(12) United States Patent
Shen et al.

(10) Patent No.: US 11,154,041 B2
(45) Date of Patent: Oct. 26, 2021

(54) GENETICALLY MODIFIED NON-HUMAN ANIMAL WITH HUMAN OR CHIMERIC GENES

(71) Applicants: Biocytogen Pharmaceuticals (Beijing) Co., Ltd., Beijing (CN); Biocytogen JiangSu Co., Ltd., Haimen (CN)

(72) Inventors: Yuelei Shen, Beijing (CN); Yanan Guo, Beijing (CN); Yang Bai, Beijing (CN); Rui Huang, Beijing (CN); Xiaofei Zhou, Beijing (CN); Chengzhang Shang, Beijing (CN); Meiling Zhang, Beijing (CN); Jiawei Yao, Beijing (CN); Chaoshe Guo, Beijing (CN)

(73) Assignees: Biocytogen Pharmaceuticals (Beijing) Co., Ltd., Beijing (CN); Biocytogen JiangSu Co., Ltd., Haimen (CN)

( * ) Notice: Subject to any disclaimer, the term of this patent is extended or adjusted under 35 U.S.C. 154(b) by 0 days.

(21) Appl. No.: 17/010,054

(22) Filed: Sep. 2, 2020

(65) Prior Publication Data

US 2021/0045367 A1   Feb. 18, 2021

Related U.S. Application Data

(63) Continuation of application No. PCT/CN2019/110819, filed on Oct. 12, 2019.

(30) Foreign Application Priority Data

Oct. 12, 2018 (CN) .......................... 201811194052.1
Dec. 28, 2018 (CN) .......................... 201811628008.7

(51) Int. Cl.
*A01K 67/027* (2006.01)
*C07K 14/715* (2006.01)
*C12N 15/85* (2006.01)

(52) U.S. Cl.
CPC ...... *A01K 67/0278* (2013.01); *C07K 14/7155* (2013.01); *C12N 15/8509* (2013.01); *A01K 2217/072* (2013.01); *A01K 2227/105* (2013.01); *C12N 2015/8527* (2013.01)

(58) Field of Classification Search
CPC .......... A01K 67/0278; A01K 2217/072; A01K 2227/105; A01K 2267/0325; A01K 2267/0387; A01K 2217/15; A01K 2267/0331; C07K 14/7155; C07K 14/5406; C07K 2319/03; C07K 2319/02; C12N 15/8509; C12N 2015/8527; C12N 15/907; C12N 15/11; C12N 2310/20; C12N 15/113

See application file for complete search history.

(56) References Cited

U.S. PATENT DOCUMENTS

| | | | |
|---|---|---|---|
| 4,683,195 A | | 7/1987 | Mullis et al. |
| 5,599,905 A | * | 2/1997 | Mosley .............. C07K 16/2866 530/350 |
| 5,942,435 A | * | 8/1999 | Wheeler ............ A01K 67/0275 435/325 |
| 2015/0106961 A1 | | 4/2015 | Rojas et al. |
| 2015/0320021 A1 | * | 11/2015 | Wang ................. A01K 67/0278 800/3 |
| 2016/0366862 A1 | * | 12/2016 | Flavell ............... A01K 67/0278 |

FOREIGN PATENT DOCUMENTS

| CN | 104755495 | 7/2015 |
|---|---|---|
| CN | 106470545 | 3/2017 |
| WO | WO 2015171861 | 11/2015 |
| WO | WO 2018001241 | 1/2018 |
| WO | WO 2018041118 | 3/2018 |
| WO | WO 2018041119 | 3/2018 |
| WO | WO 2018041120 | 3/2018 |
| WO | WO 2018041121 | 3/2018 |
| WO | WO 2018068756 | 4/2018 |
| WO | WO 2018086583 | 5/2018 |
| WO | WO 2018086594 | 5/2018 |
| WO | WO 2018113774 | 6/2018 |
| WO | WO 2018121787 | 7/2018 |

OTHER PUBLICATIONS

Hall, V. "Porcine Embryonic Stem Cells: A Possible Source for Cell Replacement Therapy." Stem Cell Rev 4, 275-282 (2008) (Year: 2008).*
Genovese et al. "Enhanced Development of Skeletal Myotubes from Porcine Induced Pluripotent Stem Cells." Scientific Reports 7 (4):pp. 1-11 (2017) (Year: 2017).*
Vesikansa, A. "Unraveling of Central Nervous System Disease Mechanisms Using CRISPR Genome Manipulation." J Cent Nerv Syst Dis.10. pp. 1-13. (2018) (Year: 2018).*
Goldstein et al. "Variation in zygotic CRISPR/Cas9 gene editing outcomes generates novel reporter and deletion alleles at the Gdf11 locus." Scientific Reports 9 (18613) pp. 1-19 (2019) (Year: 2019).*
McCarty et al. "Multiplexed CRISPR technologies for gene editing and transcriptional regulation." Nature Communications vol. 11, Article No. 1281 (2020) (Year: 2020).*
You et al. "Effects of Melanocortin 3 and 4 Receptor Deficiency on Energy Homeostasis in Rats." Sci Rep. 2016; 6: 34938. (Year: 2016).*
He et al. "Use of CRISPR/Cas9 technology efficiently targetted goat myostatin through zygotes microinjection resulting in double-muscled phenotype in goats." Biosci Rep.Nov. 1, 20183;38(6):BSR20180742. (Year: 2018).*

(Continued)

*Primary Examiner* — Titilayo Moloye
(74) *Attorney, Agent, or Firm* — Fish & Richardson P.C.

(57) ABSTRACT

The present disclosure relates to genetically modified non-human animals that express a human or chimeric (e.g., humanized) IL4R and/or IL4, and methods of use thereof.

17 Claims, 29 Drawing Sheets

Specification includes a Sequence Listing.

(56) References Cited

OTHER PUBLICATIONS

Silha, J and Murphy, L. "Unexpected and unexplained phenotypes in transgenic models." Growth Horm IGF Res. Oct. 2000;10(5):233-5. (Year: 2000).*

Brouwers et al. "Unexpected Phenotypes in Mouse Models Carrying the Human Growth Hormone Minigene to Enhance Transgene Expression." Journal of Steroids & Hormonal Science 6.2 (2015): 2. (Year: 2015).*

Yin et al. "Generation of an MC3R knock-out pig by CRSPR/Cas9 combined with somatic cell nuclear transfer (SCNT) technology." Lipids Health Dis. 2019; 18: 122. (Year: 2019).*

Auerbach et al., "Establishment and Chimera Analysis of 129/SvEv- and C57BL/6-Derived Mouse Embryonic Stem Cell Lines," Biotechniques, 2000, 26:1024-1032.

Bankaitis et al. "Targeting IL4/IL4R for the treatment of epithelial cancer metastasis." Clinical & experimental metastasis, 2015, 32(8):847-856.

Festing et al., "Revised nomenclature for strain 129 mice," Mammalian Genome, 1999, 10: 836.

GenBank Accession No. NP_001008700, "interleukin-4 receptor subunit alpha isoform 1 precursor [Mus musculus]," dated Jul. 31, 1991, 4 pages.

International Search Report and Written Opinion in International Appln. No. PCT/CN2019/110819, dated Jan. 17, 2020, 9 pages.

Ito, M. et al., "NOD/SCID/ γcnull mouse: an excellent recipient mouse model for engraftment of human cells," Blood, 2002, 100(9): 3175-3182.

Kruse et al., "Characterization of the membrane-bound and a soluble form of human IL-4 receptor beta produced by alternative splicing," International Immunology, 1999, 11(12):1965-1969.

Li-Weber et al. "Regulation of IL4 gene expression by T cells and therapeutic perspectives." Nature Reviews Immunology, 2003, 3(7):534.

Pillai et al. "Evolution of IL4 and pathogen antagonism." Growth Factors, 2011, 29(4):153-160.

Rogam, "Analysis of intergenic transcription in the human IL-4/IL-13 gene cluster," PNAS, 2004, 101(8):2446-2451.

Yin et al., "Delivery technologies for genome editing," Nature Reviews Drug Discovery, 2017, 16(6):387-399.

PCT International Preliminary Report on Patentability in International Appln. No. PCT/CN2019/110819, dated Apr. 22, 2021, 6 pages.

* cited by examiner

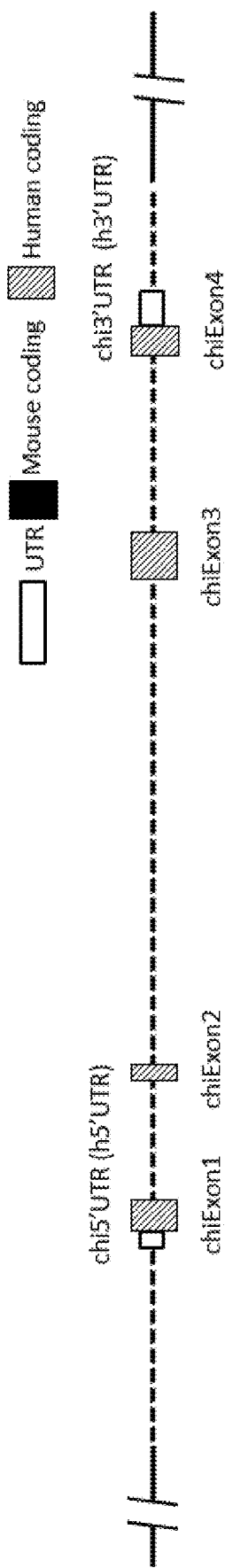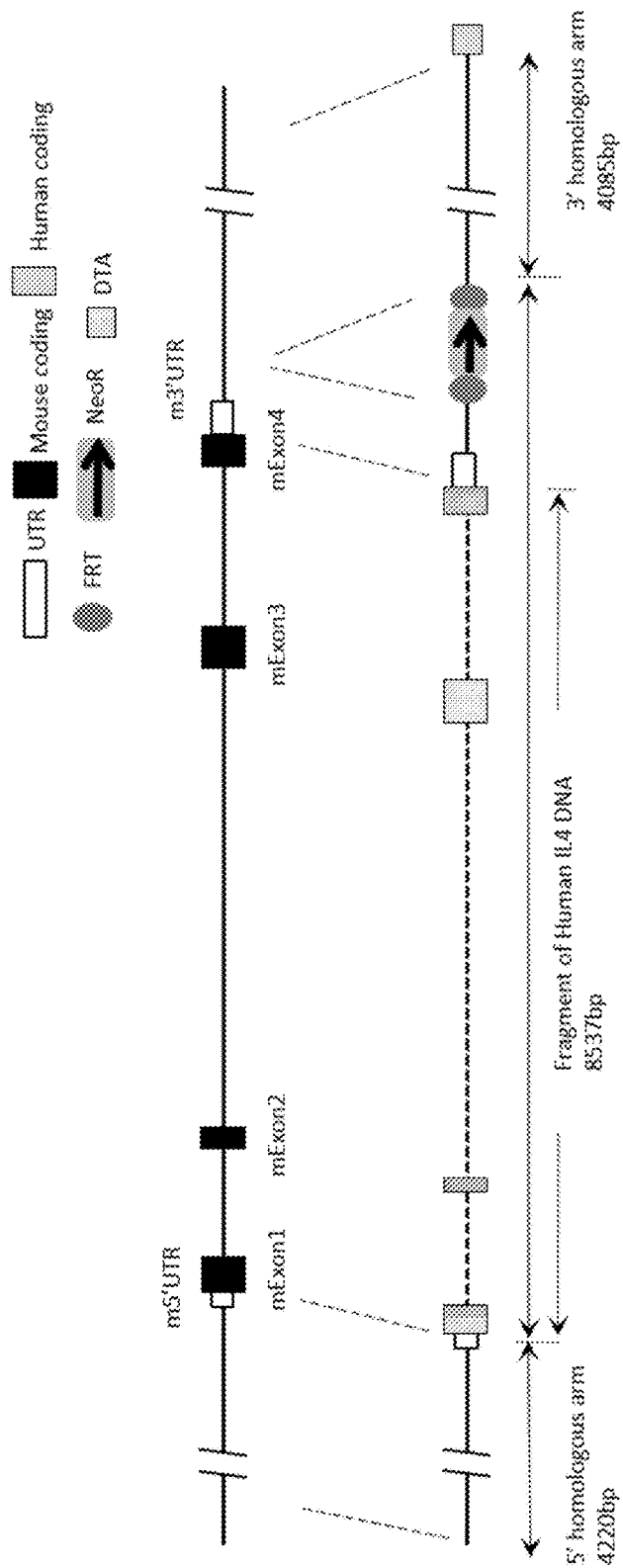
FIG. 3
FIG. 4

Neutrophils

Serum

| Score | Expect | Method | Identities | Positives | Gaps |
|---|---|---|---|---|---|
| 102 bits(254) | 2e-33() | Compositional matrix adjust. | 62/150(41%) | 87/150(58%) | 11/150(7%) |

```
Human   1    MGLTSQLLPPLFFLLACAGNFVHGHKCDIT-LQEIIKTLNSLTEQKTLCTELTVTDIFAA   59
             MGL QL+  L F L C + +HG  CD   L+EII  LN +T + T CTE+ V ++  A
Mouse   1    MGLNPQLVVILLFFLECTRSHIHG--CDKNHLREIIGILNEVTGEGTPCTEMDVPNVLTA   58

Human   60   SKNTTEKETFCRAATVLRQFYSHHEKDTRCLGATAQQFHRHKQLIRFLKRLDRNLWGLAG   119
             +KNTTE E  CRA+ VLR FY  H K T CL  +        ++L R  + LD ++
Mouse   59   TKNTTESELVCRASKVLRIFYLKHGK-TPCLKKNSSVLMELQRLFRAFRCLDSSI-----   112

Human   120  LNSCPVKEANQSTLENFLERLKTIMREKYS   149
                SC + E+  ++L++FLE LK+IM+  YS
Mouse   113  --SCTMNESKSTSLKDFLESLKSIMQMDYS   140
```

| Score | Expect | Method | Identities | Positives | Gaps |
|---|---|---|---|---|---|
| 743 bits(1919) | 0.0() | Compositional matrix adjust. | 427/816(52%) | 519/816(63%) | 21/816(2%) |

```
Human    1  MGWLCSGLLFPVSCLVLLQVASSGNMKVLQEPTCVSDYMSISTCEWKMNGPTNCSTELRL  60
            MG LC+  L V CL+LL V SG++KVL EPTC SDY+  STCEW ++   +CS++L L
Mouse    1  MGRLCTKFLTSVGCLILLLVTGSGSIKVLGEPTCFSDYIRTSTCEWFLDSAVDCSSQLCL  60

Human   61  LYQLVFL-LSEAHTCIPENNGGAGCVCHLLMDDVVSADNYTLDLWAGQQLLWKGSFKPSE  119
            Y+L+F  SE  TCIP N+    CVCH+ M+  V +D Y ++LWA  + LW+GSF PS
Mouse   61  HYRLMFFEFSENLTCIPRNSASTVCVCHMEMNRPVQSDRYQMELWAEHRQLWQGSFSPSG  120

Human  120  HVKPRAPGNLTVHTNVSDTLLLTWSNPYPPDNYLYNHLTYAVNIWSENDPADFRIYNVTY  179
            +VKP AP NLT+HTNVSD  LLTW+N YP +N LY  L   VNI  E++PA+F +YNVTY
Mouse  121  NVKPLAPDNLTLHTNVSDEWLLTWNNLYPSNNLLYKDLISMVNISREDNPAEFIVYNVTY  180

Human  180  LEPSLRIAASTLKSGISYRARVRAWAQCYNTTWSEWSPSTKWHNSYREPFEQHLLLGVSV  239
               EP L   + L SG+ Y ARVR +Q    TWSEWSPS  W+N ++ P  Q L LGV++
Mouse  181  KEPRLSFPINILMSGVYYTARVRVRSQILTGTWSEWSPSITWYNHFQLPLIQRLPLGVTI  240

Human  240  SCIVILAVCLLCYVSITKIKKEWWDQIPNPARSRLVAIIIQDAQGSQWEKRSRGQEPAKC  299
            SC+ I   CL CY SITKIKK WWDQIP PARS LVAIIIQDAQ  W+K++R QE  K
Mouse  241  SCLCIPLFCLFCYFSITKIKKIWWDQIPTPARSPLVAIIIQDAQVPLWDKQTRSQESTKY  300

Human  300  PHWKNCLTKLLPCFLEHNMKRDEDPHKAAKEMPFQGSGKSAWCPVEISKTVLWPE--SIS  357
            PHWK CL KLLPC L+H +K+ D  KAA        Q  GK+ WCP+E+S+TVLWPE  S+S
Mouse  301  PHWKTCLDKLLPCLLKHRVKKKTDFPKAAPTKSLQSPGKAGWCPMEVSRTVLWPENVSVS  360

Human  358  VVRCVELFEAPVECEEEEEVEEEKGSFCASPESSRD-DFQEGREGIVARLTESLFLDLLG  416
            VVRC+ELFEAPV+  EEEE E K     SPE+S    FQE +  I+ARLTE+LF DLL
Mouse  361  VVRCMELFEAPVQNVEEEEDEIVKEDLSMSPENSGGCGFQESQADIMARLTENLFSDLLE  420

Human  417  EENGGFCQQDMGESCLLPPSGSTSAHMPWDEFPSAGPKEAPPWGKEQPLHLEPSP-PASP  475
            E NGG Q  + ESC  PSGS  A +  W  P +EA    EQP H  P P   SP
Mouse  421  AENGGLGQSALAESCSPLPSGSGQASVSWACLPMGPSEEATCQVTEQPSH--PGPLSGSF  478

Human  476  TQSPDNLTCTETPLVIAGNPAYRSFSNSLSQSPCPRELGPDPLLARHLEEVEPEMPCVPQ  535
             QS    L CT+  PLV+A NPAYRSFS+  S +P  EL P+   A HLEE EP  P  P
Mouse  479  AQSAPTLACTQVPLVLADNPAYRSFSDCCSPAPNPGELAPEQQQADHLEEEEPPSPADPH  538

Human  536  LSEPTTVPQPEPETWEQILRRNVLQHGAAAPVSAPTSGYQEFVHAVEQGGTQASAVVGL  595
             S P   P   E+WEQIL  +VLQHGAAA    AP  GYQEFV AV+QG  Q   V G+
Mouse  539  SSGPPMQPV---ESWEQILHMSVLQHGAAAGSTPAPAGGYQEFVQAVKQGAAQDPGVPGV  595

Human  596  GPPGEAGYKAFSSLLASSAVSPEKCGFGASSGEEGYKPFQDLIPGCPGDPAPVPVPLFTF  655
             P G+ GYKAFSSLL+S+  +   G   G  GYKPFQ+ +P    + +P  VPLFTF
Mouse  596  RPSGDPGYKAFSSLLSSNGIRGDTAAAGTDDGHGGYKPFQNPVP----NQSPSSVPLFTF  651

Human  656  GLDREPPRSPQSSHLPSSSPEHLGLEPGEKVEDMPKPPLPQEQATDPLVDSLGSGIVYSA  715
            GLD E   SP +S  P SS PE LGLE G K  D  KP P +Q   P  D LG GIVYS+
Mouse  652  GLDTELSPSPLNSDPPKSPPECLGLELGLKGGDWVKAPPPADQVPKPFGDDLGFGIVYSS  711

Human  716  LTCHLCGHLKQCHGQEDGGQTPVMASPCCGCCCGDRSSPPTTPLRAPDPSPGGVPLEASL  775
            LTCHLCGHLKQ H QE+GGQ+P++ASP CGCC  DRS   +  A +  P G+P EA+L
Mouse  712  LTCHLCGHLKQHHSQEEGGQSPIVASPGCGCCYDDRSPSLGSLSGALESCPEGIPPEANL  771

Human  776  CPASLAPSGISEKSKSSSSFHPAPGNAQSSSQTPKI  811
             A    PS +S +  K         PG++    SQT ++
Mouse  772  MSAPKTPSNLSGEGK-------GPGHSPVPSQTTEV  800
```

GENETICALLY MODIFIED NON-HUMAN ANIMAL WITH HUMAN OR CHIMERIC GENES

CLAIM OF PRIORITY

Pursuant to 35 U.S.C. § 119(e), this application is a continuation of International Application PCT/CN2019/110819, with an international filing date of Oct. 12, 2019 which claims the benefit of Chinese Patent Application App. No. 201811194052.1, filed on Oct. 12, 2018, and Chinese Patent Application App. No. 201811628008.7, filed on Dec. 28, 2018. The entire contents of the foregoing are incorporated herein by reference.

TECHNICAL FIELD

This disclosure relates to genetically modified animal expressing human or chimeric (e.g., humanized) genes, and methods of use thereof.

BACKGROUND

Interleukin-4 (IL4) is a cytokine produced by several different cell types, including e.g., activated T cells, mast cells and basophils. The immuno-regulatory role of IL4 in allergic diseases and activation of Th2 type responses has been well established. There is substantial evidence showing that targeting IL4/IL4R pathway can be a therapeutic strategy for treating immune-related disorders (e.g., allergy and autoimmune diseases) in humans.

The traditional drug research and development for therapeutic agents that target IL4/IL4R pathway typically use in vitro screening approaches. However, these screening approaches are still different from what happens in the in vivo environment (such as cell microenvironment, extracellular matrix components and immune cell interaction, etc.), resulting in a high rate of failure in drug development. There is a need for humanized animal models that are suitable for human antibody screening and efficacy evaluation.

SUMMARY

This disclosure is related to an animal model with human IL4R and/or IL4 or chimeric IL4R and/or IL4. The animal model can express human IL4R and/or IL4 or chimeric IL4R and/or IL4 (e.g., humanized IL4R and/or IL4) protein in its body. It can be used in the studies on the function of IL4R and/or IL4 gene, and can be used in the screening and evaluation of anti-human IL4R and anti-IL4 antibodies. In addition, the animal models prepared by the methods described herein can be used in drug screening, pharmacodynamics studies, treatments for immune-related diseases (e.g., autoimmune disease, allergies). They can also be used to facilitate the development and design of new drugs, and save time and cost. In summary, this disclosure provides a powerful tool for studying the function of IL4R and/or IL4 protein and a platform for screening treatments for immune-related diseases.

In one aspect, the disclosure provides a genetically-modified, non-human animal whose genome comprises at least one chromosome comprising a sequence encoding a human or chimeric IL4R.

In some embodiments, the sequence encoding the human or chimeric IL4R is operably linked to an endogenous regulatory element at the endogenous IL4R gene locus in the at least one chromosome.

In some embodiments, the sequence encoding a human or chimeric IL4R comprises a sequence encoding an amino acid sequence that is at least 70%, 75%, 80%, 85%, 90%, 95%, 99%, or 100% identical to human IL4R (NP 000409.1; SEQ ID NO: 42).

In some embodiments, the sequence encoding a human or chimeric IL4R comprises a sequence encoding an amino acid sequence that is at least 70%, 75%, 80%, 85%, 90%, 95%, 99%, or 100% identical to SEQ ID NO: 44.

In some embodiments, the sequence encoding a human or chimeric IL4R comprises a sequence that is at least 70%, 75%, 80%, 85%, 90%, 95%, 99%, or 100% identical to amino acids 30-216 of SEQ ID NO: 42.

In some embodiments, the animal comprises a sequence that is at least 70%, 75%, 80%, 85%, 90%, 95%, 99%, or 100% identical to SEQ ID NO: 48, 49, 50, or 51.

In some embodiments, the animal is a mammal, e.g., a monkey, a rodent or a mouse. In some embodiments, the animal is a mouse.

In some embodiments, the animal does not express endogenous IL4R. In some embodiments, the animal has one or more cells expressing human or chimeric IL4R.

In some embodiments, the animal has one or more cells expressing human or chimeric IL4R, and the expressed human or chimeric IL4R can bind to endogenous IL4.

In some embodiments, the animal has one or more cells expressing human or chimeric IL4R, and the expressed human or chimeric IL4R cannot bind to endogenous IL4.

In another aspect, the disclosure is related to a genetically-modified, non-human animal, in some embodiments, the genome of the animal comprises a replacement of a sequence encoding a region of endogenous IL4R with a sequence encoding a corresponding region of human IL4R at an endogenous IL4R gene locus.

In some embodiments, the sequence encoding the corresponding region of human IL4R is operably linked to an endogenous regulatory element at the endogenous IL4R locus, and one or more cells of the animal express a chimeric IL4R.

In some embodiments, the animal does not express endogenous IL4R.

In some embodiments, the replaced locus is the extracellular region of IL4R.

In some embodiments, the animal has one or more cells expressing a chimeric IL4R having an extracellular region, in some embodiments, the extracellular region comprises a sequence that is at least 50%, 60%, 70%, 80%, 90%, 95%, or 99% identical to the extracellular region of human IL4R.

In some embodiments, the extracellular region of the chimeric IL4R has a sequence that has at least 10, 20, 30, 40, 50, 60, 70, 80, 90, 100, or 150 contiguous amino acids that are identical to a contiguous sequence present in the extracellular region of human IL4R.

In some embodiments, the animal is a mouse, and the replaced endogenous IL4R region is exon 4, exon 5, exon 6, and/or exon 7 of the endogenous mouse IL4R gene.

In some embodiments, the animal is heterozygous with respect to the replacement at the endogenous IL4R gene locus. In some embodiments, the animal is homozygous with respect to the replacement at the endogenous IL4R gene locus.

In one aspect, the disclosure relates to methods for making a genetically-modified, non-human animal. The methods involve replacing in at least one cell of the animal, at an endogenous IL4R gene locus, a sequence encoding a region of an endogenous IL4R with a sequence encoding a corresponding region of human IL4R.

In some embodiments, the sequence encoding the corresponding region of human IL4R comprises exon 4, exon 5, exon 6, and/or exon 7 of a human IL4R gene.

In some embodiments, the sequence encoding the corresponding region of IL4R comprises at least 100, 200, or 300 nucleotides of exon 4, exon 5, exon 6 and/or exon 7 of a human IL4R gene.

In some embodiments, the sequence encoding the corresponding region of human IL4R encodes a sequence that is at least 90% identical to amino acids 30-216 of SEQ ID NO: 42.

In some embodiments, the locus is located within the extracellular region of IL4R.

In some embodiments, the animal is a mouse, and the locus is exons 4, exon5, exon 6 and/or exon 7 of the mouse IL4R gene.

In one aspect, the disclosure relates to a non-human animal comprising at least one cell comprising a nucleotide sequence encoding a chimeric IL4R polypeptide, in some embodiments, the chimeric IL4R polypeptide comprises at least 50 contiguous amino acid residues that are identical to the corresponding contiguous amino acid sequence of a human IL4R. In some embodiments, the animal expresses the chimeric IL4R.

In some embodiments, the chimeric IL4R polypeptide has at least 50 contiguous amino acid residues that are identical to the corresponding contiguous amino acid sequence of a human IL4R extracellular region.

In some embodiments, the chimeric IL4R polypeptide comprises a sequence that is at least 90%, 95%, or 99% identical to amino acids 30-216 of SEQ ID NO: 42.

In some embodiments, the nucleotide sequence is operably linked to an endogenous IL4R regulatory element of the animal.

In some embodiments, the chimeric IL4R polypeptide comprises an endogenous IL4R transmembrane region and/or an endogenous cytoplasmic region.

In some embodiments, the nucleotide sequence is integrated to an endogenous IL4R gene locus of the animal.

In some embodiments, the chimeric IL4R has at least one mouse IL4R activity and/or at least one human IL4R activity.

In one aspect, the disclosure relates to methods of making a genetically-modified mouse cell that expresses a chimeric IL4R. The methods involve replacing, at an endogenous mouse IL4R gene locus, a nucleotide sequence encoding a region of mouse IL4R with a nucleotide sequence encoding a corresponding region of human IL4R, thereby generating a genetically-modified mouse cell that includes a nucleotide sequence that encodes the chimeric IL4R. In some embodiments, the mouse cell expresses the chimeric IL4R.

In some embodiments, the chimeric IL4R comprises: an extracellular region of human IL4R; a transmembrane region of mouse IL4R; and/or a cytoplasmic region of mouse IL4R.

In some embodiments, the nucleotide sequence encoding the chimeric IL4R is operably linked to an endogenous IL4R regulatory region, e.g., promoter.

In some embodiments, the animal further comprises a sequence encoding an additional human or chimeric protein (e.g., IL4, IL33, IL13, programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), CD137, TNF Receptor Superfamily Member 4 (OX40), CD47, or Signal regulatory protein α (SIRPa)). In some embodiments, the additional human or chimeric protein is IL4.

In one aspect, the disclosure provides a genetically-modified, non-human animal whose genome comprises at least one chromosome comprising a sequence encoding a human or chimeric IL4.

In some embodiments, the sequence encoding the human or chimeric IL4 is operably linked to an endogenous regulatory element at the endogenous IL4 gene locus in the at least one chromosome. In some embodiments, the sequence encoding the human or chimeric IL4 is operably linked to a human regulatory element at the endogenous IL4 gene locus in the at least one chromosome.

In some embodiments, the sequence encoding a human or chimeric IL4 comprises a sequence encoding an amino acid sequence that is at least 70%, 75%, 80%, 85%, 90%, 95%, 99%, or 100% identical to human IL4 (NP 000580.1; SEQ ID NO: 4).

In some embodiments, the animal comprises a sequence that is at least 70%, 75%, 80%, 85%, 90%, 95%, 99%, or 100% identical to SEQ ID NO: 8, 9, 10, 11, 23, 24, or 25.

In some embodiments, the animal is a mammal, e.g., a monkey, a rodent or a mouse. In some embodiments, the animal is a mouse.

In some embodiments, the animal does not express endogenous IL4. In some embodiments, the animal has one or more cells expressing human IL4. In some embodiments, the animal has one or more cells expressing human or chimeric IL4, and the expressed human or chimeric IL4 can bind to endogenous IL4R. In some embodiments, the animal has one or more cells expressing human or chimeric IL4, and the expressed human or chimeric IL4 cannot bind to endogenous IL4R.

In one aspect, the disclosure provides a genetically-modified, non-human animal. In some embodiments, the genome of the animal comprises a replacement of a sequence encoding a region of endogenous IL4 with a sequence encoding a corresponding region of human IL4 at an endogenous IL4 gene locus.

In some embodiments, the sequence encoding the corresponding region of human IL4 is operably linked to an endogenous regulatory element at the endogenous IL4 locus, and one or more cells of the animal expresses a human IL4.

In some embodiments, the sequence encoding the corresponding region of human IL4 is operably linked to a human regulatory element at the endogenous IL4 locus, and one or more cells of the animal expresses a human IL4.

In some embodiments, the animal does not express endogenous IL4.

In some embodiments, the replaced locus comprises a sequence of SEQ ID NO: 8, SEQ ID NO: 9, SEQ ID NO: 23, SEQ ID NO: 24, or SEQ ID NO: 25.

In some embodiments, the animal is a mouse, and the replaced endogenous IL4 region is exon 1, exon 2, exon 3 and/or exon 4 of the endogenous mouse IL4 gene.

In some embodiments, the animal is heterozygous with respect to the replacement at the endogenous IL4 gene locus. In some embodiments, the animal is homozygous with respect to the replacement at the endogenous IL4 gene locus.

In another aspect, the disclosure relates to methods for making a genetically-modified, non-human animal. The methods involve replacing in at least one cell of the animal, at an endogenous IL4 gene locus, a sequence encoding a region of an endogenous IL4 with a sequence encoding a corresponding region of human IL4.

In some embodiments, the sequence encoding the corresponding region of human IL4 comprises exon 1, exon 2, exon 3 and/or exon 4 of a human IL4 gene. In some embodiments, the sequence encoding the corresponding region of IL4 comprises at least 50, 100, 150, or 200 nucleotides of exon 1, exon 2, exon 3 and/or exon 4 of a human IL4 gene.

In some embodiments, the sequence encoding the corresponding region of human IL4 encodes a sequence that is at least 90% identical to SEQ ID NO: 4. In some embodiments, replaced locus comprises a sequence of SEQ ID NO: 8, SEQ ID NO: 9, SEQ ID NO: 10, SEQ ID NO: 11, SEQ ID NO: 23, SEQ ID NO: 24, or SEQ ID NO: 25.

In some embodiments, the animal is a mouse, and the locus is exon 1, exon 2, exon 3 and/or exon 4 of the mouse IL4 gene.

In another aspect, the disclosure provides a non-human animal comprising at least one cell comprising a nucleotide sequence encoding a chimeric IL4 polypeptide, in some embodiments, the chimeric IL4 polypeptide comprises at least 50 contiguous amino acid residues that are identical to the corresponding contiguous amino acid sequence of a human IL4. In some embodiments, the animal expresses the chimeric IL4.

In some embodiments, the chimeric IL4 polypeptide has at least 100 contiguous amino acid residues that are identical to the corresponding contiguous amino acid sequence of a human IL4.

In some embodiments, the nucleotide sequence is operably linked to an endogenous IL4 regulatory element of the animal. In some embodiments, the nucleotide sequence is operably linked to a human IL4 regulatory element of the animal.

In some embodiments, the nucleotide sequence is integrated to an endogenous IL4 gene locus of the animal.

In some embodiments, the chimeric IL4 has at least one mouse IL4 activity and/or at least one human IL4 activity.

In one aspect, the disclosure relates to methods of making a genetically-modified mouse cell that expresses a chimeric IL4 or a human IL4. The methods involve replacing, at an endogenous mouse IL4 gene locus, a nucleotide sequence encoding a region of mouse IL4 with a nucleotide sequence encoding a corresponding region of human IL4, thereby generating a genetically-modified mouse cell that includes a nucleotide sequence that encodes the chimeric IL4. In some embodiments, the mouse cell expresses the chimeric IL4 or human IL4.

In some embodiments, the nucleotide sequence encoding the chimeric IL4 is operably linked to an endogenous IL4 regulatory region, e.g., promoter, 5'-UTR, or 3'-UTR.

In some embodiments, the nucleotide sequence encoding the chimeric IL4 is operably linked to a human IL4 regulatory region, e.g., promoter, 5'-UTR, or 3'-UTR.

In some embodiments, the animal or mouse further comprises a sequence encoding an additional human or chimeric protein (e.g., IL4R, IL33, IL13, PD-1, CTLA-4, LAG-3, BTLA, PD-L1, CD27, CD28, TIGIT, TIM-3, GITR, CD137, OX40, CD47, or SIRPa). In some embodiments, the additional human or chimeric protein is IL4R.

In one aspect, the disclosure relates to methods of determining effectiveness of an IL4-IL4R pathway inhibitor for treating an allergic disorder. The methods involve administering the IL4-IL4R pathway inhibitor to the animal as described herein, where the animal has an allergic disorder; and determining the inhibitory effects of the IL4-IL4R pathway inhibitor. In some embodiments, the allergic disorder is asthma. In some embodiments, the allergic disorder is atopic dermatitis. In some embodiments, the allergic disorder is chromic sinusitis.

In some embodiments, the IL4-IL4R pathway inhibitor is an anti-IL4 antibody (e.g., anti-human IL4 antibody). In some embodiments, the IL4-IL4R pathway inhibitor is an anti-IL4R antibody (e.g., anti-human IL4R antibody). In some embodiments, the IL4-IL4R pathway inhibitor is an anti-IL13 antibody (e.g., anti-human IL13 antibody).

In some embodiments, the inhibitory effects are evaluated by serum IgE levels; pathological lung histology features; number of leukocytes (CD45+ cells), eosinophils (Eos) or neutrophils in bronchoalveolar lavage fluid (BALF); or ratio of eosinophils or neutrophils cells in CD45+ cells in bronchoalveolar lavage fluid (BALF).

In one aspect, the disclosure also provides methods of determining effectiveness of an IL4-IL4R pathway inhibitor for reducing inflammation. The methods involve administering the IL4-IL4R pathway inhibitor to the animal as described herein, where the animal has inflammation; and determining the inhibitory effects of the IL4-IL4R pathway inhibitor.

In one aspect, the disclosure also provides methods of determining effectiveness of an IL4-IL4R pathway inhibitor for treating autoimmune disorder. The methods involve administering the IL4-IL4R pathway inhibitor to the animal as described herein, where the animal has autoimmune disorder; and determining the inhibitory effects of the IL4-IL4R pathway inhibitor.

In another aspect, the disclosure also provides methods of determining effectiveness of an IL4-IL4R pathway inhibitor for treating cancer. The methods involve administering the IL4-IL4R pathway inhibitor to the animal as described herein, where the animal has a tumor; and determining the inhibitory effects of the IL4-IL4R pathway inhibitor. In some embodiments, determining the inhibitory effects of the treatment involves measuring the tumor volume in the animal.

In one aspect, the disclosure also provides methods of determining toxicity of an anti-IL4R antibody or an anti-IL4 antibody, the methods involve administering the anti-IL4R antibody or the anti-IL4 antibody to the animal as described herein; and determining weight change of the animal. In some embodiments, the method further comprising performing a blood test (e.g., determining red blood cell count).

In one aspect, the disclosure relates to proteins comprising an amino acid sequence, in some embodiments, the amino acid sequence is one of the following:

(a) an amino acid sequence set forth in SEQ ID NO: 44;
(b) an amino acid sequence that is at least 90%, 91%, 92%, 93%, 94%, 95%, 96%, 97%, 98%, or 99% identical to SEQ ID NO: 44;
(c) an amino acid sequence that is different from the amino acid sequence set forth in SEQ ID NO: 44 by no more than 10, 9, 8, 7, 6, 5, 4, 3, 2 or 1 amino acid; and
(d) an amino acid sequence that comprises a substitution, a deletion and/or insertion of one, two, three, four, five or more amino acids to the amino acid sequence set forth in SEQ ID NO: 44.

In one aspect, the disclosure relates to nucleic acids comprising a nucleotide sequence, in some embodiments, the nucleotide sequence is one of the following:

(a) a sequence that encodes the protein as described herein;
(b) SEQ ID NO: 8, 9, 10, 11, 23, 24, 25, 43, 48, 49, 50, or 51; or (c) a sequence that is at least 90%, 91%, 92%, 93%, 94%, 95%, 96%, 97%, 98%, or 99% identical to SEQ ID NO: 8, 9, 10, 11, 23, 24, 25, 43, 48, 49, 50, or 51.

In some embodiments, the mice described in the present disclosure can be mated with the mice containing other human or chimeric genes (e.g., chimeric IL4, chimeric PD-1, chimeric PD-L1, chimeric CTLA-4, or other immunomodulatory factors), so as to obtain a mouse expressing two or more human or chimeric proteins. The mice can also, e.g., be used for screening antibodies in the case of a combined use of drugs, as well as evaluating the efficacy of the combination therapy.

In one aspect, the disclosure also provides a genetically-modified, non-human animal whose genome comprise a disruption in the animal's endogenous IL4R gene, wherein the disruption of the endogenous IL4R gene comprises deletion of exon 4, exon 5, exon 6, and/or exon 7, or part thereof of the endogenous IL4R gene.

In some embodiments, the disruption of the endogenous IL4R gene further comprises deletion of one or more exons or part of exons selected from the group consisting of exon 1, exon 2, exon 3, exon 4, exon 5, exon 6, exon 7, exon 8, exon 9, exon 10 and/or exon 11 of the endogenous IL4R gene.

In some embodiments, the disruption of the endogenous IL4R gene further comprises deletion of one or more introns or part of introns selected from the group consisting of intron 1, intron 2, intron 3, intron 4, intron 5, intron 6, intron 7, intron 8, intron 9 and/or intron 10 of the endogenous IL4R gene.

In some embodiments, wherein the deletion can comprise deleting at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, 300, 350, 400, 450, 500, 550, 600, 650, or more nucleotides.

In some embodiments, the disruption of the endogenous IL4R gene comprises the deletion of at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, or 300 nucleotides of exon 1, exon 2, exon 3, exon 4, exon 5, exon 6, exon 7, exon 8, exon 9, exon 10 and/or exon 11 (e.g., deletion of at least 100 nucleotides of exon 5).

In one aspect, the disclosure also provides a genetically-modified, non-human animal whose genome comprise a disruption in the animal's endogenous IL4 gene, wherein the disruption of the endogenous IL4 gene comprises deletion of exon 1, exon 2, exon 3, and/or exon 4, or part thereof of the endogenous IL4 gene.

In some embodiments, the disruption of the endogenous IL4 gene further comprises deletion of one or more exons or part of exons selected from the group consisting of exon 1, exon 2, exon 3, and/or exon 4 of the endogenous IL4 gene.

In some embodiments, the disruption of the endogenous IL4 gene further comprises deletion of one or more introns or part of introns selected from the group consisting of intron 1, intron 2, and/or intron 3 of the endogenous IL4 gene.

In some embodiments, wherein the deletion can comprise deleting at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, 300, 350, 400, 450, 500, 550, 600, 650, or more nucleotides.

In some embodiments, the disruption of the endogenous IL4 gene comprises the deletion of at least 1, 2, 3, 4, 5, 6, 7, 8, 9, 10, 20, 30, 40, 50, 60, 70, 80, 90, 100, 110, 120, 130, 140, 150, 160, 170, 180, 190, or 200 nucleotides of exon 1, exon 2, exon 3, and/or exon 4 (e.g., deletion of at least 100 nucleotides of exon 3).

The disclosure also relates to a method for establishing a genetically-modified non-human animal expressing two human or chimeric (e.g., humanized) genes. The method includes the steps of (a) using the method for establishing a IL4R gene humanized animal model to obtain a IL4R gene genetically modified humanized mouse; (b) mating the IL4R gene genetically modified humanized mouse obtained in step (a) with another humanized mouse, and then screening to obtain a double humanized mouse model. In some embodiments, in step (b), the IL4R gene genetically modified humanized mouse obtained in step (a) is mated with an IL4 humanized mouse to obtain a IL4R and IL4 double humanized mouse model.

The disclosure also relates to a method for establishing a genetically-modified non-human animal expressing two human or chimeric (e.g., humanized) genes. The method includes the steps of (a) using the method for establishing a IL4 gene humanized animal model to obtain a IL4 gene genetically modified humanized mouse; (b) mating the IL4 gene genetically modified humanized mouse obtained in step (a) with another humanized mouse, and then screening to obtain a double humanized mouse model. In some embodiments, in step (b), the IL4 gene genetically modified humanized mouse obtained in step (a) is mated with an IL4R humanized mouse to obtain an IL4 and IL4R double humanized mouse model.

The disclosure also relates to non-human mammal generated through the methods as described herein. In some embodiments, the genome thereof contains human gene(s).

In some embodiments, the non-human mammal is a rodent. In some embodiments, the non-human mammal is a mouse. In some embodiments, the non-human mammal expresses a protein encoded by a humanized IL4R and/or IL4 gene.

The disclosure also relates to an offspring of the non-human mammal.

In one aspect, the disclosure relates to a non-human mammal model, characterized in that the non-human mammal model is obtained through the methods as described herein. In some embodiments, the non-human mammal is a rodent. In some embodiments, the non-human mammal is a mouse.

The disclosure also relates to a cell (e.g., stem cell or embryonic stem cell) or cell line, or a primary cell culture thereof derived from the non-human mammal or an offspring thereof, or the tumor bearing non-human mammal. The disclosure further relates to the tissue, organ or a culture thereof derived from the non-human mammal or an offspring thereof, or the tumor bearing non-human mammal.

In one aspect, the disclosure relates to a tumor tissue derived from the non-human mammal or an offspring thereof when it bears a tumor, or the tumor bearing non-human mammal.

The disclosure further relates to a IL4R and/or IL4 genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the non-human mammal, the animal model generated through the method as described herein in the production and utilization of an animal experimental disease model of immunization processes involving human cells, the study on a pathogen, or the development of a new diagnostic strategy and/or a therapeutic strategy.

The disclosure further relates to the use of the non-human mammal or an offspring thereof, or the non-human mammal, the animal model generated through the methods as described herein, in the screening, verifying, evaluating or studying the IL4R and/or IL4 gene function, human IL4R and/or IL4 antibodies, the drugs or efficacies for human IL4R and/or IL4 targeting sites, and the drugs for immune-related diseases.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 3 is a schematic diagram showing humanized IL4 gene (replacing coding sequencing and 5'-UTR and 3'-UTR).

FIG. 4 is a schematic diagram showing an IL4 gene targeting strategy.

FIG. 42 shows amino acid sequence alignment result between human IL4 protein and mouse IL4 protein.

FIG. 43 shows amino acid sequence alignment result between human IL4Ra protein and mouse IL4Ra protein.

SEQUENCE LISTING

Figure 1:
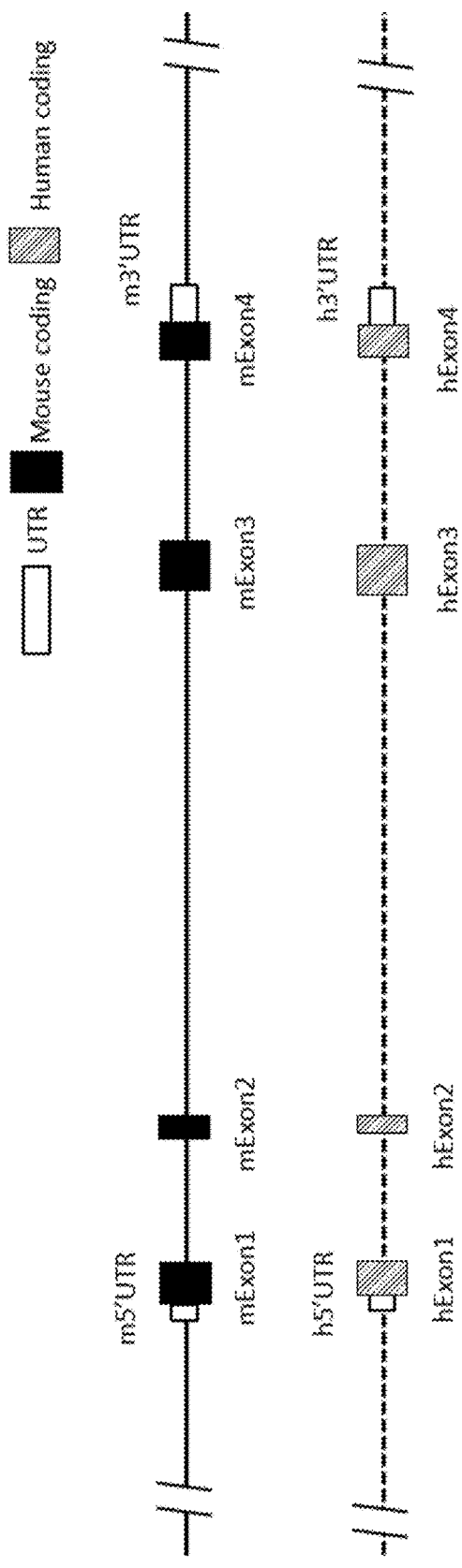
FIG. 1 is a schematic diagram showing mouse and human IL4 gene locus.

The instant application contains a Sequence Listing which has been submitted electronically in ASCII format and is hereby incorporated by reference in its entirety. Said ASCII copy, created on Nov. 10, 2020, is named Updated_SEQ.txt and is 135,121 bytes in size.

DETAILED DESCRIPTION

This disclosure relates to transgenic non-human animal with human or chimeric (e.g., humanized) IL4R and/or IL4, and methods of use thereof.

IL4/IL4R signaling is implicated in many immune diseases including e.g., allergies, autoimmune diseases, asthma, and atopic dermatitis. In the immune system, IL4 controls the development, survival, and maturation of B cells and the proliferation and differentiation of Th2 T lymphocytes. IL4 supports this enhanced proliferation and survival in part by inducing glucose uptake and metabolism. IL4 can also polarize macrophages to the 'M2' or alternatively activated phenotype.

In normal tissues, IL4 receptor α (IL4Ra) is often expressed on T and B lymphocytes, eosinophils, macrophages, endothelial cells, lung fibroblasts, bronchial epithelial cells, myeloid-derived suppressor cells (MDSCs), and smooth muscle cells. There are two types of IL4 receptors. Each type of receptors has two protein subunits that heterodimerize upon IL4 binding the IL4Ra subunit. The type I receptor is predominantly expressed by hematopoietic cells, and has the IL4Ra and common gamma C (γc) subunits. The type II receptor can be expressed by non-hematopoetic cells, and has the IL13Rα1 and IL4Ra subunits. Interestingly, while the majority of normal epithelial tissues do not express IL4 receptors, the type II receptor is overexpressed on the surface of many solid tumors including, but not limited to, renal cell carcinoma, melanoma, breast cancer, ovarian cancer, colon cancer, AIDS-related kaposi's sarcoma, and head and neck squamous cell carcinoma, suggesting targeting the IL4/IL4R signaling axis can be a potential anti-tumor therapy (Bankaitis et al. "Targeting IL4/IL4R for the treatment of epithelial cancer metastasis." Clinical & experimental metastasis 32.8 (2015): 847-856).

Unlike type I receptor, the type II receptor can also bind to IL13. IL13 signaling through the type II receptor on airway epithelial cells can lead to the airway hyper-responsiveness and increased mucus secretion in asthma. It was hypothesized that continued IL13 signaling through the type II receptor may contribute to the limited clinical efficacy of IL4-targeted treatments in asthma. Therefore, blocking the receptor subunit, IL4Ra, to inhibit both IL4- and IL13-induced signaling was an enticing alternative. However, the use of monoclonal antibodies against IL4Ra has yielded mixed results in patients. The humanized anti-IL4Ra antibody, AMG317, showed no clinical efficacy in asthma patients, and development was abandoned after phase II clinical trials. A second monoclonal antibody directed against IL4Ra, Dupilumab, has shown efficacy in the treatment of atopic dermatitis, and is possibly more effective for the treatment of asthma.

Experimental animal models are an indispensable research tool for studying the effects of these antibodies before clinical trials. Common experimental animals include mice, rats, guinea pigs, hamsters, rabbits, dogs, monkeys, pigs, fish and so on. However, there are differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models have various important applications. For example, due to the presence of human or humanized genes, the animals can express or express in part of the proteins with human functions, so as to greatly reduce the differences in clinical trials between humans and animals, and provide the possibility of drug screening at animal levels. Furthermore, because of interaction between human IL4R and human IL4, a desirable animal model for the investigation of anti-IL4R or anti-IL4 antibodies should faithfully mimic the interaction between human IL4R and human IL4, elicit robust responses from both the innate and adaptive immunity, and recapitulate side effects of IL4 blockade in human patients.

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Gloverd., 1985); Oligonucleotide Synthesis (M. J. Gaited., 1984); Mullisetal U.S. Pat. No. 4,683,195; Nucleic Acid Hybridization (B. D. Hames& S. J. Higginseds. 1984); Transcription And Translation (B. D. Hames& S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wuetal. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N.Y., 1986); each of which is incorporated herein by reference in its entirety.

Interleukin 4 (IL4)

The interleukin 4 (IL4) has a compact, globular fold (similar to other cytokines), stabilized by 3 disulfide bonds. One half of the structure is dominated by a 4 alpha-helix bundle with a left-handed twist. The helices are anti-parallel, with 2 overhand connections, which fall into a 2-stranded anti-parallel beta-sheet.

IL4 is a cytokine that induces differentiation of naive helper T cells (Th0 cells) to Th2 cells. Upon activation by IL4, Th2 cells subsequently produce additional IL4 in a positive feedback loop. The cell that initially produces IL4, thus inducing Th2 differentiation, has not been identified, but recent studies suggest that basophils may be the effector cell. It is closely related and has functions similar to interleukin 13.

Tissue macrophages play an important role in chronic inflammation and wound repair. The presence of IL4 in extravascular tissues promotes alternative activation of macrophages into M2 cells and inhibits classical activation of macrophages into M1 cells. An increase in repair macrophages (M2) is coupled with secretion of IL10 and TGF-β that result in a diminution of pathological inflammation. Release of arginase, proline, polyaminase and TGF-β by the activated M2 cell is tied with wound repair and fibrosis.

A detailed description of IL4 and its function can be found, e.g., in Pillai et al. "Evolution of IL4 and pathogen antagonism." Growth Factors 29.4 (2011): 153-160; Li-Weber et al. "Regulation of IL4 gene expression by T cells and therapeutic perspectives." Nature Reviews Immunology 3.7 (2003): 534; which are incorporated by reference herein in the entirety.

In human genomes, IL4 gene (Gene ID: 3565) locus has 4 exons, exon 1, exon 2, exon 3, and exon 4. The nucleotide sequence for human IL4 mRNA is NM_000589.3 (SEQ ID NO: 3), and the amino acid sequence for human IL4 is NP_000580.1 (SEQ ID NO: 4). The location for each exon and each region in human IL4 nucleotide sequence and amino acid sequence is listed below:

TABLE 1

Figure 8:
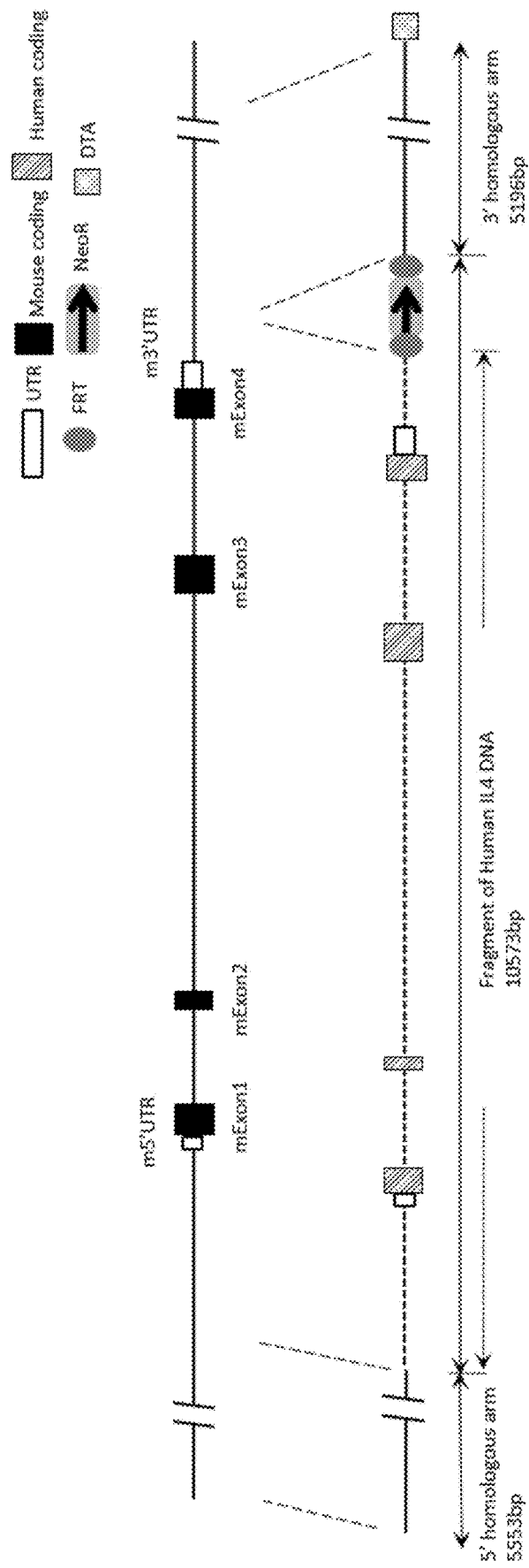
FIG. 8 is a schematic diagram showing an IL4 gene targeting strategy.

| Human IL4 (approximate location) | NM_000589.3 642 bp (SEQ ID NO: 3) | NP_000580.1 153 aa (SEQ ID NO: 4) |
| --- | --- | --- |
| Exon 1 | 1-200 | 1-45 |
| Exon 2 | 201-248 | 46-61 |
| Exon 3 | 249-425 | 62-120 |
| Exon 4 | 426-618 | 121-153 |
| Signal peptide | 66-137 | 1-24 |
| Donor region in Example FIG. 4 | 66-527 | 1-153 |
| Donor region in Example FIG. 8 | 1-642 | 1-153 |

In mice, IL4 gene locus has 4 exons, exon 1, exon 2, exon 3, and exon 4. The nucleotide sequence for mouse IL4 mRNA is NM_021283.2 (SEQ ID NO: 1), the amino acid sequence for mouse IL4 is NP_067258.1 (SEQ ID NO: 2). The location for each exon and each region in the mouse IL4 nucleotide sequence and amino acid sequence is listed below:

TABLE 2

| Mouse IL-4 (approximate location) | NM_021283.2 605 bp (SEQ ID NO: 1) | NP_067258.1 140 aa (SEQ ID NO: 2) |
| --- | --- | --- |
| Exon 1 | 1-191 | 1-44 |
| Exon 2 | 192-239 | 45-60 |
| Exon 3 | 240-392 | 61-111 |
| Exon 4 | 393-586 | 112-140 |
| Signal peptide | 60-119 | 1-20 |
| Replaced region in Example FIG. 4 | 60-482 | 1-140 |
| Replaced region in Example FIG. 8 | 1-605 | 1-140 |

The mouse IL4 gene (Gene ID: 16189) located in Chromosome 11 of the mouse genome, which is located from 53612460 to 53618665, of NC_000077.6 (GRCm38.p4, GCF_000001635.24). The 5'-UTR is from 53618669 to 53618607, exon 1 is from 53618606 to 53618475, the first intron is from 53618474 to 53618218, exon 2 is from 53618217 to 53618170, the second intron is from 53618169 to 53614057, exon 3 is from 53614056 to 53613904, the third intron is from 53613903 to 53612654, exon 4 is from 53612653 to 53612564, the 3'-UTR is from 53612563 to 53612460, based on transcript NM_021283.2. All relevant information for mouse IL4 locus can be found in the NCBI website with Gene ID: 16189, which is incorporated by reference herein in its entirety.

FIG. 42 shows the alignment between human IL4 amino acid sequence (NP_000580.1; SEQ ID NO: 4) and mouse IL4 amino acid sequence (NP_067258.1; SEQ ID NO: 2). Thus, the corresponding amino acid residue or region between human and mouse IL4 can also be found in FIG. 42.

IL4 genes, proteins, and locus of the other species are also known in the art. For example, the gene ID for IL4 in *Rattus norvegicus* is 287287, the gene ID for IL4 in *Macaca mulatta* (Rhesus monkey) is 574281, the gene ID for IL4 in *Canis lupus familiaris* (dog) is 403785, and the gene ID for IL4 in *Cavia porcellus* (domestic guinea pig) is 100720403. The relevant information for these genes (e.g., intron sequences, exon sequences, amino acid residues of these proteins) can be found, e.g., in NCBI database, which are incorporated herein by reference in the entirety.

The present disclosure provides human or chimeric (e.g., humanized) IL4 nucleotide sequence and/or amino acid sequences. In some embodiments, the entire sequence of mouse signal peptide, exon 1, exon 2, exon 3, and/or exon 4, are replaced by the corresponding human sequence.

In some embodiments, a "region" or "portion" of mouse signal peptide, exon 1, exon 2, exon 3, and/or exon 4 is replaced by the corresponding human sequence.

In some embodiments, the "region" or "portion" can be at least 50%, 55%, 60%, 65%, 70%, 75%, 80%, 85%, 90%, 95%, or 99% identical to signal peptide, exon 1, exon 2, exon 3, and/or exon 4. In some embodiments, a region, a portion, or the entire sequence of mouse signal peptide, exon 1, exon 2, exon 3 and/or exon 4 is replaced by a region, a portion, or the entire sequence of human signal peptide, exon 1, exon 2, exon 3, and/or exon 4.

In some embodiments, a "region" or "portion" of mouse signal peptide, exon 1, exon 2, exon 3, and/or exon 4 is deleted.

Thus, in some embodiments, the present disclosure also provides a chimeric (e.g., humanized) IL4 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse IL4 mRNA sequence (e.g., SEQ ID NO: 1), mouse IL4 amino acid sequence (e.g., SEQ ID NO: 2), or a portion thereof (e.g., exon 1, exon 2, exon 3, and/or exon 4); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human IL4 mRNA sequence (e.g., SEQ ID NO: 3), human IL4 amino acid sequence (e.g., SEQ ID NO: 4), or a portion thereof (e.g., exon 1, exon 2, exon 3, and/or exon 4).

In some embodiments, the sequence encoding full-length amino acid sequence of mouse IL4 (SEQ ID NO: 2) is replaced. In some embodiments, the sequence is replaced by a sequence encoding a corresponding region of human IL4 (e.g., full-length amino acid sequence of human IL4 (SEQ ID NO: 4)).

In some embodiments, the nucleic acids as described herein are operably linked to a promotor or regulatory element, e.g., an endogenous mouse IL4 promotor, a human IL4 promotor, an inducible promoter, a human enhancer, a mouse enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, or 60 nucleotides, e.g., contiguous or non-contiguous nucleotides) that are different from a portion of or the entire mouse IL4 nucleotide sequence (e.g., exon 1, exon 2, exon 3, exon 4, or SEQ ID NO: 1).

In some embodiments, the nucleic acid sequence has at least a portion (e.g., at least 1, 2, 3, 4, 5, 6, 7, 8, 9, 10, 11, 12, 13, 14, 15, 20, 30, 40, 50, or 60 nucleotides, e.g., contiguous or non-contiguous nucleotides) that is the same as a portion of or the entire mouse IL4 nucleotide sequence (e.g., exon 1, exon 2, exon 3, exon 4, or SEQ ID NO: 1).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire human IL4 nucleotide sequence (e.g., exon 1, exon 2, exon 3, exon 4, or SEQ ID NO: 3).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human IL4 nucleotide sequence (e.g., exon 1, exon 2, exon 3, exon 4, or SEQ ID NO: 3).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse IL4 amino acid sequence (e.g., exon 1, exon 2, exon 3, exon 4, SEQ ID NO: 2).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse IL4 amino acid sequence (e.g., exon 1, exon 2, exon 3, exon 4, SEQ ID NO: 2).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human IL4 amino acid sequence (e.g., exon 1, exon 2, exon 3, exon 4, or SEQ ID NO: 4).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human IL4 amino acid sequence (e.g., exon 1, exon 2, exon 3, exon 4, or SEQ ID NO: 4).

In some embodiments, the percentage identity with the sequence shown in SEQ ID NO: 2 or 4 is at least about 90%, 91%, 92%, 93%, 94%, 95%, 96%, 97%, 98%, or at least 99%. In some embodiments, the foregoing percentage identity is at least about 60%, 61%, 62%, 63%, 64%, 65%, 66%, 67%, 68%, 69%, 70%, 71%, 72%, 73%, 74%, 75%, 80%, or 85%.

Cells, tissues, and animals (e.g., mouse) are also provided that comprise the nucleotide sequences as described herein, as well as cells, tissues, and animals (e.g., mouse) that express human or chimeric (e.g., humanized) IL4 from an endogenous non-human IL4 locus.

In one aspect, the disclosure provides a genetically-modified, non-human animal whose genome comprises at least one chromosome comprising a sequence encoding a human or chimeric IL4.

In some embodiments, the sequence encoding the human or chimeric IL4 is operably linked to an endogenous regulatory element, or a human regulatory element at the endogenous IL4 gene locus in the at least one chromosome.

In some embodiments, the sequence encoding a human or chimeric IL4 comprises a sequence encoding an amino acid sequence that is at least 50%, 55%, 65%, 70%, 75%, 80%, 85%, 90%, 95%, 99%, or 100% identical to human IL4 (SEQ ID NO: 4).

In some embodiments, the animal is a mammal, e.g., a monkey, a rodent or a mouse. In some embodiments, the animal is a BALB/c mouse or a C57BL/6 mouse.

In some embodiments, the animal does not express endogenous IL4. In some embodiments, the animal has one or more cells expressing human or chimeric IL4.

In some embodiments, the animal has one or more cells expressing human or chimeric IL4, and the expressed human or chimeric IL4 can bind to endogenous IL4R. In some embodiments, the animal has one or more cells expressing human or chimeric IL4, and the expressed human or chimeric IL4 cannot bind to endogenous IL4R.

In another aspect, the disclosure is related to a genetically-modified, non-human animal, wherein the genome of the animal comprises a replacement of a sequence encoding a region of endogenous IL4 with a sequence encoding a corresponding region of human IL4 at an endogenous IL4 gene locus.

In some embodiments, the sequence encoding the corresponding region of human IL4 is operably linked to an endogenous regulatory element, or a human regulatory element at the endogenous IL4 locus, and one or more cells of the animal expresses a chimeric IL4.

In some embodiments, the animal is a mouse, and the replaced endogenous IL4 locus is exon 1, exon 2, exon 3, and/or exon 4 of the endogenous mouse IL4 gene.

In some embodiments, the animal is heterozygous with respect to the replacement at the endogenous IL4 gene locus. In some embodiments, the animal is homozygous with respect to the replacement at the endogenous IL4 gene locus.

In another aspect, the disclosure is related to methods for making a genetically-modified, non-human animal. The methods involve replacing in at least one cell of the animal, at an endogenous IL4 gene locus, a sequence encoding a region of an endogenous IL4 with a sequence encoding a corresponding region of human IL4.

In some embodiments, the sequence encoding the corresponding region of human IL4 comprises exon 1, exon 2, exon 3 and/or exon 4 of a human IL4 gene.

In some embodiments, the sequence encoding the corresponding region of IL4 comprises at least 50, 75, 100, 125, 150, 175, or 200 nucleotides of exon 1, exon 2, exon 3 and/or exon 4 of a human IL4 gene.

In some embodiments, the sequence encoding the corresponding region of human IL4 encodes a sequence that is at least 90% identical to full-length amino acid sequence of SEQ ID NO: 4.

In some embodiments, the animal is a mouse, and the locus is exon 1, exon 2, exon 3, and/or exon 4 of the mouse IL4 gene.

In another aspect, the disclosure is also related to a non-human animal comprising at least one cell comprising a nucleotide sequence encoding a chimeric IL4 polypeptide, wherein the chimeric IL4 polypeptide comprises at least 50 contiguous amino acid residues that are identical to the corresponding contiguous amino acid sequence of a human IL4, wherein the animal expresses the chimeric IL4.

In some embodiments, the chimeric IL4 polypeptide comprises a sequence that is at least 90%, 95%, or 99% identical to full-length amino acid sequence of SEQ ID NO: 4.

In some embodiments, the nucleotide sequence is operably linked to an endogenous IL4 regulatory element of the animal, a human IL4 regulatory element, a mouse 5'-UTR, a mouse 3'-UTR, a human 5'-UTR, or a human 3'-UTR.

In some embodiments, the nucleotide sequence is integrated to an endogenous IL4 gene locus of the animal.

In some embodiments, the chimeric IL4 has at least one mouse IL4 activity and/or at least one human IL4 activity.

In another aspect, the disclosure is also related to methods of making a genetically-modified mouse cell that expresses a chimeric IL4. The methods involve replacing, at an endogenous mouse IL4 gene locus, a nucleotide sequence encoding a region of mouse IL4 with a nucleotide sequence encoding a corresponding region of human IL4, thereby generating a genetically-modified mouse cell that includes a nucleotide sequence that encodes the chimeric IL4, wherein the mouse cell expresses the chimeric IL4.

In some embodiments, the nucleotide sequence encoding the chimeric IL4 is operably linked to an endogenous regulatory region, or a human IL4 regulatory region, e.g., promoter.

In some embodiments, the animal further comprises a sequence encoding an additional human or chimeric protein (e.g., IL4R, Interleukin 33 (IL33), Interleukin 13 (IL13), programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, T-Cell Immunoreceptor with Ig and ITIM Domains (TIGIT), T-cell Immunoglobulin and Mucin-Domain Containing-3 (TIM-3), Glucocorticoid-Induced TNFR-Related Protein (GITR), CD137, TNF Receptor Superfamily Member 4 (OX40), CD47, or Signal Regulatory Protein alpha (SIRPa)).

In some embodiments, the additional human or chimeric protein is IL4R.

In one aspect, the disclosure also provides methods of determining effectiveness of an IL4 antagonist (e.g., an anti-IL4 antibody) for reducing inflammation. The methods involve administering the IL4 antagonist to the animal described herein, wherein the animal has an inflammation; and determining the inhibitory effects of the IL4 antagonist to the reduction of inflammation.

In one aspect, the disclosure also provides methods of determining effectiveness of an IL4 antagonist (e.g., an anti-IL4 antibody) for treating autoimmune disorder or allergy. The methods involve administering the IL4 antagonist to the animal described herein, wherein the animal has an autoimmune disorder or allergy; and determining the inhibitory effects of the IL4 antagonist to the treatment of autoimmune disorder or allergy.

In one aspect, the disclosure also provides methods of determining effectiveness of an IL4 antagonist (e.g., an anti-IL4 antibody) for treating cancer. The methods involve administering the IL4 antagonist to the animal as described herein, wherein the animal has a tumor; and determining the inhibitory effects of the IL4 antagonist to the tumor.

In some embodiments, the animal further comprises a sequence encoding a human or chimeric IL4R. In some embodiments, the additional therapeutic agent is an anti-IL4R antibody.

In some embodiments the additional therapeutic agent is an anti-PD-1 antibody, an anti-PD-L1 antibody, an anti-CTLA4 antibody, an anti-CD20 antibody, an anti-EGFR antibody, or an anti-CD319 antibody.

In another aspect, the disclosure further provides methods of determining toxicity of an agent (e.g., an IL4 antagonist). The methods involve administering the agent to the animal as described herein; and determining weight change of the animal. In some embodiments, the method further involve performing a blood test (e.g., determining red blood cell count).

In one aspect, the disclosure relates to proteins comprising an amino acid sequence, wherein the amino acid sequence is one of the following:
  (a) an amino acid sequence set forth in SEQ ID NO: 4;
  (b) an amino acid sequence that is at least 90%, 91%, 92%, 93%, 94%, 95%, 96%, 97%, 98%, or 99% identical to SEQ ID NO: 4;
  (c) an amino acid sequence that is different from the amino acid sequence set forth in SEQ ID NO: 4 by no more than 10, 9, 8, 7, 6, 5, 4, 3, 2 or 1 amino acid; and
  (d) an amino acid sequence that comprises a substitution, a deletion and/or insertion of one, two, three, four, five or more amino acids to the amino acid sequence set forth in SEQ ID NO: 4.

In some embodiments, provided herein are cells comprising the proteins disclosed herein. In some embodiments, provided herein are animals having the proteins disclosed herein.

In another aspect, the disclosure relates to nucleic acids comprising a nucleotide sequence, wherein the nucleotide sequence is one of the following:
  (a) a sequence that encodes the protein as described herein;
  (b) SEQ ID NO: 3;
  (c) a sequence that is at least 90%, 91%, 92%, 93%, 94%, 95%, 96%, 97%, 98%, or 99% identical to SEQ ID NO: 3, 8, 9, 10, 11, 23, 24, or 25;

In some embodiments, provided herein are cells comprising the nucleic acids disclosed herein. In some embodiments, provided herein are animals having the nucleic acids disclosed herein.

In another aspect, the disclosure also provides a genetically-modified, non-human animal whose genome comprise a disruption in the animal's endogenous IL4 gene, wherein the disruption of the endogenous IL4 gene comprises deletion of exon1, exon2, exon 3 and/or exon 4 or part thereof of the endogenous IL4 gene.

In some embodiments, the disruption of the endogenous IL4 gene further comprises deletion of one or more exons or part of exons selected from the group consisting of exon 1, exon 2, exon 3 and/or exon 4 of the endogenous IL4 gene.

In some embodiments, the disruption of the endogenous IL4 gene further comprises deletion of one or more introns or part of introns selected from the group consisting of intron 1, intron 2, and/or intron 3 of the endogenous IL4 gene.

In some embodiments, wherein the deletion can comprise deleting at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, 300, 350, 400, 450, 500 or more nucleotides.

In some embodiments, the disruption of the endogenous IL4 gene comprises the deletion of at least 1, 2, 3, 4, 5, 6, 7, 8, 9, 10, 20, 30, 40, 50, 60, 70, 80, 90, 100, 110, 120, 130, 140, 150, 160, 170, 180, 190, or 200 nucleotides of exon 1, exon 2, exon 3, and/or exon 4 (e.g., deletion of the entire exon 1, exon 2, exon 3, and exon 4).

Interleukin 4 Receptor (IL4R)

The interleukin 4 receptor (IL4R), also named as interleukin 4 receptor subunit alpha, or interleukin 4 receptor α (IL4Ra), is a type I cytokine receptor. It is encoded by IL4Ra gene. The N-terminal (extracellular) portion of interleukin-4 receptor is related in overall topology to fibronectin type III modules and folds into a sandwich comprising seven antiparallel beta sheets arranged in a three-strand and a four-strand beta-pleated sheet. They are required for binding of IL4 to the receptor alpha chain, which is a crucial event for the generation of a Th2-dominated early immune response.

The IL4Ra gene encodes the alpha chain of the IL4 receptor. The IL4 receptor is a type I transmembrane protein that can bind IL4 and IL13 to regulate IgE antibody production in B cells. Among T cells, the encoded protein also can bind IL4 to promote differentiation of Th2 cells. A soluble form of the encoded protein can be produced by an alternate splice variant or by proteolysis of the membrane-bound protein, and this soluble form can inhibit IL4-mediated cell proliferation and IL5 upregulation by T-cells. Allelic variations in this gene have been associated with atopy, a condition that can manifest itself as allergic rhinitis, sinusitis, asthma, or eczema. Two transcript variants encoding different isoforms, a membrane-bound and a soluble form, have been found for this gene. Interactions of IL4 with TNFα promote structural changes to vascular endothelial cells, thus playing an important role in tissue inflammation.

The binding of IL4 or IL13 to the IL4 receptor on the surface of macrophages results in the alternative activation of those macrophages. Alternatively activated macrophages (AAMΦ) downregulate inflammatory mediators such as IFNγ during immune responses, particularly with regards to helminth infections.

A detailed description of IL4R and its function can be found, e.g., in Bankaitis et al. "Targeting IL4/IL4R for the treatment of epithelial cancer metastasis." Clinical & experimental metastasis 32.8 (2015): 847-856; Zhang et al. "Association of IL4 and IL4R polymorphisms with multiple sclerosis susceptibility in Caucasian population: a meta-analysis." Journal of the neurological sciences 363 (2016): 107-113; which are incorporated by reference herein in the entirety.

In human genomes, IL4Ra gene (Gene ID: 3566) locus has 11 exons, exon 1, exon 2, exon 3, exon 4, exon 5, exon 6, exon 7, exon 8, exon 9, exon 10, and exon 11. The IL4R protein has an extracellular region, a transmembrane region, and a cytoplasmic region. The nucleotide sequence for human IL4Ra mRNA is NM_000418.3 (SEQ ID NO: 41), and the amino acid sequence for human IL4R is NP_000409.1 (SEQ ID NO: 42). The location for each exon and each region in human IL4Ra nucleotide sequence and amino acid sequence is listed below:

TABLE 3

| Human IL4R (approximate location) | NM_000418.3 3710 bp (SEQ ID NO: 41) | NP_000409.1 825 aa (SEQ ID NO: 42) |
| --- | --- | --- |
| Exon 1 | 1-112 | Non-coding sequence |
| Exon 2 | 48-245 | Non-coding sequence |
| Exon 3 | 224-333 | 1-23 |
| Exon 4 | 312-472 | 24-70 |
| Exon 5 | 454-624 | 71-121 |
| Exon 6 | 606-776 | 122-171 |
| Exon 7 | 758-933 | 172-223 |
| Exon 8 | 915-1033 | 224-257 |
| Exon 9 | 1015-1112 | 258-283 |
| Exon 10 | 1094-1162 | 284-300 |
| Exon 11 | 1144-3689 | 301-825 |
| Signal peptide | 264-338 | 1-25 |
| Extracellular | 339-959 | 26-232 |
| Transmembrane | 960-1031 | 233-256 |
| Cytoplasmic | 1032-2738 | 257-825 |
| Donor Range | 351-911 | 30-216 |

Figures 15, 16:
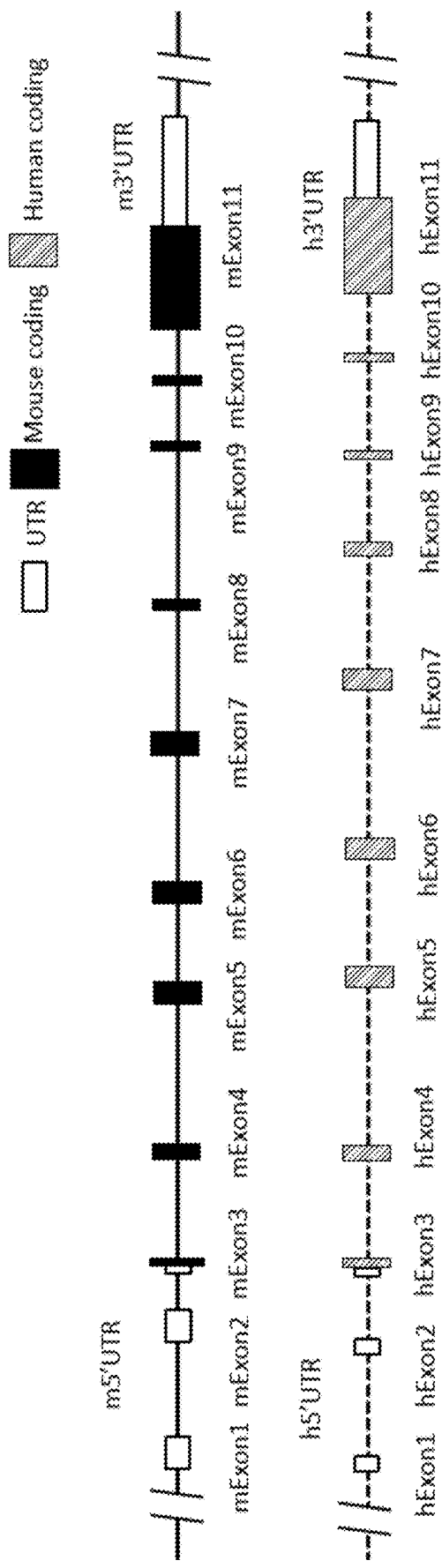
FIG. 15 is a schematic diagram showing mouse and human IL4R gene locus.
FIG. 16 is a schematic diagram showing humanized IL4R gene locus.

In mice, IL4Ra gene locus has 11 exons, exon 1, exon 2, exon 3, exon 4, exon 5, exon 6, exon 7, exon 8, exon 9, exon 10 and exon 11 (FIG. 15). The mouse IL4R protein also has an extracellular region, a transmembrane region, and a cytoplasmic region. The nucleotide sequence for mouse IL4Ra mRNA is NM_001008700.3 (SEQ ID NO: 39), the amino acid sequence for mouse IL4R is NP_001008700.1 (SEQ ID NO: 40). The location for each exon and each region in the mouse IL4Ra nucleotide sequence and amino acid sequence is listed below:

TABLE 4

| Mouse IL4Ra (approximate location) | NM_001008700.3 5122 bp (SEQ ID NO: 39) | NP_001008700.1 810 aa (SEQ ID NO: 40) |
| --- | --- | --- |
| Exon 1 | 1-47 | Non-coding sequence |
| Exon 2 | 48-223 | Non-coding sequence |
| Exon 3 | 224-311 | 1-23 |
| Exon 4 | 312-453 | 24-71 |
| Exon 5 | 454-605 | 72-121 |
| Exon 6 | 606-757 | 122-172 |
| Exon 7 | 758-914 | 173-224 |
| Exon 8 | 915-1014 | 225-258 |
| Exon 9 | 1015-1093 | 259-284 |
| Exon 10 | 1094-1143 | 285-301 |
| Exon 11 | 1144-5094 | 302-810 |
| Signal peptide | 242-316 | 1-25 |
| Extracellular | 317-940 | 26-233 |
| Transmembrane | 941-1012 | 234-257 |
| Cytoplasmic | 1013-2671 | 258-810 |
| Replaced region in Example | 329-892 | 30-217 |

The mouse IL4Ra gene (Gene ID: 16190) located in Chromosome 7 of the mouse genome, which is located from 125552282 to 125579474, of NC_000073.6 (GRCm38.p4, GCF_000001635.24). The 5'-UTR is from 125,552,120 to 125,552,328, 125,564,552 to 125,564,727 and, 125,565,637 to 125,565,654, exon 1 is from 125,552,120 to 125,552,328, the first intron is from 125,552,329 to 125,564,551, exon 2 is from 125,564,552 to 125,564,727, the second intron is from 125,564,728 to 125,565,636, exon 3 is from 125,565,637 to 125,565,724, the third intron is from 125,565,725 to 125,567,155, exon 4 is from 125,567,156 to 125,567,297, the fourth intron is from 125,567,298 to 125,569,022, exon 5 is from 125,569,023 to 125,569,174, the fifth intron is from 125,569,175 to 125,569,941, exon 6 is from 125,569,942 to 125,570,093, the sixth intron is from 125,570,094 to 125,571,433, exon 7 is from 125,571,434 to 125,571,590, the seventh intron is from 125,571,591 to 125,572,850, exon 8 is from 125,572,851 to 125,572,950, the eighth intron is from 125,572,951 to 125,574,637, exon 9 is from 125,574,638 to 125,574,716, the ninth intron is from 125,574,717 to 125,575,139, exon 10 is from 125,575,140 to 125,575,189, the ten intron is from 125,575,190 to 125,575,523, exon 11 is from 125,575,524 to 125,579,474, the 3'-UTR is from 125577055 to 125,579,474, based on transcript NM_001008700.3. All relevant information for mouse IL4Ra locus can be found in the NCBI website with Gene ID: 16190, which is incorporated by reference herein in its entirety.

FIG. 43 shows the alignment between human IL4R amino acid sequence (NP_000409.1; SEQ ID NO: 42) and mouse IL4R amino acid sequence (NP_001008700.1; SEQ ID NO: 40). Thus, the corresponding amino acid residue or region between human and mouse IL4R can also be found in FIG. 43.

IL4Ra genes, proteins, and locus of the other species are also known in the art. For example, the gene ID for IL4Ra in *Rattus norvegicus* is 25084, the gene ID for IL4Ra in *Macaca mulatta* (Rhesus monkey) is 705404, the gene ID for IL4Ra in *Canis lupus familiaris* (dog) is 489957, and the gene ID for IL4Ra in *Sus scrofa* (pig) is 397614. The relevant information for these genes (e.g., intron sequences, exon sequences, amino acid residues of these proteins) can be found, e.g., in NCBI database.

The present disclosure provides human or chimeric (e.g., humanized) IL4Ra nucleotide sequence and/or amino acid sequences. In some embodiments, the entire sequence of mouse exon 1, exon 2, exon 3, exon 4, exon 5, exon 6, exon 7, exon 8, exon 9, exon 10, exon 11, the signal peptide, the extracellular region, the transmembrane region, and/or the cytoplasmic region are replaced by the corresponding human sequence.

In some embodiments, a "region" or "portion" of mouse exon 1, exon 2, exon 3, exon 4, exon 5, exon 6, exon 7, exon 8, exon 9, exon 10, exon 11, signal peptide, the extracellular region, the transmembrane region, and/or the cytoplasmic region is replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 150, 200, 250, 300, 350, or 400 nucleotides, or at least 1, 2, 3, 4, 5, 6, 7, 8, 9, 10, 20, 30, 40, 50, 60, 70, 80, 90, 100, 110, 120, 130, or 150 amino acid residues.

In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, exon 6, exon 7, exon 8, exon 9, exon 10, exon 11, signal peptide, the extracellular region, the transmembrane region, and/or the cytoplasmic region. In some embodiments, a region, a portion, or the entire sequence of mouse exon 1, exon 2, exon 3, exon 4, exon 5, exon 6, exon 7, exon 8, exon 9, exon 10, and/or exon 11 (e.g., exon 4, exon 5, exon 6, and exon 7) is replaced by a region, a portion, or the entire sequence of human exon 1, exon 2, exon 3, exon 4, exon 5, exon 6, exon 7, exon 8, exon 9, exon 10, and/or exon 11 (e.g., exon 4, exon 5, exon 6, and exon 7).

In some embodiments, a "region" or "portion" of mouse exon 1, exon 2, exon 3, exon 4, exon 5, exon 6, exon 7, exon 8, exon 9, exon 10, exon 11, signal peptide, the extracellular region, the transmembrane region, and/or the cytoplasmic region is deleted. For example, a region or a portion of exon 4, exon 5, exon 6, and exon 7 is deleted.

Thus, in some embodiments, the present disclosure also provides a chimeric (e.g., humanized) IL4Ra nucleotide sequence and/or amino acid sequences, wherein in some to embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse IL4Ra mRNA sequence (e.g., SEQ ID NO: 39), mouse IL4R amino acid sequence (e.g., SEQ ID NO: 40), or a portion thereof (e.g., exon 1, exon 2, exon 3, exon 4, exon 5, exon 6, exon 7, exon 8, exon 9, exon 10, and/or exon 11). In some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human IL4Ra mRNA sequence (e.g., SEQ ID NO: 41), human IL4R amino acid sequence (e.g., SEQ ID NO: 42), or a portion thereof (e.g., exon 1, exon 2, exon 3, exon 4, exon 5, exon 6, exon 7, exon 8, exon 9, exon 10, and/or exon 11).

In some embodiments, the sequence encoding amino acids 30-217 of mouse IL4R (SEQ ID NO: 40) is replaced. In some embodiments, the sequence is replaced by a sequence encoding a corresponding region of human IL4R (e.g., amino acids 30-216 of human IL4R (SEQ ID NO: 42).

In some embodiments, the nucleic acids as described herein are operably linked to a promotor or regulatory element, e.g., an endogenous mouse IL4R promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse IL4Ra nucleotide sequence (e.g., exon 1, exon 2, exon 3, exon 4, exon 5, exon 6, exon 7, exon 8, exon 9, exon 10, exon 11, or SEQ ID NO: 39).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse IL4Ra nucleotide sequence (e.g., exon 1, exon 2, exon 3, exon 4, exon 5, exon 6, exon 7, exon 8, exon 9, exon 10, exon 11, or SEQ ID NO: 39).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire human IL4Ra nucleotide sequence (e.g., exon 1, exon 2, exon 3, exon 4, exon 5, exon 6, exon 7, exon 8, exon 9, exon 10, exon 11, or SEQ ID NO: 41).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human IL4Ra nucleotide sequence (e.g., exon 1, exon 2, exon 3, exon 4, exon 5, exon 6, exon 7, exon 8, exon 9, exon 10, exon 11, or SEQ ID NO: 41).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse IL4R amino acid sequence (e.g., exon 1, exon 2, exon 3, exon 4, exon 5, exon 6, exon 7, exon 8, exon 9, exon 10, exon 11, or NP_001008700.1 (SEQ ID NO: 40)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse IL4R amino acid sequence (e.g., exon 1, exon 2, exon 3, exon 4, exon 5, exon 6, exon 7, exon 8, exon 9, exon 10, exon 11, or NP_001008700.1 (SEQ ID NO: 40)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human IL4R amino acid sequence (e.g., exon 1, exon 2, exon 3, exon 4, exon 5, exon 6, exon 7, exon 8, exon 9, exon 10, exon 11, or SEQ ID NO: 42).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human IL4R amino acid sequence (e.g., exon 1, exon 2, exon 3, exon 4, exon 5, exon 6, exon 7, exon 8, exon 9, exon 10, exon 11, or SEQ ID NO: 42).

The present disclosure also provides a humanized IL4R mouse amino acid sequence, wherein the amino acid sequence is selected from the group consisting of:

a) an amino acid sequence shown in SEQ ID NO: 44;

b) an amino acid sequence having a homology of at least 90% with or at least 90% identical to the amino acid sequence shown in SEQ ID NO: 44;

c) an amino acid sequence encoded by a nucleic acid sequence, wherein the nucleic acid sequence is able to hybridize to a nucleotide sequence encoding the amino acid shown in SEQ ID NO: 44 under a low stringency condition or a strict stringency condition;

d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 44;

e) an amino acid sequence that is different from the amino acid sequence shown in SEQ ID NO: 44 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 44.

The present disclosure also relates to a nucleic acid (e.g., DNA or RNA) sequence, wherein the nucleic acid sequence can be selected from the group consisting of:

a) a nucleic acid sequence as shown in SEQ ID NO: 39, 41, or 43, or a nucleic acid sequence encoding a homologous IL4R amino acid sequence of a humanized mouse;

b) a nucleic acid sequence that is able to hybridize to the nucleotide sequence as shown in SEQ ID NO: 39, 41, or 43 under a low stringency condition or a strict stringency condition;

c) a nucleic acid sequence that has a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the nucleotide sequence as shown in SEQ ID NO: 39, 41, 43, 48, 49, 50, or 51;

d) a nucleic acid sequence that encodes an amino acid sequence, wherein the amino acid sequence has a homology of at least 90% with or at least 90% identical to the amino acid sequence shown in SEQ ID NO: 40, 42, or 44;

e) a nucleic acid sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 40, 42, or 44;

f) a nucleic acid sequence that encodes an amino acid sequence, wherein the amino acid sequence is different from the amino acid sequence shown in SEQ ID NO: 40, 42, or 44 by no more than 10, 9, 8, 7, 6, 5, 4, 3, 2 or no more than 1 amino acid; and/or g) a nucleic acid sequence that encodes an amino acid sequence, wherein the amino acid sequence comprises a substitution, a deletion and/or insertion of one or more amino acids to the amino acid sequence shown in SEQ ID NO: 40, 42, or 44.

The present disclosure further relates to an IL4R genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 39, 41, or 43.

The disclosure also provides an amino acid sequence that has a homology of at least 90% with, or at least 90% identical to the sequence shown in SEQ ID NO: 40, 42, or 44, and has protein activity. In some embodiments, the homology with the sequence shown in SEQ ID NO: 40, 42, or 44 is at least about 90%, 91%, 92%, 93%, 94%, 95%, 96%, 97%, 98%, or at least 99%. In some embodiments, the foregoing homology is at least about 60%, 61%, 62%, 63%, 64%, 65%, 66%, 67%, 68%, 69%, 70%, 71%, 72%, 73%, 74%, 75%, 80%, or 85%.

In some embodiments, the percentage identity with the sequence shown in SEQ ID NO: 40, 42, or 44 is at least or about 90%, 91%, 92%, 93%, 94%, 95%, 96%, 97%, 98%, or at least 99%. In some embodiments, the foregoing percentage identity is at least about 60%, 61%, 62%, 63%, 64%, 65%, 66%, 67%, 68%, 69%, 70%, 71%, 72%, 73%, 74%, 75%, 80%, or 85%.

The disclosure also provides a nucleotide sequence that has a homology of at least 90%, or at least 90% identical to the sequence shown in SEQ ID NO: 39, 41, or 43, and encodes a polypeptide that has protein activity. In some embodiments, the homology with the sequence shown in SEQ ID NO: 39, 41, or 43 is at least about 90%, 91%, 92%, 93%, 94%, 95%, 96%, 97%, 98%, or at least 99%. In some embodiments, the foregoing homology is at least about 50%, 55%, 60%, 65%, 66%, 67%, 68%, 69%, 70%, 71%, 72%, 73%, 74%, 75%, 80%, or 85%.

Cells, tissues, and animals (e.g., mouse) are also provided that comprise the nucleotide sequences as described herein, as well as cells, tissues, and animals (e.g., mouse) that express human or chimeric (e.g., humanized) IL4R from an endogenous non-human IL4R locus.

In one aspect, the disclosure also provides methods of determining effectiveness of an IL4R antagonist (e.g., an anti-IL4R antibody) for reducing inflammation. The methods involve administering the IL4R antagonist to the animal described herein, wherein the animal has an inflammation; and determining the inhibitory effects of the IL4R antagonist to the reduction of inflammation.

In one aspect, the disclosure also provides methods of determining effectiveness of an IL4R antagonist (e.g., an anti-IL4R antibody) for treating autoimmune disorder or allergy. The methods involve administering the IL4R antagonist to the animal described herein, wherein the animal has an autoimmune disorder or allergy; and determining the inhibitory effects of the IL4R antagonist to the treatment of autoimmune disorder or allergy.

In one aspect, the disclosure also provides methods of determining effectiveness of an IL4R antagonist (e.g., an anti-IL4R antibody) for treating cancer. The methods involve administering the IL4R antagonist to the animal described herein, wherein the animal has a tumor; and determining the inhibitory effects of the IL4R antagonist to the tumor. In some embodiments, the tumor comprises one or more cancer cells that are injected into the animal. In some embodiments, determining the inhibitory effects of the IL4R antagonist (e.g., an anti-IL4R antibody) to the tumor involves measuring the tumor volume in the animal.

In another aspect, the disclosure also provides a genetically-modified, non-human animal whose genome comprise a disruption in the animal's endogenous IL4R gene, wherein the disruption of the endogenous IL4R gene comprises deletion of exon 1, exon 2, exon 3, exon 4, exon 5, exon 6, exon 7, exon 8, exon 9, exon 10, exon 11 (e.g., exon 4, exon 5, exon 6 and/or exon 7) or part thereof of the endogenous IL4R gene.

In some embodiments, the disruption of the endogenous IL4R gene comprises deletion of one or more exons or part of exons selected from the group consisting of exon 4, exon 5, exon 6 and/or exon 7 of the endogenous IL4R gene.

In some embodiments, the disruption of the endogenous IL4R gene further comprises deletion of one or more introns or part of introns selected from the group consisting of intron 4, intron 5, and/or intron 6 of the endogenous IL4R gene.

In some embodiments, wherein the deletion can comprise deleting at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, 300, 350, 400, 450, 500 or more nucleotides.

In some embodiments, the disruption of the endogenous IL4R gene comprises the deletion of at least 1, 2, 3, 4, 5, 6, 7, 8, 9, 10, 20, 30, 40, 50, 60, 70, 80, 90, 100, 110, 120, 130, 140, 150, 160, 170, 180, 190, or 200 nucleotides of exon 1, exon 2, exon 3, exon 4, exon 5, exon 6, exon 7, exon 8, exon 9, exon 10, exon 11 (e.g., exon 4, exon 5, exon 6 and/or exon 7)

Genetically Modified Animals

As used herein, the term "genetically-modified non-human animal" refers to a non-human animal having genetic modification (e.g., exogenous DNA) in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the genetic modification in its genome. The cell having exogenous DNA can be various kinds of cells, e.g., an endogenous cell, a somatic cell, an immune cell, a T cell, a B cell, a germ cell, a blastocyst, or an endogenous tumor cell. In some embodiments, genetically-modified non-human animals are provided that comprise a modified endogenous IL4R or IL4 locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wild-type nucleic acid in the animal. In some embodiments, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one portion of the sequences of the protein or the polypeptide does not correspond to wild-type amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized IL4R gene or a humanized IL4R nucleic acid. In some embodiments, at least one or more portions of the gene or the nucleic acid is from the human IL4R gene, at least one or more portions of the gene or the nucleic acid is from a non-human IL4R gene. In some embodiments, the gene or the nucleic acid comprises a sequence that encodes an IL4R protein. The encoded IL4R protein is functional or has at least one activity of the human IL4R protein or the non-human IL4R protein, e.g., binding to human or non-human IL4, and/or upregulating immune response.

In some embodiments, the chimeric protein or the chimeric polypeptide is a humanized IL4R protein or a humanized IL4R polypeptide. In some embodiments, at least one or more portions of the amino acid sequence of the protein or the polypeptide is from a human IL4R protein, and at least one or more portions of the amino acid sequence of the protein or the polypeptide is from a non-human IL4R protein. The humanized IL4R protein or the humanized IL4R polypeptide is functional or has at least one activity of the human IL4R protein or the non-human IL4R protein.

In some embodiments, the humanized IL4R protein or the humanized IL4R polypeptide can bind to mouse IL4, and/or upregulate immune response. In some embodiments, the humanized IL4R protein or the humanized IL4R polypeptide cannot bind to mouse IL4, thus cannot upregulate immune response.

In some embodiments, the chimeric gene or the chimeric nucleic acid is a humanized IL4 gene or a humanized IL4 nucleic acid. In some embodiments, at least one or more portions of the gene or the nucleic acid is from the human IL4 gene, at least one or more portions of the gene or the nucleic acid is from a non-human IL4 gene. In some embodiments, the gene or the nucleic acid comprises a sequence that encodes an IL4 protein. The encoded IL4 protein is functional or has at least one activity of the human IL4 protein or the non-human IL4 protein, e.g., binding to human or non-human IL4R, and/or upregulating immune response.

In some embodiments, the chimeric protein or the chimeric polypeptide is a humanized IL4 protein or a humanized IL4 polypeptide. In some embodiments, at least one or more portions of the amino acid sequence of the protein or the polypeptide is from a human IL4 protein, and at least one or more portions of the amino acid sequence of the protein or the polypeptide is from a non-human IL4 protein. The humanized IL4 protein or the humanized IL4 polypeptide is functional or has at least one activity of the human IL4 protein or the non-human IL4 protein.

In some embodiments, the humanized IL4 protein or the humanized IL4 polypeptide can bind to mouse IL4R, and/or upregulate immune response. In some embodiments, the humanized IL4 protein or the humanized IL4 polypeptide cannot bind to mouse IL4R, thus cannot upregulate immune response.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable embryonic stem (ES) cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In some embodiments, the genetically modified rodent is selected from a true mouse or rat (family Muridae), a gerbil, a spiny mouse, and a crested rat. In some embodiments, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 12959/SvEvH, 129S6 (129/SvEvTac), 129S7, 129S8, 129T1, 129T2. These mice are described, e.g., in Festing et al., Revised nomenclature for strain 129 mice, Mammalian Genome 10: 836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiments, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized IL4R or IL4 animal is made. For example, suitable mice for maintaining a xenograft, can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/SCID/γcnull mice (Ito, M. et al., NOD/SCID/γcnull mouse: an excellent recipient mouse model for engraftment of human cells, Blood 100(9): 3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human IL4R or IL4 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γc null mice, nude mice, Rag1 and/or Rag2 knockout mice, and a combination thereof. These genetically modified animals are described, e.g., in US20150106961, which is incorporated herein by reference in its entirety. In some embodiments, the mouse can include a replacement of all or part of mature IL4R or IL4 coding sequence with human mature IL4R or IL4 coding sequence.

Genetically modified non-human animals can comprise a modification of an endogenous non-human IL4 or IL4R locus. In some embodiments, the modification can comprise a human nucleic acid sequence encoding at least a portion of a mature IL4 or IL4R protein (e.g., at least 10%, 20%, 30%, 40%, 50%, 60%, 70%, 80%, 90%, 95%, 96%, 97%, 98%, or 99% identical to the mature IL4 or IL4R protein sequence). Although genetically modified cells are also provided that can comprise the modifications described herein (e.g., ES cells, somatic cells), in many embodiments, the genetically modified non-human animals comprise the modification of the endogenous IL4 or IL4R locus in the germline of the animal.

Genetically modified animals can express a human IL4 or IL4R (or a chimeric IL4 or IL4R) from endogenous mouse loci, wherein the endogenous mouse gene has been replaced with a human gene and/or a nucleotide sequence that encodes a region of human IL4 or IL4R sequence or an amino acid sequence that is at least 10%, 20%, 30%, 40%, 50%, 60%, 70&, 80%, 90%, 95%, 96%, 97%, 98%, or 99% identical to the human IL4 or IL4R sequence. In various embodiments, an endogenous non-human locus is modified in whole or in part to comprise human nucleic acid sequence encoding at least one protein-coding sequence of a mature protein.

In some embodiments, the genetically modified mice express the human IL4 or IL4R (or chimeric IL4 or IL4R) from endogenous loci that are under control of mouse promoters and/or mouse regulatory elements. The replacement(s) at the endogenous mouse loci provide non-human animals that express human protein or chimeric protein in appropriate cell types and in a manner that does not result in the potential pathologies observed in some other transgenic mice known in the art. The human protein or the chimeric protein expressed in animal can maintain one or more functions of the wild-type mouse or human protein in the animal. For example, IL4R can bind to human or non-human IL4, and upregulate immune response, e.g., upregulate immune response by at least 10%, 20%, 30%, 40%, or 50%. As used herein, the term "endogenous IL4R" refers to IL4R protein that is expressed from an endogenous IL4R nucleotide sequence of the non-human animal (e.g., mouse) before any genetic modification. Similarly, the term "endogenous IL4" refers to IL4 protein that is expressed from an endogenous IL4 nucleotide sequence of the non-human animal (e.g., mouse) before any genetic modification.

The genome of the animal can comprise a sequence encoding an amino acid sequence that is at least 70%, 75%, 80%, 85%, 90%, 95%, 99%, or 100% identical to SEQ ID NO: 40, 42, or 44, and/or a sequence encoding an amino acid sequence that is at least 70%, 75%, 80%, 85%, 90%, 95%, 99%, or 100% identical to SEQ ID NO: 4.

The genome of the genetically modified animal can comprise a replacement at an endogenous IL4R gene locus of a sequence encoding a region of endogenous IL4R with a sequence encoding a corresponding region of human IL4R. In some embodiments, the sequence that is replaced is any sequence within the endogenous IL4R gene locus, e.g., exon 1, exon 2, exon 3, exon 4, exon 5, exon 6, exon 7, exon 8, exon 9, exon 10, exon 11 5'-UTR, 3'UTR, the first intron, the second intron, and the third intron, the fourth intron, the fifth intron, the sixth intron, the seventh intron, the eighth intron, the ninth intron, the tenth intron or the eleventh intron, etc. In some embodiments, the sequence that is replaced is within the regulatory region of the endogenous IL4R gene. In some embodiments, the sequence that is replaced is exon 4, exon 5, exon 6 and/or exon 7 or part thereof, of an endogenous mouse IL4R gene locus.

The genetically modified animal can have one or more cells expressing a human or chimeric IL4R (e.g., humanized IL4R) having an extracellular region and a cytoplasmic region, wherein the extracellular region comprises a sequence that is at least 50%, 60%, 70%, 80%, 90%, 95%, 99% identical to the extracellular region of human IL4R. In some embodiments, the extracellular region of the humanized IL4R has a sequence that has at least 10, 20, 30, 40, 50, 60, 70, 80, 90, 100, 110, 120, 130, 140, 150, 160, 170, or 180 amino acids (e.g., contiguously or non-contiguously) that are identical to human IL4R.

The genome of the genetically modified animal can comprise a replacement at an endogenous IL4 gene locus of a sequence encoding a region of endogenous IL4 with a sequence encoding a corresponding region of human IL4. In some embodiments, the sequence that is replaced is any sequence within the endogenous IL4 gene locus, e.g., exon 1, exon 2, exon 3, exon 4, 5'-UTR, 3'UTR, the first intron, the second intron, or the third intron, etc. In some embodiments, the sequence that is replaced is within the regulatory region of the endogenous IL4 gene. In some embodiments, the sequence that is replaced is within the regulatory region of the human IL4 gene.

Because human protein and non-human protein sequences, in many cases, are different, antibodies that bind to human protein will not necessarily have the same binding affinity with non-human protein or have the same effects to non-human protein. Therefore, the genetically modified animal expressing human IL4 and the genetically modified animal having a human or a humanized extracellular region of IL4R can be used to better evaluate the effects of anti-IL4 or IL4R antibodies in an animal model. In some embodiments, the genome of the genetically modified animal comprises a sequence encoding an amino acid sequence that corresponds to part or the entire sequence of exon 4, exon 5, exon 6 and/or exon 7 of human IL4R, part or the entire sequence of the extracellular region of human IL4R (with or without signal peptide), or part or the entire sequence of amino acids 30-216 of SEQ ID NO: 42.

In some embodiments, the non-human animal can have, at an endogenous IL4R gene locus, a nucleotide sequence encoding a chimeric human/non-human IL4R polypeptide, wherein a human portion of the chimeric human/non-human IL4R polypeptide comprises a portion of human IL4R extracellular region, and wherein the animal expresses a functional IL4R on a surface of a cell of the animal. The human portion of the chimeric human/non-human IL4R polypeptide can comprise a portion of exon 4, exon 5, exon 6 and/or exon 7 of human IL4R. In some embodiments, the human portion of the chimeric human/non-human IL4R polypeptide can comprise a sequence that is at least 80%, 85%, 90%, 95%, or 99% identical to amino acids 30-216 of SEQ ID NO: 42.

In some embodiments, the non-human portion of the chimeric human/non-human IL4R polypeptide comprises the transmembrane region, and/or the cytoplasmic region of an endogenous non-human IL4R polypeptide. There may be several advantages that are associated with the transmembrane and/or cytoplasmic regions of an endogenous non-human IL4R polypeptide. For example, once IL4 binds to IL4R, they can properly transmit extracellular signals into the cells and regulate the downstream pathway. A human or humanized transmembrane and/or cytoplasmic regions may not function properly in non-human animal cells. In some embodiments, a few extracellular amino acids that are close to the transmembrane region of IL4R are also derived from endogenous sequence.

In some embodiments, the humanized IL4R locus lacks a human IL4R 5'-UTR. In some embodiment, the humanized IL4R locus comprises a rodent (e.g., mouse) 5'-UTR. In some embodiments, the humanization comprises a human 3'-UTR. In appropriate cases, it may be reasonable to presume that the mouse and human IL4R genes appear to be similarly regulated based on the similarity of their 5'-flanking sequence. As shown in the present disclosure, humanized IL4R mice that comprise a replacement at an endogenous mouse IL4R locus, which retain mouse regulatory elements but comprise a humanization of IL4R encoding sequence, do not exhibit obvious pathologies. Both genetically modified mice that are heterozygous or homozygous for humanized IL4R are grossly normal.

In some embodiments, the humanized IL4 locus has a human IL4 5'-UTR or an endogenous IL4 5'-UTR. In some embodiment, the humanized IL4 locus comprises a rodent (e.g., mouse) 5'-UTR. In some embodiments, the humanization comprises a human 3'-UTR or an endogenous 3'-UTR. In appropriate cases, it may be reasonable to presume that the mouse and human IL4 genes appear to be similarly regulated based on the similarity of their 5'-flanking sequence. As shown in the present disclosure, humanized IL4 mice that comprise a replacement at an endogenous mouse IL4 locus, which has mouse or human regulatory elements, do not exhibit obvious pathologies. Both genetically modified mice that are heterozygous or homozygous for humanized IL4 are grossly normal.

The present disclosure further relates to a non-human mammal generated through the method mentioned above. In some embodiments, the genome thereof contains human gene(s). In some embodiments, the non-human mammal is a rodent, and preferably, the non-human mammal is a mouse.

In some embodiments, the non-human mammal expresses a protein encoded by a humanized IL4R or IL4 gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human or humanized IL4R or IL4 in the genome of the animal.

In some embodiments, the non-human mammal comprises the genetic construct as described herein. In some embodiments, a non-human mammal expressing human or humanized IL4R or IL4 is provided. In some embodiments, the tissue-specific expression of human or humanized IL4R or IL4 protein is provided.

In some embodiments, the expression of human or humanized IL4R or IL4 in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human IL4R or IL4 protein can be detected by a variety of methods.

There are many analytical methods that can be used to detect exogenous DNA, including methods at the level of nucleic acid (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human or humanized IL4R or IL4 protein.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, or 200 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The percentage of residues conserved with similar physicochemical properties (percent homology), e.g. leucine and isoleucine, can also be used to measure sequence similarity.

Families of amino acid residues having similar physicochemical properties have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The homology percentage, in many cases, is higher than the identity percentage.

Cells, tissues, and animals (e.g., mouse) are also provided that comprise the nucleotide sequences as described herein, as well as cells, tissues, and animals (e.g., mouse) that express human or chimeric (e.g., humanized) amino acid sequence from an endogenous non-human IL4R or IL4 locus.

Vectors

The present disclosure relates to a targeting vector, comprising: a) a DNA fragment homologous to the 5' end of a region to be altered (5' arm), which is selected from the IL4Ra or IL4 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the IL4Ra or IL4 gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000077.6; c) the DNA fragment homologous to the 3' end of the region to be altered (3' arm) is selected from the nucleotide sequences that have at least 90% homology to the NCBI accession number NC_000077.6.

In some embodiments, a) the DNA fragment homologous to the 5' end of a region to be altered (5' arm) is selected from the nucleotides from the position 53622826 to the position 53618607 of the NCBI accession number NC_000077.6; c) the DNA fragment homologous to the 3' end of the region to be altered (3' arm) is selected from the nucleotides from the position 53612065 to the position 53607981 of the NCBI accession number NC_000077.6.

In some embodiments, a) the DNA fragment homologous to the 5' end of a region to be altered (5' arm) is selected from the nucleotides from the position 53625623 to the position 53620071 of the NCBI accession number NC_000077.6; c) the DNA fragment homologous to the 3' end of the region to be altered (3' arm) is selected from the nucleotides from the position 53612200 to the position 53607005 of the NCBI accession number NC_000077.6.

In some embodiments, a) the DNA fragment homologous to the 5' end of a conversion region to be altered (5' arm) is selected from the nucleotide sequences that have at least 90% homology to the NCBI accession number NC_000073.6; c) the DNA fragment homologous to the 3' end of the region to be altered (3' arm) is selected from the nucleotide sequences that have at least 90% homology to the NCBI accession number NC_000073.6.

In some embodiments, a) the DNA fragment homologous to the 5' end of a region to be altered (5' arm) is selected from the nucleotides from the position 125562909 to the position 125567172 of the NCBI accession number NC_000073.6; c) the DNA fragment homologous to the 3' end of the region to be altered (3' arm) is selected from the nucleotides from the position 125572100 to the position 125576624 of the NCBI accession number NC_000073.6.

In some embodiments, the length of the selected genomic nucleotide sequence in the targeting vector can be about or at least 3 kb, 4 kb, 5 kb, 6 kb, 7 kb, 8 kb, 9 kb or 10 kb.

In some embodiments, the region to be altered is exon 1, exon 2, exon 3, and/or exon 4 of IL4 gene (e.g., exon 1, exon 2, exon 3 and/or exon 4 of mouse IL4 gene).

In some embodiments, the region to be altered is exon 4, exon 5, exon 6, and/or exon 7 of IL4Ra gene (e.g., exon 4, exon 5, exon 6 and/or exon 7 of mouse IL4Ra gene).

The targeting vector can further include a selected gene marker.

In some embodiments, the sequence of the 5' arm is shown in SEQ ID NO: 5; and the sequence of the 3' arm is shown in SEQ ID NO: 6.

In some embodiments, the sequence of the 5' arm is shown in SEQ ID NO: 20; and the sequence of the 3' arm is shown in SEQ ID NO: 21.

In some embodiments, the sequence of the 5' arm is shown in SEQ ID NO: 45; and the sequence of the 3' arm is shown in SEQ ID NO: 46.

In some embodiments, the sequence is derived from human (e.g., 132674051-132682587 of NC_000005.10, or 132672342-132682914 of NC_000005.10). For example, the target region in the targeting vector is a part or entirety of the nucleotide sequence of a human IL4, preferably exon 1, exon 2, exon 3 and/or exon 4 of the human IL4. In some embodiments, the nucleotide sequence of the humanized IL4 encodes the entire or the part of human IL4 protein (e.g., SEQ ID NO: 4).

In some embodiments, the sequence is derived from human (e.g., 27342138-27352674 of NC_000016.10). For example, the target region in the targeting vector is a part or entirety of the nucleotide sequence of a human IL4Ra, preferably exon 4, exon 5, exon 6 and/or exon 7 of the human IL4Ra. In some embodiments, the nucleotide sequence of the humanized IL4Ra encodes the entire or the part of human IL4Ra protein (e.g., SEQ ID NO: 42).

In some embodiments, the target region is derived from human. In some embodiments, the target region is a part or entirety of the nucleotide sequence of a humanized IL4R. In some embodiments, the nucleotide sequence is shown as one or more of exon 1, exon 2, exon 3, exon 4, exon 5, exon 6, exon 7, exon 8, exon 9, exon 10 and/or exon 11 of the human IL4R. In some embodiments, the target region is a part or entirety of the nucleotide sequence of a humanized IL4. In some embodiments, the nucleotide sequence is shown as one or more of exon 1, exon 2, exon 3, and/or exon 4 of the human IL4.

In some embodiments, the nucleotide sequence of the human IL4R encodes the human IL4R protein with the NCBI accession number NP_000409.1 (SEQ ID NO: 42). In some emboldens, the nucleotide sequence of the human IL4R is selected from the nucleotides from the position 27342138 to the position 27352674 of NC_000016.10 (SEQ ID NO: 47).

In some embodiments, the nucleotide sequence of the human IL4 encodes the human IL4 protein with the NCBI accession number NP_000580.1 (SEQ ID NO: 4). In some emboldens, the nucleotide sequence of the human IL4R is selected from the nucleotides from the position 132674051 to the position 132682587 of NC_000005.10 (SEQ ID NO: 7), or position 132672342 to the position 132682914 of NC_000005.10 (SEQ ID NO: 22).

The disclosure also relates to a cell comprising the targeting vectors as described herein.

In addition, the present disclosure further relates to a non-human mammalian cell, having any one of the foregoing targeting vectors, and one or more in vitro transcripts of the construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous IL4Ra or IL4 gene locus, a sequence encoding a region of an endogenous IL4R or IL4 with a sequence encoding a corresponding region of human or chimeric IL4R or IL4. In some embodiments, the replacement occurs in a germ cell, a somatic cell, a blastocyst, or a fibroblast, etc. The nucleus of a somatic cell or the fibroblast can be inserted into an enucleated oocyte.

Figure 17:
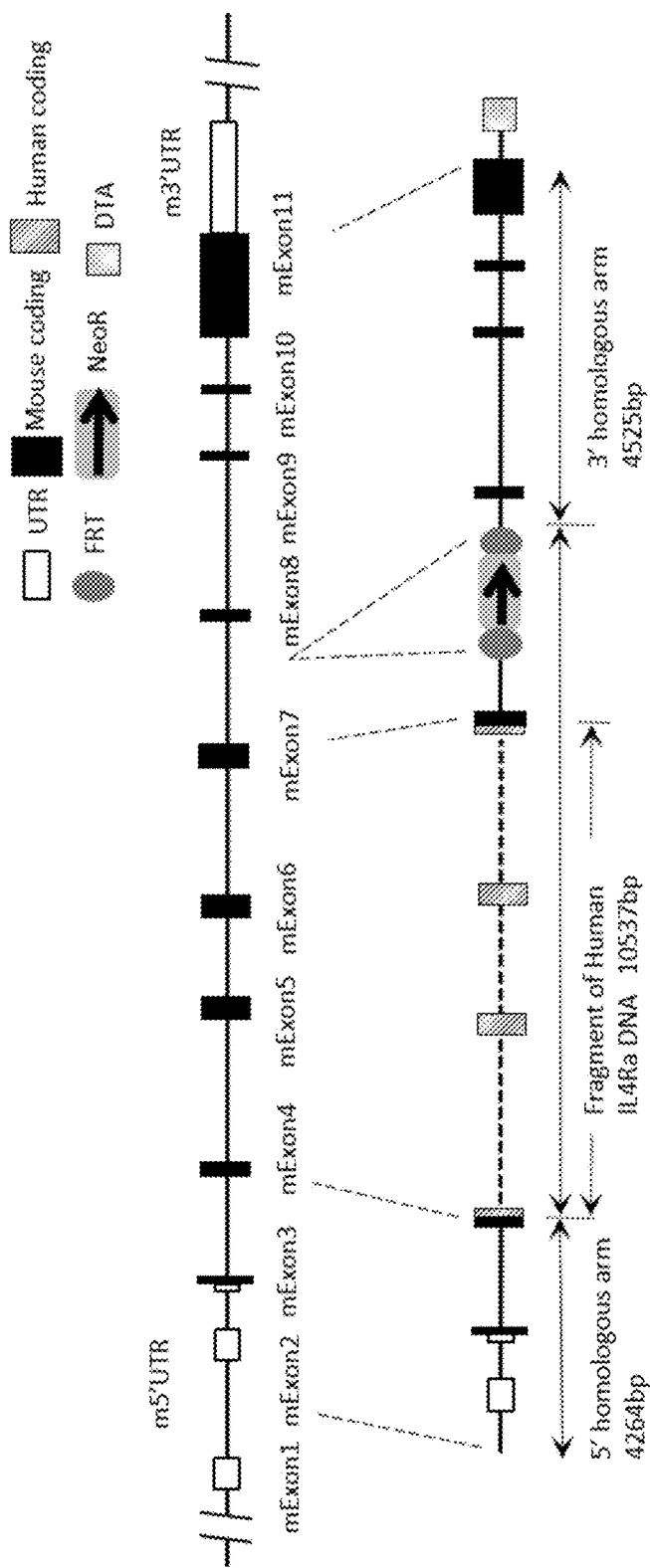
FIG. 17 is a schematic diagram showing the targeting strategy for IL4R gene locus.

FIG. 17 shows a humanization strategy for a mouse IL4R locus. In FIG. 17, the targeting strategy involves a vector comprising the 5' end homologous arm, human IL4Ra gene fragment, 3' homologous arm. The process can involve replacing endogenous IL4Ra sequence with human sequence by homologous recombination. FIG. 4 and FIG. 8 show a humanization strategy for a mouse IL4 locus. In FIG. 4 and FIG. 8, the targeting strategy involves a vector comprising the 5' end homologous arm, human IL4 gene fragment, 3' homologous arm. The process can involve replacing endogenous IL4 sequence with human sequence by homologous recombination. In some embodiments, the cleavage at the upstream and the downstream of the target site (e.g., by zinc finger nucleases, TALEN or CRISPR) can result in DNA double strand break, and the homologous recombination is used to replace endogenous IL4Ra or IL4 sequence with human IL4Ra or IL4 sequence.

Thus, in some embodiments, the methods for making a genetically modified, humanized animal, can include the step of replacing at an endogenous IL4Ra locus (or site), a nucleic acid encoding a sequence encoding a region of endogenous IL4R with a sequence encoding a corresponding region of human IL4R. The sequence can include a region (e.g., a part or the entire region) of exon 1, exon 2, exon 3, exon 4, exon 5, exon 6, exon 7, exon 8, exon 9, exon 10 and/or exon 11 of a human IL4Ra gene. In some embodiments, the sequence includes a region of exon 4, exon 5, exon 6 and/or exon 7 of a human IL4Ra gene (e.g., amino acids 30-216 of SEQ ID NO: 42). In some embodiments, the region is located within the extracellular region of IL4R. In some embodiments, the endogenous IL4Ra locus is exon 4, exon 5, exon 6 and/or exon 7 of mouse IL4Ra.

Thus, in some embodiments, the methods for making a genetically modified, humanized animal, can include the step of replacing at an endogenous IL4 locus (or site), a nucleic acid encoding a sequence encoding a region of endogenous IL4 with a sequence encoding a corresponding region of human IL4. The sequence can include a region (e.g., a part or the entire region) of exon 1, exon 2, exon 3, and/or exon 4 of a human IL4 gene. In some embodiments, the sequence includes a region of exon 1, exon 2, exon 3 and/or exon 4 of a human IL4 gene (e.g., full-length sequence of SEQ ID NO: 4). In some embodiments, the endogenous IL4 locus is exon 1, exon 2, exon 3 and/or exon 4 of mouse IL4.

In some embodiments, the methods of modifying an IL4Ra or IL4 locus of a mouse to express a chimeric human/mouse IL4R or IL4 peptide can include the steps of replacing at the endogenous mouse IL4Ra or IL4 locus a nucleotide sequence encoding a mouse IL4R or IL4 with a nucleotide sequence encoding a human IL4R or IL4, thereby generating a sequence encoding a chimeric human/mouse IL4R or IL4.

In some embodiments, the nucleotide sequence encoding the chimeric human/mouse IL4R can include a first nucleotide sequence encoding a region of the extracellular region of mouse IL4R (with or without the mouse or human signal peptide sequence); a second nucleotide sequence encoding a region of the extracellular region of human IL4R; a third nucleotide sequence encoding the transmembrane region, and/or the cytoplasmic region of a mouse IL4R.

In some embodiments, the nucleotide sequences as described herein do not overlap with each other (e.g., the first nucleotide sequence, the second nucleotide sequence, and/or the third nucleotide sequence do not overlap). In some embodiments, the amino acid sequences as described herein do not overlap with each other.

The present disclosure further provides a method for establishing an IL4Ra or IL4 gene humanized animal model, involving the following steps:

(a) providing the cell (e.g. a fertilized egg cell) based on the methods described herein;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 or BALB/c mouse).

In some embodiments, the non-human mammal in step (c) is a female with pseudo pregnancy (or false pregnancy).

In some embodiments, the fertilized eggs for the methods described above are C57BL/6 or BALB/c fertilized eggs. Other fertilized eggs that can also be used in the methods as described herein include, but are not limited to, FVB/N fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the method described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate in the context of the humanized animal's physiology.

Genetically modified animals that express human or humanized IL4R and/or IL4 protein, e.g., in a physiologically appropriate manner, provide a variety of uses that include, but are not limited to, developing therapeutics for human diseases and disorders, and assessing the toxicity and/or efficacy of these human therapeutics in the animal models.

In various aspects, genetically modified animals are provided that express human or humanized IL4R and/or IL4, which are useful for testing agents that can decrease or block the interaction between IL4R and IL4 or the interaction between IL4R and other IL4R ligands, testing whether an agent can increase or decrease the immune response, and/or determining whether an agent is an IL4R or IL4 agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In one aspect, the disclosure also provides methods of determining effectiveness of an IL4R or IL4 antagonist (e.g., an anti-IL4R or an anti-IL4 antibody) for reducing inflammation. The methods involve administering the IL4R or IL4 antagonist to the animal described herein, wherein the animal has an inflammation; and determining the inhibitory effects of the IL4R or IL4 antagonist to the reduction of inflammation.

In one aspect, the disclosure also provides methods of determining effectiveness of an IL4R or IL4 antagonist (e.g., an anti-IL4R or anti-IL4 antibody) for treating an immune disorder (e.g., an autoimmune disorder or allergy). The methods involve administering the IL4R or IL4 antagonist to the animal described herein, wherein the animal has an immune disorder; and determining the inhibitory effects of the IL4R or IL4 antagonist.

In one aspect, the disclosure also provides methods of determining effectiveness of an IL4R or IL4 antagonist (e.g., an anti-IL4R or anti-IL4 antibody) for treating cancer. The methods involve administering the IL4R or IL4 antagonist to the animal described herein, wherein the animal has a tumor; and determining the inhibitory effects of the IL4R or IL4 antagonist to the tumor. In some embodiments, the tumor comprises one or more cancer cells that are injected into the animal. The inhibitory effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MM or CT.

In some embodiments, the anti-IL4R antibody or anti-IL4 antibody prevents IL4 from binding to IL4R. In some embodiments, the anti-IL4R antibody or anti-IL4 antibody cannot prevent IL4 from binding to IL4R (e.g., endogenous IL4R).

In some embodiments, the genetically modified animals can be used for determining whether an anti-IL4R antibody is an IL4R agonist or antagonist. In some embodiments, the genetically modified animals can be used for determining whether an anti-IL4 antibody is an IL4 agonist or antagonist. In some embodiments, the methods as described herein are also designed to determine the effects of the agent (e.g., anti-IL4R or anti-IL4 antibodies) on IL4R and/or IL4, e.g., whether the agent can stimulate macrophages, and/or whether the agent can upregulate the immune response or downregulate immune response. In some embodiments, the genetically modified animals can be used for determining the effective dosage of a therapeutic agent for treating a disease in the subject, e.g., an immune disorder, an allergy, or autoimmune diseases.

In some embodiments, the inhibitory effects of treating inflammation are evaluated by serum IgE levels; pathological lung histology features; number of leukocytes (CD45+ cells), eosinophils (Eos) or neutrophils in bronchoalveolar lavage fluid (BALF); or ratio of eosinophils or neutrophils cells in CD45+ cells in bronchoalveolar lavage fluid (BALF).

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the anti-IL4R or anti-IL4 antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. As IL-4 blockade improves the response to anti-OX40 antibody or CpG oligodeoxynucleotide immunotherapies, in some embodiments, the anti-IL4R antibody or anti-IL4 antibody are used in connection with anti-OX40 antibody or CpG oligodeoxynucleotide immunotherapies.

In some embodiments, the antibody is designed for treating various autoimmune diseases or allergy (e.g., allergic rhinitis, sinusitis, asthma, or eczema). Thus, the methods as described herein can be used to determine the effectiveness of an antibody in inhibiting immune response.

The present disclosure also provides methods of determining toxicity of an antibody (e.g., anti-IL4R antibody or anti-IL4 antibody). The methods involve administering the antibody to the animal as described herein. The animal is then evaluated for its weight change, red blood cell count, hematocrit, and/or hemoglobin. In some embodiments, the antibody can decrease the red blood cells (RBC), hematocrit, or hemoglobin by more than 20%, 30%, 40%, or 50%.

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the methods as described herein in the screening, verifying, evaluating or studying the IL4R or IL4 gene function, human IL4R or IL4 antibodies, drugs for human IL4R or IL4 targeting sites, the drugs or efficacies for human IL4R or IL4 targeting sites, the drugs for immune-related diseases and antitumor drugs.

Genetically Modified Animal Model with Two or More Human or Chimeric Genes

The present disclosure further relates to methods for generating genetically modified animal model with two or more human or chimeric genes. The animal can comprise a human or chimeric IL4Ra gene and a sequence encoding one or more additional human or chimeric protein (e.g., IL4). Alternatively, the animal can comprise a human or chimeric IL4 gene and a sequence encoding one or more additional human or chimeric protein (e.g., IL4R).

In some embodiments, the additional human or chimeric protein can be IL4, IL4R, Interleukin 33 (IL33), Interleukin 13 (IL13), programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, T-Cell Immunoreceptor with Ig and ITIM Domains (TIGIT), T-cell Immunoglobulin and Mucin-Domain Containing-3 (TIM-3), Glucocorticoid-Induced TNFR-Related Protein (GITR), CD137, TNF Receptor Superfamily Member 4 (TNFRSF4 or OX40), CD47 or SIRPa.

The methods of generating genetically modified animal model with two or more human or chimeric genes (e.g., humanized genes) can include the following steps:

(a) using the methods of introducing human IL4R gene or chimeric IL4Ra gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric IL4, IL33, IL13, PD-1, CTLA-4, LAG-3, BTLA, PD-L1, CD27, CD28, TIGIT, TIM-3, GITR, OX40, CD137, CD47, CD40, CD3e or SIRPa. Some of these genetically modified non-human animal are described, e.g., in PCT/CN2017/090320, PCT/CN2017/099577, PCT/CN2017/099575, PCT/CN2017/099576, PCT/CN2017/099574, PCT/CN2017/106024, PCT/CN2017/110494, PCT/CN2017/110435, PCT/CN2017/117984, PCT/CN2017/120388, PCT/CN2018/091846, PCT/CN2018/091845, PCT/CN2018/120713, PCT/CN2018/110069; each of which is incorporated herein by reference in its entirety.

Similarly, the methods of generating genetically modified animal model can include the following steps:

(a) using the methods of introducing human IL4 gene or chimeric IL4 gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, the humanization is directly performed on a genetically modified animal having a human or chimeric IL4, IL4R, IL33, IL13, PD-1, CTLA-4, BTLA, PD-L1, CD27, CD28, TIGIT, TIM-3, GITR, CD137, OX40, CD47, CD40, CD3e or SIRPa gene.

In some embodiments, the IL4R humanization is directly performed on a genetically modified animal having a human or chimeric IL4. In some embodiments, the IL4 humanization is directly performed on a genetically modified animal having a human or chimeric IL4R.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-IL4R antibody and an additional therapeutic agent for the treatment. The methods include administering the anti-IL4R antibody and/or the anti-IL4 antibody, and the additional therapeutic agent to the animal, wherein the animal has a tumor; and determining the inhibitory effects of the combined treatment to the tumor. In some embodiments, the additional therapeutic agent is an antibody that specifically binds to IL4, IL4R, IL33, IL13, PD-1, CTLA-4, BTLA, PD-L1, CD27, CD28, TIGIT, TIM-3, GITR, CD137, OX40, CD47, CD40, CD3e or SIRPa. In some embodiments, the additional therapeutic agent is an anti-CTLA4 antibody (e.g., ipilimumab), an anti-CD20 antibody (e.g., rituximab), an anti-EGFR antibody (e.g., cetuximab), and an anti-CD319 antibody (e.g., elotuzumab), or anti-PD-1 antibody (e.g., nivolumab).

EXAMPLES

The invention is further described in the following examples, which do not limit the scope of the invention described in the claims.
Materials and Methods
The following materials were used in the following examples.

C57BL/6 mice were purchased from the China Food and Drugs Research Institute National Rodent Experimental Animal Center.

AIO kit was obtained from Beijing Biocytogen Co., Ltd. (Catalog number: BCG-DX-004).

Mouse IL-4 ELISA kit was obtained from RayBiotech, Inc. (Catalog number ELM-IL4-1).

Human IL-4 ELISA kit was obtained from RayBiotech, Inc. (Catalog number ELH-IL4-5).

BamHI, HindIII, XhoI, EcoRI, EcoRV, NotI, NdeI, SacI, BglII, AseI, MfeI and SmaI restriction enzymes were purchased from NEB with Catalog numbers: R3136M, R3104M, R0146S, R3101M, R0195S, R3189M, R3193M, R3156M, R0144M, R0526M, R3589S and R0141S, respectively.

Bacterial Artificial Chromosome (BAC) bacteria containing mouse IL4 and IL4R genes, and BAC bacteria containing human IL4 and IL4R genes were ordered from Invitrogen (Catalog number RPCI23.0 and RPCI11.C).

Purified NA/LE Hamster anti-mouse CD3e (mCD3) antibody was purchased from Becton, Dickinson and Company (BD Biosciences, Catalog number 553057).

FITC anti-mouse CD19 antibody (mCD19 FITC) was purchased from Biolegend (Catalog number 115506).

APC anti-human CD124 (IL4Ra) antibody (hIL4RA APC) was purchased from Biolegend (Catalog number: 355006).

PE anti-mouse CD124 (IL4Ra) antibody (mIL4RA PE) was purchased from Biolegend (Catalog number 144804).

APC/Cy7 anti-mouse CD19 antibody (mCD19 APC-Cy7) was purchased from Biolegend (Catalog number: 115530).

PE anti-human CD124 (IL-4Ra) antibody (hIL4RA PE) was purchased from Biolegend (Catalog number 355003).

Alexa Fluor® 647 AffiniPure F(ab')₂ Fragment Goat Anti-Human IgG, Fcγ fragment specific (anti-hIgG-AF647) was purchased from Jackson ImmunoResearch Inc. (Catalog number: 109-606-170).

In vivo Grade Human IgG4 kappa Isotype Control—CrownVivo™ Antibody (anti-IgG4-kappa hIgG-APC) was purchased from Crown Bio Inc. (Catalog number: C0004).

Example 1: Mice with Humanized IL4 Gene

The transcript of mouse IL4 gene (NCBI Gene ID: 16189, Primary source: MGI: 96556, UniProt ID: P07750) is NM_021283.2 (SEQ ID NO: 1) with the corresponding protein NP_067258.1 (SEQ ID NO: 2). The transcript of human IL4 gene (NCBI Gene ID: 3565, Primary source: HGNC: 6014, UniProt ID: P05112) is NM_000589.3 (SEQ ID NO: 3) with the corresponding protein NP_000580.1 (SEQ ID NO: 4). A schematic diagram that compares the mouse IL4 gene and the human IL4 gene was shown in FIG. 1.

Figure 2:
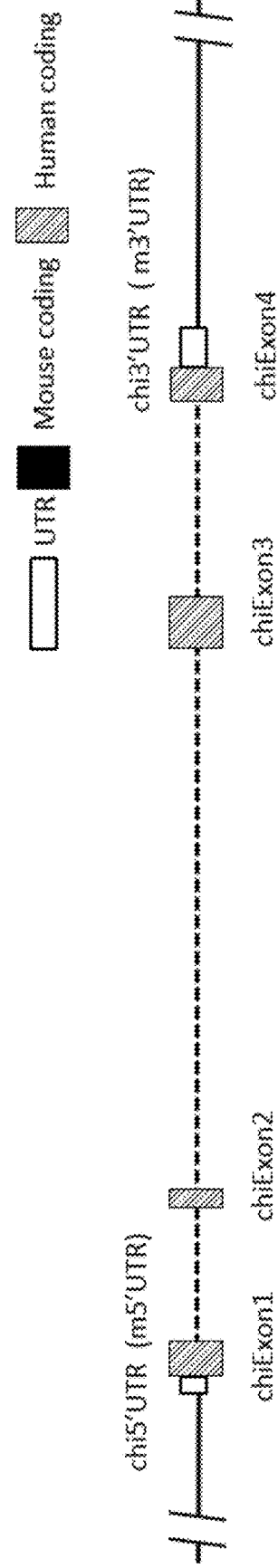
FIG. 2 is a schematic diagram showing humanized IL4 gene locus (replacing coding sequence).

Two humanization strategies were used to introduce a gene sequence encoding a human IL4 protein into the endogenous mouse IL4 locus. In one method, the mouse IL4 gene sequence was replaced with human IL4 gene sequences at the endogenous IL4 locus. About ~8.5 kb sequence starting from ATG (start codon) to TGA (stop codon) was replaced with the corresponding human DNA sequence to obtain a humanized IL4 locus (FIG. 2; version 1, the mRNA sequence of the engineered mouse IL4 after humanization was shown in SEQ ID NO: 80). The sequence is still under the control of mouse IL4 regulatory elements, and has mouse 5'-UTR and 3'-UTR. Another humanization strategy is shown in FIG. 3 (version 2). A longer sequence at the IL4 locus was replaced. The sequence includes human 5'-UTR and human 3'-UTR, and is under the control of human IL4 regulatory elements.

Mouse and human IL4 DNA were obtained using Bacterial Artificial Chromosome (BAC) RP23-464K4 and RP11-17K19, respectively. As shown in the schematic diagram of the targeting strategy in FIG. 4, the recombinant vector contained the homology arm sequence upstream and downstream of mouse IL4 (4220 bp upstream of ATG of endogenous IL4 gene and 4085 bp downstream of TGA), and 8537 bp human IL4 Sequence (extending from start codon ATG in exon 1 to stop codon TGA in exon 4). The upstream homology arm sequence (5' homology arm, SEQ ID NO: 5) was identical to the nucleotide sequence of 53622826-53618607 with NCBI accession number NC_000077.6, and the downstream homology arm sequence (3' homology arm, SEQ ID NO: 6) was identical to the nucleotide sequence of 53612065-53607981 with NCBI accession number NC_000077.6. The DNA fragment sequence of human IL4 (SEQ ID NO: 7) was identical to the nucleotide sequence of 132674051-132682587 with NCBI accession number NC_000005.10. The sequence containing the human IL4 gene and the upstream connection site at the mouse locus was designed as 5'-ACTTTAACTCTATATATAGAGA-GACCTCTGCCAGCATTGCATTGTTAGCAT CTCTT-GATAAACTTAATTGTCTCTCGT-CACTGACGGCACAGAGC<u>TATTG</u>ATGG GTCTCACCTCC-CAACTGCTTCCCCCTCTGTTCTTCCTGCTAG-CATGTGCCGGCA ACTTTGTC-CACGGACACAAGTGCGATATCACCTTACAGGAGA-3' (SEQ ID NO: 8), wherein the "G" in the sequence "TATTG" was the last nucleotide of the mouse sequence, and the "A" in the sequence "ATGGG" was the first nucleotide of the human sequence.

The sequence containing the human IL4 gene and the downstream connection site at the mouse locus was designed as 5'-TGGAAAACTTCTTGGAAAGGCTAAA-GACGATCATGAGAGAGAAATATTCA AAGTGTTCGAGCTGA <u>TACTG</u>AGCCACCATGCTTTAACTTATGAATTTTTA ATG GTTTTATTTTTAATATTTATATATTTATAATTCAT-AAAATAAAATA-3' (SEQ ID NO: 9), wherein the "A" in the sequence "GCTGA" was the last nucleotide of the human sequence, and the "T" in the sequence "TACTG" was the first nucleotide of the mouse sequence.

The targeting vector also included an antibiotic resistance gene for positive clone screening (neomycin phosphotransferase Neo), and two Frt recombination sites on both sides of the antibiotic resistance gene. The locus formed a Neo cassette. The connection between the 5' end of the Neo cassette and the mouse IL4 locus was designed as 5'-ACATGCCTGTAGGCAAGACACCCACACACAT-AAAAACAAAATAAAATAA GGA- TAGAAAGGCCAGGGGGAT GAATCCTCGAGGTCGACGGTATCGATAAGC TTGATATCGAATTCCGAAGTTCCTATTCTCTAGAAAGTATAGGAACTTCAGGT CT-3' (SEQ ID NO: 10), wherein the "C" of the sequence "GAATC" was the last nucleotide of the mouse sequence, and the "C" of the sequence "CTCGA" was the first nucleotide of the Neo cassette. The connection between the 3' end of the Neo cassette with the mouse IL4 locus was designed as 5'-AGAAAGTATAGGAACTTCATCAGTCAGGTACATAATGG TGGATCCATTAAT CAGAGGTAGAAGAAAACTTATTCC-3' (SEQ ID NO: 11), wherein the last "T" of the sequence "TTAAT" was the last nucleotide of the Neo cassette, and the "C" of the sequence "CAGAG" was the first nucleotide of the mouse sequence. In addition, a coding gene with a negative selectable marker (a gene encoding diphtheria toxin A subunit (DTA)) was also inserted downstream of the 3' homology arm of the recombinant vector.

Figure 5A:
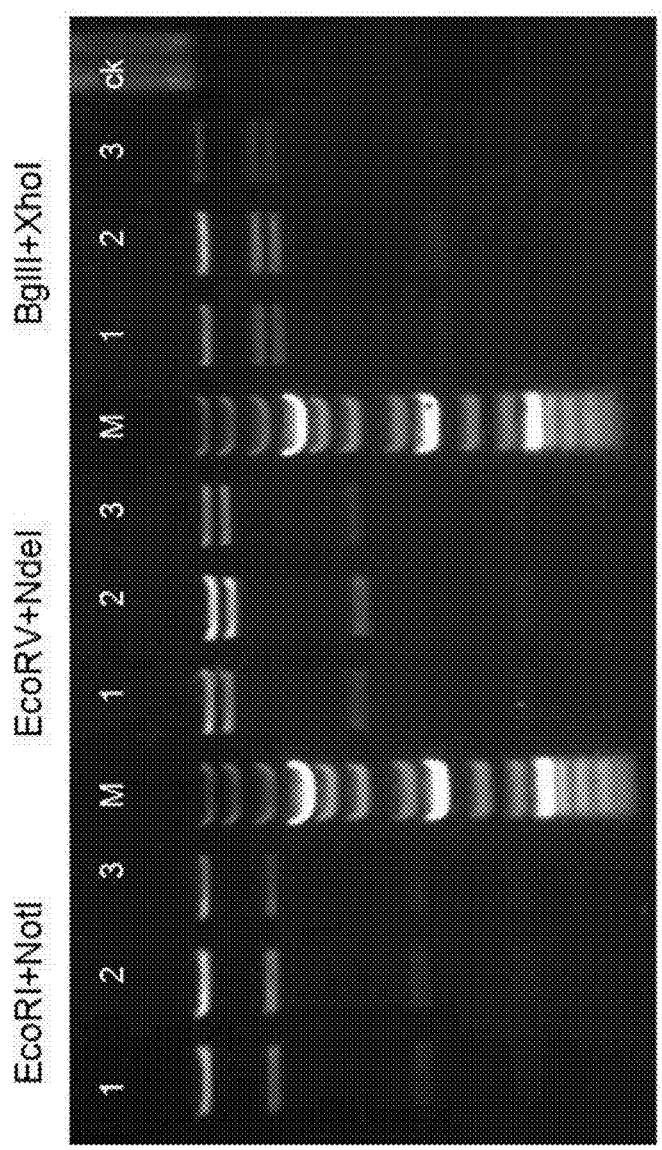
FIG. 5A is a graph showing recombinant vector digestion results, wherein No. 1, 2, 3 refer to 3 vector plasmids respectively, ck represents the undigested plasmid control, M is the Marker.
Figure 5B:
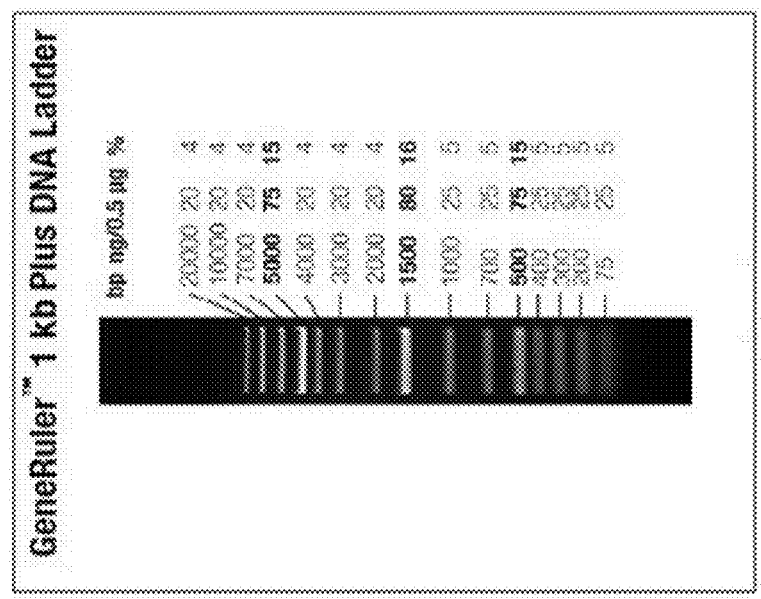
FIG. 5B is a graph showing DNA ladder for the Marker.

Vector construction can be carried out by restriction enzyme digestion and ligation. The constructed recombinant vector sequence can be initially verified by restriction enzyme digestion. The verification results were shown in FIGS. 5A-5B. The restriction enzyme digestion results were verified by using three groups of enzymes. Among them, EcoRI+NotI should generate 634 bp+1678 bp+5953 bp+16413 bp fragments, EcoRV+NdeI should generate 587 bp+2637 bp+8928 bp+12526 bp fragments, BglII+XhoI should generate 1183 bp+5178 bp+6292 bp+12025 bp fragments. The results of restriction enzyme digestion were in line with expectations and the sequences of plasmids 1 and 2 were verified by sequencing.

Figure 6:
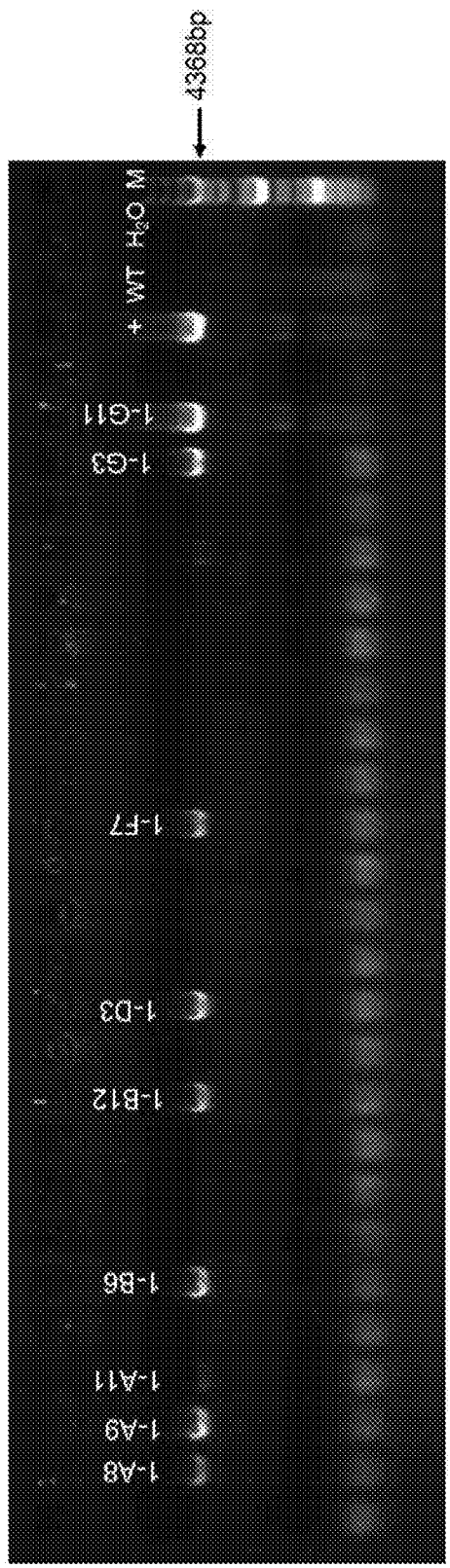
FIG. 6 is a graph showing PCR identification results of cells, wherein + is the positive control, WT is the wild-type control, M is the Marker, $H_2O$ is a blank control. The clones marked with the clone numbers were identified as positive clones.
Figure 7:
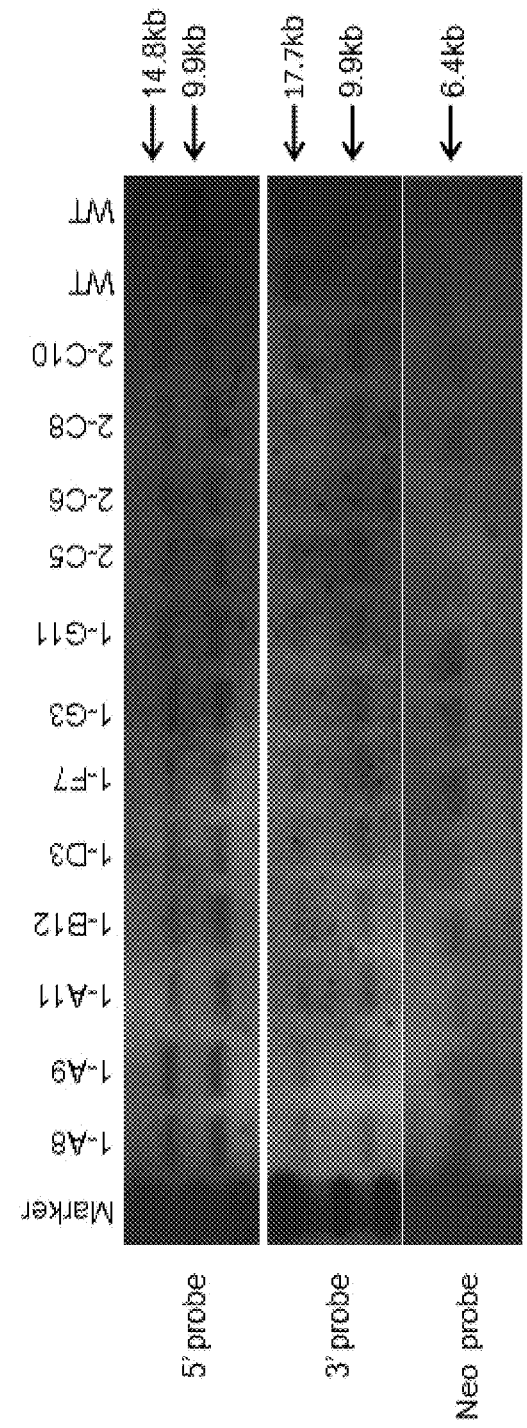
FIG. 7 is a graph showing Southern blot results.

The correct recombinant vector was electroporated and transfected into embryonic stem cells of C57BL/6 mice. The positive selectable marker gene was used to screen the cells, and the integration of exogenous genes was confirmed by PCR and Southern Blot. PCR and Southern Blot results (digested with EcoRI or AseI, respectively, and hybridized with 3 probes) for some of the clones were shown in FIG. 6 and FIG. 7. As shown in FIG. 7, among the 12 PCR-positive clones, 11 clones were selected and identified as positive heterozygous clones and no random insertions were detected.

The following primers were used in PCR:

```
F:
                                    (SEQ ID NO: 12)
5'-GACAACTTTCAGGGAGGGAGTCAG-3',

R:
                                    (SEQ ID NO: 13)
5'-ATCGCACTTGTGTCCGTGGAC-3'.
```

The following probes were used in Southern Blot assays:

```
5' Probe:
F:
                                    (SEQ ID NO: 14)
5'-GCCTCTCTCAACCCAGTATAAC-3', R:
                                    (SEQ ID NO: 15)
5'-CTTGGAGTCAACCACCTCTG-3';

3' Probe:
F:
                                    (SEQ ID NO: 16)
5'-GATCTTTCACTGAAACTTGACTG-3', R:
                                    (SEQ ID NO: 17)
5'-CTCCAACTACATCTACTTTCTG-3';

Neo Probe:
F:
                                    (SEQ ID NO: 18)
5'-GGATCGGCCATTGAACAAGATGG-3', R:
                                    (SEQ ID NO: 19)
5'-CAGAAGAACTCGTCAAGAAGGCG-3'.
```

Another IL4 mouse humanization strategy was to perform a sequence substitution for a longer sequence near the IL4 locus. The humanized mouse IL4 locus was shown in FIG. 3, and the targeting strategy was shown in FIG. 8. The recombinant vector contained an upstream homology arm sequence of 5553 bp and a downstream homology arm sequence of 5196 bp of the mouse IL4 locus, and a 10573 bp sequence containing human IL4 DNA fragments. The upstream homology arm sequence (5' homology arm, SEQ ID NO: 20) was identical to the nucleotide sequence of 53625623-53620071 of NCBI accession number NC_000077.6, and the downstream homology arm sequence (3' homology arm, SEQ ID NO: 21) was identical to the nucleotide sequence at position 53612200-53607005 of NCBI Accession No. NC_000077.6; the sequence of human IL4 DNA fragment (SEQ ID NO: 22) was identical to the nucleotide sequence of 132672342-132682914 with NCBI accession number NC_000005.10.

The sequence containing the human IL4 gene and the upstream connection site of the mouse locus was designed as 5'-TGGGGTATGGTGGCTTATATCTGTAACTTCAACACTTGAGAGGTGGAG GCAGGAGAGTGACCATGAATCTGAGGG CTTCCAGAATAAATTCATAGGGAG GCCCAGGCACAGTGGCTCACGCCTGTAATCCCAGCACTTTGGGAGG-3' (SEQ ID NO: 23), wherein the last "G" of the sequence "GAGGG" was the last nucleotide of the mouse sequence, and the first "C" of the sequence "CTTCC" was the first nucleotide of the human sequence.

Downstream of the sequence containing the human IL4 gene was linked to the Neo cassette, and the connection site was designed as 5'-GGGGTTCCCTCTCGAGTTAGGGACATAACACACAAGATAATTAAAGAACA CAAGGCCATACAAGATGTAAATAAGACACCTTGGGTCCAA GAGTGCGTCGA CGGTATCGATAAGCTTGATATCGAATTCCGAAGTTCCTATTCTCTAGAAAGTA TAGGAACTTCAGGTCTGAAGAGGAGTTTACGTCCAGCCAAGC-3' (SEQ ID NO: 24), wherein the "C" of the sequence "GAGTGC" was the last nucleotide of the human sequence, and the first "G" of the sequence "GTCGA" was the first nucleotide of the Neo cassette.

The Neo cassette downstream was connected to the mouse sequence, and the connection sequence was designed as 5'-TGCGGAACCCTTCGAAGTTCCTATTCTCTAGAAAGTATA GGAACTTCATCAGTCAGGTACATAATGGTGGATCCTAACTCAAGTTCTGGGG GAGCTGATGCTCTCCTCTGGCCTCCTGTGGAGGTACACAGACCACATGCCTGT AGGCAA-3' (SEQ ID NO: 25), wherein the last "C" of the sequence "GATCC" was the last nucleotide of the Neo cassette, and the first "T" of the sequence "TAACT" was the first nucleotide of the mouse sequence.

Figure 9A:
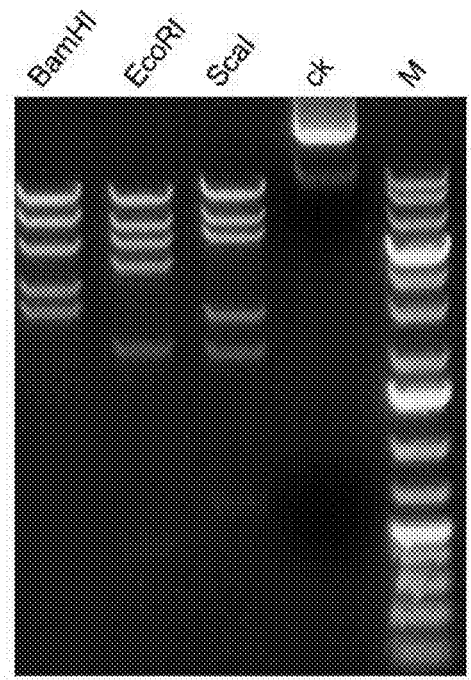
FIG. 9A is a graph showing recombinant vector digestion results, wherein ck represents the undigested plasmid control, M is the Marker. The plasmids were treated with BamHI, EcoRI or ScaI, respectively.
Figure 9B:
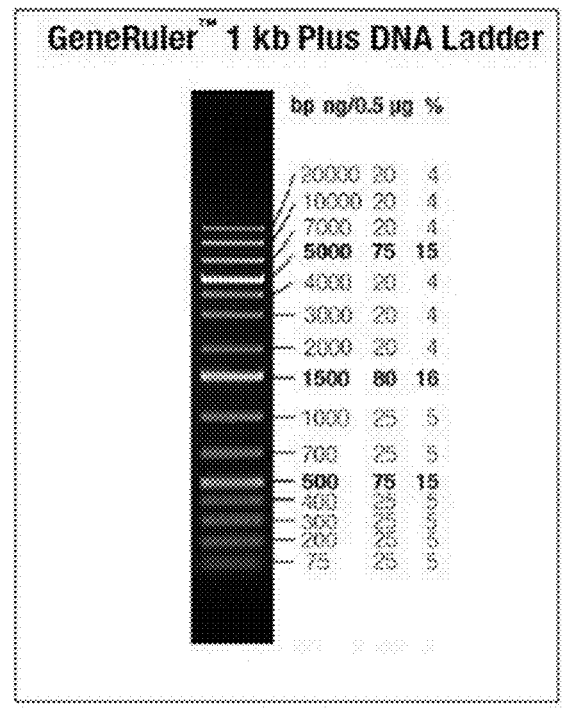
FIG. 9B is a graph showing DNA ladder for the Marker.

In addition, a coding gene with a negative selectable marker (a gene encoding the diphtheria toxin A subunit (DTA)) was also inserted downstream of the 3' homology arm of the recombinant vector. The verified results of the constructed recombinant vector digestion were shown in FIGS. 9A-9B, wherein BamHI should generate 9938 bp+6990 bp+5266 bp+3577 bp+2930 bp fragments, EcoRI should generate 9606 bp+6558 bp+5432 bp+4470 bp+2178 bp+457 bp fragments, ScaI should generate 10389 bp+7026 bp+5739 bp+2818 bp+2074 bp+655 bp fragments. The results of restriction enzyme digestion were in line with expectations and the plasmid was verified by sequencing.

Figure 10:
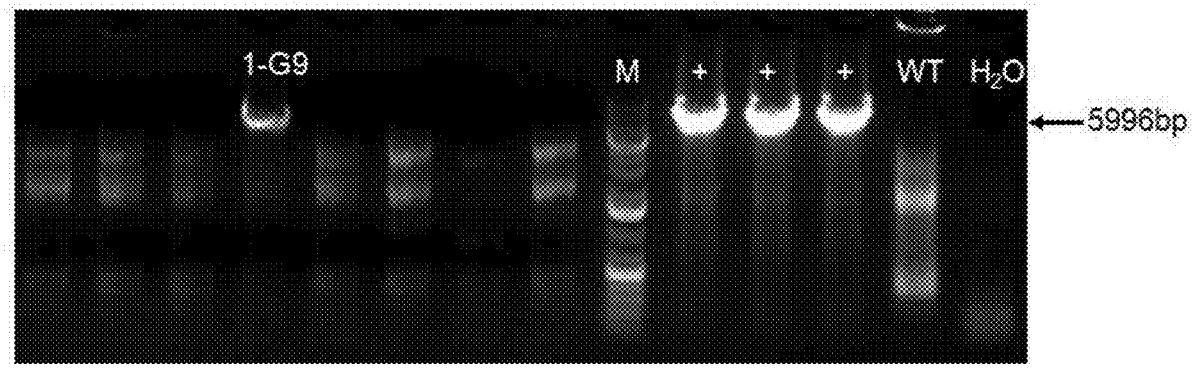
FIG. 10 is a graph showing PCR identification results, wherein M is the Marker, + is the positive control, WT is the wild-type control, and $H_2O$ is a blank control. The lane marked with clone number 1-G9 was identified as a positive clone.
Figure 11:
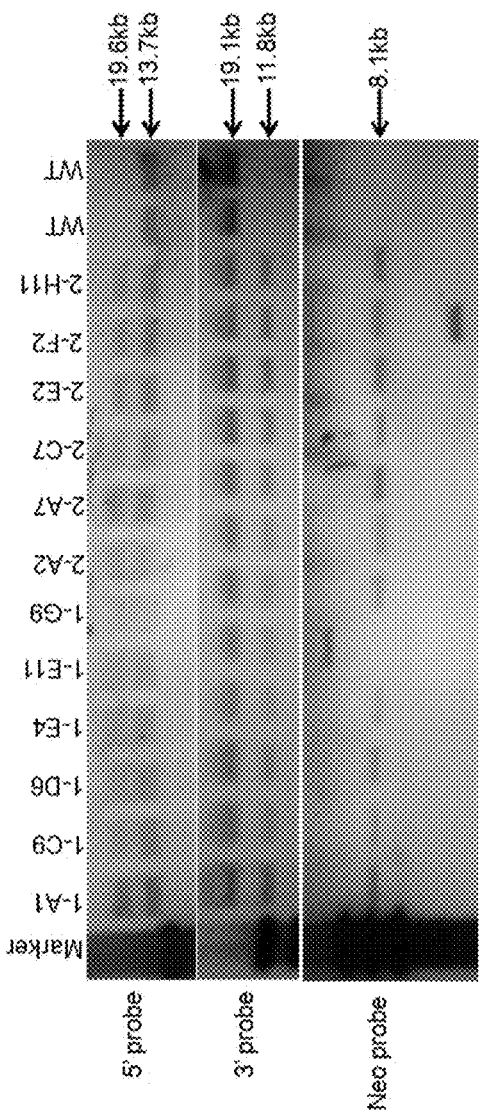
FIG. 11 is a graph showing Southern blot results.

The embryonic stem cells from C57BL/6 mice were transfected with the correct recombinant vector, screened, then confirmed by PCR and Southern Blot. Some of the PCR and Southern Blot (digested with MfeI, BamHI or EcoRV, respectively, and hybridized with 3 probes) results were shown in FIG. 10 and FIG. 11. As shown in FIG. 11, the results showed that among the 12 PCR-positive clones, except for 1-E11 and 2-F2, the remaining 10 clones were confirmed as positive heterozygous clones and no random insertions were detected.

The following primers were used in PCR:

```
F:
                                   (SEQ ID NO: 26)
5'-CTGTGATCATGGTTCCTTATCTGG-3',

R:
                                   (SEQ ID NO: 27)
5'-CCTCCCCGAGTAGCTGGGACTAC-3'.
```

The following probe were used in Southern Blot assays:

```
5' Probe:
F:
                                   (SEQ ID NO: 28)
5'-CCACTAGGGGTCCACAGCTAGTCAT-3', R:
                                   (SEQ ID NO: 29)
5'-CTTCAGTGAAACCTCCTGAGCCTGG-3';

3' Probe:
F:
                                   (SEQ ID NO: 30)
5'- AGTCAGAGCTACAGAAGTGGAGGGT-3', R:
                                   (SEQ ID NO: 31)
5'- CTGCTCTGCAGGAAGTAAGGGTTCC-3';

Neo Probe F: SEQ ID NO: 18;

Neo Probe R: SEQ ID NO: 19.
```

Figure 12:
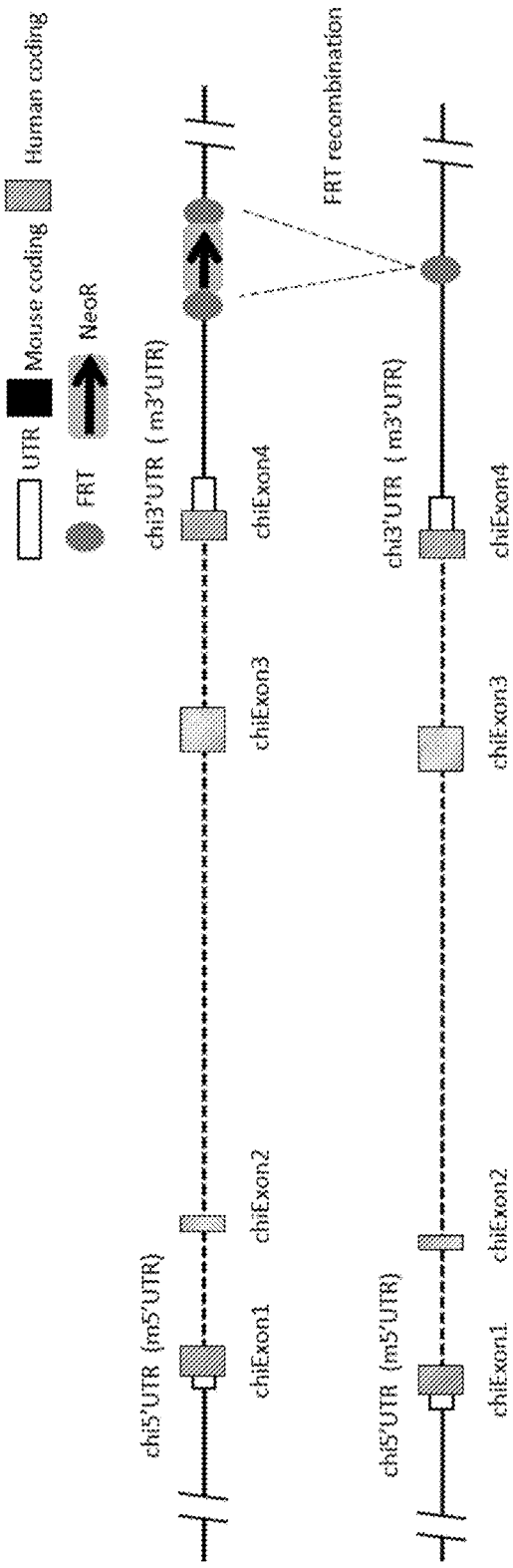
FIG. 12 is a schematic diagram showing the FRT recombination process.
Figures 13A, 13B, 13C, 13D:
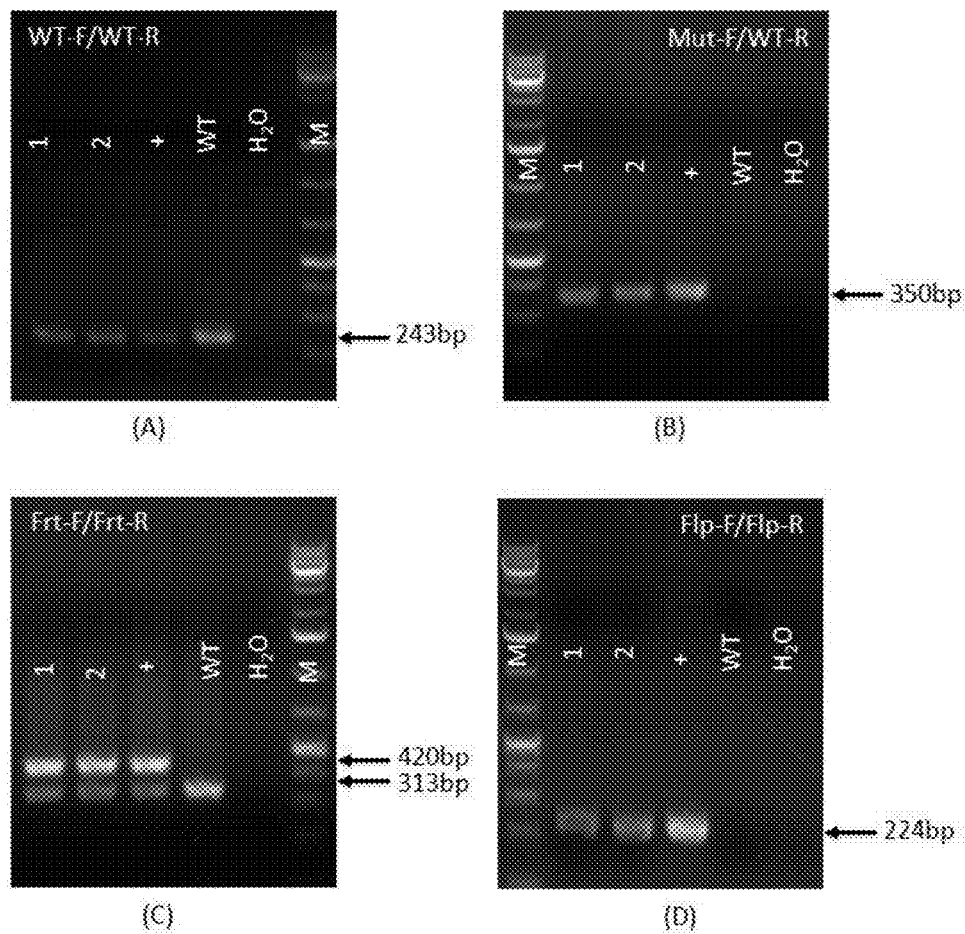
FIG. 13A shows PCR identification results for F1 generation mice (short fragment replacement), wherein primer pairs WT-F and WT-R were used to amplify wild-type mouse IL4 gene exon 4. WT is wild-type, $H_2O$ is a blank control, and + is the positive control.
FIG. 13B shows PCR identification results for F1 generation mice (short fragment replacement), wherein primer pairs Mut-F and WT-R were used to amplify the engineered exon 4 of the mouse IL4 gene to verify the correct insertion of the recombinant vector into the genomic locus; wherein WT is wild-type and + is the positive control.
FIG. 13C shows PCR identification results for F1 generation mice (short fragment replacement), wherein primer pairs Frt-F and Frt-R are used to amplify the Neo fragment to determine whether the resistance gene NeoR was removed; wherein WT is wild-type, and + is the positive control.
FIG. 13D shows PCR identification results for F1 generation mice (short fragment replacement), wherein primer pairs Flp-F and Flp-R were used to confirm the presence of the Flp fragment; wherein WT is wild-type and + is the positive control.

The positive clones that had been screened (black mice) were introduced into isolated blastocysts (white mice), and the obtained chimeric blastocysts were transferred to the culture medium for short-term culture and then transplanted to the fallopian tubes of the recipient mother (white mice) to produce the F0 chimeric mice (black and white). The F2 generation homozygous mice can be obtained by backcrossing the F0 generation chimeric mice with wild-type mice to obtain the F1 generation mice, and then mating the F1 generation heterozygous mice with each other. The positive mice can also be mated with the Flp tool mice to remove the positive selectable marker gene (the schematic diagram of the process was shown in FIG. 12), and then the humanized IL4 homozygous mice expressing human IL4 protein can be obtained by mating with each other. The genotype of the progeny mice can be identified by PCR, and the results for the F1 generation mice (Neo-removed) were shown in FIGS. 13A-13D, wherein the mice numbered 1 and 2 were positive heterozygous mice. The following primers were used in PCR:

```
WT-F:
                                   (SEQ ID NO: 32)
5'-ccacatcactgaaagacttcctgg-3';

WT-R:
                                   (SEQ ID NO: 33)
5'-gatcaagtagacaggcaggcaagac-3';

Mut-F:
                                   (SEQ ID NO: 34)
5'-ctgtgatcatggttccttatctgg-3';

WT-R: (SEQ ID NO: 33);

Frt-F:
                                   (SEQ ID NO: 35)
5'-agggacagatgcaggctggg-3';

Frt-R:
                                   (SEQ ID NO: 36)
5'-gagatgcgtgttagaggttttggga-3';

Flp-F:
                                   (SEQ ID NO: 37)
5'-tcagcgatattaagaacgttgatccg-3';

Flp-R:
                                   (SEQ ID NO: 38)
5'-tgaagaattgccggtcctatttactcg-3'.
```

Figure 14A:
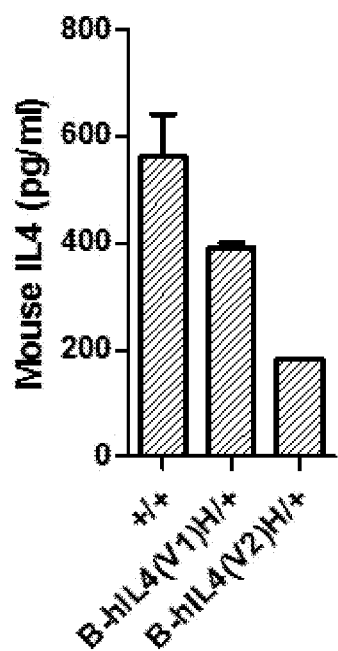
FIG. 14A is a graph showing the ELISA detection results of the mouse IL4 protein in IL4 humanized mice. One wild-type C57BL/6 mouse and two IL4 humanized heterozygotes were selected, wherein +/+ represents wild-type C57BL/6 mice; B-hIL4 (V1) H/+ represents the IL4 humanized mouse heterozygote obtained by short fragment replacement (replacing coding sequences); and B-hIL4 (V2) H/+ represents the IL4 humanized mouse heterozygote obtained by long fragment replacement (replacing coding sequences and 5'- and 3'-UTR).
Figure 14B:
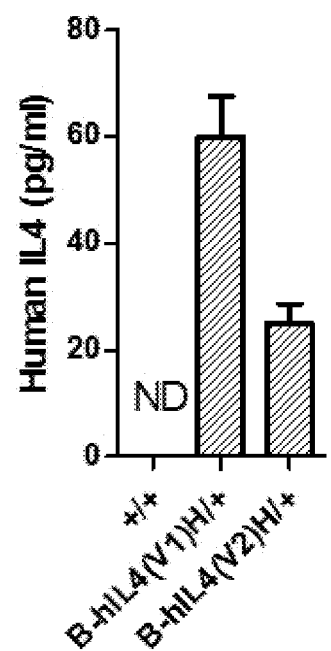
FIG. 14B is a graph showing the ELISA detection results of the human IL4 protein in IL4 humanized mice. One wild-type C57BL/6 mouse and two IL4 humanized heterozygotes were selected, wherein +/+ represents wild-type C57BL/6 mice; B-hIL4 (V1) H/+ represents the IL4 humanized mouse heterozygote obtained by short fragment replacement; and B-hIL4 (V2) H/+ represents the IL4 humanized mouse heterozygote obtained by long fragment replacement.

The expression of humanized IL4 protein in positive mice can be confirmed by ELISA. 7.5 µg of anti-mouse CD3 antibody (mCD3) was intraperitoneally injected into the mice. After 1.5 hours, serum was taken and diluted 5× to measure the levels of mouse IL4 and human IL4 protein. The measurement results were shown in FIGS. 14A-14B. FIG. 14A showed that the expression of mouse IL4 protein was detected in wild-type C57BL/6 mice and the two versions of IL4 humanized heterozygotes. FIG. 14B showed that the expression of human IL4 protein was not detected in wild-type C57BL/6 mice, and human IL4 protein expression was detected in both versions of IL4 humanized mice.

Example 2: Mice with Humanized IL4Ra Genes

The transcript of mouse IL4Ra gene (NCBI Gene ID: 16190, Primary source: MGI: 105367, UniProt ID: P16382) is NM_001008700.3 (SEQ ID NO: 39) with the corresponding protein NP_001008700.1 (SEQ ID NO: 40). The transcript of human IL4Ra gene (NCBI Gene ID: 3566, Primary source: HGNC: 6015, UniProt ID: P24394) is NM_000418.3 (SEQ ID NO: 41) with the corresponding protein NP_000409.1 (SEQ ID NO: 42). A schematic diagram that compared the mouse IL4Ra gene locus and the human IL4Ra gene locus was shown in FIG. 15.

The extracellular region of the endogenous mouse IL4Ra gene was replaced with the human IL4Ra gene sequence. Two humanization strategies were used. One was to replace a 4.4 kb sequence encoding the extracellular region of the mouse IL4Ra from exon 4 to exon 7 with a 10.5 kb sequence spanning from exon 4 to exon 7 of the human IL4Ra locus. This humanized strategy resulted in a humanized IL4Ra gene as shown in FIG. 16. The mRNA sequence of the engineered mouse IL4Ra after humanization and its encoded protein sequence were shown in SEQ ID NO: 43 and SEQ ID NO: 44, respectively.

Mouse and human IL4Ra DNA were obtained using Bacterial Artificial Chromosome (BAC) RP23-261H16 and RP11-16E24, respectively. As shown in the schematic diagram of the targeting strategy in FIG. 17, the recombinant vector contained the homology arm sequence upstream and downstream of mouse IL4Ra sequence (4264 bp upstream of exon 4 of endogenous IL4Ra gene and 4525 bp downstream of exon 7), and 10537 bp human IL4Ra sequence (extending from part of exon 4 to exon 7). The upstream homology arm sequence (5' homology arm, SEQ ID NO: 45) was identical to the nucleotide sequence of 125562909-125567172 with NCBI accession number NC_000073.6, and the downstream homology arm sequence (3' homology arm, SEQ ID NO: 46) was identical to the nucleotide sequence of 125572100-125576624 with NCBI accession number NC_000073.6; the DNA fragment sequence of human IL4Ra (SEQ ID NO: 47) was identical to the nucleotide sequence of 27342138-27352674 with NCBI accession number NC_000016.10. The sequence containing the human IL4Ra gene and the upstream of the connecting site at the mouse locus was designed as 5'-CCTCCCTCTGACCTTAGTGGTGG-GAGCCCCTGACCATGCCACCACTGATCT GGCCGTTCTGTCTCTGCAGGGAGCAT-CAAGGTCCTGCAGGAGCCCACCTGCG TCTCCGAC-TACATGAGCATCTCTACTTGCGAGTGGAAGAT-GAATGGTCCCACC AATTGCAGCACCGAGCTCCGCCTGTTG-3' (SEQ ID NO: 48), wherein the "G" of the sequence "TCCTG" was the last nucleotide of the mouse sequence, and the "C" of the sequence "CAGGA" was the first nucleotide of the human sequence. The sequence containing the human IL4Ra gene and the downstream of the connection site at the mouse locus was designed as 5'-CAGCACCCTGAAGTCTGG-GATTTCCTACAGGGCA CGGGTGAGGGCCT GGGCTCAGTGCTATAACACCACCTGGAGTGAGTG-GAGCCCTAGCATCACGTG GTACAACCGT-GAGTATCAGGGTCGTAGGCTGTGAGGATCTCTA-CAGCCGTGT ATATTCTCTGTTCAGAAATTCCCTCTGGCTGA-3' (SEQ ID NO: 49), wherein the "C" of the sequence "GGAGC" was the last nucleotide of the human sequence, and the first "C" of the sequence "CCTAG" was the first nucleotide of the mouse sequence.

The connection sequence between the 5' end of the Neo cassette and the mouse IL4Ra locus was designed as 5'-AGGCCCGGAGTTTAAATCCCCAGAGCC-CACGTAAAAGCCTGATATCGAA TTCCGAAGTTCCT-ATTCTCTAGAAAGTATAGGAACTTC-3' (SEQ ID NO: 50), wherein the "T" of the sequence "AGCCT" was the last nucleotide of the mouse sequence, and the first "G" of the sequence "GATAT" was the first nucleotide of the Neo cassette. The connection sequence of the 3' end of the Neo cassette with the mouse IL4Ra locus was designed as 5'-GAAGTTCCTATTCTCTAGAAAGTATAGGAACTT-CATCAGTCAGGTACATAATG GTGGATCCAAGCTT TGCGCAGTAGCACGCATGCGTAATCCTGATGGAGC AAT TAG-GAGAAGCCGGTGGCCGGCTAGCCTGTGCA-GACTGTGAAAACAGAGCATC TGAAGCTGTGT-GAAAGGCTAGCTCGC-3' (SEQ ID NO: 51), wherein the last "T" of the sequence "AGCTT" was the last nucleotide of the Neo cassette, and the "T" of the sequence "TGCGC" was the first nucleotide of the mouse sequence. In addition, a coding gene with a negative selectable marker (a gene encoding the diphtheria toxin A subunit (DTA)) was also added downstream of the 3' homology arm of the recombinant vector.

Figure 18:
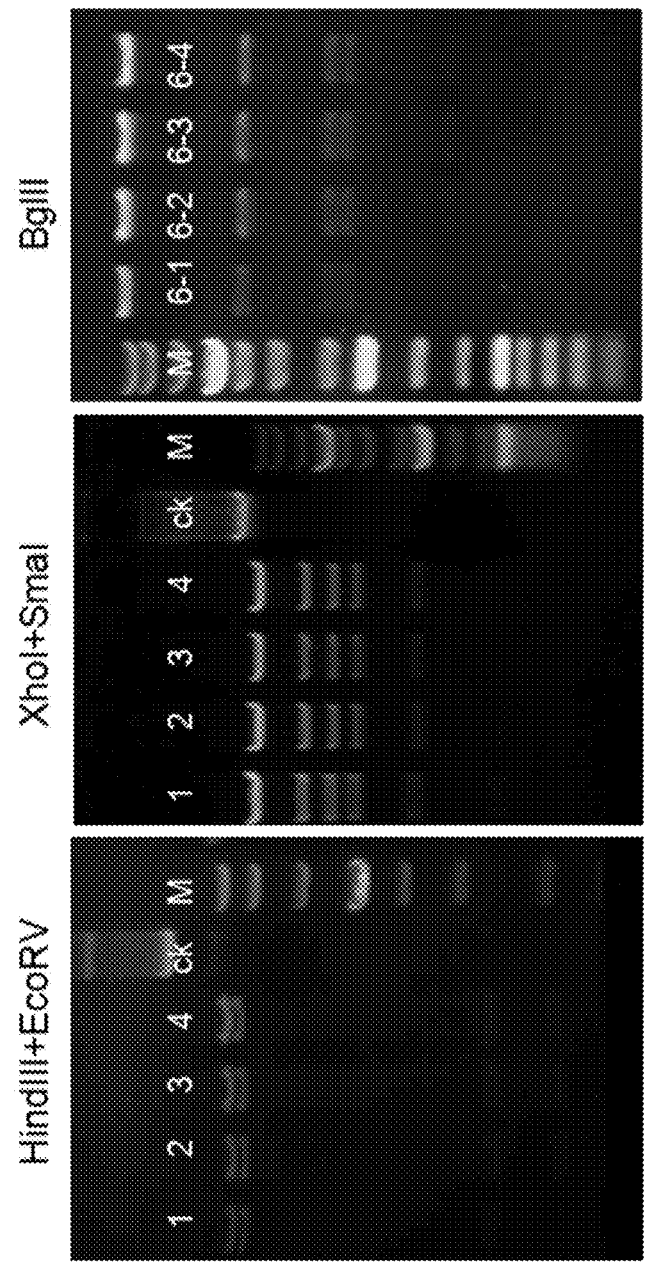
FIG. 18 is a graph showing the recombinant vector restriction enzyme digestion results, wherein No. 1, 2, 3, 4 refer to 4 vector plasmids respectively, ck represents the undigested plasmid control, and M is the Marker.

The constructed recombinant vector sequences were verified by restriction enzyme digestion as shown in FIG. 18. The restriction enzyme digestion results were verified by using three groups of enzymes. Among them, HindIII+EcoRV should generate 1866 bp+2513 bp+10385 bp+12455 bp fragments, XhoI+SmaI should generate 481 bp+1375 bp+2818 bp+3815 bp+5670 bp+13060 bp fragments, BglII should generate 754 bp+1610 bp+1856 bp+3705 bp+19294 bp fragments, and the results of restriction enzyme digestion were in line with expectations. Plasmid 3 was selected and the sequence was further verified by sequencing.

Figure 19A:
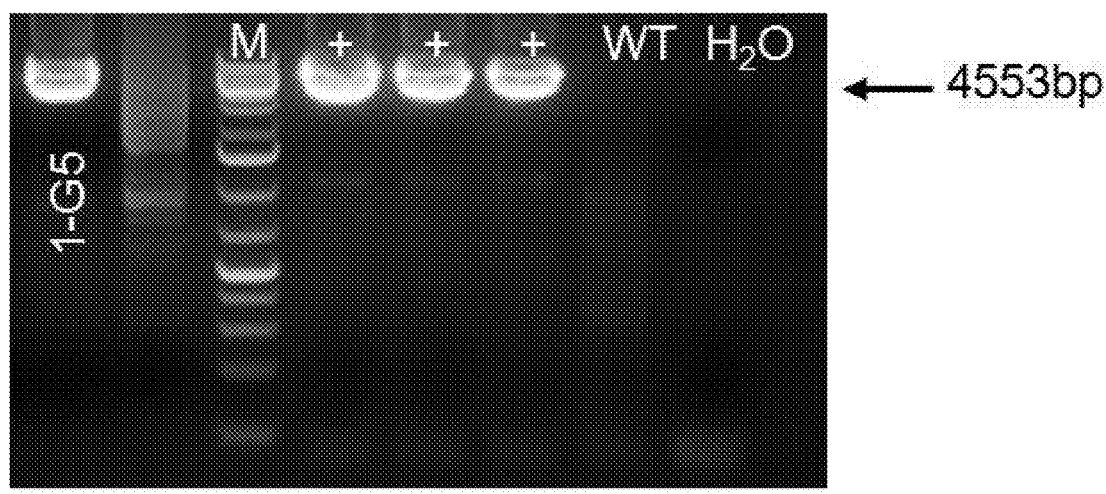
FIG. 19A is a graph showing the PCR identification results using primer pairs F1/R1, wherein + is the positive control, WT is the wild-type control, and M is the Marker.
Figure 19B:
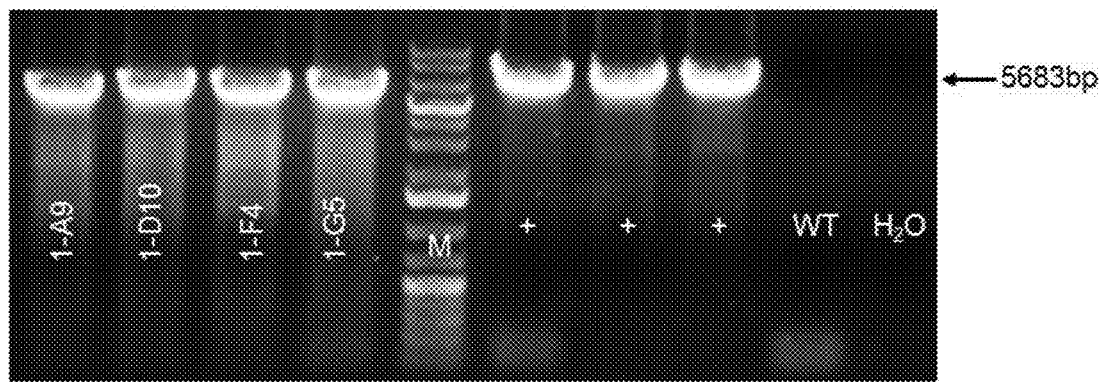
FIG. 19B is a graph showing the PCR identification results using primer pairs F2/R2, wherein + is the positive control, WT is the wild-type control, M is the Marker.
Figure 20:
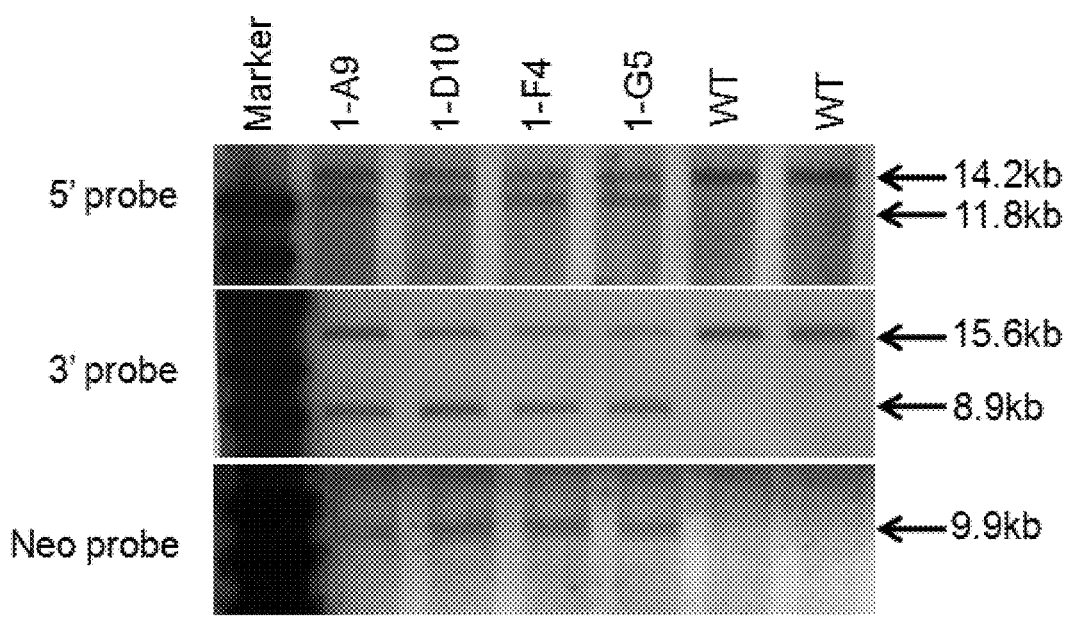
FIG. 20 is a graph showing Southern blot results. WT is the wild-type.

The recombinant vector was electroporated and transfected into embryonic stem cells of C57BL/6 mice. The positive selectable marker gene was used to screen the cells, and the integration of exogenous genes was confirmed by PCR and Southern Blot. Positive clones identified by PCR (see FIGS. 19A-19B for part of the cloning result) were then confirmed by Southern Blot (digested with SacI, HindIII or BglII, respectively, and hybridized with 3 probes). As shown in FIG. 20, the results indicated that four clones (1-A9, 1-D10, 1-F4, A-G5) were positive heterozygous clones and no random insertions were detected.

The following primers were used in PCR assays:

```
F1:
                                     (SEQ ID NO: 81)
    5'-GGGAGGGTGAGTGGAGTCCCA-3';

R1:
                                     (SEQ ID NO: 82)
    5'-CAGCGCAGGCTTACTCGGAGAG-3';

F2:
                                     (SEQ ID NO: 52)
    5'-CGCATTGTCTGAGTAGGTGTC-3';

R2:
                                     (SEQ ID NO: 53)
    5'-GCTGTTCAATGAATGGCCTCTGTG-3';
```

The following probes were used in Southern Blot assays:
5' Probe:

```
F:
                                     (SEQ ID NO: 54)
    5'-GTGGCCACCGTTTCTGGGAAC-3';

R:
                                     (SEQ ID NO: 55)
    5'- TCAACAATCTAAGCACGGACCT-3';

3' Probe:
F:
                                     (SEQ ID NO: 56)
    5'- GTGCTGAGGCCAGGGTTCCTC-3';

R:
                                     (SEQ ID NO: 57)
    5'-GCTGTTCAATGAATGGCCTCTGTG-3';

Neo Probe:
F: SEQ ID NO: 18,

R: SEQ ID NO: 19.
```

Figures 21A, 21B:
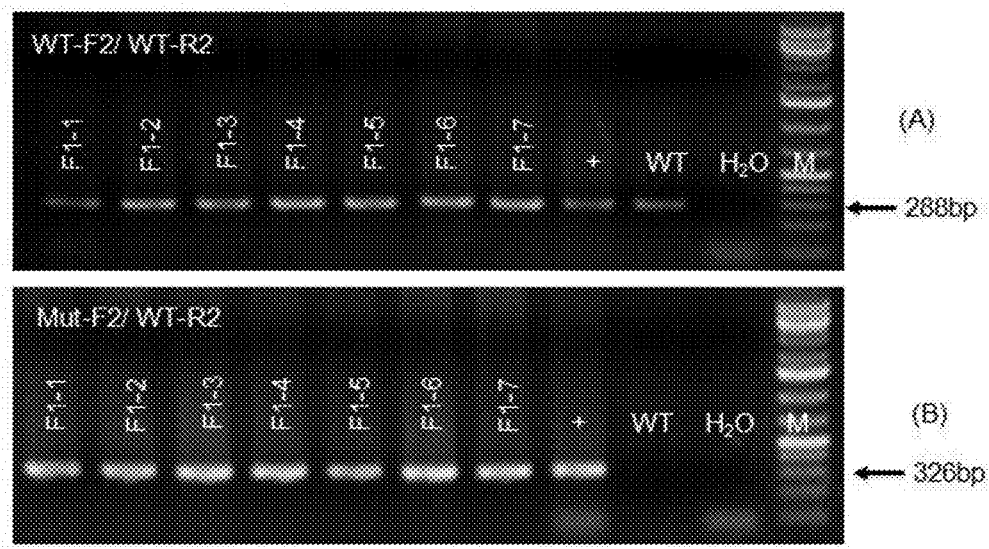
FIG. 21A shows PCR identification results of F1 generation mice, wherein primer pairs WT-F2 and WT-R2 were used to amplify wild-type mouse IL4Ra gene exon 7; wherein WT is wild-type, + is the positive control, H₂O is a blank control, and M is the Marker.
FIG. 21B shows PCR identification results of F1 generation mice, wherein primer pairs Mut-F2 and WT-R2 were used to amplify modified exon 7 of the mouse IL4Ra gene to confirm the insertion of the recombinant vector into the genomic locus; wherein WT is wild-type, + is the positive control and, M is the Marker.
Figures 22A, 22B:
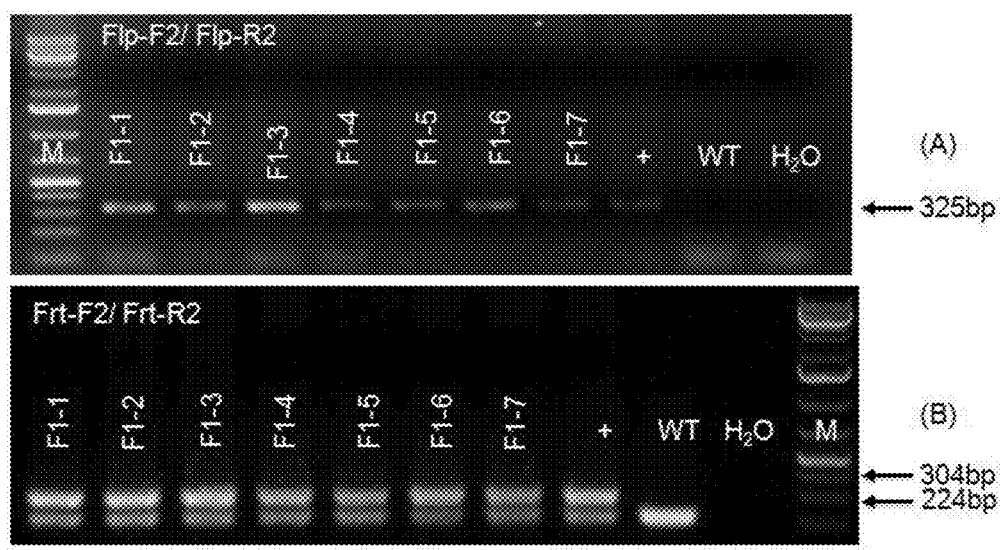
FIG. 22A shows PCR identification results of F1 generation mice, wherein primer pairs Flp-F2 and Flp-R2 were used to confirm the presence of the Flp fragment; wherein WT is wild-type, and + is the positive control.
FIG. 22B shows PCR identification results of F1 generation mice, wherein primer pairs Frt-F2 and Frt-R2 were used to amplify the Neo fragment to verify whether the resistance gene Neo was removed; wherein WT is wild-type, and + is the positive control.

The positive clones (black mice) were introduced into isolated blastocysts (white mice), according to the techniques known in the art (for example, the method as described in A. Nagy, et al., "Manipulating the Mouse Embryo: A Laboratory Manual (Third Edition)," Cold Spring Harbor Laboratory Press, 2003). The obtained chimeric blastocysts were transferred to a culture medium for a short-term culture and then transplanted into the fallopian tubes of the recipient mother mice (white mice) to produce the F0 generation chimeric mice (black and white). The F1 generation mice were obtained by backcrossing the F0 generation chimeric mice with wild-type mice. F2 generation homozygous mice were then obtained by mating the F1 generation heterozygous mice with each other. The positive mice were also mated with the Flp tool mice to remove the positive selectable marker gene, and then the humanized IL4Ra gene homozygous mice expressing human IL4Ra protein were obtained by mating with each other. The genotype of the progeny mouse can be identified by PCR and the identification results of the F1 generation mice (Neo-removed) were shown in FIG. 21 and FIG. 22, wherein the mice number F1-1 to F1-7 were positive heterozygous mice in FIG. 20.

The following primers were used in PCR assays:

```
WT-F2:
                              (SEQ ID NO: 58)
5'-gacacacgtgtctgccagctctgt-3';

WT-R2:
                              (SEQ ID NO: 59)
5'-cacggtcagccagagggaatttctg-3';

Mut-F2:
                              (SEQ ID NO: 60)
5'-gtggggtcagctaacgacagcaac-3';

Frt-F2:
                              (SEQ ID NO: 61)
5'-cgtgtcaaaagcagaaacgcaggag-3';

Frt-R2:
                              (SEQ ID NO: 62)
5'-gcgtatgtcaggatctgaggagcac-3';

Flp-F2:
                              (SEQ ID NO: 63)
5'- gacaagcgttagtaggcacatatac-3';

Flp-R2:
                              (SEQ ID NO: 64)
5'-gctccaatttcccacaacattagt-3'.
```

Figures 23A, 23B, 23C, 23D, 23E, 23F:
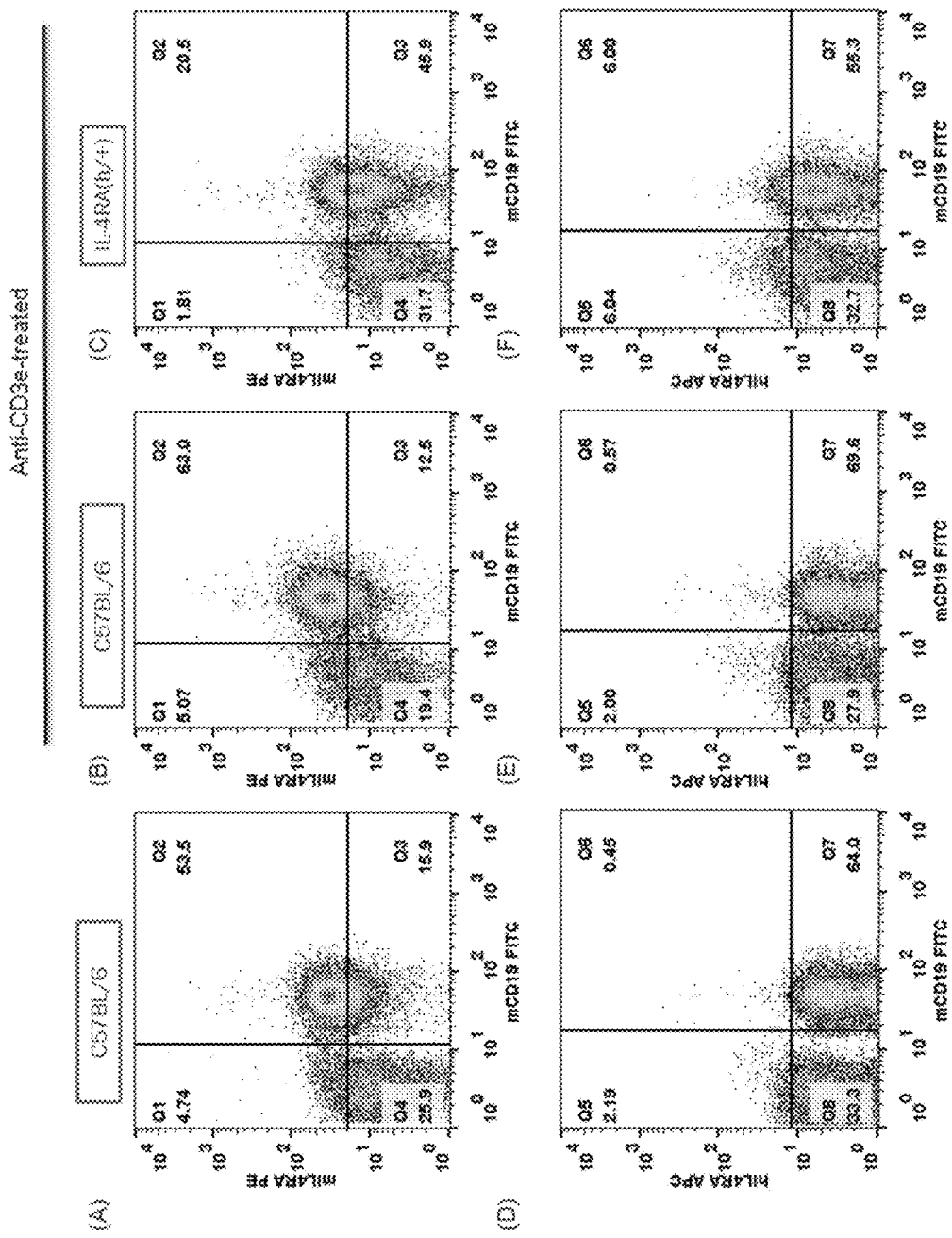
FIG. 23A is a graph showing the flow cytometry analysis result of wild-type C57BL/6 mice, wherein cells were stained by anti-mouse IL4Ra antibody (mIL4RA PE) and anti-mouse CD19 antibody (mCD19 FITC).
FIG. 23B is a graph showing the flow cytometry analysis result of anti-mouse CD3 antibody-stimulated wild-type C57BL/6 mice, wherein cells were stained by anti-mouse IL4Ra antibody (mIL4RA PE) and anti-mouse CD19 antibody (mCD19 FITC).
FIG. 23C is a graph showing the flow cytometry analysis result of anti-mouse CD3 antibody-stimulated humanized IL4Ra gene heterozygous mice, wherein cells were stained by anti-mouse IL4Ra antibody (mIL4RA PE) and anti-mouse CD19 antibody (mCD19 FITC).
FIG. 23D is a graph showing the flow cytometry analysis result of wild-type C57BL/6 mice, wherein cells were stained by anti-human IL4Ra antibody (hIL4RA APC) and anti-mouse CD19 antibody (mCD19 FITC).
FIG. 23E is a graph showing the flow cytometry analysis result of anti-mouse CD3 antibody-stimulated wild-type C57BL/6 mice, wherein cells were stained by anti-human IL4Ra antibody (hIL4RA APC) and anti-mouse CD19 antibody (mCD19 FITC).
FIG. 23F is a graph showing the flow cytometry analysis result of anti-mouse CD3 antibody-stimulated humanized IL4Ra gene heterozygous mice, wherein cells were stained by anti-human IL4Ra antibody (hIL4RA APC) and anti-mouse CD19 antibody (mCD19 FITC).

The expression of humanized IL4Ra protein in mice can be confirmed by routine detection methods. For example, IL4Ra protein expression can be detected by staining the mouse spleen cells with anti-mouse IL4Ra antibody (mIL4RA PE) combined with anti-mouse CD19 antibody (mCD19 FITC), or anti-human IL4Ra antibody (hIL4RA APC) combined with anti-mouse CD19 antibody (mCD19 FITC), followed by flow cytometry analysis. The results of the flow cytometry analysis (see FIGS. 23A-23F) showed that the mouse IL4Ra protein (FIG. 23C) and the humanized IL4Ra protein (FIG. 23F) were detected in the spleen of the humanized IL4Ra gene heterozygous mice upon stimulation by anti-mCD3 antibody. In the spleen of wild-type C57BL/6 mice, the mouse IL4Ra protein was detected regardless whether the mouse was stimulated by anti-mCD3 antibody (FIGS. 23A-23B), and no expression of human or humanized IL4Ra protein were detected in the wildtype mice (FIGS. 23D-23E).

A CRISPR/Cas system was also used in gene editing to obtain humanized IL4Ra mice. The target sequence in this system determines sgRNA targeting specificity and the efficiency of Cas9-induced cleavage at the target gene. Therefore, selection and design of an efficient and specific target sequence are prerequisites for the construction of sgRNA expression vector. A group of sgRNA sequences recognizing the 5'-end target site (sgRNA1-sgRNA7) and the 3'-end target site (sgRNA8-sgRNA15) were designed and synthesized. The 5'-end target site and the 3'-end target site were located in exon 4 and exon 7 of the IL4Ra gene, respectively. The sequence of the target site of each sgRNA on IL4Ra was as follows:

```
sgRNA1 target site sequence (SEQ ID NO: 65):
5'-AACATAGACTGGCGTTCACCTGG-3' sgRNA2 target site sequence (SEQ ID NO: 66):
5'-TCCGCACTTCCACGTGTGAGTGG-3' sgRNA3 target site sequence (SEQ ID NO: 67):
5'-GTGGTTCCTGGATAGCGCTGTGG-3' sgRNA4 target site sequence (SEQ ID NO: 68):
5'-ATCCAGGAACCACTCACACGTGG-3' sgRNA5 target site sequence (SEQ ID NO: 69):
5'-TATGTTGTGCTGTATGCTTGTGG-3' sgRNA6 target site sequence (SEQ ID NO: 70):
5'-CTCAGCTCTGCCTACACTACAGG-3' sgRNA7 target site sequence (SEQ ID NO: 71):
5'-AGAACATCAGCCTGTAGTGTAGG-3' sgRNA8 target site sequence (SEQ ID NO: 72):
5'-CTACTATACGGCGCGTGTGAGGG-3' sgRNA9 target site sequence (SEQ ID NO: 73):
5'-GATGTCAGGGGTCTACTATACGG 3' sgRNA10 target site sequence (SEQ ID NO: 74):
5'-TATAGTAGACCCCTGACATCAGG-3' sgRNA11 target site sequence (SEQ ID NO: 75):
5'-ACGTGTGTCGGTTCCCAGCCTGG-3' sgRNA12 target site sequence (SEQ ID NO: 76):
5'-CTGACATCAGGATGTTGATCGGG-3' sgRNA13 target site sequence (SEQ ID NO: 77)
5'-GTTGATCGGGAAGCTCAGCCTGG-3' sgRNA14 target site sequence (SEQ ID NO: 78):
5'-ATGTGACCTACAAGGAACCCAGG-3' sgRNA15 target site sequence (SEQ ID NO: 79):
5'-AGTCTATAATGTGACCTACAAGG-3'
```

Figure 24A:
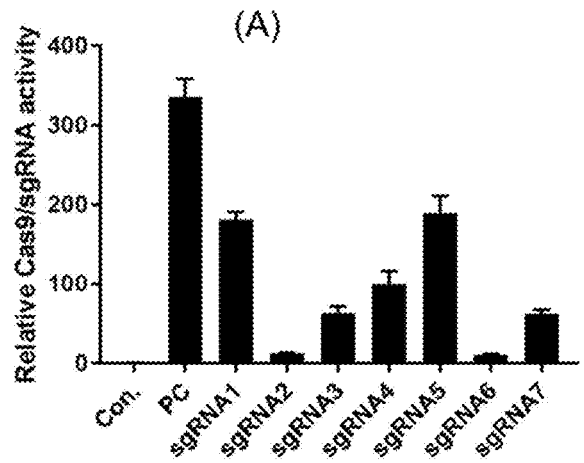
FIG. 24A is a graph showing the results of sgRNA1-sgRNA7 activity assay, in which Con. is the negative control and PC is the positive control.
Figure 24B:
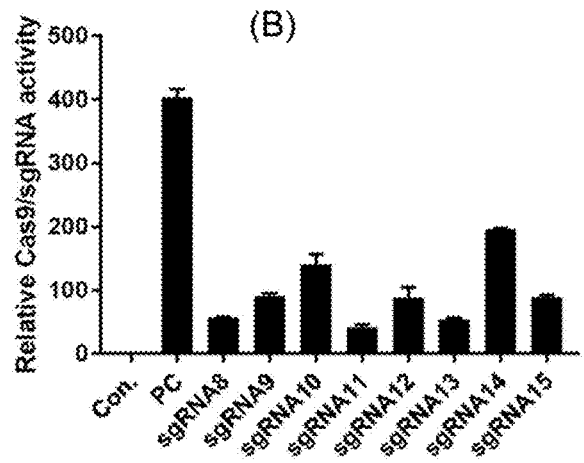
FIG. 24B is a graph showing the results of sgRNA8-sgRNA15 activity assay, in which Con. is the negative control and PC is the positive control.

The activity of multiple sgRNAs were detected using the UCA kit. The results showed that sgRNAs had different activities, and the detection results were shown in FIGS. 24A-24B and the table below. Two of the sgRNAs (sgRNA1 and sgRNA14 respectively) were selected for subsequent experiments. The positive clones can be obtained by transfecting the embryonic stem cells of C57BL/6 mice with the sgRNA1, sgRNA14 and Cas9 mRNAs together with the recombinant vector. In addition, due to the double-strand breakage of genomic DNA caused by Cas9-induced cleavage, the homologous recombination repair mechanism can randomly introduce insertions/deletions. Therefore, this method can also generate IL4Ra knockout mice.

TABLE 5

| sgRNA activity test results | | | |
| --- | --- | --- | --- |
| 5'-end target site detection result | | 3'-end target site detection result | |
| Con. | 1.00 | Con. | 1.00 |
| PC | 335.74 | PC | 403.91 |
| sgRNA-1 | 181.76 | sgRNA-8 | 57.47 |
| sgRNA-2 | 13.08 | sgRNA-9 | 90.55 |

TABLE 5-continued sgRNA activity test results

| 5'-end target site detection result | | 3'-end target site detection result | |
|---|---|---|---|
| sgRNA-3 | 63.34 | sgRNA-10 | 141.49 |
| sgRNA-4 | 100.09 | sgRNA-11 | 41.83 |
| sgRNA-5 | 189.77 | sgRNA-12 | 88.48 |
| sgRNA-6 | 10.68 | sgRNA-13 | 53.77 |
| sgRNA-7 | 62.37 | sgRNA-14 | 196.53 |
| / | / | sgRNA-15 | 89.55 |

Example 3: Mice with Both Humanized IL4/IL4Ra Genes

Mice containing the humanized IL4 or IL4Ra gene prepared using the methods as described in the present disclosure can also be used to further prepare an animal model with double-humanized IL4/IL4Ra genes or additional humanized genes. For example, the fertilized egg cells used in the microinjection and embryo transfer process can be selected from the embryos of genetically modified mice (e.g., the fertilized egg cells of IL4 mice and/or IL4Ra mice) and can be genetically edited to obtain IL4 and IL4Ra double humanized mice, or mice with additional gene modifications. Mice with humanized IL4 mice and mice with humanized IL4Ra (homozygous or heterozygous) can also mate each other or mate with other genetically modified homozygous or heterozygous mice. Their offspring can be screened. According to Mendel's laws, there is a chance to obtain the IL4 and IL4Ra double humanized mice, or multiple-gene modified heterozygous mice. The obtained heterozygotes can mate each other to finally obtain homozygotes with double- or multiple modified genes.

Figures 25A, 25B, 25C, 25D:
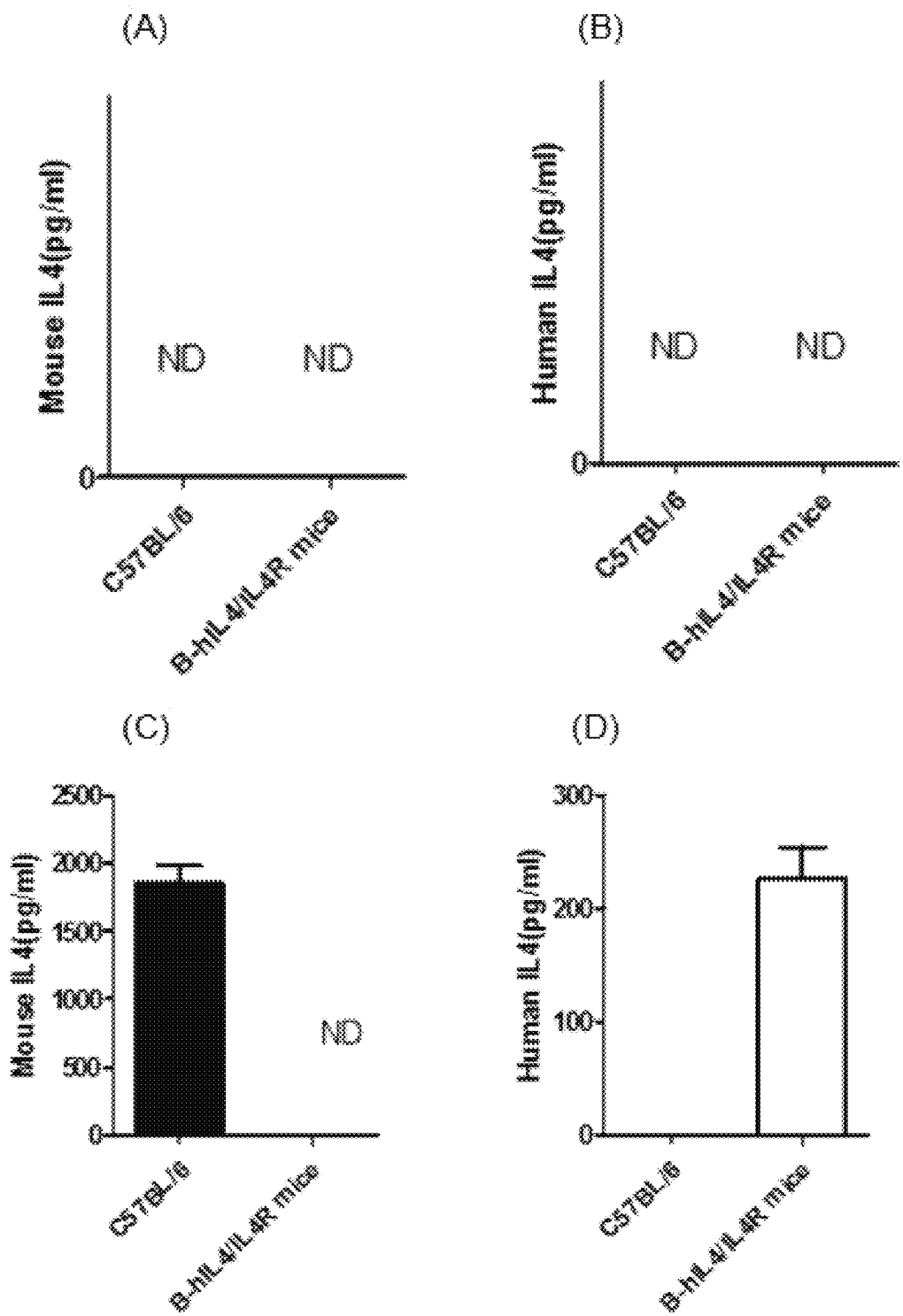
FIG. 25A is the ELISA detection result showing mouse IL4 protein levels in unstimulated mouse serum, wherein three wild-type C57BL/6 mice and three double-humanized IL4/IL4Ra homozygous mice (B-hIL4/IL4R mice) were selected.
FIG. 25B is the ELISA detection result showing human IL4 protein levels in unstimulated mouse serum, wherein three wild-type C57BL/6 mice and three double-humanized IL4/IL4Ra homozygous mice (B-hIL4/IL4R mice) were selected.
FIG. 25C is the ELISA detection result showing mouse IL4 protein levels in stimulated mouse serum, wherein three wild-type C57BL/6 mice and three double-humanized IL4/IL4Ra homozygous mice (B-hIL4/IL4R mice) were selected.
FIG. 25D is the ELISA detection result showing human IL4 protein levels in stimulated mouse serum, wherein three wild-type C57BL/6 mice and three double-humanized IL4/IL4Ra homozygous mice (B-hIL4/IL4R mice) were selected.
Figures 26A, 26B, 26C, 26D, 26E, 26F, 26G, 26H:
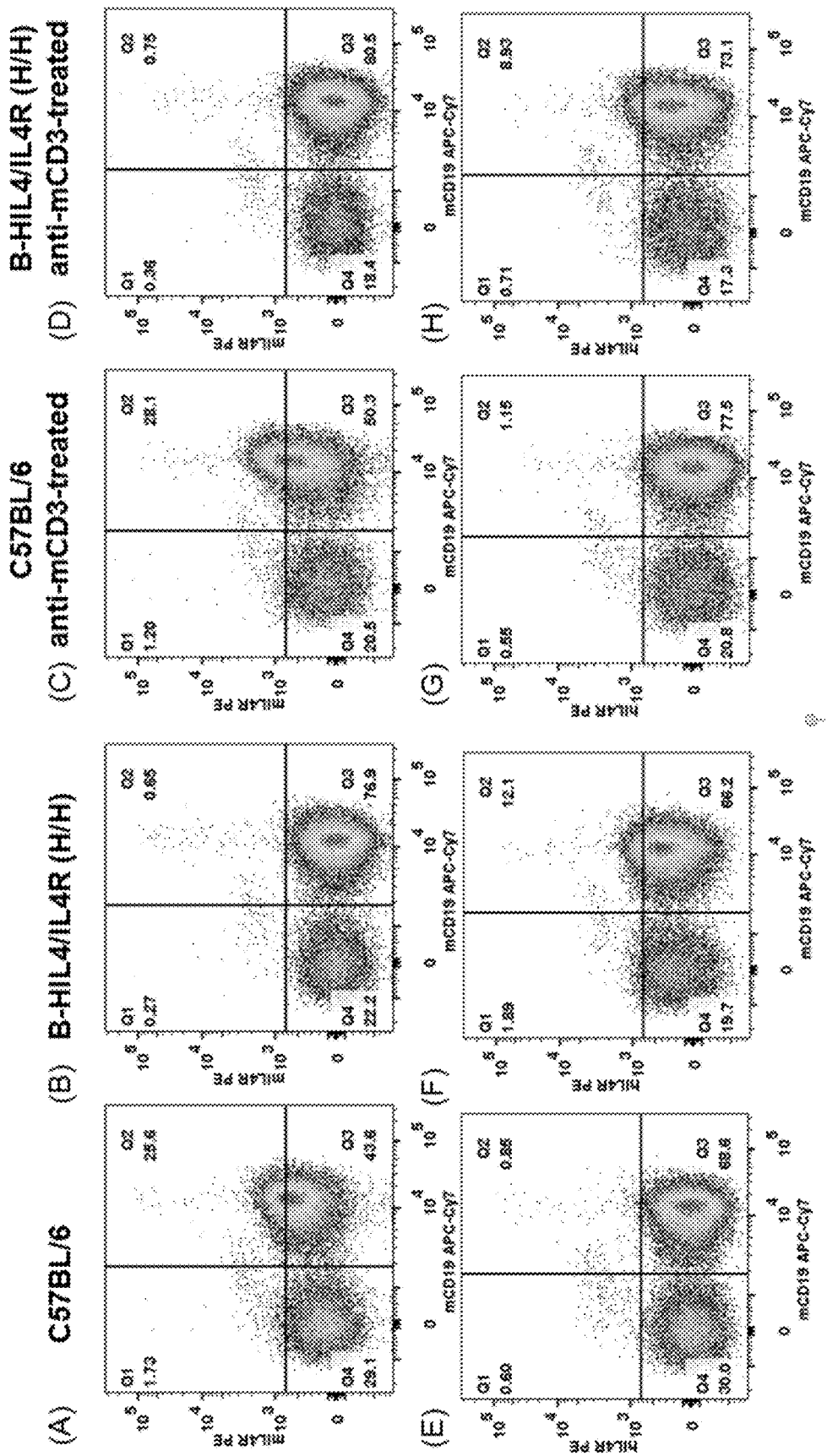
FIG. 26A is a graph showing the flow cytometry analysis result of three unstimulated wild-type C57BL/6 mice, wherein cells were labeled by anti-mouse IL4Ra antibody (mIL4RA PE) and anti-mouse CD19 antibody (mCD19 APC-Cy7).
FIG. 26B is a graph showing the flow cytometry analysis result of three unstimulated double-humanized IL4/IL4Ra homozygous (B-HIL4/IL4R (H/H)) mice, wherein cells were labeled by anti-mouse IL4Ra antibody (mIL4RA PE) and anti-mouse CD19 antibody (mCD19 APC-Cy7).
FIG. 26C is a graph showing the flow cytometry analysis result of three anti-mouse CD3 antibody-stimulated wild-type C57BL/6 mice, wherein cells were labeled by anti-mouse IL4Ra antibody (mIL4RA PE) and anti-mouse CD19 antibody (mCD19 APC-Cy7).
FIG. 26D is a graph showing the flow cytometry analysis result of three anti-mouse CD3 antibody-stimulated double-humanized IL4/IL4Ra homozygous (B-HIL4/IL4R (H/H)) mice, wherein cells were labeled by anti-mouse IL4Ra antibody (mIL4RA PE) and anti-mouse CD19 antibody (mCD19 APC-Cy7).
FIG. 26E is a graph showing the flow cytometry analysis result of three unstimulated wild-type C57BL/6 mice, wherein cells were labeled by anti-human IL4Ra antibody (hIL4RA PE) and anti-mouse CD19 antibody (mCD19 APC-Cy7).
FIG. 26F is a graph showing the flow cytometry analysis result of three unstimulated double-humanized IL4/IL4Ra homozygous (B-HIL4/IL4R (H/H)) mice, wherein cells were labeled by anti-human IL4Ra antibody (hIL4RA PE) and anti-mouse CD19 antibody (mCD19 APC-Cy7).
FIG. 26G is a graph showing the flow cytometry analysis result of three anti-mouse CD3 antibody-stimulated wild-type C57BL/6 mice, wherein cells were labeled by anti-human IL4Ra antibody (hIL4RA PE) and anti-mouse CD19 antibody (mCD19 APC-Cy7).
FIG. 26H is a graph showing the flow cytometry analysis result of three anti-mouse CD3 antibody-stimulated double-humanized IL4/IL4Ra homozygous (B-HIL4/IL4R (H/H)) mice, wherein cells were labeled by anti-human IL4Ra antibody (hIL4RA PE) and anti-mouse CD19 antibody (mCD19 APC-Cy7).

The mouse IL4 and IL4Ra genes are located on chromosomes 11 and 7, respectively. IL4 humanized mice (V1) and IL4Ra humanized mice were selected for mating. Positive cloned progeny mice were screened to obtain double-humanized IL4/IL4Ra mice (B-hIL4/hIL4Ra mouse). The protein expression of double-humanized IL4/IL4Ra mice was examined. Three double-humanized IL4/IL4Ra homozygous mice and three wild-type C57BL/6 mice were selected. Retro-orbital blood from these mice was collected. The mice were then stimulated by intraperitoneal injection of 7.5 µg anti-mouse CD3 (mCD3) antibody. Serum and spleen samples were taken after 1.5 hours of stimulation, and the protein levels of IL4 and IL4Ra were detected by ELISA and flow cytometry. ELISA results showed that expression of mouse or human IL4 protein cannot be detected in either unstimulated double-humanized IL4/IL4Ra mouse homozygotes or wild-type C57BL/6 mice (FIG. 25A and FIG. 25B); however, human IL4 but not mouse IL4 protein expression was detected in anti-mCD3 antibody stimulated double-humanized IL4/IL4Ra homozygous mice. In contrast, in anti-mCD3 antibody stimulated wild-type C57BL/6 mice, only mouse IL4 protein expression was detected but no human IL4 protein was detected (FIGS. 25C-25D).

The anti-mouse IL4Ra antibody (mIL4RA PE) combined with anti-mouse CD19 antibody (mCD19 APC-Cy7), or anti-human IL4Ra antibody (hIL4RA PE) combined with anti-mouse CD19 antibody (mCD19 APC-Cy7) were used to detect the expression of IL4Ra protein in mouse spleen cells by flow cytometry. The results showed that the expression of humanized IL4Ra protein was detected in double-humanized IL4/IL4Ra mice, but the expression of mouse IL4Ra protein was not detected. No human or humanized IL4Ra protein was detected in wild type C57BL/6 mice. The detection results were shown in FIGS. 26A-26H.

Figures 27A, 27B, 27C:
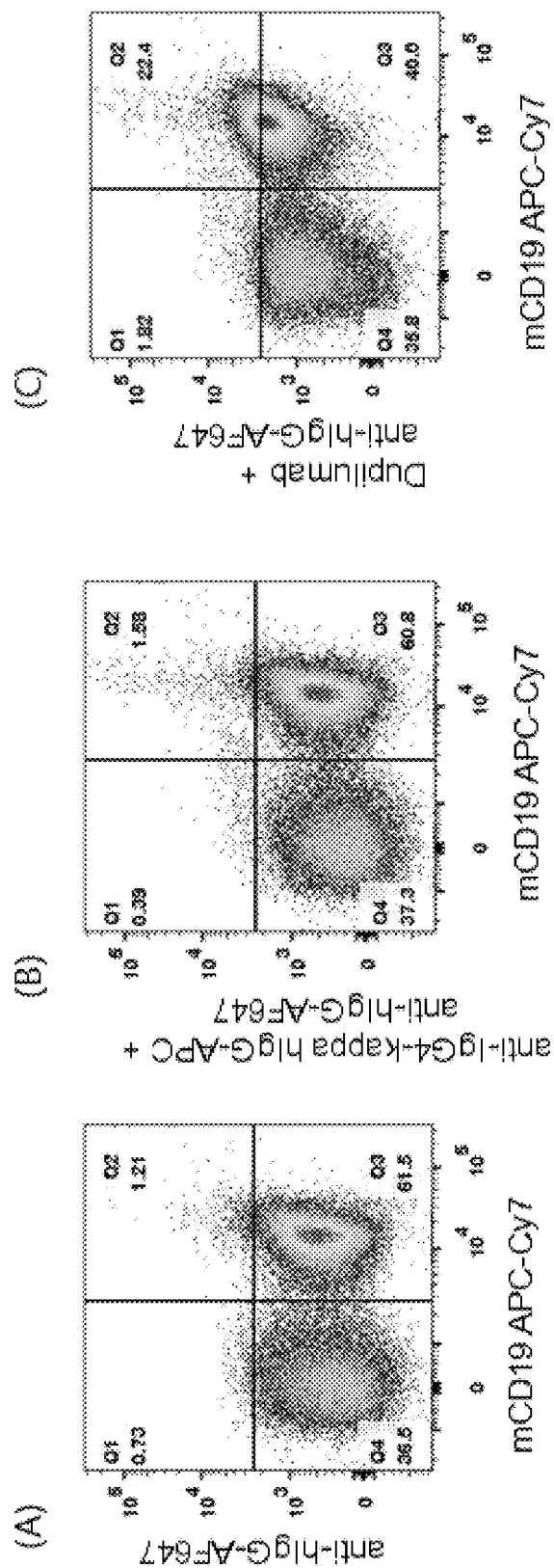
FIG. 27A is a graph showing the flow cytometry analysis result of double-humanized IL4/IL4Ra homozygous mice, wherein the cells were labeled by anti-hIgG-AF647 and anti-mCD19 antibody (mCD19APC-Cy7).
FIG. 27B is a graph showing the flow cytometry analysis result of double-humanized IL4/IL4Ra homozygous mice, wherein the cells were labeled by anti-IgG4-kappa hIgG-APC/anti-hIgG-AF647 and anti-mouse CD19 antibody (mCD19APC-Cy7).
FIG. 27C is a graph showing the flow cytometry analysis result of double-humanized IL4/IL4Ra homozygous mice, wherein the cells were labeled by anti-human IL4Ra antibody (Dupilumab)/anti-hIgG-AF647 and anti-mouse CD19 antibody (mCD19APC-Cy7). The results show that Dupilumab binds well to IL4Ra expressed in the double-humanized homozygous mice.

The binding activity of humanized IL4Ra expressed in homozygous double-humanized IL4/IL4Ra mice to anti-human IL4Ra antibody was analyzed. Spleen cells from double-humanized IL4/IL4Ra homozygous mice stimulated by anti-mCD3 antibody were selected and divided into 3 groups. One randomly selected group was added with anti-human IL4Ra antibody (Dupilumab)/anti-hIgG-AF647 and anti-mouse CD19 antibody (mCD19 APC-Cy7) for staining. The control group was added with anti-IgG4-kappa (hIgG-APC)/anti-hIgG-AF647 or only anti-hIgG-AF647, and anti-mouse CD19 antibody (mCD19 APC-Cy7) for staining. The stained cells were washed with PBS, and then protein expression was detected by flow cytometry. The results showed that the anti-human IL4Ra antibody (Dupilumab) binds well to IL4Ra expressed in the double-humanized homozygotes (FIG. 27C) compared to the control groups (FIG. 27A or 27B).

Spleen cells from unstimulated double-humanized IL4/IL4Ra mice were further analyzed, and lymphocytes were sorted and compared to cells from wild-type C57BL/6 mice. Blood tests and other biochemical tests were performed on double-humanized IL4/IL4Ra mice and no obvious differences were observed as compared to wildtype mice.

Figure 28:
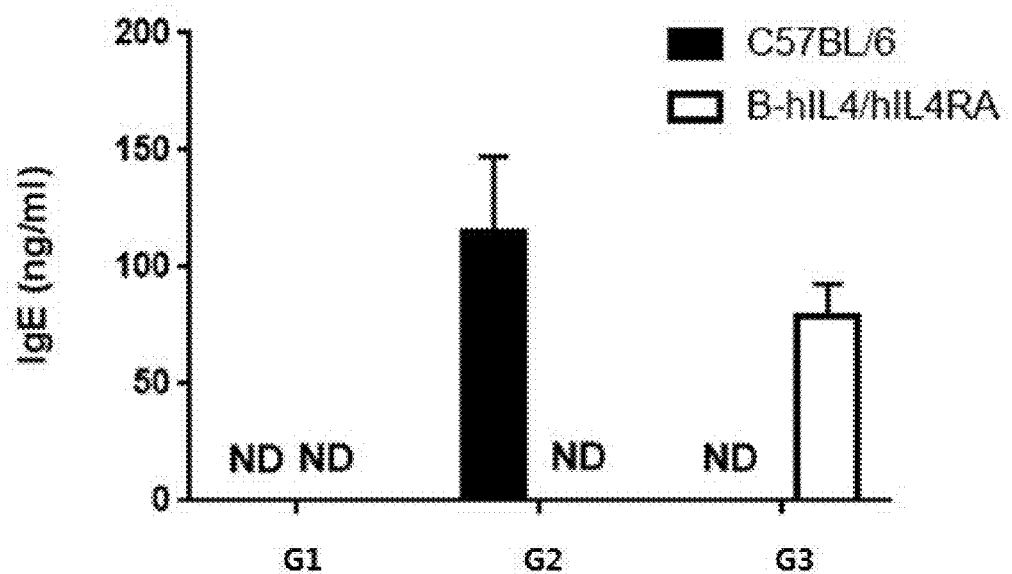
FIG. 28 is a graph showing LPS-induced spleen lymphocyte proliferation result, wherein G1 was induced only by LPS, G2 was induced by LPS and mIL4, G3 was induced by LPS and hIL4. The result shows that the level of IgE in double-humanized IL4/IL4Ra mice was comparable to that of wild-type C57BL/6 mice, and the lymphocytes of wild-type mice can only be induced by mIL4 to produce IgE, while lymphocytes of double-humanized IL4/IL4Ra mice can only be induced by hIL4.

In addition, spleen lymphocytes from double-humanized IL4/IL4Ra mice and wild-type C57BL/6 mice were divided into 3 groups. Lipopolysaccharide (LPS) was added to group G1, mIL4 was added to group G2, and hIL4 (50 ng/mL) was added to group G3. IgE levels of each group were determined on day 6, and the results were shown in FIG. 28, indicating that the in vitro induced IgE levels of spleen lymphocytes from double-humanized IL4/IL4Ra mice were comparable to the IgE levels from wild-type C57BL/6 mice. It further indicated that spleen cells isolated from double-humanized IL4/IL4Ra mice had functional IL4/IL4Ra signaling pathway.

Figure 29:
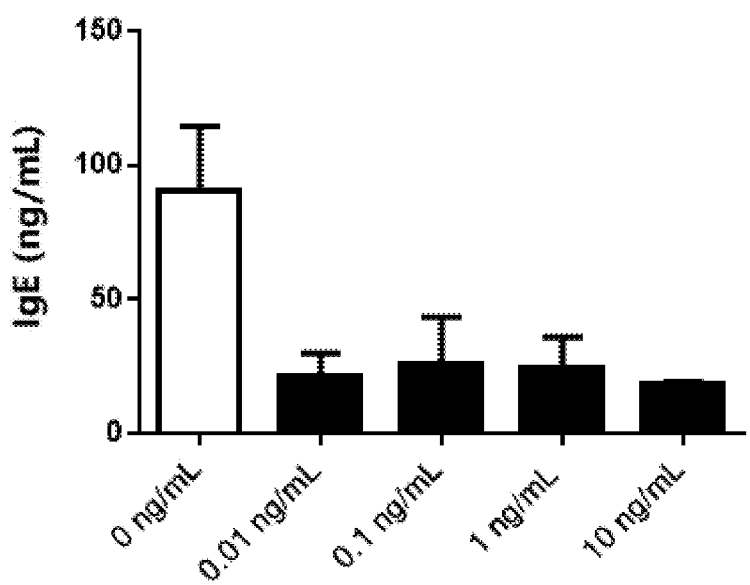
FIG. 29 is a graph showing IgE production induced by hIL4 in double-humanized IL4/IL4Ra mice was effectively blocked by anti-human IL4Ra antibody Dupilumab.

In another experiment, double-humanized IL4/IL4Ra mouse spleen lymphocytes were first treated with different doses of anti-human IL4Ra antibody Dupilumab (0.01 ng/mL, 0.1 ng/mL, 1 ng/mL, 10 ng/mL). After incubation for 0.5 hours, LPS and hIL4 (50 ng/mL) were added, and IgE levels of each group were determined on day 6. The results were shown in FIG. 29, indicating that at each test concentration, in vitro IgE production by exposing B cells to hIL4 was effectively blocked by anti-human IL4Ra antibody Dupilumab.

Figure 30:
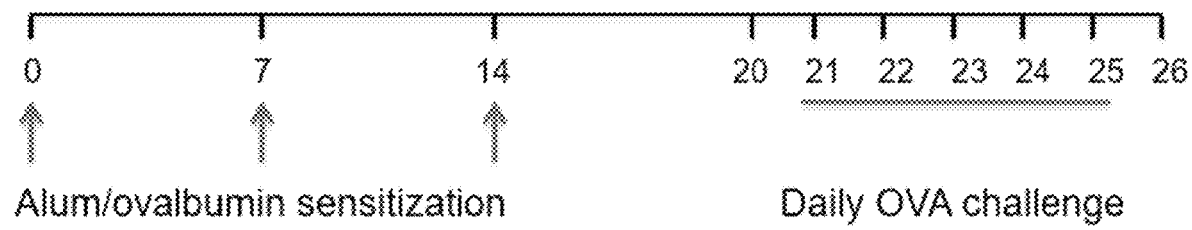
FIG. 30 is the experimental protocol of using double-humanized IL4/IL4Ra mice to make an inducible asthma model.
Figure 31:
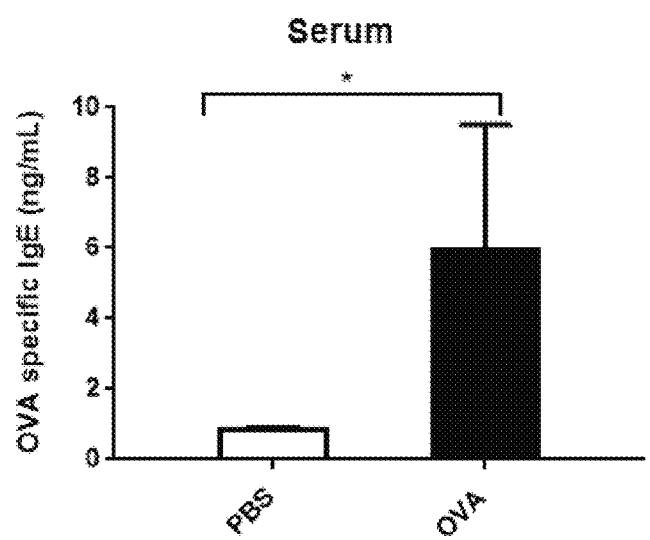
FIG. 31 is a graph showing serum IgE levels of control group (PBS) and the asthma model (OVA). The serum IgE levels in the asthma model mice are significantly higher than those in the PBS control group.
Figure 32:
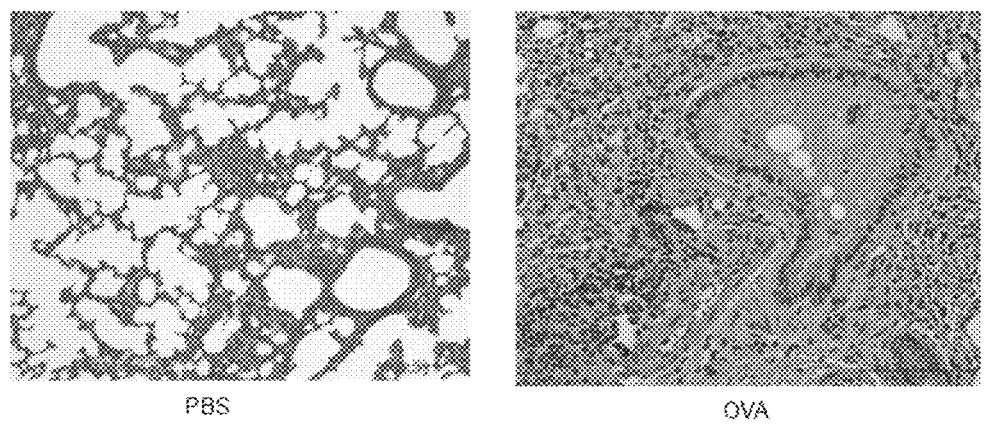
FIG. 32 is a graph showing lung histology results of double-humanized IL4/IL4Ra mice induced by ovalbumin combined with aluminum hydroxide (OVA) or PBS (control group). The OVA-induced group had more darkly stained area than the PBS control group, showing higher rate of inflammatory cell infiltration and obvious pathological features of asthma.
Figure 33A:
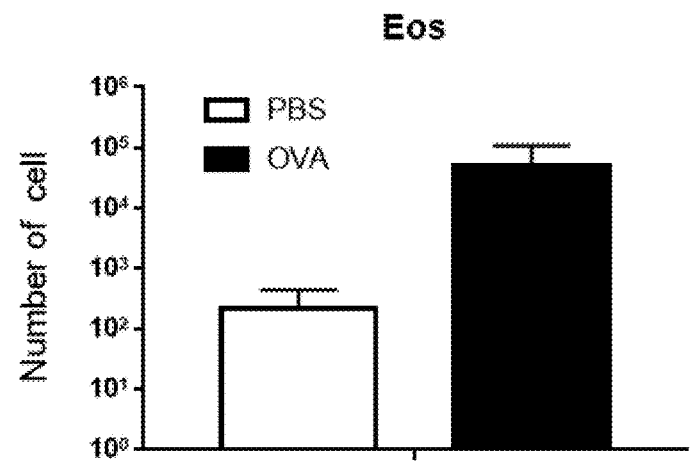
FIG. 33A is a graph showing total number of eosinophils (Eos) cells in bronchoalveolar lavage fluid (BALF) of double-humanized IL4/IL4Ra mice induced by ovalbumin combined with aluminum hydroxide or PBS (control group), wherein OVA-induced group had more Eos cells than the PBS control group.
Figure 33B:
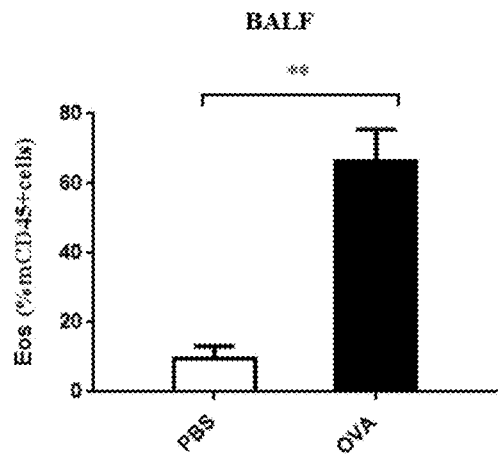
FIG. 33B is a graph showing the proportion of eosinophils cells (Eos %) in bronchoalveolar lavage fluid (BALF) of double-humanized IL4/IL4Ra mice induced by ovalbumin combined with aluminum hydroxide (OVA) or PBS (control group). The result shows mice in the OVA-induced group had significantly more eosinophils compared than the PBS control group, indicating a sensitizing phenotype.
Figure 33C:
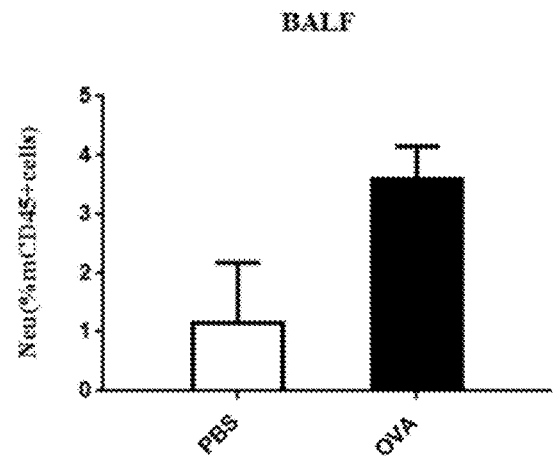
FIG. 33C is a graph showing the proportion of neutrophil cells (Neu %) in bronchoalveolar lavage fluid (BALF) of double-humanized IL4/IL4Ra mice induced by ovalbumin combined with aluminum hydroxide (OVA) or PBS (control group). The result shows mice in OVA-induced group had significantly more neutrophils compared with the PBS control group, indicating a sensitizing phenotype.

Example 4: Ovalbumin (OVA) Combined with Aluminum Hydroxide-Induced Asthma Model Single-gene (IL4Ra) or double-humanized IL4/IL4Ra mice (5-8 weeks) were selected and exposed 3 times to ovalbumin (OVA) combined with aluminum hydroxide by intraperitoneal injection. After 3 weeks of the first injection, nebulization with 2% OVA was performed continuously for 5 days to make an inducible asthma model (modeling protocol was shown in FIG. 30). In the control group, OVA was replaced by PBS. All samples were obtained for analysis on day 26. When modeled with double-humanized IL4/IL4Ra mice, compared to the control group (PBS), the mice had typical symptoms such as elevated serum IgE levels and pathological lung histology features (FIGS. 31-32). Infiltrating cell analysis in bronchoalveolar lavage fluid (BALF) suggested an increase in total number and proportion of eosinophils (Eos) cells among CD45+ cells (FIGS. 33A-33C), indicating that double-humanized IL4/IL4Ra mice have IL4/IL4Ra signaling pathway in vivo. Treatment results with anti-human IL4 antibody or anti-human IL4Ra antibody can be evaluated by routine methods such as airway reactivity test, hematoxylin and eosin (HE) staining, immunohistochemistry (IHC) pathology detection, inflammatory cells and IgE detection to assess the efficacy of antibodies.

Figure 34:
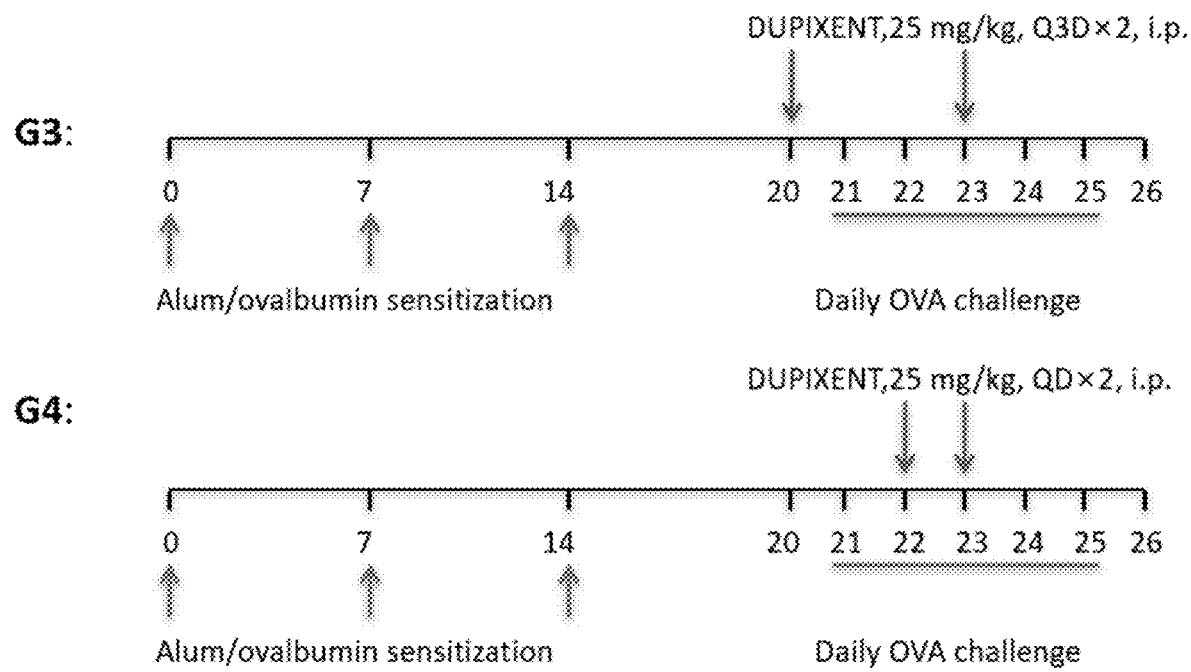
FIG. 34 is the experimental design to assess treatment efficacy of anti-human IL4Ra antibody Dupilumab in the double-humanized IL4/IL4Ra mice induced by ovalbumin combined with aluminum hydroxide.
Figure 35A:
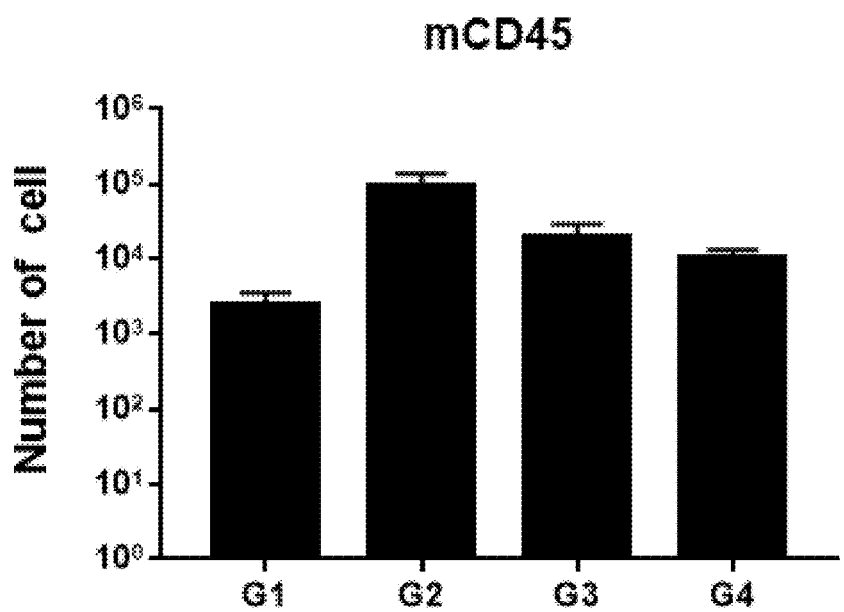
FIG. 35A is a graph showing total number of leukocytes (CD45+ cells) in bronchoalveolar lavage fluid (BALF) of double-humanized IL4/IL4Ra mice induced by ovalbumin combined with aluminum hydroxide and control group, wherein OVA-induced group (G2) had slightly more leukocytes than the control group (G1) and the treatment groups (G3, G4).
Figure 35B:
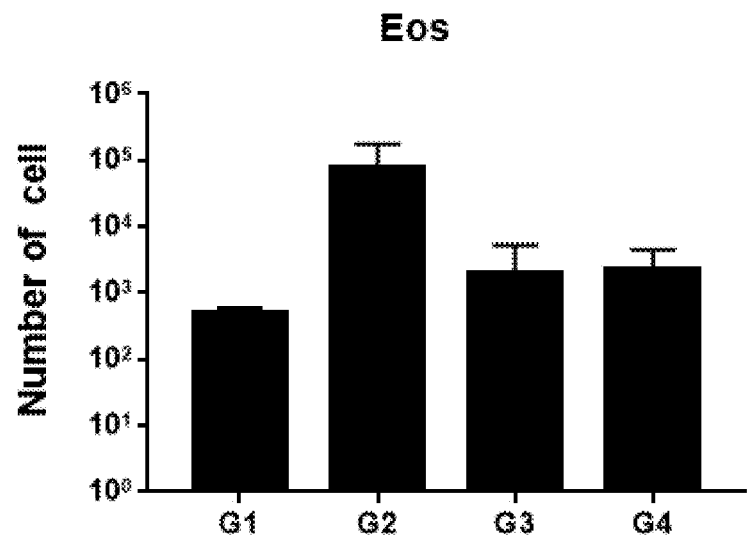
FIG. 35B is a graph showing total number of eosinophils (Eos) cells in bronchoalveolar lavage fluid (BALF) of double-humanized IL4/IL4Ra mice induced by ovalbumin combined with aluminum hydroxide, wherein OVA-induced group (G2) had the most eosinophils cells, and the treatment group (G3, G4) had slightly more eosinophils cells than the control group (G1).
Figure 35C:
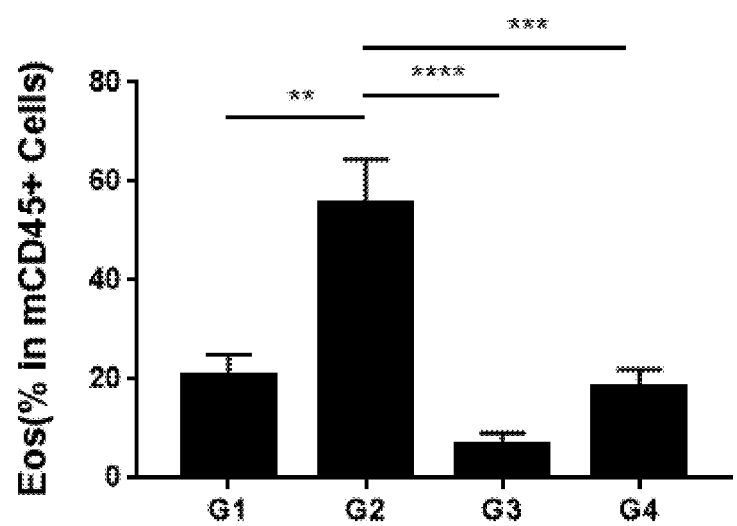
FIG. 35C is a graph showing the proportion of eosinophils (Eos %) cells in leukocytes (CD45+ cells) in bronchoalveolar lavage fluid (BALF) of double-humanized IL4/IL4Ra mice induced by ovalbumin combined with aluminum hydroxide, wherein OVA-induced group (G2) had the highest proportion, the treatment group (G3) had the lowest proportion, and the treatment group (G4) had slightly lower proportion than the control group (G1).
Figure 36:
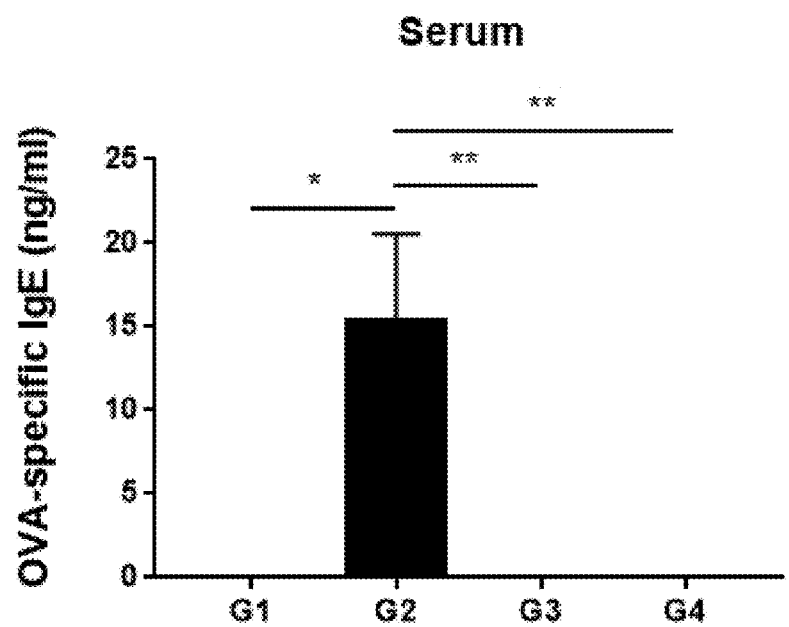
FIG. 36 is a graph showing serum IgE levels of double-humanized IL4/IL4Ra mice induced by ovalbumin combined with aluminum hydroxide, wherein high serum IgE levels were only detected in OVA-induced group (G2).
Figure 37:
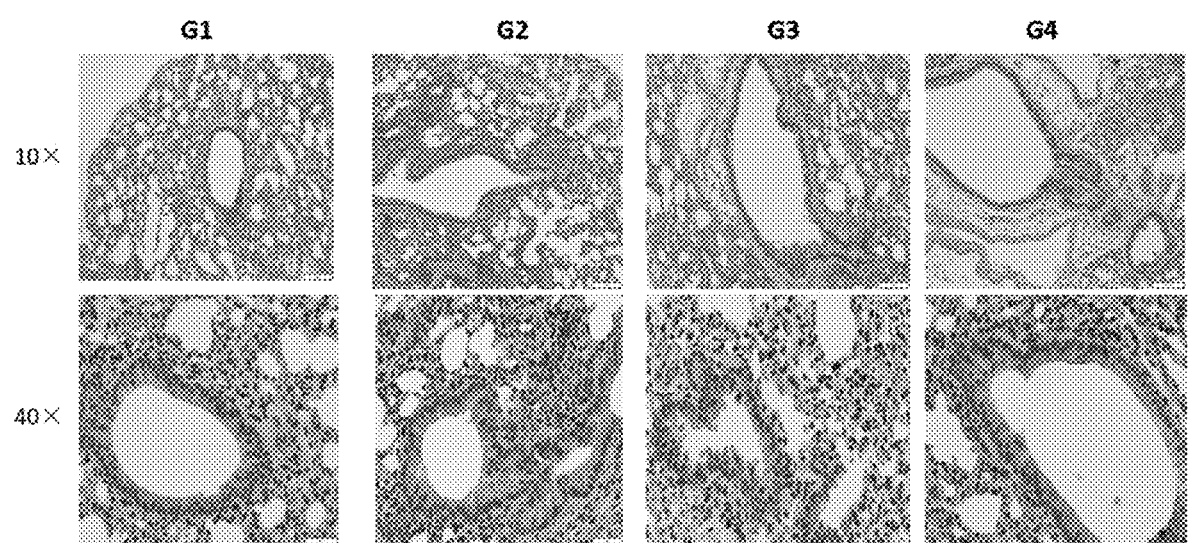
FIG. 37 is a graph showing airway tissue section H&E staining result of double-humanized IL4/IL4Ra mice induced by ovalbumin combined with aluminum hydroxide, wherein airway of the control group (G1) mice showed no inflammation while the OVA-induced group (G2) had peribronchial and perivascular inflammation and increased mucus secretion levels. The mice in the treatment group (G3, G4) had decreased inflammatory infiltration and mucus secretion as compared to the G2 group.

A number of double-humanized IL4/IL4Ra mice were randomly divided into 4 groups. The asthma model was induced according to the method above, in which the G3 and G4 groups were administered with Dupilumab. Different dosing schedules were followed after sensitization by intraperitoneal injection with anti-human IL4RA antibody Dupilumab (25 mg/kg) (see FIG. 34 for the dosing schedule). The results showed that the number of leukocytes (CD45+ cells) and eosinophils cells (Eos) in bronchoalveolar lavage fluid (BALF) was slightly higher in the OVA-inducing group (G2) than in the control group (G1) and the treatment group (G3, G4). The ratio of eosinophils cells (Eos) in CD45+ cells was the highest in the OVA-induced group (G2), the lowest in the G3 treatment group, and slightly lower in the G4 treatment group than in the control group (G1) (FIGS. 35A-35C). High serum IgE levels were only detected in the OVA-inducing group (G2) (FIG. 36). H&E staining showed that the airway of the control (G1) (PBS) mice had no inflammation, whereas peribronchial and perivascular inflammation was significantly increased in the OVA-induced group (G2) mice, with increased mucus secretion levels. In both of the treatment groups (G3, G4), inflammatory infiltration and mucus secretion were observed (compared to the G2 group) at reduced levels (FIG. 37).

TABLE 6

| Group | Mice | Alum/ovalbumin sensitization | Challenge | Drug |
| --- | --- | --- | --- | --- |
| G1 | B-hIL4/hIL4Ra | PBS | PBS | NA |
| G2 | B-hIL4/hIL4Ra | Al (OH)$_3$ + OVA | 2% OVA | NA |
| G3 | B-hIL4/hIL4Ra | Al (OH)$_3$ + OVA | 2% OVA | Dupilumab (25 mg/kg) |
| G4 | B-hIL4/hIL4Ra | Al (OH)$_3$ + OVA | 2% OVA | Dupilumab (25 mg/kg) |

Figure 38:
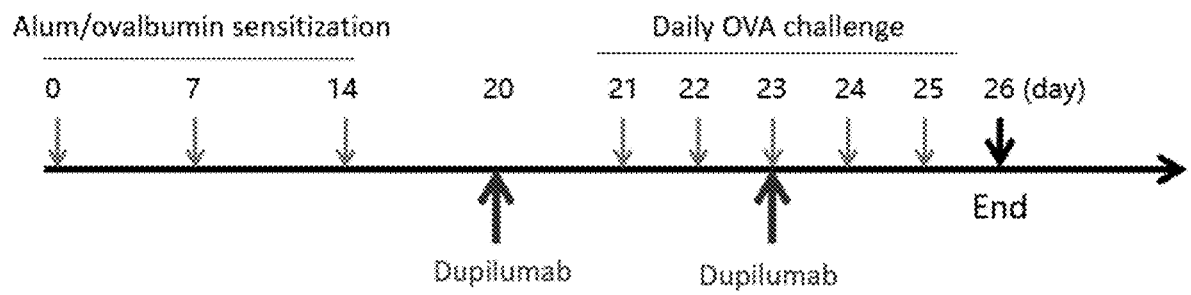
FIG. 38 is the experimental design to assess treatment efficacy of anti-human IL4Ra antibody Dupilumab in the double-humanized IL4/IL4Ra mouse asthma model.
Figure 39A:
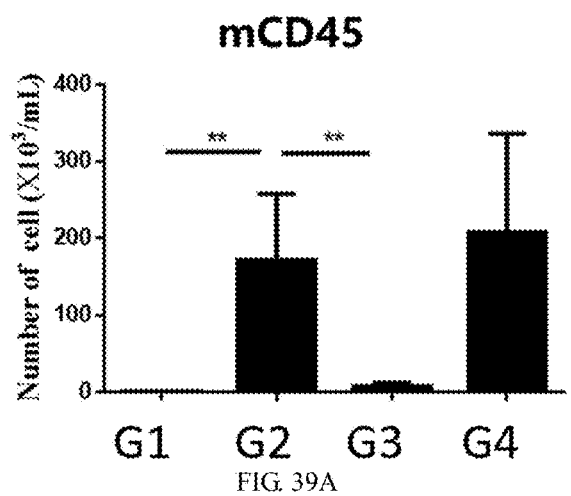
FIG. 39A is a graph showing total number of leukocytes (CD45+ cells) in BALF in the double-humanized IL4/IL4Ra mouse asthma model, wherein OVA-induced groups (G2, G4) have significantly more leukocytes than the control group (G1) and the treatment group (G3).
Figure 39B:
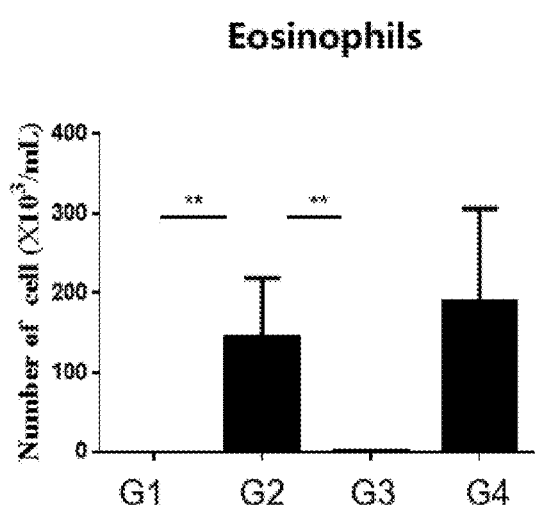
FIG. 39B is a graph showing total number of eosinophils cells in BALF in the double-humanized IL4/IL4Ra mouse asthma model, wherein OVA-induced groups (G2, G4) had significantly more eosinophils cells than the control group (G1) and the treatment group (G3).
Figure 39C:
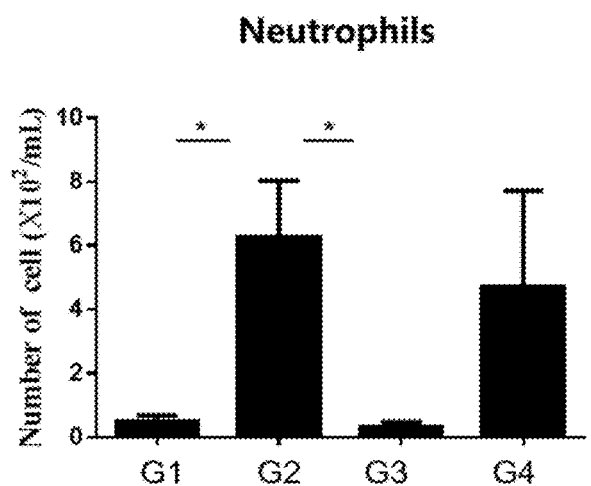
FIG. 39C is a graph showing total number of neutrophils cells in BALF in the double-humanized IL4/IL4Ra mouse asthma model, wherein OVA-induced groups (G2, G4) had significantly more neutrophils cells than the control group (G1) and the treatment group (G3).
Figure 40:
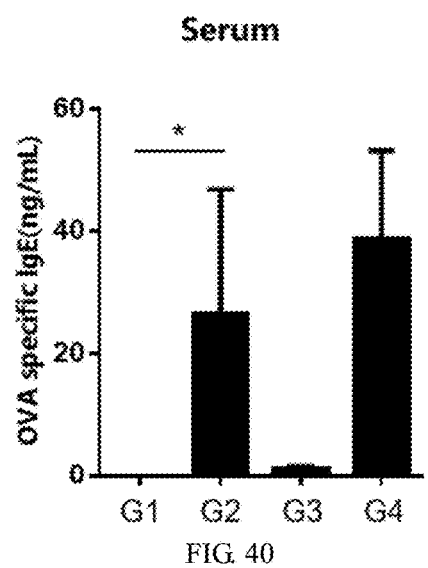
FIG. 40 is a graph showing serum IgE levels in the double-humanized IL4/IL4Ra mouse asthma model, wherein OVA-induced groups (G2, G4) had significantly higher serum IgE levels than the control group (G1) and the treatment group (G3).
Figure 41:
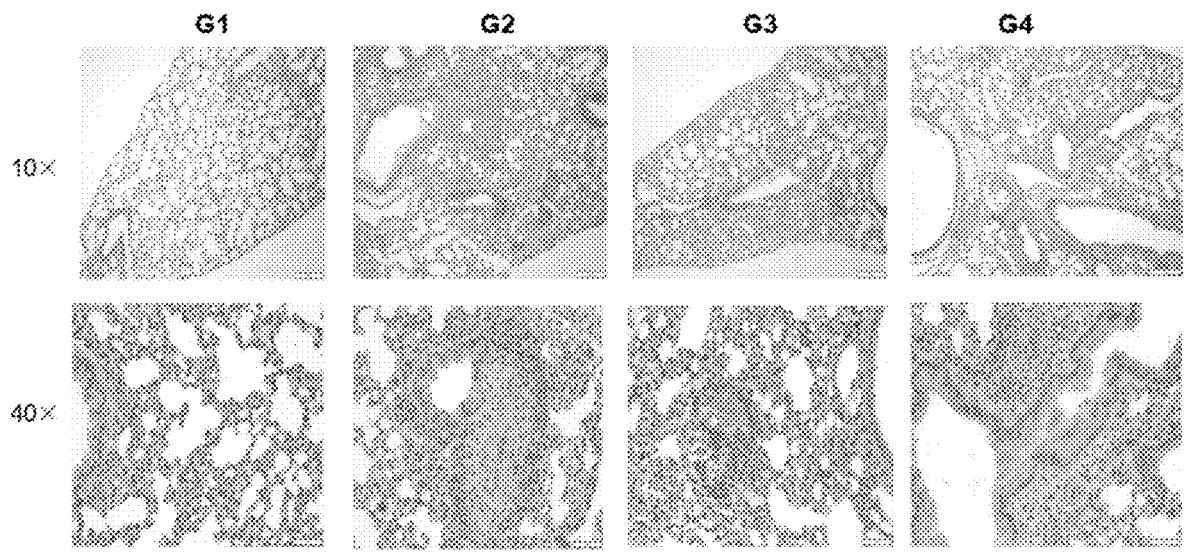
FIG. 41 is a graph showing airway tissue section H&E staining results in the double-humanized IL4/IL4Ra mouse asthma model, wherein airway of the control group (G1) mice had no inflammation while OVA-induced groups (G2, G4) had peribronchial and perivascular inflammation and increased mucus secretion levels. Decreased inflammatory infiltration and mucus secretion were observed in the treatment group (G3) as compared to the OVA-induced groups.

In another experiment, C57BL/6 wild-type mice and humanized IL4/IL4Ra mice were selected according to a similar scheme. The specific groupings were shown in the table below. The treatment group (G3) dosage schedule was shown in FIG. 38. All samples were obtained for analysis on day 26, and the results were consistent with the previous ones. The number of leukocytes (CD45+ cells), eosinophils (Eos) and neutrophils in bronchoalveolar lavage fluid (BALF) was higher in the OVA induction group (G2, G4), and was lower in the control group (G1) and the treatment group (G3) (see FIG. 39). Higher serum IgE levels were detected in the OVA-induced group (G2, G4) (FIG. 40). H&E staining results showed that the airway of the control (G1) (PBS) mice showed no inflammation, while the peribronchial and perivascular inflammation of the G2 and G4 mice in the OVA-induced group increased significantly with increased mucus secretion levels. Decreased inflammatory infiltration and mucus secretion were observed in the treatment group (G3) mice compared to the OVA-induced groups (see FIG. 41).

TABLE 7

| Group | Mice | Alum/ovalbumin sensitization | Challenge | Drug |
| --- | --- | --- | --- | --- |
| G1 | B-hIL4/hIL4Ra | PBS | PBS | NA |
| G2 | B-hIL4/hIL4Ra | Al (OH)$_3$ + OVA | 2% OVA | NA |
| G3 | B-hIL4/hIL4Ra | Al (OH)$_3$ + OVA | 2% OVA | Dupilumab (25 mg/kg) |
| G4 | C57BL/6 WT | Al (OH)$_3$ + OVA | 2% OVA | NA |

Figures 44A, 44B:
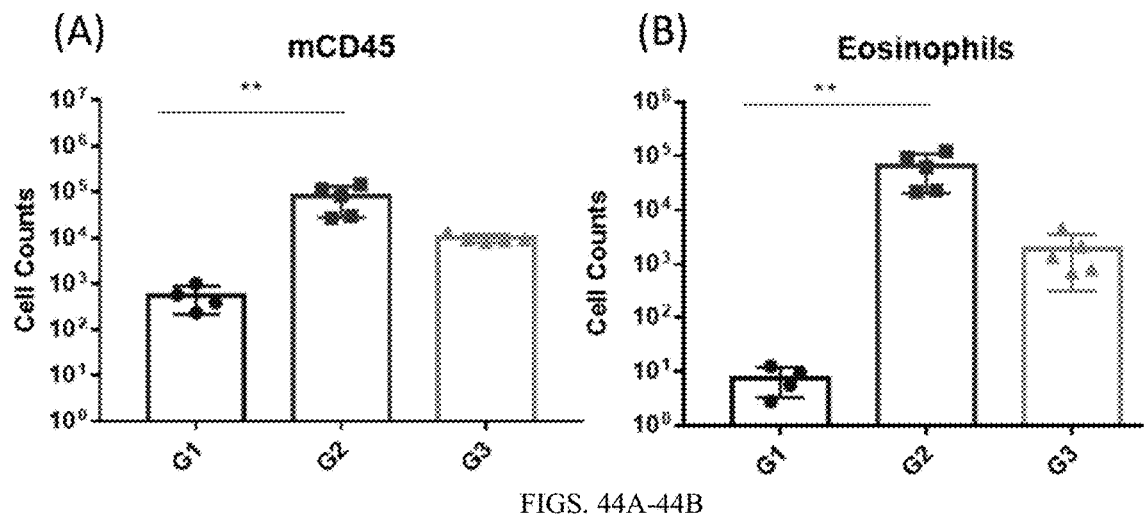
FIG. 44A is a graph showing total number of leukocytes (CD45+ cells) in BALF in the double-humanized IL4/IL4Ra mouse asthma model.
FIG. 44B is a graph showing total number of eosinophils cells in BALF in the double-humanized IL4/IL4Ra mouse asthma model.
Figures 45A, 45B:
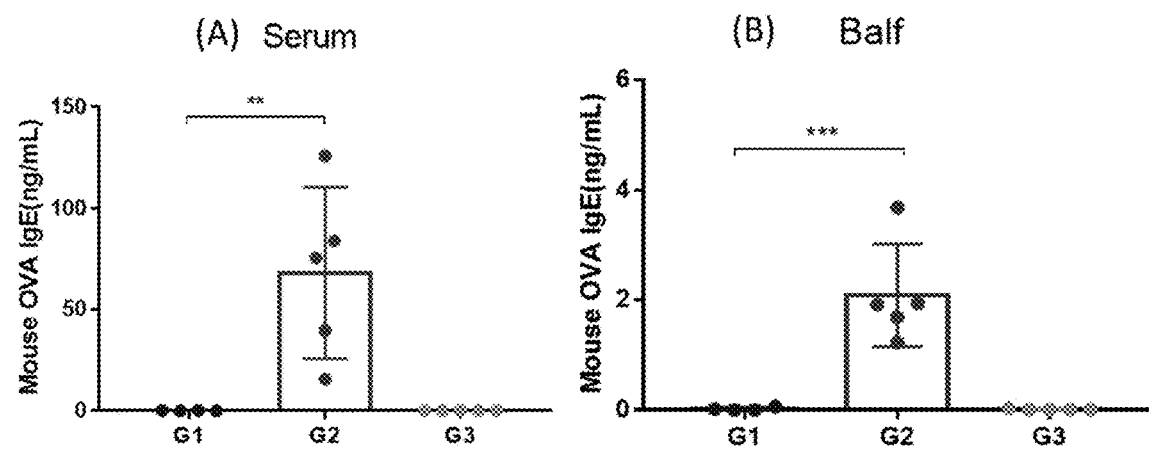
FIG. 45A is a graph showing serum IgE levels in the double-humanized IL4/IL4Ra mouse asthma model.
FIG. 45B is a graph showing IgE levels in BALF of the double-humanized IL4/IL4Ra mouse asthma model.

Example 5: Mouse Asthma Models with Both Humanized IL4 (Version 2) and IL4Ra Genes IL4 humanized mice (Version 2) and IL4Ra humanized mice were selected for mating to obtain double-humanized IL4/IL4Ra mice (B-hIL4 (V2)/hIL4Ra mouse). Similar protein expression and phenotypic analysis were performed using B-hIL4 (V2)/hIL4Ra mouse. The mice appeared normal. A few B-hIL4 (V2)/hIL4Ra mice were selected and randomly divided into 3 groups. The asthma model mice were induced and treated according to the G3 dosing schedule in FIG. 34. Different groups were shown in Table 8. All samples were collected for analysis on day 26, and the results were consistent with the results in Example 4. The number of leukocytes (CD45+ cells), eosinophils (Eos) and neutrophils in bronchoalveolar lavage fluid (BALF) in isotype control group (G2) was higher than treatment group (G3). The control group (G1) had the lowest level of leukocytes (CD45+ cells), eosinophils (Eos) and neutrophils in BALF (FIGS. 44A-44B). Higher serum IgE levels were detected in the isotype control group (G2) (FIGS. 45A-45B). H&E staining results were consistent with the B-hIL4/hIL4Ra mouse results in Example 4.

TABLE 8

| Group | Mice | Alum/ovalbumin sensitization | Challenge | Drug |
| --- | --- | --- | --- | --- |
| G1 | B-hIL4(V2)/hIL4Ra | PBS | PBS | NA |
| G2 | B-hIL4(V2)/hIL4Ra | Al (OH)$_3$ + OVA | 2% OVA | hIgG4 (25 mg/kg) |
| G3 | B-hIL4(V2)/hIL4Ra | Al (OH)$_3$ + OVA | 2% OVA | DUPIXENT (25 mg/kg) |

The experiments above (both Examples 4 and 5) showed that the anti-human IL4Ra antibody Dupilumab can block the IL4/IL4Ra signaling pathway in humanized IL4/IL4Ra mice, thereby reducing the number of eosinophils (Eos) in bronchoalveolar lavage fluid (BALF) and reducing IgE levels in serum to reduce inflammatory symptom. The results indicated that the humanized IL4/IL4Ra mice can be used as asthma models, can be used in the preclinical studies to screen and evaluate the in vivo efficacy of anti-human IL4/IL4Ra antibodies, and can be used to characterize anti-human IL4 and/or IL4Ra antibody characteristics.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified rodent whose genome comprises a replacement of an endogenous gene sequence encoding the extracellular region of endogenous IL4R protein with a human gene sequence encoding the extracellular region of human IL4R protein, forming a chimeric IL4R gene sequence, wherein the chimeric IL4R gene sequence is operably linked to an endogenous regulatory element of the rodent, wherein the rodent detectably expresses a functional chimeric IL4R protein on the surface of an activated T cell of the rodent, wherein the chimeric IL4R protein comprises an amino acid sequence that is at least 90% identical to SEQ ID NO: 44, wherein the chimeric IL4R protein comprises an endogenous signal peptide.

2. The rodent of claim 1, wherein the chimeric IL4R protein comprises an amino acid sequence that is identical to SEQ ID NO: 44.

3. The rodent of claim 1, wherein the chimeric IL4R protein consists of an amino acid sequence that is identical to SEQ ID NO: 44.

4. The rodent of claim 1, wherein the rodent is a mouse.

5. The rodent of claim 1, wherein the rodent does not express endogenous IL4R protein.

6. The rodent of claim 1, wherein the rodent further comprises a sequence encoding a human or chimeric IL4 protein.

7. The rodent of claim 1, whose genome further comprises at least one chromosome comprising a sequence encoding a human IL4 protein, wherein the sequence is operably linked to:
   1) a human regulatory element at an endogenous IL4 gene locus in the at least one chromosome; or
   2) an endogenous regulatory element and an endogenous 3' UTR at an endogenous IL4 gene locus in the at least one chromosome.

8. The rodent of claim 7, wherein the sequence encoding the human IL4 protein is operably linked to a human regulatory element at the endogenous IL4 gene locus in the at least one chromosome, and the human regulatory element comprises a 5' UTR of human IL4 gene.

9. The rodent of claim 7, wherein the rodent is a mouse.

10. The rodent of claim 7, wherein the rodent does not express endogenous IL4 protein.

11. The rodent of claim 7, wherein the sequence encoding the human IL4 protein is operably linked to a human regulatory element at an endogenous IL4 gene locus in the at least one chromosome.

12. The rodent of claim 7, wherein the sequence encoding the human IL4 protein is operably linked to an endogenous regulatory element and an endogenous 3' UTR at an endogenous IL4 gene locus in the at least one chromosome.

13. The rodent of claim 1, wherein the chimeric IL4R protein comprises an amino acid sequence that is at least 95% identical to SEQ ID NO: 44.

14. A genetically-modified rodent whose genome comprises a replacement of an endogenous IL4R gene sequence encoding a portion of the extracellular region of endogenous IL4R protein with a human IL4R gene sequence encoding a corresponding portion of the extracellular region of human IL4R protein, wherein the human IL4 gene sequence is operably linked to an endogenous regulatory element to the rodent thereby forming a chimeric IL4R gene, wherein the rodent detectably expresses a functional chimeric IL4R protein on the surface of an activated T cell of the rodent, wherein the chimeric IL4R protein comprises an amino acid sequence that is at least 90% identical to SEQ ID NO: 44, wherein the chimeric IL4R protein comprises an endogenous signal peptide.

15. The rodent of claim 14, wherein the chimeric IL4R protein comprises an amino acid sequence that is 95% identical to SEQ ID NO: 44.

16. The rodent of claim 14, wherein the rodent is a mouse.

17. The rodent of claim 14, wherein the rodent further comprises a sequence encoding a human or chimeric IL4 protein.

* * * * *

SEQUENCE LISTING

<160> NUMBER OF SEQ ID NOS: 82

<210> SEQ ID NO 1
<211> LENGTH: 605
<212> TYPE: DNA
<213> ORGANISM: Mus musculus

<400> SEQUENCE: 1

```
ttgttagcat ctcttgataa acttaattgt ctctcgtcac tgacggcaca gagctattga      60
tgggtctcaa cccccagcta gttgtcatcc tgctcttctt tctcgaatgt accaggagcc     120
atatccacgg atgcgacaaa aatcacttga gagagatcat cggcattttg aacgaggtca     180
caggagaagg gacgccatgc acggagatgg atgtgccaaa cgtcctcaca gcaacgaaga     240
acaccacaga gagtgagctc gtctgtaggg cttccaaggt gcttcgcata ttttatttaa     300
aacatgggaa aactccatgc ttgaagaaga actctagtgt tctcatggag ctgcagagac     360
tctttcgggc ttttcgatgc ctggattcat cgataagctg caccatgaat gagtccaagt     420
ccacatcact gaaagacttc ctggaaagcc taaagagcat catgcaaatg gattactcgt     480
agtactgagc caccatgctt taacttatga atttttaatg gttttatttt taatatttat     540
atatttataa ttcataaaat aaaatatttg tataatgtaa cagaaaaaaa aaaaaaaaaa     600
aaaaa                                                                  605
```

<210> SEQ ID NO 2
<211> LENGTH: 140
<212> TYPE: PRT
<213> ORGANISM: Mus musculus

<400> SEQUENCE: 2

```
Met Gly Leu Asn Pro Gln Leu Val Val Ile Leu Leu Phe Phe Leu Glu
1               5                   10                  15

Cys Thr Arg Ser His Ile His Gly Cys Asp Lys Asn His Leu Arg Glu
            20                  25                  30

Ile Ile Gly Ile Leu Asn Glu Val Thr Gly Glu Gly Thr Pro Cys Thr
        35                  40                  45

Glu Met Asp Val Pro Asn Val Leu Thr Ala Thr Lys Asn Thr Thr Glu
    50                  55                  60

Ser Glu Leu Val Cys Arg Ala Ser Lys Val Leu Arg Ile Phe Tyr Leu
65                  70                  75                  80

Lys His Gly Lys Thr Pro Cys Leu Lys Lys Asn Ser Ser Val Leu Met
                85                  90                  95

Glu Leu Gln Arg Leu Phe Arg Ala Phe Arg Cys Leu Asp Ser Ser Ile
            100                 105                 110

Ser Cys Thr Met Asn Glu Ser Lys Ser Thr Ser Leu Lys Asp Phe Leu
        115                 120                 125

Glu Ser Leu Lys Ser Ile Met Gln Met Asp Tyr Ser
    130                 135                 140
```

<210> SEQ ID NO 3
<211> LENGTH: 642
<212> TYPE: DNA
<213> ORGANISM: Homo sapiens

<400> SEQUENCE: 3

```
tgcatcgtta gcttctcctg ataaactaat tgcctcacat tgtcactgca atcgacacc       60
tattaatggg tctcacctcc caactgcttc cccctctgtt cttcctgcta gcatgtgccg    120
```

```
gcaactttgt ccacggacac aagtgcgata tcaccttaca ggagatcatc aaaactttga      180
acagcctcac agagcagaag actctgtgca ccgagttgac cgtaacagac atctttgctg      240
cctccaagaa cacaactgag aaggaaacct tctgcagggc tgcgactgtg ctccggcagt      300
tctacagcca ccatgagaag gacactcgct gcctgggtgc gactgcacag cagttccaca      360
ggcacaagca gctgatccga ttcctgaaac ggctcgacag gaacctctgg ggcctggcgg      420
gcttgaattc ctgtcctgtg aaggaagcca accagagtac gttggaaaac ttcttggaaa      480
ggctaaagac gatcatgaga gagaaatatt caaagtgttc gagctgaata ttttaattta      540
tgagtttttg atagctttat tttttaagta tttatatatt tataactcat cataaaataa      600
agtatatata gaatctaaaa aaaaaaaaaa aaaaaaaaa aa                          642
```

<210> SEQ ID NO 4
<211> LENGTH: 153
<212> TYPE: PRT
<213> ORGANISM: Homo sapiens

<400> SEQUENCE: 4

```
Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150
```

<210> SEQ ID NO 5
<211> LENGTH: 4220
<212> TYPE: DNA
<213> ORGANISM: Artificial Sequence
<220> FEATURE:
<223> OTHER INFORMATION: Synthetic primer

<400> SEQUENCE: 5

```
gtcatcagat tttgatctga gtcacctcac tggagtcctg actccaggtc ttaactctac       60
catgatactg ctaagccgct caaagccacg gggtaccttc ccactctcac actcgggcca      120
ctctcaagga aactgcagat ctaactgccc ctatccatc cgttctccct ttctgacacc       180
cttcacttcc tctagggctt cctcgacacc acactgggcc ttccacaggc ttcctcttgc      240
ctggttctgg cactgagccc acagtgcca gtcccagctc ctagcctctg aggagctgga       300
aggggcgcct tcctcagctg caggagagaa gggaaggcaa gtctgggctg ggcaagcag       360 gctgtaggga cagacagcca ggcctaagga cacagcgggg ctgcttgttt ctgatccttt      420
```

-continued

```
ctccttaaat ggtgcatgtg acaccatggt ttgacatttc ctagtggcaa gtctgagcat      480
ctgctgaagt gactctgggt ggagatggtt tctccagaga gctaggcatg cagaacaaa      540 ggtgacgctg tcttcctcgc ccagtgggct atgaggacac caagtttcct tctggaatga     600
ctcggcaggt tgaaaggtca tcacagctgc atctcagcat cgtgtcaccc aagctccagg     660
cccttctcag agtcctaggc acagtgtgcg cacacccact cccacagccc tctcaacact     720
ccacctgcat ccacctccct ttcctgaatg aagtgcccat ggtgtatcat ggtcagcttc     780
ctctgctatc caggttcata aatctaagga ctgaaaccca acactgaaac tcctcagaaa     840
caagtgtggg gaccaaagcg tgaatgtcca gacttgagta ttatagtcat tcagccaacc     900
aaaatgtgat gagtaatgaa gtacccactg cgtgcagggt gcttaactaa gtacctgaac     960
ttagtactta gaacaacctc acaagacaag tacaactgtc actcctcagt ttcgggactg    1020
aggttgagtg tatgcccaaa gtcacatgag aggacacaga acagctaggt ctgacaagca    1080 gcggggtgg gggtgggtg ggtggggtg tagagtcttt ttccttagtc ttgtcgcaat       1140
ggtatatcag gtgactcagg ctaagtgctt tctccataga tctcagactt gtggtcacag    1200 gagcccagg ggaggggtg cacagctttc tcctcactgt gtagaaaccc ggccacaagc      1260
ccctgccttc tggactccac actctggtac acaaaactgc tcaatggctc tcggctcaca    1320
aagggctgga gagggtctat gacagtcact ttcctgccct gtccctccac tgaccaccac    1380
tggctggctg acactcttca tcccactttt ccagcctctg ccttatctgc tccattcaca    1440
gataatgtga atctgtcact tggggtggcc ttggacgtcc tttctagtct ttgggaagac    1500
ttggagtctg ggactattca gactcttttc tctgactcct tccaaccact gaaacaagca    1560
agacaaacgg aactttgctt ctgagcgag ttgccttact ctatcccttt ctgactatca     1620
tcttcccaca gagcccagca gttaaggtgc tgagaggaaa acctgaatgg tctattcttt    1680
gctccaggga cactgtggga tccagccctc cccttcccta ggtgtccttc tgtgcccctt    1740
cttagcagga ttcttccagc tatggatgac aagttcctgc tggatctcag ccactcgatg    1800
ccccaccctg gctctcgcgc aaggtcaacc ccagccaagc tcaactgagg cgggatagtt    1860
gcttctccta gaggcgaccg acctttcaaa tgcttctaga gaagcccacc ctcggttaag    1920
agcactggct gctcttccag aggacgctaa ttcagttctc agtacctaca agaaggctca    1980
caaccacctg taacttcagt gtcagggtc tcaacactct cttccggacc ccagaggcat     2040
cgggtatatg tttggtacac acatgaaagc aaaataatca gatgtataaa attaataatt    2100
ctaaaaaaaa aaaaaagcca aattgaaaca agaatactc ctctacctgt acagcgaagg     2160
atcagcttca gagccagaga gatgctcatc ggggagacgc tcgctcacca tgtggctgag    2220
tggatctgta ggacatcaca gaagtggaag agggaaacca agcccaagcc ataagtaaat    2280
aactcattta tctactaatt tattttaggt tttcgagaca gggtttctct gtactctgtg    2340
tagccctggc tgtcctgaaa ctcactctgt agaccaggct gctctgaact caagagatcc    2400
ccctgcctct gcctcccagt gctgggatta aaggtgtgcg ccaccactgc tcagcttaat    2460 ctttttttt tttcttgtaa tgaaccccctt tcacccaaag agagctcagg cctttaccct    2520
ggctcgtcgc ccaggggaac agacttgaaa tttgcctcgt tgcttatcat cagtggctgg    2580
aaggtaacag tttcccaaga attgactgtg tccctaggcc tacagaacat gactgtgtcc    2640
aactttacaa cagtcacagt taatatatat atatttgtaa gtggggtatg gtggcttata    2700
tctgtaactt caacacttga gaggtggagg caggagagtg accatgaatc tgagggcagc    2760
```

| | |
|---|---|
| cttacctata taagttccta ggtagctttg acttcagagt gagacccttc aaattttttt | 2820 |
| attttaaaag ttaaaaagaa agaaagaaaa aagaaagaa agaagaaag aaagaaagaa | 2880 |
| agaaagaaag aaagaaagaa agaaaggagg aaggaaggaa agaagaaggg aaggaaggct | 2940 |
| tatatattat aaacatcttc agttttatt aattaaataa cagtaatgga aaaataattt | 3000 |
| aacacacaat gacaaccta gcaacaacta tttctagatg gtcttccaga aatgagaagt | 3060 |
| cagaattgga ggcagggact tgggggatat gaagaaccct ttctactctg taaaacagag | 3120 |
| cttcgcttcc aagcagatgg cagggtgcg gtgctcactg ctggtggggg gcaatgagta | 3180 |
| cctcgacagg gcctgcattc gttagattaa ggcagtgggc tgggggcagg gtgctgactg | 3240 |
| agagggtgag agagggctgt tcctggtta gtgaaggata tgttttaagt tcattgaaaa | 3300 |
| ggcagccagc cattcttggg ccaatgagat ggctcaggag ggaaggtgct tgccgccaag | 3360 |
| cttgtgagtc tgagttcaag gatccacacg gtgcaaagag agacccggtc tcctgacctc | 3420 |
| cacactgatg ctgtagtgca catagataca cacatgctca catgaagtaa tttaaaaaaa | 3480 |
| ttttttttta aatcagccat ttctcaggct tctgtctaag gtaggaaaaa tcttcaacct | 3540 |
| agcccagaac ctccatatag gtaaagcctc attccatggt cctgcctgcc ccactccatg | 3600 |
| tcacctctct gtcccaaag accacaaact tgtaagatca gctggtctag gatgcgagaa | 3660 |
| ggtctgcctc catcatcctt ctatgaggta agaccccaga gtcagctttc ccaagatatc | 3720 |
| agagttttcca aggggcccc atagcaggaa gcagctaggc ccaggtgtgc tcaaggcaga | 3780 |
| ctttcttgat attactctgt ctttccccag ggcgacacca gcaccctcgg acacctgtga | 3840 |
| cctcttcctt ctctgcagga ggagagccag tggcaaccct acgctgataa gattagtctg | 3900 |
| aaaggccgat tatggtgtaa tttcctatgc tgaaactttg tagatttaaa aaaaaagggg | 3960 |
| ggggagggg gtttcatttt ccaattggtc tgatttcaca ggaaaattta cctgtttctc | 4020 |
| ttttttctcc tggaagagag gtgctgattg gcccagaata actgacaatc tggtgtaata | 4080 |
| aaattttcca atgtaaactc attttccctt ggtttcagca actttaactc tatatataga | 4140 |
| gagacctctg ccagcattgc attgttagca tctcttgata aacttaattg tctctcgtca | 4200 |
| ctgacggcac agagctattg | 4220 |

```
<210> SEQ ID NO 6
<211> LENGTH: 4085
<212> TYPE: DNA
<213> ORGANISM: Artificial Sequence
<220> FEATURE:
<223> OTHER INFORMATION: Synthetic primer

<400> SEQUENCE: 6
```

| | |
|---|---|
| cagaggtaga agaaaactta ttccctggaa ttgtcctctg actcccctcc caaaacctct | 60 |
| aacacgcatc tctctctctc tctctctctc tctctctctc acacacacat | 120 |
| acacacacac atacacacac acacacacaa atgaggggta tgcatatata cacatgtata | 180 |
| cacatacata cacacaaatg agatggtatg catactcaca catgtgcaca cacacagatg | 240 |
| aggagtatgt acacacacac acatgcacac acactaagta aataaaacag agaagaacag | 300 |
| aggcatggca ctacacccta ccttccatgg ggagggatta ctgagacaac agagcctgcg | 360 |
| gcttgtgaaa caagaaccag aaatcaaaaa ataatttttt gaaaggacaa ggaatcggta | 420 |
| gcacttacct acaatccagt ttgaagcagg ccagcatgca tcccagaat ccacataaaa | 480 |
| gtggaaagag aaaatcaact ctacaaagat gtgttctgac ctccacatac gcatcataca | 540 |
| tacacacagt catcatatat atatatat atatatat atatatat atatatat | 600 |

```
atatattaga gaaaatcaag agatttaagt gtttaaaact gctaacacag tagaactaca    660
aaacttgact acaaaacatg tcatagggaa gccacacatg tgggtgtggc ctgagacctg    720
tgggggactg tggtggattg aacgaaaatg gccgccatag acccatatgc ttgaatactt    780
ggtccaccgt tggtggaact gtttgggaag gattaggagg tgtggccccg ttggaggagg    840
agtgtcactg gggcaggctt tgaggtttca aaagcccagg ctattcccag tgtgttctct    900
ctgcccccag ctttcagatc aagacatgag ctctgacaca gtgcctctgt tctgccatca    960
tgtactctaa acccagaaac ctatagtccc aaattaaaca cttccttta taagttgctt    1020 tggtcatggt gtcttgtcca ttaagagcag taactaagac agggcaggga gactgtttaa    1080
agaacaggag taattggtta ggtgtggtgg agtacacttt taattccagc acttgggaag    1140
cacaggcagg ggtagctctg tgagtctgaa gccagcctgg tcggtatatt gagctccagg    1200
ccagccagag ctacataatg agaacctgtt tctaaagtgg gggggtgggg ggtgtgagtt    1260
gctgggcagg aatgatggct cagtggctaa gaccacctgc tgctcttggt tgtttccaag    1320
caaccacata ctggctcaca attatctgta gctccagggg atttgacacc tctggcttct    1380
gtgggcactg aactcacatg cacatatcca tgtgcagaca cacacatcta cacataactt    1440
acagaaaaaa aaattacata tatatatata tatatatata catatacata tatatatata    1500
tacacatata catatatata catatatata tatatatata tatatgtatg taaagttgat    1560
aattaaaaat atagctaagg atagtcacga attgggctg gagagacagc tcagtggtta    1620
tgagcaccaa ctgctcttcc agaggaccct ggttcaagtc ccagcaacca catggtggat    1680
cacaaccatc tgtaactcca gttcttgggc atctgacacc atttcctgac ctctgtgagt    1740
acttcgtgca gaacagac atgcatgcag tcaatgccct cacacacaca aaagcaattt    1800
gaacaaatct caatcttaat taacgctgtt attaaaaggg aaggaatcga gaggagagaa    1860
cccaacggag ctccacactg tcaagcttgc ccgtcagaag atgctctatg cagtctcttc    1920
tactagaggg atctagtaac agtgacttgg cactcttctg accctcaatc acatgcatgt    1980
gacaaaaatt aacaccaaca ctgacatcac cccaaaaata cataccaact ttttaacccc    2040
ttcaaaataa ggggaaaaaa atcaaaagct taaaatctca ccctgaccac aggcagtttc    2100
accctgccca catgaaatac cagcatgcca agggcaatag cggcttctaa ggccaatcag    2160
ggaaggtatg cagtgaaaaa tttaattcc tctcttttga ttgaaactca tttgcatgtc    2220
ctggctaatg tgagccctgt ctgccacagg atatgagttg tgggtttgca cttggtatat    2280
gaggctgaga tgataaagga acggctgtca aaagaaaga cctaaaatag accacgggac    2340
ccaggcaggt tctaggtcag tcagtcacac ctacacttgg atggtcagaa cacactaact    2400
cttttgtttg cctccacata gggagcccta gactctggac ttaaacatcc aatgctcagc    2460
ctctgattcg atcaagggaa gaagaggtaa ggccagccat aaaacacgcg tggattaagg    2520
gaacttgagg attaagtaag tcgtgaggct tgtgactgga gcagttactg aggccaccag    2580
ccacagtcag tgctcagtgg agtgtgttcg ccacagatgg tgaaggtgga actgttaact    2640
ctctctccca tgatgcacat gggctctgct tttgccctca gccagtggat gggttatctc    2700
taactggcat ctggcaatgg gcaataagta cctcatggat aaatgcctaa caaaaccata    2760
tatagctgtg tcttgcattc ttggggagcc gggaagaaat gctggcctgg gctggagaga    2820
tggctcagtg gttaagagca ctgattgctc ttccagaggt cctgagttca attcccagca    2880
accacatggc tcacaacctt ctgtaatggg gtctggtgtg tctgaagaca gctacagtgc    2940
```

```
actcatacac ataaaataga gacaggtgga tctctgtaag tttgaggcca gcctggtcta    3000
cagagtgagt tctaggacat ccagggctat acagagaaac cctgtctcaa aaaaccaaaa    3060
gcaagtttaa agtagatttc cccctcctgc tgtactaggg cttgaaccca tggccttgtg    3120
cacagcaggg aagcactgta ctatgaggta tacctctaga cctcctggtc tcccatccta    3180
aagctatgat gttttcacct tagctctcta gactgccttt gtgtgtgtgc acaagcatgt    3240
atgtacatgt gccttgacac taccatgtga agcccagaga tctgggtctt tcttaatcac    3300
tatcttactt tttttttttt taataaatgt tagtgtgtgt gcatgtgtgc acataatgtg    3360
tgcacctgtg tggcatggtg cgcacgttga agtatgtgag tatctgagat ggaactcagg    3420
ccttgaggtt gtgcagcaag tgtcttttac ccgctgagcc atctcccgg catgcggtcc      3480 cctcccttct gattagctct tcctgccagt ttcttcccag tgcaagctgc ggaagggacc    3540
tgttccttct tggggagaac ctcctgtgta ctgtgaggaa gcatccgtca cctgtcaata    3600
aagctggcgg ttggtctatt aactgaggca ggaaatgggg tggaagttcc agtagggaga    3660
gaggaactct gggataggca ggtttaggaa gacattctcc cgggattctg agactcaaga    3720
aactgaggca aggtaactag ccgtgtagca ctcacagaat agaataaatg gttaattaag    3780
gtactgggta gtcaaggagt gggccaaagc ttgtggtcta ggtgtttatt cataaacagt    3840
aagtctcaga gtcactgttt tgggcactag ggtgtcagtg gaaaagcctg aggttaaacc    3900
ttcttgttct gtattggcca gtgttaaagc agacaaagtc tgctttcatg ctgtgggccc    3960
agtgcatgcc cagtgtccat ttgacactac atttgaaaga catgtttgtc cccttggtct    4020
aagagtggaa gctggcatat ctacctattg tctctccagc ccacgactgg cgtgtctgtt    4080
ctcag                                                                4085

<210> SEQ ID NO 7
<211> LENGTH: 8537
<212> TYPE: DNA
<213> ORGANISM: Artificial Sequence
<220> FEATURE:
<223> OTHER INFORMATION: Synthetic primer

<400> SEQUENCE: 7
atgggtctca cctcccaact gcttccccct ctgttcttcc tgctagcatg tgccggcaac      60
tttgtccacg gacacaagtg cgatatcacc ttacaggaga tcatcaaaac tttgaacagc     120
ctcacagagc agaaggtgag tacctatctg gcaccatctc tccagatgtt ctggtgatgc     180
tctcagtatt tctaggcatg aaaacgttaa cagctgctag agaagttgga actggtggtt     240
ggtggcagtc cagggcacac agcgaggctt ctcccctgcc actctttttt ctgagggttt     300
gtaggaagtt tcctcagttg gagggagtga gagctgctca tcaaggactt ctctgtccgg     360
ttggaggtta actctgtctc ttgctctctc atttctgcct ggaccaagac tctgtgcacc     420
gagttgaccg taacagacat ctttgctgcc tccaaggtaa gaagccgtcc cacggtctgt     480
tttagcaaat ggggagatcc atccccaaat gtctgaacaa gaaacttgtc taatggaaaa     540
cgagcgggcc caaattaact ctaaggtgtt agatgttttc aaagaacgag aagtctgatc     600
tttactctta agcatgtttt ggtctttctg gtttcacttg atttagaaga catgtaatag     660
aaagcttaca tgctgtagtc ctgactcaga tcctggtcaa agaaaagccc tcttgggttt     720
tacttagctt tggcatagtg cctggaacgt aggaggcact caataaatgc ctgttgaatg     780
agagaatttt tctggcccat acatttctga aaaaccaaat actctcacag aaacagatat     840
tgagatgaca ggttgaggga gctttcattt tgtctaagag acttcctatg gcaacagaaa     900
```

```
aggtatcgcc agagccctc ctcttccaca gcctggccac ctaacagccc tctgggttcc        960
ggggctggcc gtccagagct cctcagcttg ctctggccgg ccgaactccc ctccagctcg       1020
gtctggaacc atcctgctgg gcagcgtcca gcacatccct gcttcgggct gcctgggcac       1080
ctcgcctctc tgcctcctgt gctgcctcac ccccaccccct ctatctgtag tgggaggaga      1140
tagatttgac agctgatagt gcattttctc tgacaaacac atgactacag ccgtatcaat       1200
agttttgtgc atttcagttc ctgttttcat ggaaacacac ggctgagaat gaaagcccca       1260
aagcctcaat ttcacagtgg tctcctaact acctgctttc catgcaaact agggagatga      1320
tatggccagg agtgaagccc tgtgtgttgg gcagggtcac actccagcac ccagaccata      1380
gaacagggcc catcctgctt catgagggaa actgctcttc gggcctttag ctggactatc      1440
tcatttcatt agttatcccg ggagtccgat acaggatgag attctgaagg gcaaatacac      1500 acttttttt tttttgaga tagggtcttg ttctgtcacc caggctggag tgcagtggtg        1560
cgatttcagc tcatagcagc ctccacctcc caggctcaag ctatcttcct acctcagcct      1620
cccaagtagc cgggacgaca ggtgtgcacc accacgcctg gctaattttt gtattttttt      1680
gtagagatgg agtcttgcca ttttgcccag gcttgtctcg aacttctggg ctcaagcaat      1740
ccgtccacct cggcctctca aagtgctggg attagccact gcacctgggc aacagtttat      1800
gtgtgtgtgt gtgtgtgtgt gtgtgtgtat atatgtgtgt gtgtatatat atgtgtgtat      1860
gtatatatgt gtatgtatat gtgtgtgtgt gtgtgtgtgt gtgtgtataa aatctccaag      1920
tccatccaac cgagatggct cctactagaa gccaagagtc caccgggttg agcactgggt      1980
ctctggaggc ctgtggcact gctgagaagg ctctaacaaa gccaagggaa gggccacctc      2040
actagaagcc aggcctggag gaagggtgag ggctgagggc ctggaggtaa gactgcctgt      2100
ggttttagac ccagctctgc cactgactag ctgtgtggct ggccttcagc acatcttcac      2160
acctctctgc acctcagttt ccacatgtga agatatgaaa gtgattctga aggtgattgc      2220
aaggttgatt ggaatccagc tcttgagtta gtgcaaagtg ttattgtgag atgatataac      2280
cacgattaaa agcaagaaca ggtgcagaga agcgatgatt ctaagaagga ggggaccggg      2340
ttggaaagga tcaaaccatc caggatgccg agtctggggc aatccatctg ggctgttttct     2400 ggaagaccc cgggtgcagg ccaggacact gctgccctcc cgtccttaac tcccctcttc      2460
actcagtcct cactcacctc cctctcacac acacaaacat ctcctagaat aatcccact       2520 gcctgccttc actcttaccc gtctcatttg cctccctga acttcatcct cctggagttc      2580
acgatctcac tcttcactct tttcttcccc tcgaagattc agcactgctt acttacatgt      2640
taagatattt cagaacagtg aaatgttgct attttcaaaa acctacaaag gtggtatgca      2700
gaggaaaagg tacttctttg tgttcccaaa gaaaacatct ttccaaaatc cagcctattg      2760 atttttatttc ttcgggggaa caagaatttt agtatctcta agttgggtag cattctactc     2820
ttggcagttg ctggaaagaa ggcactggtc taggtcctgg gcttcacagg taacacctgt      2880
cagggtgtct atgaagtcaa ggctgtctga ggaacagcaa agtgggaaga agcaagctgg      2940
ctggctgatg aagggtttct tgggtggaca agtagtggga gctatttcct atttaccaaa     3000
gagagctaaa gttcataatt ctacagagag ttccataatg aacctcaaat acctctgttt      3060
tttgaaggag tttctcatat acagcactag ctgactatcc tgggcaggat gggagataat      3120
gaatgcagtg ccaatcgggc tggatttata tggtcctcag tgaggctggt caagaaccga      3180
gttagaactc tcacagagtc actgccacag aagaaatctc ccaagtggct gtttcctgac      3240
```

-continued

```
attcccggga gggacaggcc tccttctgag tcactcccta agcagttctg aactgtgagg    3300
tcagccaggc tgtccaagtg cactccctga gccactggca gacacactca gcagccagag    3360
ctagacaggc aggtggtagg agtccagggc cacggcaggg atggagtgtc gcccctcgc    3420 tgcgatacca gagcaactaa aacgttaagg ccttgcacta aagctgccct taggatgcat    3480
tcttttaaag tttttccatt taatgcagac tcttttcaat tcttatttta tccttgtttc    3540
ctttagaaag tcctttcaaa aatatcttta gagggttttt tcctatacta tgtggccata    3600
tacgggtcaa aattaagttt aatttccagg ctccaagcca gcgtttcaga aaaatctcac    3660
caaggtttgt ggtaaaagaa gcaaagggct gactttttgg ttttcttgaa tctcactgtt    3720
ccctctgcag cagcatgcat gtctgcccac ctccagacac acaggcacca tctgccgccc    3780
cccatcagcc cgtgtccctt ccacctcgac tcgcctacaa agcccagaga ggtctgtttc    3840
ttggccccca gagcccaaag atactgacac actcttacat ttccaactag aatcaggaac    3900
gaggagtgac tctcagtcag ttcattaagt aaatgtcttt ctaaccgctc tgcccatggg    3960
acatcacgcc ccacagggga aaggggaagc ttctgtagcc tgggattctg gtgcctcagt    4020
ctgggtctag actttcctga aaaacgtta aaatatgaac tgcattccta gaatttagcc     4080
tacataaata agagatgaac acaaagattt ctatagttta ctcactgccg cttatttaca    4140
gaagcaaaaa tctgccacga taggggcctg acaaatgaca gtaccactgt gcaatgcgtt    4200
tctacgcagc tctcaatccc atgttctcta ataccaccga agggcttagg aaatgcttat    4260
ggtatatgta aagagtaaag aagttacaaa acagtatcaa cagttgaccc ctattttaaa    4320
aagtattttt aaagtgtga cgatatttac caaaatatta acagcaatag ttacctctgg     4380
ctggtgggat gagtgaatgt attttttgttg aatatatgtt acctttatag taaatatatg    4440
ttatcttgat catcagaaaa aaaaatatgt aagaacttga aagctgcttg acagcgctg     4500 ctgatagaaa cccctgagca tcttgtcact gttcttctga ttcagagggt ctgggtgggg    4560
caggggtggt ctgagattct gtatttctaa gaagctccca gtgatgtcca tgctgctggt    4620
ccatggacca cactttgagt atcaagggac cagagcatgt cggggagag gctggggata     4680 gctttctttta tctgaactgg ataaaggaac tgggctcaag ctaagaaccc tctccaggtt    4740
ctgcatcttt gttcttcagt gaaaaatgag aggacacacc aggccaggtt cagactgaga    4800
cacaatccct ctcctgggtt cccaatgact tgtctcttgt ccattccctt ctctaaggct    4860
aagggccccc aggaagagcc atgtggccag accctcacag ttgctggcat tccaaggaga    4920
ttctcactcc gcatcatttg gggccaaaag gccccttaca gaagctctgc caaggctca    4980 gatcaatggc acctgctccc agagcctcct ctgatctccc aggacacctt tccctgatct    5040
gtgcacttat ctcttgctgc ctggcaaaat gtcttagctc ctcacttggg ccatgtgctg    5100
ctctcctctc ccatggggag agccacacgg agagtgctgg ccaaagcagc agagttcagg    5160
ccaaaggatg tgcactcatt tattcaacag gcatgcagga tttccaggga aagctggatt    5220
ttaaaacctc tgggaacaag agcagaacct gactgagagc tcatgtgggc acttttcata    5280
gcagaatagc tcatgaggta tagagacacg gacgcagaac gtgggctgta gcgacagatg    5340
gtcctgcatt ctagtcccca ctgtgccttt tcctcatggg atgactttat tcaggtaccc    5400
tttcggcaaa atcctccaag agaaaggaaa ctggagggtt ctggggagaa ggctgctgcg    5460
tttgcaattg ggagaggttg ttgacagagg tttatgtctg tggcaagcag ccttccttca    5520
gtggaatact tgaagacagg tctgtagttg agcaaactca cctccatttg tcctcctgga    5580
aagaagaaat caagaggaaa aatctctctc ccatcctcca aatggagctg gcacattgct    5640
```

```
atctgtggca tttgtctttc cagaacacaa ctgagaagga aaccttctgc agggctgcga    5700
ctgtgctccg gcagttctac agccaccatg agaaggacac tcgctgcctg ggtgcgactg    5760
cacagcagtt ccacaggcac aagcagctga tccgattcct gaaacggctc gacaggaacc    5820 tctgggggcct ggcgggcttg gtaagctgca ctgtattcct ggcaagccgg ccgcgtggct    5880
cctggtggac agcagcctca cttctaaaca ctccttagga gctgcagcac ccttggtcaa    5940
cccattcatt cattcactca ttcaataagt atttgctgaa gttccacaag tgctgggtgt    6000
ggttctaggt gctgaggacg tgtcactaaa gacacgcagg ccgagtccct gttctcatgg    6060
aatgttctaa tgggagagtt agaaaaacaa acatgtaaaa tgatggccag cagtgatacg    6120
tgctacaaag aaaaacatag aaataaagaa cataagagtc atgggggagg gggctgactt    6180
aggagctggt gacattatct gagcagatat ttgaattgag ggagcaggcc acatgactaa    6240
ctagggagac cattccaggc agaaggagga ggtatgcaaa ggccttagga tggaaatgaa    6300
ctaacttcct gtatttaaag accagtagga aggccagtgt ggctggatca gagtgagtga    6360
ggggtagttt ccaggacagc agatcacaca aggcctttag attccaccac gagtatggca    6420
gggaacacct gcagagcttt gggcaggaca aagactgtac aatctgattt acgtgattta    6480
aaagggtcag tctggctact gtgtggtaaa taggctgaaa gggggaaagc atagaagcaa    6540
gatggcctgt tgggaggcta ccacagtaaa ccaggctaga gatgatggtg gcgtggacag    6600
aatgaagcaa gatggcctgt tgggaggcta ccacagtaaa ccaggctaga gacgatggtg    6660
gcgtggacag aatgaagcaa gatggcctgt tgggaggcta ccacagtaaa ccaggctaga    6720
gatgatggtg gcgtggacag aatgggagca gttgaggtga acagatttgg gatatgacta    6780
aaaataaaac cagaaggatt tgctgacaga tcggttgtag ggggtaagat acaggggagg    6840
aaaagatgac ctctttgttc ctgcccaaac ccctctggcg atggtcagta ctgtttacag    6900
agagatgaaa gactggcggc aaggcagggc tggaggttca gcagaagatc aagagttcaa    6960
ttttgtacat cgtacatgta aggtggctct tggatagcca agtgaaggtg ttgagaagat    7020
ggttagaaaa gtctggaact taggggagag gtcagaactt gcaatacaaa aaggagagtc    7080
cttagataga tactgctgaa aatctgaatg acagaaaggg agagatcaaa ggactgagcc    7140
tgagatcaac acatggaggt caggagagga ggatccagcc aagggggcctg aggaggagtg    7200 accagtgagg caggagaaca ctggagagtg ggcggtaccc caggaagccg ttgaggcac    7260 tcaaggaggg agggttgact gtgtcaaatg tactgaaagg acaggtcagg tgaggaccaa    7320
gaaaggcccc tgggtttggc tgatggaggc catgggtgag gctgatgtaa atggagaggc    7380
aggaaggaaa gcccagctgg agtgggctca ccgaggatag ggtggcgaga ggagacaaag    7440
aaggaacagt gagggcagaa cactctttga agatgtttag ctataaggct gcagagaaac    7500
tgacccacag ctgcagggtg gttatggagt gagggaagct cttttaaggt tgggggtata    7560
cccagcatgt taatgcacct ggggggaatgg tccagtggag caggaagaac tgaagagagc    7620
agaaagagga agaatcatta gggggcagaa gtccttgtag cccagagtgg atgttatcta    7680
atatcgagtg gaggaattaa ttggctttag aggagaacaa ggacatgtat cccctctctg    7740
ggcctatcac cttgtagaca atgggatagg tcatgggata ggaacttggc acaacacatg    7800
ttctctcttt taattctctc cattatctta tgaagcaggc aagtaggcaa acaattgtcc    7860
caactttaca aaagaaactg aagctttat aaattaagta gtacatccta agcaatacaa    7920
ttaataaatg gtagagctga gattcaaact gaagcagtgg cctgggggta gcatctggaa    7980
```

| | |
|---|---|
| tccttcccac ctttagggct gctgtgctgc ggtgctgctg tttaatggca caggagggcc | 8040 |
| acatgactga atctctctca gcagtccagg cagtcatgca gaaggcccag tagagcaccg | 8100 |
| ggcaggtctg agccagcatc ttcaagttcc accctctgag caagcaccta gctgtgacac | 8160 |
| acctctccag agactgcact ccccccgcg ccacccaccc caaaagcaga taggtaatgg | 8220 |
| tatacagtaa ccatttctag aagtgtaagt agtatgcacc caaataggc aaaacctgct | 8280 |
| ggcctagtga tagagacaac tcccagtcag gctagactgg aggccttggt tttataagtg | 8340 |
| ttcaggtgac aagtgccaca gtaggcttga tcaagtagac aggcaggcaa gacaaatgct | 8400 |
| taccaatgca agctaatgaa atgtttcttt tgcagaattc ctgtcctgtg aaggaagcca | 8460 |
| accagagtac gttggaaaac ttcttggaaa ggctaaagac gatcatgaga gagaaatatt | 8520 |
| caaagtgttc gagctga | 8537 |

<210> SEQ ID NO 8
<211> LENGTH: 200
<212> TYPE: DNA
<213> ORGANISM: Artificial Sequence
<220> FEATURE:
<223> OTHER INFORMATION: Synthetic primer

<400> SEQUENCE: 8

| | |
|---|---|
| actttaactc tatatataga gagacctctg ccagcattgc attgttagca tctcttgata | 60 |
| aacttaattg tctctcgtca ctgacggcac agagctattg atgggtctca cctcccaact | 120 |
| gcttccccct ctgttcttcc tgctagcatg tgccggcaac tttgtccacg gacacaagtg | 180 |
| cgatatcacc ttacaggaga | 200 |

<210> SEQ ID NO 9
<211> LENGTH: 149
<212> TYPE: DNA
<213> ORGANISM: Artificial Sequence
<220> FEATURE:
<223> OTHER INFORMATION: Synthetic primer

<400> SEQUENCE: 9

| | |
|---|---|
| tggaaaactt cttggaaagg ctaaagacga tcatgagaga gaaatattca aagtgttcga | 60 |
| gctgatactg agccaccatg ctttaactta tgaatttta atggttttat ttttaatatt | 120 |
| tatatattta taattcataa aataaaata | 149 |

<210> SEQ ID NO 10
<211> LENGTH: 155
<212> TYPE: DNA
<213> ORGANISM: Artificial Sequence
<220> FEATURE:
<223> OTHER INFORMATION: Synthetic primer

<400> SEQUENCE: 10

| | |
|---|---|
| acatgcctgt aggcaagaca cccacacaca taaaaacaaa ataaaataag gatagaaagg | 60 |
| ccagggggat gaatcctcga ggtcgacggt atcgataagc ttgatatcga attccgaagt | 120 |
| tcctattctc tagaaagtat aggaacttca ggtct | 155 |

<210> SEQ ID NO 11
<211> LENGTH: 75
<212> TYPE: DNA
<213> ORGANISM: Artificial Sequence
<220> FEATURE:
<223> OTHER INFORMATION: Synthetic primer

<400> SEQUENCE: 11

```
agaaagtata ggaacttcat cagtcaggta cataatggtg gatccattaa tcagaggtag    60
aagaaaactt attcc                                                     75

<210> SEQ ID NO 12
<211> LENGTH: 24
<212> TYPE: DNA
<213> ORGANISM: Artificial Sequence
<220> FEATURE:
<223> OTHER INFORMATION: Synthetic primer

<400> SEQUENCE: 12
gacaactttc agggagggag tcag                                           24

<210> SEQ ID NO 13
<211> LENGTH: 21
<212> TYPE: DNA
<213> ORGANISM: Artificial Sequence
<220> FEATURE:
<223> OTHER INFORMATION: Synthetic primer

<400> SEQUENCE: 13
atcgcacttg tgtccgtgga c                                              21

<210> SEQ ID NO 14
<211> LENGTH: 22
<212> TYPE: DNA
<213> ORGANISM: Artificial Sequence
<220> FEATURE:
<223> OTHER INFORMATION: Synthetic primer

<400> SEQUENCE: 14
gcctctctca acccagtata ac                                             22

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
cttggagtca accacctctg                                                20

<210> SEQ ID NO 16
<211> LENGTH: 23
<212> TYPE: DNA
<213> ORGANISM: Artificial Sequence
<220> FEATURE:
<223> OTHER INFORMATION: Synthetic primer

<400> SEQUENCE: 16
gatctttcac tgaaacttga ctg                                            23

<210> SEQ ID NO 17
<211> LENGTH: 22
<212> TYPE: DNA
<213> ORGANISM: Artificial Sequence
<220> FEATURE:
<223> OTHER INFORMATION: Synthetic primer

<400> SEQUENCE: 17
ctccaactac atctactttc tg                                             22

<210> SEQ ID NO 18
```

```
<211> LENGTH: 23
<212> TYPE: DNA
<213> ORGANISM: Artificial Sequence
<220> FEATURE:
<223> OTHER INFORMATION: Synthetic primer

<400> SEQUENCE: 18
ggatcggcca ttgaacaaga tgg                                              23

<210> SEQ ID NO 19
<211> LENGTH: 23
<212> TYPE: DNA
<213> ORGANISM: Artificial Sequence
<220> FEATURE:
<223> OTHER INFORMATION: Synthetic primer

<400> SEQUENCE: 19
cagaagaact cgtcaagaag gcg                                              23

<210> SEQ ID NO 20
<211> LENGTH: 5553
<212> TYPE: DNA
<213> ORGANISM: Artificial Sequence
<220> FEATURE:
<223> OTHER INFORMATION: Synthetic primer

<400> SEQUENCE: 20
ctcagggatt cactgcagcc ttaccaggta ccacggatct ggttcctgag cacagcaagg        60
ttaggttaca tccagtgaga cagtgagaca acatagagca acagcacaga ggtgccaggc       120
acctcggaag ccacagagga gaagccactg gccagtggtt ggggcagagc acaggaagcc       180
aagtacacct cactcgtgag atgggtgaaa acagaggtct ggctggctgg agagagtctg       240
tgtgagagac gttctttgca ttagcaagac caaagcatca acaagagta ctggagtgac        300 ccaagtcttg atcagacaga cgcacagcac atgaagccta actccggcac tcaggaggta       360
taggtaggag ggacaggagt ttgaggactg tgaaaaatgt ctaagacctt gaggccaagc       420
cgtatctgaa tcagatttta gcagagccat tctggcagtg agggctgcaa agggcagggt       480
cagggagact gcttatcagg ttcctgtaga gacccgggtg ggacaggatg gcagtagaga       540
ggggagagtc taattctgga gaggtgtgta tgcaaattac atgtttatac tttatataat       600
ataaagtaaa catgcatacg atatctactg cctcttaata tacacactca gtttctatga       660
attctatgtt tgtgtagagg atgaatgtct gtgtacaaca tgtagaggca gatgagaagg       720
tcaagtatct cccttcttct gaagacagtg tctctcacgg agcctggagc taggctggca       780
gccagcgatc ccagtcactc ttctgtcccc atctccacag tgaggggtt cccaggtgcc        840 tgtgggacca cgttggcttt tttatatggg tgctggggat ctgaacccag ccctcacgct       900
tgcttggcaa gctctcttag cctgaaacat cttcccagcc cagtacttaa atataaaccc       960
atgcacactt ttctgcagag ctgcacacat tacccatgtg cactaccact gagctatgcc      1020
tctgagccac atatcaactt ttttggtttg gttttatttg tttctagttt tgttttgttt      1080
ttgagacaac gtagccctgg ctgtcctgga gcttgctgtg tagaccaggc tggccttgaa      1140
ctcacagaga tcatcctacc tctgctgccc aaatactggt attaaaggca tgaaccatca      1200
tgccctggcc ccaaatcagt ttttgttttg ttttgttttt gtttttaaa agtgtgtgtg       1260 tgtgtgtgtg tgtgtgtgca atgcccccaa aggccaggag agggcatccg atccctggga      1320
gctggagtta caggtggtgg aaagtcaact gatgtgggtg ctgggaacct aactgggccc      1380
tctgcaagca cggtacaaac tcttgactgc tgagccacct ccccaccttc taagggattt      1440
```

```
attctaaaaa tgtcaaatat ttacaaaata cccctgagga acccattacc cagcctcaat    1500
ggttagcatg tgagggtcga tttgtctcat ctctaccttc cttattcccc tagtgacaat    1560
gactggatcc agagtctagg tgagagcaga agctgggtgg ggtggatgta gcctgtgagg    1620
tctggacaca ctacgtgtga gaaacctgag ctccagtatg ccatcaaagc tggattgtgg    1680
acgccatgtt ccttcctgga gcgtggcacg gcctggcctc ccaagtctca ggccacagca    1740
cagggtctcc atcttctccg tcctcccagc ttaccaccgt tccactgcac agagaagtca    1800
ctttgctgat gtcacagtgt tatcaatcca tcacccttat ctcctgtcac ctcccacggg    1860
cctcggtgac cctcacttct gcttcttgag actcccactc cctggggctc tgaccctgcc    1920
tgtgcccggc tcttggttag gcctcctacc cttcttccgg tattaccagt gggtagtggg    1980
tcatttctta tccccccttgc ctctctcaac ccagtataac tccatttatg ggaatgcctc    2040
catgttcagg gccacagagg ccgctcagct cagcattgct gatctctgac catatctcat    2100
acctgctaaa ctcccagaag ctcctgggtc acctgcagcc gacttctcac tcaatccaac    2160
gtgcattcgt tgtgagtggt gacccatggc cgccactgct gctggtgatg atcacagctg    2220
ggtttggggt tgttttatgt ttgtctttca aacattgtat acttacatat ttttttctaa    2280
tgtgccaaat gccacaccaa cactcgacac ttattaccac acatgatttt ctcacaccac    2340
ttttctactg ccagccggtt ttactggaat acccagacag aataactttc tcaaagccac    2400
tcagaaagat gtctagagct ggattcagag gtggttgact ccaagtcttt ctttgtgtgt    2460
gcatatgcat gtgtgtatag atatgtgtgt gcatacgcat gtgtgtatag atgtgtgtgc    2520
atatgcatgt atgtatagat atgtgtatag atgtttgtat atgcatgtgt atatagatgc    2580
atgtgtgtat agatatgtgt gcatatgcat gtgtgtatag atgcatgtgc atatgcatgt    2640
gtgtatagat gtgtgtgcat atgcatgtgt gtatagatgt gtgtatagat gtgtgtgcat    2700
atgtgcatgt ttagatgtgt gtggaagtca gaagacaact ttcagggagg gagtcagtta    2760
ccccttcctc tgtgtgggcc ctggggattg aacttgggtc atcagatttt gatctgagtc    2820
acctcactgg agtcctgact ccaggtctta actctaccat gatactgcta agccgctcaa    2880
agccacgggg taccttccca ctctcacact cgggccactc tcaaggaaac tgcagattct    2940
aactgcccct atccatccgt tctccctttc tgacacccTt cacttcctct agggcttcct    3000
cgacaccaca ctgggccttc acaggcttc ctcttgcctg ttctggcac tgagccccac    3060 agtgccagtc ccagctccta gcctctgagg agctggaagg ggcgccttcc tcagctgcag    3120
gagagaaggg aaggcaagtc tgggctgggg caagcaggct gtagggacag acagccaggc    3180
ctaaggacac agcggggctg cttgtttctg atcctttctc cttaaatggt gcatgtgaca    3240
ccatggtttg acatttccta gtggcaagtc tgagcatctg ctgaagtgac tctgggtgga    3300
gatggtttct ccagagagct aggcatggca gaacaaaggt gacgctgtct cctcgccca    3360 gtgggctatg aggacaccaa gtttccttct ggaatgactc ggcaggttga aggtcatca    3420 cagctgcatc tcagcatcgt gtcacccaag ctccaggccc ttctcagagt cctaggcaca    3480
gtgtgcgcac acccactccc acagccctct caacactcca cctgcatcca cctccctttc    3540
ctgaatgaag tgcccatggt gtatcatggt cagcttcctc tgctatccag gttcataaat    3600
ctaaggactg aaacccaaca ctgaaactcc tcagaaacaa gtgtggggac caaagcgtga    3660
atgtccagac ttgagtatta tagtcattca gccaaccaaa atgtgatgag taatgaagta    3720
cccactgcgt gcagggtgct taactaagta cctgaactta gtacttagaa caacctcaca    3780
```

```
agacaagtac aactgtcact cctcagtttc gggactgagg ttgagtgtat gcccaaagtc    3840
acatgagagg acacagaaca gctaggtctg acaagcagcg ggggtggggg tggggtgggg    3900
tggggtgtag agtcttttc cttagtcttg tcgcaatggt atatcaggtg actcaggcta    3960
agtgctttct ccatagatct cagacttgtg gtcacaggag ccccagggga ggggggtgcac   4020 agctttctcc tcactgtgta gaaacccggc cacaagcccc tgccttctgg actccacact   4080
ctggtacaca aaactgctca atggctctcg gctcacaaag ggctggagag ggtctatgac   4140
agtcactttc ctgccctgtc cctccactga ccaccactgg ctggctgaca ctcttcatcc   4200
cacttttcca gcctctgcct tatctgctcc attcacagat aatgtgaatc tgtcacttgg   4260
ggtggccttg gacgtccttt ctagtctttg ggaagacttg gagtctggga ctattcagac   4320
tcttttctct gactccttcc aaccactgaa acaagcaaga caaacggaac tttgcttctg   4380
agcggagttg ccttactcta tccctttctg actatcatct tcccacagag cccagcagtt   4440
aaggtgctga ggaaaaacc tgaatggtct attctttgct ccaggacac tgtgggatcc     4500 agccctcccc ttccctaggt gtccttctgt gcccttctt agcaggattc ttccagctat    4560
ggatgacaag ttcctgctgg atctcagcca ctcgatgccc caccctggct ctcgcgcaag    4620
gtcaacccca gccaagctca actgaggcgg atagttgct tctcctagag gcgaccgacc     4680
tttcaaatgc ttctagagaa gcccaccctc ggttaagagc actggctgct cttccagagg    4740
acgctaattc agttctcagt acctacaaga aggctcacaa ccacctgtaa cttcagtgtc    4800
aggggtctca acactctctt ccggacccca gaggcatcgg gtatatgttt ggtacacaca    4860
tgaaagcaaa ataatcagat gtataaaatt aataattcta aaaaaaaaa aaagccaaat    4920 tgaaacaaag aatactcctc tacctgtaca gcgaaggatc agcttcagag ccagagagat    4980
gctcatcggg gagacgctcg ctcaccatgt ggctgagtgg atctgtagga catcacagaa    5040
gtggaagagg gaaaccaagc ccaagccata agtaaataac tcatttatct actaatttat    5100
tttaggtttt cgagacaggg tttctctgta ctctgtgtag ccctggctgt cctgaaactc    5160
actctgtaga ccaggctgct ctgaactcaa gagatccccc tgcctctgcc tcccagtgct    5220
gggattaaag gtgtgcgcca ccactgctca gcttaatctt tttttttttt cttgtaatga    5280 accccttca cccaaagaga gctcaggcct ttaccctggc tcgtcgccca ggggaacaga    5340
cttgaaattt gcctcgttgc ttatcatcag tggctggaag gtaacagttt cccaagaatt    5400
gactgtgtcc ctaggcctac agaacatgac tgtgtccaac tttacaacag tcacagttaa    5460
tatatatata tttgtaagtg gggtatggtg gcttatatct gtaacttcaa cacttgagag    5520
gtggaggcag gagagtgacc atgaatctga ggg                                 5553
```

<210> SEQ ID NO 21
<211> LENGTH: 5196
<212> TYPE: DNA
<213> ORGANISM: Artificial Sequence
<220> FEATURE:
<223> OTHER INFORMATION: Synthetic primer

<400> SEQUENCE: 21

```
taactcaagt tctgggggag ctgatgctct cctctggcct cctgtggagg tacacagacc      60
acatgcctgt aggcaagaca cccacacaca taaaaacaaa ataaaataag gatagaaagg     120 ccaggggggat gaatccagag gtagaagaaa acttattccc tggaattgtc ctctgactcc    180
cctcccaaaa cctctaacac gcatctctct ctctctctct ctctctctct                240
ctctcacaca cacatacaca cacacataca cacacacaca cacaaatgag gggtatgcat    300
```

```
atatacacat gtatacacat acatacacac aaatgagatg gtatgcatac tcacacatgt    360
gcacacacac agatgaggag tatgtacaca cacacacatg cacacacact aagtaaataa    420
aacagagaag aacagaggca tggcactaca ccctaccttc catggggagg gattactgag    480
acaacagagc ctgcggcttg tgaaacaaga accagaaatc aaaaaataat tttttgaaag    540
gacaaggaat cggtagcact tacctacaat ccagtttgaa gcaggccagc atgcatcccc    600
agaatccaca taaaagtgga aagagaaaat caactctaca aagatgtgtt ctgacctcca    660
catacgcatc atacatacac acagtcatca tatatatata tatatatata tatatatata    720
tatatatata tatatatata ttagagaaaa tcaagagatt taagtgttta aaactgctaa    780
cacagtagaa ctacaaaact tgactacaaa acatgtcata gggaagccac acatgtgggt    840
gtggcctgag acctgtgggg gactgtggtg gattgaacga aaatggccgc catagaccca    900
tatgcttgaa tacttggtcc accgttggtg gaactgtttg ggaaggatta ggaggtgtgg    960
ccccgttgga ggaggagtgt cactggggca ggctttgagg tttcaaaagc ccaggctatt   1020
cccagtgtgt tctctctgcc cccagctttc agatcaagac atgagctctg acacagtgcc   1080
tctgttctgc catcatgtac tctaaaccca gaaacctata gtcccaaatt aaacacttcc   1140
ttttataagt tgctttggtc atggtgtctt gtccattaag agcagtaact aagacagggc   1200
agggagactt tttaaagaac aggagtaatt ggttaggtgt ggtggagtac acttttaatt   1260
ccagcacttg ggaagcacag gcaggggtag ctctgtgagt ctgaagccag cctggtcggt   1320
atattgagct ccaggccagc cagagctaca taatgagaac ctgtttctaa agtgggggggg   1380 tgggggtgt gagttgctgg gcaggaatga tggctcagtg gctaagacca cctgctgctc   1440
ttggttgttt ccaagcaacc acatactggc tcacaattat ctgtagctcc aggggatttg   1500
acacctctgg cttctgtggg cactgaactc acatgcacat atccatgtgc agacacacac   1560
atctacacat aacttacaga aaaaaaaatt acatatatat atatatatat atatacatat   1620
acatatatat atatatacac atatacatat atatacatat atatatatat atatatatat   1680
gtatgtaaag ttgataatta aaaatatagc taaggatagt cacgaattgg ggctggagag   1740
acagctcagt ggttatgagc accaactgct cttccagagg accctggttc aagtcccagc   1800
aaccacatgg tggatcacaa ccatctgtaa ctccagttct tgggcatctg acaccatttc   1860
ctgacctctg tgagtacttc gtgcagaaca cagacatgca tgcagtcaat gccctcacac   1920
acacaaaagc aatttgaaca aatctcaatc ttaattaacg ctgttattaa aagggaagga   1980
atcgagagga gagaacccaa cggagctcca cactgtcaag cttgcccgtc agaagatgct   2040
ctatgcagtc tcttctacta gagggatcta gtaacagtga cttggcactc ttctgaccct   2100
caatcacatg catgtgacaa aaattaacac caacactgac atcaccccaa aaatacatac   2160 caactttta accccttcaa aataagggga aaaaatcaa aagcttaaaa tctcaccctg   2220
accacaggca gtttcaccct gcccacatga aataccagca tgccaaggc aatagcggct   2280 tctaaggcca atcagggaag gtatgcagtg aaaaattaa tttcctctct tttgattgaa   2340
actcatttgc atgtcctggc taatgtgagc cctgtctgcc acaggatatg agttgtgggt   2400
ttgcacttgg tatatgaggc tgagatgata aaggaacggc tgtcaaaaag aaagacctaa   2460
aatagaccac gggacccagg caggttctag gtcagtcagt cacacctaca cttggatggt   2520
cagaacacac taactctttt gtttgcctcc acatagggag ccctagactc tggacttaaa   2580
catccaatgc tcagcctctg attcgatcaa gggaagaaga ggtaaggcca gccataaaac   2640
```

```
acgcgtggat taagggaact tgaggattaa gtaagtcgtg aggcttgtga ctggagcagt    2700
tactgaggcc accagccaca gtcagtgctc agtggagtgt gttcgccaca gatggtgaag    2760
gtggaactgt taactctctc tcccatgatg cacatgggct ctgcttttgc cctcagccag    2820
tggatgggtt atctctaact ggcatctggc aatgggcaat aagtacctca tggataaatg    2880
cctaacaaaa ccatatatag ctgtgtcttg cattcttggg gagccgggaa gaaatgctgg    2940
cctgggctgg agagatggct cagtggttaa gagcactgat tgctcttcca gaggtcctga    3000
gttcaattcc cagcaaccac atggctcaca accttctgta atggggtctg gtgtgtctga    3060
agacagctac agtgcactca tacacataaa atagagacag gtggatctct gtaagtttga    3120
ggccagcctg gtctacagag tgagttctag gacatccagg gctatacaga gaaaccctgt    3180
ctcaaaaaac caaaagcaag tttaaagtag atttccccct cctgctgtac tagggcttga    3240
acccatggcc ttgtgcacag cagggaagca ctgtactatg aggtatacct ctagacctcc    3300
tggtctccca tcctaaagct atgatgtttt caccttagct ctctagactg cctttgtgtg    3360
tgtgcacaag catgtatgta catgtgcctt gacactacca tgtgaagccc agagatctgg    3420
gtctttctta atcactatct tactttttt tttttaata aatgttagtg tgtgtgcatg    3480
tgtgcacata atgtgtgcac ctgtgtggca tggtgcgcac gttgaagtat gtgagtatct    3540
gagatggaac tcaggccttg aggttgtgca gcaagtgtct tttacccgct gagccatctc    3600
cccggcatgc ggtcccctcc cttctgatta gctcttcctg ccagtttctt cccagtgcaa    3660
gctgcggaag ggacctgttc cttcttgggg agaacctcct gtgtactgtg aggaagcatc    3720
cgtcacctgt caataaagct ggcggttggt ctattaactg aggcaggaaa tggggtggaa    3780
gttccagtag ggagagagga actctgggat aggcaggttt aggaagacat tctcccggga    3840
ttctgagact caagaaactg aggcaaggta actagccgtg tagcactcac agaatagaat    3900
aaatggttaa ttaaggtact gggtagtcaa ggagtgggcc aaagcttgtg gtctaggtgt    3960
ttattcataa acagtaagtc tcagagtcac tgttttgggc actagggtgt cagtggaaaa    4020
gcctgaggtt aaaccttctt gttctgtatt ggccagtgtt aaagcagaca aagtctgctt    4080
tcatgctgtg ggcccagtgc atgcccagtg tccatttgac actacatttg aaagacatgt    4140
ttgtcccctt ggtctaagag tggaagctgg catatctacc tattgtctct ccagcccacg    4200
actggcgtgt ctgttctcag ggcacaata tacaccacaa gcgggaaggt ggtcagtaga    4260
gtcctgctgc agcgcaggag agacacattt taattttat gattttgtg tgtgcatgtg    4320 tgtggtgtgt gtgcaaatgt gtgcatttgc ttgtgtgggc ccacgtacac agtccagagg    4380
ataacattgg gtgtcctgtg ctatcattct gccttatgtc tttttttttt ttttttggt    4440 tttttgagac agggtttctc tgtgtagccc tggctgtcct ggaactcact tgtagacca    4500 ggctggcctc gaactcagaa atccgcctgc ctctgcctcc tgagagctgg gattaaaggc    4560
gtgcgctacc acgcccggct gccttatgtc tttaagacag gatctttcac tgaaacttga    4620
ctgtgtctgc cccagcagtg ctgggtcac aggcaccctt gaccatgctc agcctttaga    4680
tgagtgctgg agatgtgaat tcaggtcctg atgccacctt agtaagtgtt cttgccccac    4740
tgagccatct ccccaacccc aagatatact caagagggca ccagggcact taaacattgc    4800
tagtggcaaa gaaagctggg gcagctactg caggaactgt atggagggtt ctgaagaatt    4860
aaatattata tctctgttgg actgagaacc caacagagat gcttgtacat tcacaatcat    4920
tgtggcactg cacagtcatg aatatatgga accaaggcat caacagataa ctagataaag    4980
aatatgttgt gcatagacac aatggaattg tgcttaggcg tgaagaatga agtcatgttt    5040
```

```
acagaaagta gatgtagttg gagattatgt taaataaagc cagattgaga aaaaaaacaa      5100
ttttttccat tctatgcaga atctggattt aaatctgtat atttagagca tgtgtgcatg      5160
gttaaagtga gagggaatta agagaggcag gagagg                                5196

<210> SEQ ID NO 22
<211> LENGTH: 10573
<212> TYPE: DNA
<213> ORGANISM: Artificial Sequence
<220> FEATURE:
<223> OTHER INFORMATION: Synthetic primer

<400> SEQUENCE: 22
cttccagaat aaattcatag ggaggcccag gcacagtggc tcacgcctgt aatcccagca        60
ctttgggagg ccgaggcagg cggatcacga ggtcaggaga tggagaccat cctggctaac      120
acggtgaaac cccgtctcta ctaaaaatac aaaaaattag ccgggcgtgg tggcaggtgc      180
ctgtagtccc agctactcgg ggaggctgag gcaggagaac ggcatgaacc caggaggcgg      240
agcttgcagt gaactaagat cacgccactg cactccagcc tgggtgacag agcaagattc      300
catctcaaaa aaaaaaaaa aaaaagaaa ttcataggga aaagaaggtc agagaccaag        360
ggaagggaag gttctgggag aaaagcaggg ggcaggcagg gcccaagaat cctgctgccc      420
atgagccctt actgggaggt ggggtggcct tgcacagggc ccaggcacct gagtgagtgg      480
tggggtcctt acgttcactg ctggggtgag gcaatgagca ccttattgtg tccacatgaa      540
ttcaataaaa aacaagcagg gcgggtggtg gggcactgac taggagggct gatttgtaag      600
ttggtaagac tgtagctctt tttcctaatt agctgaggat gtgtttaggt tccattcaaa      660
aagtgggcat tcctggccag gcatggtggc tcacacctgt aatctcagag ctttgggaga      720
ctgaggtagg aggatcactt gagcccagga atttgagatg agcctaggca acatagtgag      780
actcttatct ctatcaaaaa ataaaaataa aaatgagcca ggcatggtgc ggtggcacgc      840
acctactgct agggggctg aggtgggagg atcacttgag cctgggaggt tgaggctgca      900
gtgatccctg atcacaacat tgcatttcag cctgggtgac agagtgagac cctgtctcag      960 aaaaaaaaa aaaaagtca ttcctgaaac ctcagaatag acctaccttg ccaagggctt       1020
ccttatgggt aaggaccttta tggacctgct gggacccaaa ctaggcctca cctgatacga      1080
cctgtccttc tcaaaacacc taaacttggg agaacattgt cccccagtgc tggggtagga      1140
gagtctgcct gttattctgc ctctatgcag agaaggagcc ccagatcagc ttttccatga      1200
caggacagtt tccaagatgc cacctgtact tggaagaagc caggttaaaa acttttcaa       1260 gtaaaacttt cttgatatta ctctatcttt ccccaggagg actgcattac aacaaattcg      1320
gacacctgtg gcctctccct tctatgcaaa gcaaaaagcc agcagcagcc caagctgat       1380 aagattaatc taaagagcaa attatggtgt aatttcctat gctgaaactt tgtagttaat      1440
tttttaaaaa ggtttcattt tcctattggt ctgatttcac aggaacattt tacctgtttg      1500
tgaggcattt tttctcctgg aagagaggtg ctgattggcc ccaagtgact gacaatctgg      1560
tgtaacgaaa atttccaatg taaactcatt ttccctcggt ttcagcaatt ttaaatctat      1620
atatagagat atctttgtca gcattgcatc gttagcttct cctgataaac taattgcctc      1680
acattgtcac tgcaaatcga cacctattaa tgggtctcac ctcccaactg cttccccctc      1740
tgttcttcct gctagcatgt gccggcaact ttgtccacgg acacaagtgc gatatcacct      1800
tacaggagat catcaaaact ttgaacagcc tcacagagca gaaggtgagt acctatctgg      1860
```

```
caccatctct ccagatgttc tggtgatgct ctcagtattt ctaggcatga aaacgttaac    1920
agctgctaga gaagttggaa ctggtggttg gtggcagtcc agggcacaca gcgaggcttc    1980
tcccctgcca ctcttttttc tgagggtttg taggaagttt cctcagttgg agggagtgag    2040
agctgctcat caaggacttc tctgtccggt tggaggttaa ctctgtctct tgctctctca    2100
tttctgcctg gaccaagact ctgtgcaccg agttgaccgt aacagacatc tttgctgcct    2160
ccaaggtaag aagccgtccc acggtctgtt ttagcaaatg gggagatcca tccccaaatg    2220
tctgaacaag aaacttgtct aatggaaaac gagcgggccc aaattaactc taaggtgtta    2280
gatgttttca agaacgagaa agtctgatct ttactcttaa gcatgttttg gtctttctgg    2340
tttcacttga tttagaagac atgtaataga aagcttacat gctgtagtcc tgactcagat    2400
cctggtcaaa gaaaagccct cttgggtttt acttagcttt ggcatagtgc ctggaacgta    2460
ggaggcactc aataaatgcc tgttgaatga gagaattttt ctggcccata catttctgaa    2520
aaaccaaata ctctcacaga aacagatatt gagatgacag gttgagggag ctttcatttt    2580
gtctaagaga cttcctatgg caacagaaaa ggtatcgcca gagcccctcc tcttccacag    2640
cctggccacc taacagccct ctgggttccg ggctggccg tccagagctc ctcagcttgc    2700 tctgccggc cgaactcccc tccagctcgg tctggaacca tcctgctggg cagcgtccag    2760
cacatccctg cttcgggctg cctgggcacc tcgcctctct gcctcctgtg ctgcctcacc    2820 cccaccccte tatctgtagt gggaggagat agatttgaca gctgatagtg cattttctct    2880
gacaaacaca tgactacagc cgtatcaata gttttgtgca tttcagttcc tgttttcatg    2940
gaaacacacg gctgagaatg aaagccccaa agcctcaatt tcacagtggt ctcctaacta    3000
cctgctttcc atgcaaacta gggagatgat atggccagga gtgaagccct gtgtgttggg    3060
cagggtcaca ctccagcacc cagaccatag aacagggccc atcctgcttc atgagggaaa    3120
ctgctcttcg ggcctttagc tggactatct catttcatta gttatcccgg gagtccgata    3180
caggatgaga ttctgaaggg caaatacaca ctttttttt tttttgagat agggtcttgt    3240
tctgtcaccc aggctggagt gcagtggtgc gatttcagct catagcagcc tccacctccc    3300
aggctcaagc tatcttccta cctcagcctc ccaagtagcc gggacgacag gtgtgcacca    3360
ccacgcctgg ctaattttg tattttttg tagagatgga gtcttgccat tttgcccagg    3420
cttgtctcga acttctgggc tcaagcaatc cgtccacctc ggcctctcaa agtgctggga    3480
ttagccactg cacctgggca acagtttatg tgtgtgtgtg tgtgtgtgtg tgtgtgtata    3540
tatgtgtgtg tgtatatata tgtgtgtatg tatatatgtg tatgtatatg tgtgtgtgtg    3600
tgtgtgtgtg tgtgtataaa atctccaagt ccatccaacc gagatggctc ctactagaag    3660
ccaagagtcc accgggttga gcactggtc tctggaggcc tgtggcactg ctgagaaggc    3720
tctaacaaag ccaagggaag ggccacctca ctagaagcca ggcctggagg aagggtgagg    3780
gctgagggcc tggaggtaag actgcctgtg gttttagacc cagctctgcc actgactagc    3840
tgtgtggctg gccttcagca catcttcaca cctctctgca cctcagtttc cacatgtgaa    3900
gatatgaaag tgattctgaa ggtgattgca aggttgattg aatccagct cttgagttag    3960 tgcaaagtgt tattgtgaga tgatataacc acgattaaaa gcaagaacag gtgcagaaa    4020 gcgatgattc taagaaggag gggaccgggt tggaaaggat caaaccatcc aggatgccga    4080
gtctggggca atccatctgg gctgtttctg gaagaccccc gggtgcaggc caggacactg    4140
ctgccctccc gtccttaact cccctcttca ctcagtcctc actcacctcc ctctcacaca    4200
cacaaacatc tcctagaata atccccactg cctgccttca ctcttacccg tctcatttgc    4260
```

```
ctcccctgaa cttcatcctc ctggagttca cgatctcact cttcactctt ttcttcccct    4320
cgaagattca gcactgctta cttacatgtt aagatatttc agaacagtga aatgttgcta    4380
ttttcaaaaa cctacaaagg tggtatgcag aggaaaaggt acttctttgt gttcccaaag    4440
aaaacatctt tccaaaatcc agcctattga ttttatttct tcggggaac aagaatttta     4500 gtatctctaa gttgggtagc attctactct tggcagttgc tggaaagaag gcactggtct    4560
aggtcctggg cttcacaggt aacacctgtc agggtgtcta tgaagtcaag gctgtctgag    4620
gaacagcaaa gtgggaagaa gcaagctggc tggctgatga agggtttctt gggtggacaa    4680
gtagttggag ctatttccta tttaccaaag agagctaaag ttcataattc tacagagagt    4740
tccataatga acctcaaata cctctgtttt ttgaaggagt ttctcatata cagcactagc    4800
tgactatcct gggcaggatg ggagataatg aatgcagtgc caatcgggct ggatttatat    4860
ggtcctcagt gaggctggtc aagaaccgag ttagaactct cacagagtca ctgccacaga    4920
agaaatctcc caagtggctg tttcctgaca ttcccgggag ggacaggcct ccttctgagt    4980
cactccctaa gcagttctga actgtgaggt cagccaggct gtccaagtgc actccctgag    5040
ccactggcag acacactcag cagccagagc tagacaggca ggtggtagga gtccagggcc    5100
acggcaggga tggagtgtcg ccccctcgct gcgataccag agcaactaaa acgttaaggc    5160
cttgcactaa agctgccctt aggatgcatt cttttaaagt ttttccatt aatgcagact      5220 cttttcaatt cttattttat ccttgtttcc tttagaaagt cctttcaaaa atatctttag    5280
agggtttttt cctatactat gtggccatat acgggtcaaa attaagttta atttccaggc    5340
tccaagccag cgtttcagaa aaatctcacc aaggtttgtg gtaaaagaag caaagggctg    5400 acttttggt tttcttgaat ctcactgttc cctctgcagc agcatgcatg tctgcccacc      5460
tccagacaca caggcaccat ctgccgcccc ccatcagccc gtgtcccttc cacctcgact    5520
cgcctacaaa gcccagagag gtctgttct tggcccccag agcccaaaga tactgacaca     5580
ctcttacatt tccaactaga atcaggaacg aggagtgact ctcagtcagt tcattaagta    5640
aatgtctttc taaccgctct gcccatggga catcacgccc cacaggggaa aggggaagct    5700
tctgtagcct gggattctgg tgcctcagtc tgggtctaga cttccctgaa aaaacgttaa    5760
aatatgaact gcattcctag aatttagcct acataaataa gagatgaaca caaagatttc    5820
tatagtttac tcactgccgc ttatttacag aagcaaaaat ctgccacgat aggggcctga    5880
caaatgacag taccactgtg caatgcgttt ctacgcagct ctcaatccca tgttctctaa    5940
taccaccgaa gggcttagga aatgcttatg gtatatgtaa agagtaaaga agttacaaaa    6000
cagtatcaac agttgacccc tattttaaaa agtattttta aaagtgtgac gatatttacc    6060
aaaatattaa cagcaatagt tacctctggc tggtgggatg agtgaatgta ttttgttga     6120 atatatgtta cctttatagt aaatatatgt tatcttgatc atcagaaaaa aaaatatgta    6180
agaacttgaa agctgcttgg acagcgctgc tgatagaaac ccctgagcat cttgtcactg    6240
ttcttctgat tcagagggtc tgggtgggc aggggtggtc tgagattctg tatttctaag      6300
aagctcccag tgatgtccat gctgctggtc catggaccac actttgagta tcaagggacc    6360
agagcatgtc gggggagagg ctgggatag cttttcttat ctgaactgga taaggaact       6420 gggctcaagc taagaaccct ctccaggttc tgcatctttg ttcttcagtg aaaaatgaga    6480
ggacacacca ggccaggttc agactgagac acaatccctc tcctgggttc ccaatgactt    6540
gtctcttgtc cattcccttc tctaaggcta agggcccca ggaagagcca tgtggccaga      6600
```

```
ccctcacagt tgctggcatt ccaaggagat tctcactccg catcatttgg ggccaaaagg    6660 cccccttacag aagctctgcc caaggctcag atcaatggca cctgctccca gagcctcctc   6720
tgatctccca ggacacctttt ccctgatctg tgcacttatc tcttgctgcc tggcaaaatg   6780
tcttagctcc tcacttgggc catgtgctgc tctcctctcc catggggaga gccacacgga   6840
gagtgctggc caaagcagca gagttcaggc caaaggatgt gcactcattt attcaacagg    6900
catgcaggat ttccagggaa agctggatttt taaaacctct gggaacaaga gcagaacctg   6960
actgagagct catgtgggca cttttcatag cagaatagct catgaggtat agagacacgg    7020
acgcagaacg tgggctgtag cgacagatgg tcctgcattc tagtccccac tgtgcctttt    7080
cctcatggga tgactttatt caggtaccct ttcggcaaaa tcctccaaga gaaaggaaac    7140
tgggaggttc tggggagaag gctgctgcgt ttgcaattgg gagaggttgt tgacagaggt    7200
ttatgtctgt ggcaagcagc cttccttcag tggaatactt gaagacaggt ctgtagttga    7260
gcaaactcac ctccatttgt cctcctggaa agaagaaatc aagaggaaaa atctctctcc    7320
catcctccaa atggagctgg cacattgcta tctgtggcat ttgtctttcc agaacacaac    7380
tgagaaggaa accttctgca gggctgcgac tgtgctccgg cagttctaca gccaccatga    7440
gaaggacact cgctgcctgg gtgcgactgc acagcagttc cacaggcaca agcagctgat    7500
ccgattcctg aaacggctcg acaggaacct ctggggcctg gcgggcttgg taagctgcac    7560
tgtattcctg gcaagccggc cgcgtggctc ctggtggaca gcagcctcac ttctaaacac    7620
tccttaggag ctgcagcacc cttggtcaac ccattcattc attcactcat tcaataagta    7680
tttgctgaag ttccacaagt gctgggtgtg gttctaggtg ctgaggacgt gtcactaaag    7740
acacgcaggc cgagtccctg ttctcatgga atgttctaat gggagagtta gaaaacaaa    7800 catgtaaaat gatggccagc agtgatacgt gctacaaaga aaaacataga aataaagaac   7860
ataagagtca tgggggaggg ggctgactta ggagctggtg acattatctg agcagatatt   7920
tgaattgagg gagcaggcca catgactaac taggagacc attccaggca gaaggaggag    7980
gtatgcaaag gccttaggat ggaaatgaac taacttcctg tatttaaaga ccagtaggaa    8040
ggccagtgtg gctggatcag agtgagtgag gggtagtttc caggacagca gatcacacaa   8100
ggcctttaga ttccaccacg agtatggcag ggaacacctg cagagctttg gcaggacaa    8160 agactgtaca atctgattta cgtgatttaa aagggtcagt ctggctactg tgtggtaaat   8220
aggctgaaag ggggaaagca tagaagcaag atggcctgtt gggaggctac cacagtaaac   8280
caggctagag atgatggtgg cgtggacaga atgaagcaag atggcctgtt gggaggctac   8340
cacagtaaac caggctagag acgatggtgg cgtggacaga atgaagcaag atggcctgtt   8400
gggaggctac cacagtaaac caggctagag atgatggtgg cgtggacaga atgggagcag   8460
ttgaggtgaa cagatttggg atatgactaa aaataaaacc agaaggattt gctgacagat   8520
cggttgtagg gggtaagata caggggagga aaagatgacc tctttgttcc tgcccaaacc   8580
cctctggcga tggtcagtac tgtttacaga gagatgaaag actggcggca aggcagggct   8640
ggaggttcag cagaagatca agagttcaat tttgtacatc gtacatgtaa ggtggctctt   8700
ggatagccaa gtgaaggtgt tgagaagatg gttagaaaag tctggaactt aggggagagg   8760
tcagaacttg caatacaaaa aggagagtcc ttagatagat actgctgaaa atctgaatga   8820
cagaaaggga gagatcaaag gactgagcct gagatcaaca catggaggtc aggagaggag   8880
gatccagcca aggggcctga ggaggagtga ccagtgaggc aggagaacac tggagagtgg   8940
gcggtacccc aggaagccgt tgaggacact caaggaggga gggttgactg tgtcaaatgt    9000
```

```
actgaaagga caggtcaggt gaggaccaag aaaggcccct gggtttggct gatggaggcc   9060
atgggtgagg ctgatgtaaa tggagaggca ggaaggaaag cccagctgga gtgggctcac   9120
cgaggatagg gtggcgagag gagacaaaga aggaacagtg agggcagaac actctttgaa   9180
gatgtttagc tataaggctg cagagaaact gacccacagc tgcagggtgg ttatggagtg   9240
agggaagctc ttttaaggtt gggggtatac ccagcatgtt aatgcacctg ggggaatggt   9300
ccagtggagc aggaagaact gaagagagca gaaagaggaa gaatcattag ggggcagaag   9360
tccttgtagc ccagagtgga tgttatctaa tatcgagtgg aggaattaat tggctttaga   9420
ggagaacaag gacatgtatc ccctctctgg gcctatcacc ttgtagacaa tgggataggt   9480
catgggatag gaacttggca caacacatgt tctctctttt aattctctcc attatcttat   9540
gaagcaggca gtaggcaaa caattgtccc aactttacaa agaaactga agcttttata    9600 aattaagtag tacatcctaa gcaatacaat taataaatgg tagagctgag attcaaactg   9660
aagcagtggc ctgggggtag catctggaat ccttcccacc tttagggctg ctgtgctgcg   9720
gtgctgctgt ttaatggcac aggagggcca catgactgaa tctctctcag cagtccaggc   9780
agtcatgcag aaggcccagt agagcaccgg gcaggtctga gccagcatct tcaagttcca   9840
ccctctgagc aagcacctag ctgtgacaca cctctccaga gactgcactc ccccccgcgc   9900
cacccacccc aaaagcagat aggtaatggt atacagtaac catttctaga agtgtaagta   9960
gtatgcaccc aaaataggca aaacctgctg gcctagtgat agagacaact cccagtcagg  10020
ctagactgga ggccttggtt ttataagtgt tcaggtgaca agtgccacag taggcttgat  10080
caagtagaca ggcaggcaag acaaatgctt accaatgcaa gctaatgaaa tgtttctttt  10140
gcagaattcc tgtcctgtga aggaagccaa ccagagtacg ttggaaaact tcttggaaag  10200
gctaaagacg atcatgagag agaaatattc aaagtgttcg agctgaatat tttaatttat  10260
gagtttttga tagctttatt ttttaagtat ttatatattt ataactcatc ataaaataaa  10320
gtatatatag aatctaacag caatggcatt taatgtattg gctatgttta cttgacaaat  10380
gaaattatgg tttgcaactt ttagggaaat caatttagtt taccaagaga ctataaatgc  10440
tatgggagca aaacaggaaa gaccacttcc ccctcgaggg gttccctctc gagttaggga  10500
cataacacac aagataatta aagaacacaa ggccatacaa gatgtaaata agacaccttg  10560
ggtccaagag tgc                                                     10573

<210> SEQ ID NO 23
<211> LENGTH: 145
<212> TYPE: DNA
<213> ORGANISM: Artificial Sequence
<220> FEATURE:
<223> OTHER INFORMATION: Synthetic primer

<400> SEQUENCE: 23
tggggtatgg tggcttatat ctgtaacttc aacacttgag aggtggaggc aggagagtga    60
ccatgaatct gagggcttcc agaataaatt catagggagg cccaggcaca gtggctcacg   120
cctgtaatcc cagcactttg ggagg                                         145

<210> SEQ ID NO 24
<211> LENGTH: 196
<212> TYPE: DNA
<213> ORGANISM: Artificial Sequence
<220> FEATURE:
<223> OTHER INFORMATION: Synthetic primer
```

<400> SEQUENCE: 24
ggggttccct ctcgagttag ggacataaca cacaagataa ttaaagaaca caaggccata    60
caagatgtaa ataagacacc ttgggtccaa gagtgcgtcg acggtatcga taagcttgat   120
atcgaattcc gaagttccta ttctctagaa agtataggaa cttcaggtct gaagaggagt   180
ttacgtccag ccaagc                                                  196

<210> SEQ ID NO 25
<211> LENGTH: 150
<212> TYPE: DNA
<213> ORGANISM: Artificial Sequence
<220> FEATURE:
<223> OTHER INFORMATION: Synthetic primer

<400> SEQUENCE: 25
tgcggaaccc ttcgaagttc ctattctcta gaaagtatag gaacttcatc agtcaggtac    60
ataatggtgg atcctaactc aagttctggg ggagctgatg ctctcctctg gcctcctgtg   120
gaggtacaca gaccacatgc ctgtaggcaa                                   150

<210> SEQ ID NO 26
<211> LENGTH: 24
<212> TYPE: DNA
<213> ORGANISM: Artificial Sequence
<220> FEATURE:
<223> OTHER INFORMATION: Synthetic primer

<400> SEQUENCE: 26
ctgtgatcat ggttccttat ctgg                                          24

<210> SEQ ID NO 27
<211> LENGTH: 23
<212> TYPE: DNA
<213> ORGANISM: Artificial Sequence
<220> FEATURE:
<223> OTHER INFORMATION: Synthetic primer

<400> SEQUENCE: 27
cctccccgag tagctgggac tac                                           23

<210> SEQ ID NO 28
<211> LENGTH: 25
<212> TYPE: DNA
<213> ORGANISM: Artificial Sequence
<220> FEATURE:
<223> OTHER INFORMATION: Synthetic primer

<400> SEQUENCE: 28
ccactagggg tccacagcta gtcat                                         25

<210> SEQ ID NO 29
<211> LENGTH: 25
<212> TYPE: DNA
<213> ORGANISM: Artificial Sequence
<220> FEATURE:
<223> OTHER INFORMATION: Synthetic primer

<400> SEQUENCE: 29
cttcagtgaa acctcctgag cctgg                                         25

<210> SEQ ID NO 30
<211> LENGTH: 25
<212> TYPE: DNA
<213> ORGANISM: Artificial Sequence
<220> FEATURE:
<223> OTHER INFORMATION: Synthetic primer

<400> SEQUENCE: 30
agtcagagct acagaagtgg agggt                                          25

<210> SEQ ID NO 31
<211> LENGTH: 25
<212> TYPE: DNA
<213> ORGANISM: Artificial Sequence
<220> FEATURE:
<223> OTHER INFORMATION: Synthetic primer

<400> SEQUENCE: 31
ctgctctgca ggaagtaagg gttcc                                          25

<210> SEQ ID NO 32
<211> LENGTH: 24
<212> TYPE: DNA
<213> ORGANISM: Artificial Sequence
<220> FEATURE:
<223> OTHER INFORMATION: Synthetic primer

<400> SEQUENCE: 32
ccacatcact gaaagacttc ctgg                                           24

<210> SEQ ID NO 33
<211> LENGTH: 25
<212> TYPE: DNA
<213> ORGANISM: Artificial Sequence
<220> FEATURE:
<223> OTHER INFORMATION: Synthetic primer

<400> SEQUENCE: 33
gatcaagtag acaggcaggc aagac                                          25

<210> SEQ ID NO 34
<211> LENGTH: 24
<212> TYPE: DNA
<213> ORGANISM: Artificial Sequence
<220> FEATURE:
<223> OTHER INFORMATION: Synthetic primer

<400> SEQUENCE: 34
ctgtgatcat ggttccttat ctgg                                           24

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35
agggacagat gcaggctggg                                                20

<210> SEQ ID NO 36
<211> LENGTH: 25
<212> TYPE: DNA
<213> ORGANISM: Artificial Sequence
<220> FEATURE:
<223> OTHER INFORMATION: Synthetic primer

<400> SEQUENCE: 36
gagatgcgtg ttagaggttt tggga                                          25

<210> SEQ ID NO 37
<211> LENGTH: 26
<212> TYPE: DNA
<213> ORGANISM: Artificial Sequence
<220> FEATURE:
<223> OTHER INFORMATION: Synthetic primer

<400> SEQUENCE: 37
tcagcgatat taagaacgtt gatccg                                        26

<210> SEQ ID NO 38
<211> LENGTH: 27
<212> TYPE: DNA
<213> ORGANISM: Artificial Sequence
<220> FEATURE:
<223> OTHER INFORMATION: Synthetic primer

<400> SEQUENCE: 38
tgaagaattg ccggtcctat ttactcg                                       27

<210> SEQ ID NO 39
<211> LENGTH: 5122
<212> TYPE: DNA
<213> ORGANISM: Mouse

<400> SEQUENCE: 39
cttctcgcag gaaagccccg cgcggcgcgt ggagcctgaa ctcgcaggtt ctggctggac      60
ttctcgaagc tgaggagaag cagagggacc tggcttctga ttttggatct gcgtgcttgc     120
tggttctggc gcctgctggt cttgttcctg taacctagga ctcggggctt gcacatgctt     180
tttttttgaa gttgctggag agggagccca ggaccttgtg caggcacctt ttgtgtcccc     240
aatggggcgg ctttgcacca agttcctgac ctctgtgggc tgtctgattt tgctgttggt     300
gactggatct gggagcatca aggtcctggg tgagcccacc tgcttctctg actacatccg     360
cacttccacg tgtgagtggt tcctggatag cgctgtggac tgcagttctc agctctgcct     420
acactacagg ctgatgttct tcgagttctc tgaaaacctc acatgcatcc cgaggaacag     480
tgccagcact gtgtgtgtgt gccacatgga aatgaatagg ccggtccaat cagacagata     540
ccagatggaa ctgtgggctg agcacagaca gctgtggcag ggctccttca gccccagtgg     600
taatgtgaag cccctagctc cagacaacct cacactccac accaatgtgt ccgacgaatg     660
gctgctgacc tggaataacc tgtacccatc gaacaactta ctgtacaaag acctcatctc     720
catggtcaac atctccagag aggacaaccc tgcagaattc atagtctata atgtgaccta     780
caaggaaccc aggctgagct cccgatcaa catcctgatg tcaggggtct actatacggc     840
gcgtgtgagg gtcagatccc agatactcac tggcacctgg agtgagtgga gtcctagcat     900
cacgtggtac aaccacttcc agctgccct gatacagcgc cttccactgg gggtcaccat     960
ctcctgcctc tgcatcccgt tgttttgcct gttctgttac ttcagcatta ccaagattaa    1020
gaagatatgg tgggaccaga ttcccacccc agcacgcagt cccttggtgg ccatcatcat    1080
tcaggatgca caggtgcccc tctgggataa gcagaccga agccaggagt caaccaagta    1140
cccgcactgg aaaacttgtc tagacaagct gctgccttgc ttgctgaagc acagagtaaa    1200
gaagaagaca gacttcccga aggctgcccc aaccaagtct ctccagagtc ctggaaaggc    1260
aggctggtgt cccatggagg tcagcaggac cgtcctctgg ccagagaatg ttagtgtcag    1320
tgtggtgcgc tgtatggagc tgtttgaggc cccagtacag aatgtggagg aggaagaaga    1380
tgagatagtc aaagaggacc tgagcatgtc acctgagaac agcggaggct gcggcttcca    1440

-continued

```
ggagagccag gcagacatca tggctcggct cactgagaac ctgttttccg acttgttgga    1500
ggctgagaat gggggccttg gccagtcagc cttggcagag tcatgctccc ctctgccttc    1560
aggaagtggg caggcttctg tatcctgggc ctgcctcccc atggggccca gtgaggaggc    1620
cacatgccag gtcacagagc agccttcaca cccaggccct ctttcaggca gcccagccca    1680
gagtgcacct actctggctt gcacgcaggt cccacttgtc cttgcagaca atcctgccta    1740
ccggagtttt agtgactgct gtagcccggc cccaaatcct ggagagctgg ctccagagca    1800
gcagcaggct gatcatctgg aagaagagga gcctccaagc ccggctgacc cccattcttc    1860
agggccacca atgcagccag tggagagctg ggagcagatc cttcacatga gtgtcctgca    1920
gcatggggca gctgctggct ccaccccagc ccctgccggt ggctaccagg agtttgtgca    1980
ggcagtgaag caggtgccg cccaggatcc tggggtgcct ggtgtcaggc cttctggaga    2040
ccccggttac aaggccttct cgagcctgct cagcagcaat ggcatccgcg ggacacagc    2100
agcagcgggg actgacgatg gcatggagg ctacaagccc ttccagaatc ctgttcctaa    2160
ccagtcccct agctccgtgc ccttatttac tttcggacta gacacggagc tgtcacccag    2220
tcctctgaac tcagacccac ccaaaagccc cccagaatgc cttggtctgg agctggggct    2280
caaaggaggt gactgggtga aggcccctcc tcctgcagat caggtgccca gccctttgg    2340
ggatgacctg ggctttggta ttgtgtactc gtccctcact tgccacttgt gtggccacct    2400
gaagcaacac cacagccagg aggaaggtgg ccagagcccc atcgttgcta gccctggctg    2460
tggctgctgc tacgatgaca gatcaccatc cctggggagc ctctcggggg ccttggaaag    2520
ctgtcctgag ggaataccac cagaagccaa cctcatgtca gcacccaaga caccctcaaa    2580
cttgtcaggg gagggcaagg gccctggtca ctctcctgtt cccagccaga cgaccgaggt    2640
gcctgtgggc gccctgggca ttgctgtttc ttaggtgagt gagtgtgctg ttgttgctga    2700
ggtctgtgct gaggccaggg ttcctccaag ccagggaagt acttcctggg agacagccca    2760
gctggcaggt ttcccagaaa tccagagaat ggtgaattga agatgtaaac ttggcctgac    2820
cctggacgct cggagcctgg ctgtctcctc ttccactggc ctgggctctc ctccctccca    2880
agggatacag gggctcactg tgcttggtcc cacagcagtg ctgacgttcc taagtcctgg    2940
gctttcctag ctgatgttgt cctacctact cagtcccatt ttgtccaccg aatagacctg    3000
tcactcaagg ctctcagcgg tcctgccata gctgctggac gctcccagct ggaagctggg    3060
cctagaaact cacagatggc ctggcagtgg catgggaggc cctaaaaatt agtggaaatt    3120
ttgagagagg acaggtattg ccccacagag gccattcatt gaacagccag gactgggact    3180
agaggcagag cctgctgtcc tccgctcagt tgtagaaagc aacaaggaca caaacttgat    3240
tgcccaaagt cactgccagt tacccacata tgaccagaag ccagggctcc tgggatgtgg    3300
aagataaaca aacacagttg ccgggtggca gggcccagcg ggcacgataa ctggcagtca    3360
aggcgatacc tcgagggaac tgtggggctg gtcctggttg gtggtcaggt ggtaggata    3420
gcagatggca gactttggtg agtgagtgag tctgactgtg ttctggaaga tgggaccggg    3480
ctcagcactg tctgctcacg tccccactgt tgcaacacct agtctgtttg caaggaggac    3540
aggacaggtc acatggagct ttatgtcaat aaagtcttta tcttgtcagg tttcctttac    3600
tatacacacg ccgagcccac agtgcacgaa agctgaaatg tgcaggcagg gggttgggga    3660
agtggggaga caaggcccca gcagttggtt taagggaatg acttgggaat ggggcagagc    3720
tgtggctact ccatctctca tccttaccct cctgctacca cagcttgtgc ccatgtgtgc    3780
```

```
ctgctcaggg gaggggtcct cctctttccc tctcctttag gcagagtgct agaggtgttg    3840
gatgctcctt agcacgcaga gggcgtgaca ctggctgcta agtgttgttg aatgtgtcaa    3900
ggcattgaca tcagtaggcc ccacatctta ggcaggggat ttggggtgtg caacctgcc    3960
aggccagcag agaacttgaa tatgatgttc agaaggaaag acagagacag gtcacttagg    4020
gaggcttgaa ggaggccact tttgagatga gcccgtggta tctgcaaaaa agcctggaag    4080
aactcagaac atgcagcaga tggctcatgt ctgaagtttg aggcacaggg atctggtgtg    4140
gtcacagcat cagagagaag ggtcctggca tgatggggac tggtgtgcag ttggatactg    4200
gtattctgcc ttagttctgc ctcttgagag gtggtccagt agaagccagc ctcagacttt    4260
cacatctcag aacagtcttt tcaaagacaa ggtctcagtg tggctcagac gggcctctag    4320
catcactcgg tctcctgagt gctgggatca caggtgtgtg ctactacacc cagcttccca    4380
gagcagtctt accacagccc ctaagcaggg gaggagagga aacggagcca tccaagatct    4440
acctcctgtg ggcatccctc ctgcctggct gaaggagaag tctgggttta aaatccccat    4500
tgctcagatt tgtatcctgg agggaagtga ctcccacagg aatgaactga ctgtcccagg    4560
aaattcttcc cgctgtgcct ttagaacttc ctctgtaaag tacctccctt cagctggtgg    4620
tgcctgtctt taacagtggc tgacagccag ggagtttgag gctagcctag gctttgacag    4680
tgagatcctg ttcaataaac gcagcttccc agtccggcac ttgaccttca agctctgacc    4740
tctggattag cccaggattt cttcactggt cctccacctt ccaccccctt ccactgctta    4800
tacccgctcc catcatttcc aacccaggaa gctgctaaga tctatgtggt agccctggct    4860
ccattaccac cctctcccca tctcctgggt gactgaggga actaaggtac aagcccgagg    4920
aacttgggat tccctgccct gctgttacct tgcctcctgt ctgccatcat taacatagga    4980
ggtgccagcc tgtgccgtcc tggctcccat actcactacc taaggctacc tgttgggaat    5040
tccaaccctc accagtccca tctcttcatt ctattaaaat tacttatcaa gcaaaaaaaa    5100
aaaaaaaaaa aaaaaaaaaa aa                                             5122
```

<210> SEQ ID NO 40
<211> LENGTH: 810
<212> TYPE: PRT
<213> ORGANISM: Mouse

<400> SEQUENCE: 40

```
Met Gly Arg Leu Cys Thr Lys Phe Leu Thr Ser Val Gly Cys Leu Ile
1               5                   10                  15

Leu Leu Leu Val Thr Gly Ser Gly Ser Ile Lys Val Leu Gly Glu Pro
            20                  25                  30

Thr Cys Phe Ser Asp Tyr Ile Arg Thr Ser Thr Cys Glu Trp Phe Leu
        35                  40                  45

Asp Ser Ala Val Asp Cys Ser Ser Gln Leu Cys Leu His Tyr Arg Leu
    50                  55                  60

Met Phe Phe Glu Phe Ser Glu Asn Leu Thr Cys Ile Pro Arg Asn Ser
65                  70                  75                  80

Ala Ser Thr Val Cys Val Cys His Met Glu Met Asn Arg Pro Val Gln
                85                  90                  95

Ser Asp Arg Tyr Gln Met Glu Leu Trp Ala Glu His Arg Gln Leu Trp
            100                 105                 110

Gln Gly Ser Phe Ser Pro Ser Gly Asn Val Lys Pro Leu Ala Pro Asp
        115                 120                 125

Asn Leu Thr Leu His Thr Asn Val Ser Asp Glu Trp Leu Leu Thr Trp
```

```
            130                 135                 140
Asn Asn Leu Tyr Pro Ser Asn Asn Leu Leu Tyr Lys Asp Leu Ile Ser
145                 150                 155                 160

Met Val Asn Ile Ser Arg Glu Asp Asn Pro Ala Glu Phe Ile Val Tyr
                165                 170                 175

Asn Val Thr Tyr Lys Glu Pro Arg Leu Ser Phe Pro Ile Asn Ile Leu
            180                 185                 190

Met Ser Gly Val Tyr Tyr Thr Ala Arg Val Arg Val Arg Ser Gln Ile
            195                 200                 205

Leu Thr Gly Thr Trp Ser Glu Trp Ser Pro Ser Ile Thr Trp Tyr Asn
            210                 215                 220

His Phe Gln Leu Pro Leu Ile Gln Arg Leu Pro Leu Gly Val Thr Ile
225                 230                 235                 240

Ser Cys Leu Cys Ile Pro Leu Phe Cys Leu Phe Cys Tyr Phe Ser Ile
                245                 250                 255

Thr Lys Ile Lys Lys Ile Trp Trp Asp Gln Ile Pro Thr Pro Ala Arg
                260                 265                 270

Ser Pro Leu Val Ala Ile Ile Gln Asp Ala Gln Val Pro Leu Trp
            275                 280                 285

Asp Lys Gln Thr Arg Ser Gln Glu Ser Thr Lys Tyr Pro His Trp Lys
            290                 295                 300

Thr Cys Leu Asp Lys Leu Leu Pro Cys Leu Leu Lys His Arg Val Lys
305                 310                 315                 320

Lys Lys Thr Asp Phe Pro Lys Ala Ala Pro Thr Lys Ser Leu Gln Ser
                325                 330                 335

Pro Gly Lys Ala Gly Trp Cys Pro Met Glu Val Ser Arg Thr Val Leu
            340                 345                 350

Trp Pro Glu Asn Val Ser Val Ser Val Val Arg Cys Met Glu Leu Phe
            355                 360                 365

Glu Ala Pro Val Gln Asn Val Glu Glu Glu Asp Glu Ile Val Lys
            370                 375                 380

Glu Asp Leu Ser Met Ser Pro Glu Asn Ser Gly Gly Cys Gly Phe Gln
385                 390                 395                 400

Glu Ser Gln Ala Asp Ile Met Ala Arg Leu Thr Glu Asn Leu Phe Ser
                405                 410                 415

Asp Leu Leu Glu Ala Glu Asn Gly Gly Leu Gly Gln Ser Ala Leu Ala
            420                 425                 430

Glu Ser Cys Ser Pro Leu Pro Ser Gly Ser Gly Gln Ala Ser Val Ser
            435                 440                 445

Trp Ala Cys Leu Pro Met Gly Pro Ser Glu Glu Ala Thr Cys Gln Val
450                 455                 460

Thr Glu Gln Pro Ser His Pro Gly Pro Leu Ser Gly Ser Pro Ala Gln
465                 470                 475                 480

Ser Ala Pro Thr Leu Ala Cys Thr Gln Val Pro Leu Val Leu Ala Asp
                485                 490                 495

Asn Pro Ala Tyr Arg Ser Phe Ser Asp Cys Cys Ser Pro Ala Pro Asn
                500                 505                 510

Pro Gly Glu Leu Ala Pro Glu Gln Gln Ala Asp His Leu Glu Glu
            515                 520                 525

Glu Glu Pro Pro Ser Pro Ala Asp Pro His Ser Ser Gly Pro Pro Met
            530                 535                 540

Gln Pro Val Glu Ser Trp Glu Gln Ile Leu His Met Ser Val Leu Gln
545                 550                 555                 560
```

His Gly Ala Ala Ala Gly Ser Thr Pro Ala Pro Ala Gly Gly Tyr Gln
            565                 570                 575

Glu Phe Val Gln Ala Val Lys Gln Gly Ala Ala Gln Asp Pro Gly Val
        580                 585                 590

Pro Gly Val Arg Pro Ser Gly Asp Pro Gly Tyr Lys Ala Phe Ser Ser
    595                 600                 605

Leu Leu Ser Ser Asn Gly Ile Arg Gly Asp Thr Ala Ala Ala Gly Thr
610                 615                 620

Asp Asp Gly His Gly Gly Tyr Lys Pro Phe Gln Asn Pro Val Pro Asn
625                 630                 635                 640

Gln Ser Pro Ser Ser Val Pro Leu Phe Thr Phe Gly Leu Asp Thr Glu
            645                 650                 655

Leu Ser Pro Ser Pro Leu Asn Ser Asp Pro Pro Lys Ser Pro Pro Glu
        660                 665                 670

Cys Leu Gly Leu Glu Leu Gly Leu Lys Gly Gly Asp Trp Val Lys Ala
    675                 680                 685

Pro Pro Pro Ala Asp Gln Val Pro Lys Pro Phe Gly Asp Asp Leu Gly
690                 695                 700

Phe Gly Ile Val Tyr Ser Ser Leu Thr Cys His Leu Cys Gly His Leu
705                 710                 715                 720

Lys Gln His His Ser Gln Glu Glu Gly Gly Gln Ser Pro Ile Val Ala
            725                 730                 735

Ser Pro Gly Cys Gly Cys Cys Tyr Asp Asp Arg Ser Pro Ser Leu Gly
        740                 745                 750

Ser Leu Ser Gly Ala Leu Glu Ser Cys Pro Glu Gly Ile Pro Pro Glu
    755                 760                 765

Ala Asn Leu Met Ser Ala Pro Lys Thr Pro Ser Asn Leu Ser Gly Glu
770                 775                 780

Gly Lys Gly Pro Gly His Ser Pro Val Pro Ser Gln Thr Thr Glu Val
785                 790                 795                 800

Pro Val Gly Ala Leu Gly Ile Ala Val Ser
            805                 810

<210> SEQ ID NO 41
<211> LENGTH: 3710
<212> TYPE: DNA
<213> ORGANISM: human

<400> SEQUENCE: 41
gggtctccgc gcccaggaaa gccccgcgcg gcgcgggcca gggaagggcc acccaggggt    60
cccccacttc ccgcttgggc gcccggacgg cgaatggagc aggggcgcgc agataattaa   120
agatttacac acagctggaa gaaatcatag agaagccggg cgtggtggct catgcctata   180
atcccagcac ttttggaggc tgaggcgggc agatcacttg agatcaggag ttcgagacca   240
gcctggtgcc ttggcatctc ccaatggggt ggctttgctc tggctcctg ttccctgtga    300 gctgcctggt cctgctgcag gtggcaagct ctgggaacat gaaggtcttg caggagccca   360
cctgcgtctc cgactacatg agcatctcta cttgcgagtg aagatgaat ggtcccacca    420 attgcagcac cgagctccgc ctgttgtacc agctggtttt tctgctctcc gaagcccaca   480
cgtgtatccc tgagaacaac ggaggcgcgg ggtgcgtgtg ccacctgctc atggatgacg   540
tggtcagtgc ggataactat acactggacc tgtgggctgg gcagcagctg ctgtggaagg   600
gctccttcaa gcccagcgag catgtgaaac ccagggcccc aggaaacctg acagttcaca   660

```
ccaatgtctc cgacactctg ctgctgacct ggagcaaccc gtatccccct gacaattacc   720
tgtataatca tctcacctat gcagtcaaca tttggagtga aaacgacccg gcagatttca   780
gaatctataa cgtgacctac ctagaaccct ccctccgcat cgcagccagc accctgaagt   840 ctggatttc ctacagggca cgggtgaggg cctgggctca gtgctataac accacctgga    900
gtgagtggag ccccagcacc aagtggcaca actcctacag ggagcccttc gagcagcacc   960
tcctgctggg cgtcagcgtt tcctgcattg tcatcctggc cgtctgcctg ttgtgctatg   1020
tcagcatcac caagattaag aaagaatggt gggatcagat tcccaaccca gcccgcagcc   1080
gcctcgtggc tataataatc caggatgctc aggggtcaca gtgggagaag cggtcccgag   1140
gccaggaacc agccaagtgc ccacactgga agaattgtct taccaagctc ttgccctgtt   1200
ttctggagca acatgaaa agggatgaag atcctcacaa ggctgccaaa gagatgcctt     1260
tccagggctc tggaaaatca gcatggtgcc cagtggagat cagcaagaca gtcctctggc  1320
cagagagcat cagcgtggtg cgatgtgtgg agttgtttga ggccccggtg gagtgtgagg   1380
aggaggagga ggtagaggaa gaaaaaggga gcttctgtgc atcgcctgag agcagcaggg   1440
atgacttcca ggagggaagg gagggcattg tggcccggct aacagagagc ctgttcctgg   1500
acctgctcgg agaggagaat gggggctttt gccagcagga catgggggag tcatgccttc   1560
ttccaccttc gggaagtacg agtgctcaca tgccctggga tgagttccca agtgcagggc   1620
ccaaggaggc acctccctgg ggcaaggagc agcctctcca cctggagcca agtcctcctg   1680
ccagcccgac ccagagtcca gacaacctga cttgcacaga gacgcccctc gtcatcgcag   1740
gcaaccctgc ttaccgcagc ttcagcaact ccctgagcca gtcaccgtgt cccagagagc   1800
tgggtccaga cccactgctg gccagacacc tggaggaagt agaacccgag atgccctgtg   1860 tccccagct ctctgagcca accactgtgc cccaacctga gccagaaacc tgggagcaga    1920
tcctccgccg aaatgtcctc agcatggggc agctgcagc cccgtctcg gccccccacca    1980 gtggctatca ggagtttgta catgcggtgg agcagggtgg cacccaggcc agtgcggtgg   2040
tgggcttggg tcccccagga gaggctggtt acaaggcctt ctcaagcctg cttgccagca   2100
gtgctgtgtc cccagagaaa tgtgggtttg ggctagcag tggggaagag gggtataagc    2160 cttttccaaga cctcattcct ggctgccctg ggaccctgc cccagtccct gtcccccttgt  2220 tcacctttgg actggacagg gagccacctc gcagtccgca gagctcacat ctcccaagca   2280
gctccccaga gcacctgggt ctggagccgg gggaaaaggt agaggacatg ccaaagcccc   2340 cacttccca ggagcaggcc acagacccc ttgtggacag cctgggcagt ggcattgtct     2400
actcagccct tacctgccac ctgtgcggcc acctgaaaca gtgtcatggc caggaggatg   2460
gtggccagac ccctgtcatg gccagtcctt gctgtggctg ctgctgtgga gacaggtcct   2520
cgccccctac aacccccctg agggcccag accctctcc aggtggggt ccactggagg      2580 ccagtctgtg tccggcctcc ctggcaccct cgggcatctc agagaagagt aaatcctcat   2640
catccttcca tcctgcccct ggcaatgctc agagctcaag ccagaccccc aaaatcgtga   2700
actttgtctc cgtgggaccc acatacatga gggtctctta ggtgcatgtc ctcttgttgc   2760
tgagtctgca gatgaggact agggcttatc catgcctggg aaatgccacc tcctggaagg   2820
cagccaggct ggcagatttc caaaagactt gaagaaccat ggtatgaagg tgattggccc   2880
cactgacgtt ggcctaacac tgggctgcag agactggacc ccgccagca ttgggctggg    2940 ctcgccacat cccatgagag tagagggcac tgggtcgccg tgcccacgg caggcccctg    3000 caggaaaact gaggcccttg ggcacctcga cttgtgaacg agttgttggc tgctccctcc   3060
```

-continued

```
acagcttctg cagcagactg tccctgttgt aactgcccaa ggcatgtttt gcccaccaga    3120
tcatggccca cgtggaggcc cacctgcctc tgtctcactg aactagaagc cgagcctaga    3180
aactaacaca gccatcaagg gaatgacttg ggcggccttg ggaaatcgat gagaaattga    3240
acttcaggga gggtggtcat tgcctagagg tgctcattca tttaacagag cttccttagg    3300
ttgatgctgg aggcagaatc ccggctgtca aggggtgttc agttaagggg agcaacagag    3360
gacatgaaaa attgctatga ctaaagcagg gacaatttgc tgccaaacac ccatgcccag    3420
ctgtatggct gggggctcct cgtatgcatg gaaccccag aataaatatg ctcagccacc     3480
ctgtgggccg gcaatccag acagcaggca taaggcacca gttaccctgc atgttggccc     3540
agacctcagg tgctagggaa ggcgggaacc ttgggttgag taatgctcgt ctgtgtgttt    3600
tagtttcatc acctgttatc tgtgtttgct gaggagagtg gaacagaagg ggtggagttt    3660
tgtataaata aagtttcttt gtctctttaa aaaaaaaaaa aaaaaaaaa              3710
```

<210> SEQ ID NO 42
<211> LENGTH: 825
<212> TYPE: PRT
<213> ORGANISM: human

<400> SEQUENCE: 42

```
Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Cys Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln His Leu Leu Leu Gly Val Ser Val Ser
225                 230                 235                 240

Cys Ile Val Ile Leu Ala Val Cys Leu Leu Cys Tyr Val Ser Ile Thr
                245                 250                 255
```

-continued

```
Lys Ile Lys Lys Glu Trp Trp Asp Gln Ile Pro Asn Pro Ala Arg Ser
            260                 265                 270

Arg Leu Val Ala Ile Ile Ile Gln Asp Ala Gln Gly Ser Gln Trp Glu
        275                 280                 285

Lys Arg Ser Arg Gly Gln Glu Pro Ala Lys Cys Pro His Trp Lys Asn
    290                 295                 300

Cys Leu Thr Lys Leu Leu Pro Cys Phe Leu Glu His Asn Met Lys Arg
305                 310                 315                 320

Asp Glu Asp Pro His Lys Ala Ala Lys Glu Met Pro Phe Gln Gly Ser
                325                 330                 335

Gly Lys Ser Ala Trp Cys Pro Val Glu Ile Ser Lys Thr Val Leu Trp
            340                 345                 350

Pro Glu Ser Ile Ser Val Val Arg Cys Val Glu Leu Phe Glu Ala Pro
        355                 360                 365

Val Glu Cys Glu Glu Glu Glu Val Glu Glu Lys Gly Ser Phe
    370                 375                 380

Cys Ala Ser Pro Glu Ser Ser Arg Asp Asp Phe Gln Glu Gly Arg Glu
385                 390                 395                 400

Gly Ile Val Ala Arg Leu Thr Glu Ser Leu Phe Leu Asp Leu Leu Gly
                405                 410                 415

Glu Glu Asn Gly Gly Phe Cys Gln Gln Asp Met Gly Glu Ser Cys Leu
            420                 425                 430

Leu Pro Pro Ser Gly Ser Thr Ser Ala His Met Pro Trp Asp Glu Phe
        435                 440                 445

Pro Ser Ala Gly Pro Lys Glu Ala Pro Pro Trp Gly Lys Glu Gln Pro
    450                 455                 460

Leu His Leu Glu Pro Ser Pro Ala Ser Pro Thr Gln Ser Pro Asp
465                 470                 475                 480

Asn Leu Thr Cys Thr Glu Thr Pro Leu Val Ile Ala Gly Asn Pro Ala
                485                 490                 495

Tyr Arg Ser Phe Ser Asn Ser Leu Ser Gln Ser Pro Cys Pro Arg Glu
            500                 505                 510

Leu Gly Pro Asp Pro Leu Leu Ala Arg His Leu Glu Glu Val Glu Pro
        515                 520                 525

Glu Met Pro Cys Val Pro Gln Leu Ser Glu Pro Thr Thr Val Pro Gln
    530                 535                 540

Pro Glu Pro Glu Thr Trp Glu Gln Ile Leu Arg Arg Asn Val Leu Gln
545                 550                 555                 560

His Gly Ala Ala Ala Pro Val Ser Ala Pro Thr Ser Gly Tyr Gln
                565                 570                 575

Glu Phe Val His Ala Val Glu Gln Gly Gly Thr Gln Ala Ser Ala Val
            580                 585                 590

Val Gly Leu Gly Pro Pro Gly Glu Ala Gly Tyr Lys Ala Phe Ser Ser
        595                 600                 605

Leu Leu Ala Ser Ser Ala Val Ser Pro Glu Lys Cys Gly Phe Gly Ala
    610                 615                 620

Ser Ser Gly Glu Glu Gly Tyr Lys Pro Phe Gln Asp Leu Ile Pro Gly
625                 630                 635                 640

Cys Pro Gly Asp Pro Ala Pro Val Pro Val Pro Leu Phe Thr Phe Gly
                645                 650                 655

Leu Asp Arg Glu Pro Pro Arg Ser Pro Gln Ser Ser His Leu Pro Ser
            660                 665                 670

Ser Ser Pro Glu His Leu Gly Leu Glu Pro Gly Glu Lys Val Glu Asp
```

```
            675                 680                 685
Met Pro Lys Pro Pro Leu Pro Gln Glu Gln Ala Thr Asp Pro Leu Val
            690                 695                 700
Asp Ser Leu Gly Ser Gly Ile Val Tyr Ser Ala Leu Thr Cys His Leu
705                 710                 715                 720
Cys Gly His Leu Lys Gln Cys His Gly Gln Glu Asp Gly Gly Gln Thr
                    725                 730                 735
Pro Val Met Ala Ser Pro Cys Cys Gly Cys Cys Cys Gly Asp Arg Ser
                740                 745                 750
Ser Pro Pro Thr Thr Pro Leu Arg Ala Pro Asp Pro Ser Pro Gly Gly
                755                 760                 765
Val Pro Leu Glu Ala Ser Leu Cys Pro Ala Ser Leu Ala Pro Ser Gly
            770                 775                 780
Ile Ser Glu Lys Ser Lys Ser Ser Ser Ser Phe His Pro Ala Pro Gly
785                 790                 795                 800
Asn Ala Gln Ser Ser Ser Gln Thr Pro Lys Ile Val Asn Phe Val Ser
                    805                 810                 815
Val Gly Pro Thr Tyr Met Arg Val Ser
            820                 825

<210> SEQ ID NO 43
<211> LENGTH: 5119
<212> TYPE: DNA
<213> ORGANISM: Artificial Sequence
<220> FEATURE:
<223> OTHER INFORMATION: Synthetic primer

<400> SEQUENCE: 43
cttctcgcag gaaagccccg cgcggcgcgt ggagcctgaa ctcgcaggtt ctggctggac      60
ttctcgaagc tgaggagaag cagagggacc tggcttctga ttttggatct gcgtgcttgc     120
tggttctggc gcctgctggt cttgttcctg taacctagga ctcggggctt gcacatgctt     180
ttttttttgaa gttgctggag agggagccca ggaccttgtg caggcacctt ttgtgtcccc     240
aatgggggcgg cttttgcacca gttcctgac ctctgtgggc tgtctgattt tgctgttggt     300
gactggatct gggagcatca aggtcctgca ggagcccacc tgcgtctccg actacatgag     360
catctctact gcgagtggga agatgaatgg tcccaccaat tgcagcaccg agctccgcct     420
gttgtaccag ctgttttttc tgctctccga agcccacacg tgtatccctg agaacaacgg     480
aggcgcgggg tgcgtgtgcc acctgctcat ggatgacgtg gtcagtgcgg ataactatac     540
actgaccctg tgggctgggc agcagctgct gtggaagggc tccttcaagc ccagcgagca     600
tgtgaaaccc agggccccag gaaacctgac agttcacacc aatgtctccg cactctgct      660
gctgacctga gcaaccccgt atccccctga caattacctg tataatcatc tcacctatgc     720
agtcaacatt tggagtgaaa cgacccggc agatttcaga atctataacg tgacctacct     780
agaaccctcc ctccgcatcg cagccagcac cctgaagtct gggatttcct acagggcacg     840
ggtgagggcc tgggctcagt gctataacac cacctggagt gagtggagcc ctagcatcac     900
gtggtacaac cacttccagc tgccccctgat acagcgcctt ccactggggg tcaccatctc     960
ctgcctctgc atcccgttgt tttgcctgtt ctgttacttc agcattacca agattaagaa    1020
gatatggtgg gaccagattc ccaccccagc acgcagtccc ttggtggcca tcatcattca    1080
ggatgcacag gtgcccctct gggataagca gacccgaagc caggagtcaa ccaagtaccc    1140
gcactggaaa acttgtctag acaagctgct gccttgcttg ctgaagcaca gagtaaagaa    1200
```

```
gaagacagac ttcccgaagg ctgccccaac caagtctctc cagagtcctg gaaaggcagg    1260
ctggtgtccc atggaggtca gcaggaccgt cctctggcca gagaatgtta gtgtcagtgt    1320
ggtgcgctgt atggagctgt ttgaggcccc agtacagaat gtggaggagg aagaagatga    1380
gatagtcaaa gaggacctga gcatgtcacc tgagaacagc ggaggctgcg gcttccagga    1440
gagccaggca gacatcatgg ctcggctcac tgagaacctg ttttccgact tgttggaggc    1500
tgagaatggg ggccttggcc agtcagcctt ggcagagtca tgctcccctc tgccttcagg    1560
aagtgggcag gcttctgtat cctgggcctg cctccccatg gggcccagtg aggaggccac    1620
atgccaggtc acagagcagc cttcacaccc aggccctctt tcaggcagcc cagcccagag    1680
tgcacctact ctggcttgca cgcaggtccc acttgtcctt gcagacaatc ctgcctaccg    1740
gagttttagt gactgctgta gcccggcccc aaatcctgga gagctggctc cagagcagca    1800
gcaggctgat catctggaag aagaggagcc tccaagcccg gctgaccccc attcttcagg    1860
gccaccaatg cagccagtgg agagctggga gcagatcctt cacatgagtg tcctgcagca    1920
tggggcagct gctggctcca ccccagcccc tgccggtggc taccaggagt ttgtgcaggc    1980
agtgaagcag ggtgccgccc aggatcctgg ggtgctggt gtcaggcctt ctggagaccc    2040
cggttacaag gccttctcga gcctgctcag cagcaatggc atccgcgggg acacagcagc    2100 agcgggact gacgatgggc atggaggcta caagcccttc cagaatcctg ttcctaacca    2160
gtcccctagc tccgtgccct tatttacttt cggactagac acgagctgt cacccagtcc    2220 tctgaactca gacccaccca aaagcccccc agaatgcctt ggtctggagc tggggctcaa    2280
aggaggtgac tgggtgaagg cccctcctcc tgcagatcag gtgcccaagc ctttggggga    2340
tgacctgggc tttggtattg tgtactcgtc cctcacttgc cacttgtgtg ccacctgaa    2400 gcaacaccac agccaggagg aaggtggcca gagcccatc gttgctagcc ctggctgtgg    2460
ctgctgctac gatgacagat caccatccct ggggagcctc tcggggcct tggaaagctg    2520 tcctgaggga ataccaccag aagccaacct catgtcagca cccaagacac cctcaaactt    2580
gtcaggggag ggcaagggcc ctggtcactc tcctgttccc agccagacga ccgaggtgcc    2640
tgtgggcgcc ctgggcattg ctgtttctta ggtgagtgag tgtgctgttg ttgctgaggt    2700
ctgtgctgag gccagggttc ctccaagcca gggaagtact tcctgggaga cagcccagct    2760
ggcaggtttc ccagaaatcc agagaatggt gaattgaaga gtaaacttg gcctgacccct    2820 ggacgctcgg agcctggctg tctcctcttc cactggcctg ggctctcctc cctcccaagg    2880
gatacagggg ctcactgtgc ttggtccac agcagtgctg acgttcctaa gtcctgggct    2940
ttcctagctg atgttgtcct acctactcag tcccattttg tccaccgaat agacctgtca    3000
ctcaaggctc tcagcggtcc tgccatagct gctggacgct cccagctgga agctgggcct    3060
agaaactcac agatggcctg gcagtggcat gggaggccct aaaaattagt ggaaattttg    3120
agagaggaca ggtattgccc cacagaggcc attcattgaa cagccaggac tgggactaga    3180
ggcagagcct gctgtcctcc gctcagttgt agaaagcaac aaggacacaa acttgattgc    3240
ccaaagtcac tgccagttac ccacatatga ccagaagcca gggctcctgg gatgtggaag    3300
ataaacaaac acagttgccg ggtggcaggg cccagcgggc acgataactg gcagtcaagg    3360
cgatacctcg agggaactgt ggggctggtc ctggttggtg gtcaggtggt agggatagca    3420
gatggcagac tttggtgagt gagtgagtct gactgtgttc tggaagatgg gaccgggctc    3480
agcactgtct gctcacgtcc ccactgttgc aacacctagt ctgtttgcaa ggaggacagg    3540
acaggtcaca tggagcttta tgtcaataaa gtctttatct tgtcaggttt cctttactat    3600
```

```
acacacgccg agcccacagt gcacgaaagc tgaaatgtgc aggcaggggg ttggggaagt    3660
ggggagacaa ggccccagca gttggtttaa gggaatgact tgggaatggg cagagctgt    3720 ggctactcca tctctcatcc ttaccctcct gctaccacag cttgtgccca tgtgtgcctg    3780
ctcaggggag gggtcctcct ctttccctct cctttaggca gagtgctaga ggtgttggat    3840
gctccttagc acgcagaggg cgtgacactg gctgctaagt gttgttgaat gtgtcaaggc    3900
attgacatca gtaggcccca catcttaggc aggggatttg gggtgtggca acctgccagg    3960
ccagcagaga acttgaatat gatgttcaga aggaaagaca gagacaggtc acttagggag    4020
gcttgaagga ggccactttt gagatgagcc cgtggtatct gcaaaaaagc ctggaagaac    4080
tcagaacatg cagcagatgg ctcatgtctg aagtttgagg cacagggatc tggtgtggtc    4140
acagcatcag agagaagggt cctggcatga tggggactgg tgtgcagttg gatactggta    4200
ttctgcctta gttctgcctc ttgagaggtg gtccagtaga agccagcctc agactttcac    4260
atctcagaac agtcttttca aagacaaggt ctcagtgtgg ctcagacggg cctctagcat    4320
cactcggtct cctgagtgct gggatcacag gtgtgtgcta ctacacccag cttcccagag    4380
cagtcttacc acagccccta agcaggggag gagaggaaac ggagccatcc aagatctacc    4440
tcctgtgggc atccctcctg cctggctgaa ggagaagtct gggtttaaaa tccccattgc    4500
tcagatttgt atcctggagg gaagtgactc ccacaggaat gaactgactg tcccaggaaa    4560
ttcttcccgc tgtgccttta gaacttcctc tgtaaagtac ctcccttcag ctggtggtgc    4620
ctgtctttaa cagtggctga cagccaggga gtttgaggct agcctaggct ttgacagtga    4680
gatcctgttc aataaacgca gcttcccagt ccggcacttg accttcaagc tctgacctct    4740
ggattagccc aggatttctt cactggtcct ccaccttcca cccccttcca ctgcttatac    4800
ccgctcccat catttccaac ccaggaagct gctaagatct atgtggtagc cctggctcca    4860
ttaccaccct ctccccatct cctgggtgac tgagggaact aaggtacaag cccgaggaac    4920
ttgggattcc ctgccctgct gttaccttgc ctcctgtctg ccatcattaa cataggaggt    4980
gccagcctgt gccgtcctgg ctcccatact cactacctaa ggctacctgt tgggaattcc    5040
aaccctcacc agtcccatct cttcattcta ttaaaattac ttatcaagca aaaaaaaaa    5100 aaaaaaaaaa aaaaaaaaa                                                  5119
```

<210> SEQ ID NO 44
<211> LENGTH: 809
<212> TYPE: PRT
<213> ORGANISM: Artificial Sequence
<220> FEATURE:
<223> OTHER INFORMATION: Synthetic primer

<400> SEQUENCE: 44

```
Met Gly Arg Leu Cys Thr Lys Phe Leu Thr Ser Val Gly Cys Leu Ile
1               5                   10                  15

Leu Leu Leu Val Thr Gly Ser Gly Ser Ile Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
```

-continued

```
                85                  90                  95
Asp Asn Tyr Thr Leu Asp Leu Trp Ala Gly Gln Gln Leu Leu Trp Lys
                100                 105                 110
Gly Ser Phe Lys Pro Ser Glu His Val Lys Pro Arg Ala Pro Gly Asn
            115                 120                 125
Leu Thr Val His Thr Asn Val Ser Asp Thr Leu Leu Leu Thr Trp Ser
        130                 135                 140
Asn Pro Tyr Pro Pro Asp Asn Tyr Leu Tyr Asn His Leu Thr Tyr Ala
145                 150                 155                 160
Val Asn Ile Trp Ser Glu Asn Asp Pro Ala Asp Phe Arg Ile Tyr Asn
                165                 170                 175
Val Thr Tyr Leu Glu Pro Ser Leu Arg Ile Ala Ala Ser Thr Leu Lys
                180                 185                 190
Ser Gly Ile Ser Tyr Arg Ala Arg Val Arg Ala Trp Ala Gln Cys Tyr
            195                 200                 205
Asn Thr Thr Trp Ser Glu Trp Ser Pro Ser Ile Thr Trp Tyr Asn His
        210                 215                 220
Phe Gln Leu Pro Leu Ile Gln Arg Leu Pro Leu Gly Val Thr Ile Ser
225                 230                 235                 240
Cys Leu Cys Ile Pro Leu Phe Cys Leu Phe Cys Tyr Phe Ser Ile Thr
                245                 250                 255
Lys Ile Lys Lys Ile Trp Trp Asp Gln Ile Pro Thr Pro Ala Arg Ser
                260                 265                 270
Pro Leu Val Ala Ile Ile Ile Gln Asp Ala Gln Val Pro Leu Trp Asp
            275                 280                 285
Lys Gln Thr Arg Ser Gln Glu Ser Thr Lys Tyr Pro His Trp Lys Thr
        290                 295                 300
Cys Leu Asp Lys Leu Leu Pro Cys Leu Leu Lys His Arg Val Lys Lys
305                 310                 315                 320
Lys Thr Asp Phe Pro Lys Ala Ala Pro Thr Lys Ser Leu Gln Ser Pro
                325                 330                 335
Gly Lys Ala Gly Trp Cys Pro Met Glu Val Ser Arg Thr Val Leu Trp
            340                 345                 350
Pro Glu Asn Val Ser Val Ser Val Arg Cys Met Glu Leu Phe Glu
        355                 360                 365
Ala Pro Val Gln Asn Val Glu Glu Glu Asp Glu Ile Val Lys Glu
370                 375                 380
Asp Leu Ser Met Ser Pro Glu Asn Ser Gly Cys Gly Phe Gln Glu
385                 390                 395                 400
Ser Gln Ala Asp Ile Met Ala Arg Leu Thr Glu Asn Leu Phe Ser Asp
            405                 410                 415
Leu Leu Glu Ala Glu Asn Gly Gly Leu Gly Gln Ser Ala Leu Ala Glu
        420                 425                 430
Ser Cys Ser Pro Leu Pro Ser Gly Ser Gly Gln Ala Ser Val Ser Trp
    435                 440                 445
Ala Cys Leu Pro Met Gly Pro Ser Glu Glu Ala Thr Cys Gln Val Thr
    450                 455                 460
Glu Gln Pro Ser His Pro Gly Pro Leu Ser Gly Ser Pro Ala Gln Ser
465                 470                 475                 480
Ala Pro Thr Leu Ala Cys Thr Gln Val Pro Leu Val Leu Ala Asp Asn
                485                 490                 495
Pro Ala Tyr Arg Ser Phe Ser Asp Cys Cys Ser Pro Ala Pro Asn Pro
            500                 505                 510
```

Gly Glu Leu Ala Pro Glu Gln Gln Ala Asp His Leu Glu Glu Glu
            515                 520                 525

Glu Pro Pro Ser Pro Ala Asp Pro His Ser Ser Gly Pro Pro Met Gln
        530                 535                 540

Pro Val Glu Ser Trp Glu Gln Ile Leu His Met Ser Val Leu Gln His
545                 550                 555                 560

Gly Ala Ala Gly Ser Thr Pro Ala Pro Ala Gly Gly Tyr Gln Glu
            565                 570                 575

Phe Val Gln Ala Val Lys Gln Gly Ala Ala Gln Asp Pro Gly Val Pro
            580                 585                 590

Gly Val Arg Pro Ser Gly Asp Pro Gly Tyr Lys Ala Phe Ser Ser Leu
            595                 600                 605

Leu Ser Ser Asn Gly Ile Arg Gly Asp Thr Ala Ala Ala Gly Thr Asp
            610                 615                 620

Asp Gly His Gly Gly Tyr Lys Pro Phe Gln Asn Pro Val Pro Asn Gln
625                 630                 635                 640

Ser Pro Ser Ser Val Pro Leu Phe Thr Phe Gly Leu Asp Thr Glu Leu
            645                 650                 655

Ser Pro Ser Pro Leu Asn Ser Asp Pro Pro Lys Ser Pro Pro Glu Cys
            660                 665                 670

Leu Gly Leu Glu Leu Gly Leu Lys Gly Gly Asp Trp Val Lys Ala Pro
            675                 680                 685

Pro Pro Ala Asp Gln Val Pro Lys Pro Phe Gly Asp Leu Gly Phe
            690                 695                 700

Gly Ile Val Tyr Ser Ser Leu Thr Cys His Leu Cys Gly His Leu Lys
705                 710                 715                 720

Gln His His Ser Gln Glu Glu Gly Gly Gln Ser Pro Ile Val Ala Ser
            725                 730                 735

Pro Gly Cys Gly Cys Cys Tyr Asp Asp Arg Ser Pro Ser Leu Gly Ser
            740                 745                 750

Leu Ser Gly Ala Leu Glu Ser Cys Pro Glu Gly Ile Pro Pro Glu Ala
            755                 760                 765

Asn Leu Met Ser Ala Pro Lys Thr Pro Ser Asn Leu Ser Gly Glu Gly
            770                 775                 780

Lys Gly Pro Gly His Ser Pro Val Pro Ser Gln Thr Thr Glu Val Pro
785                 790                 795                 800

Val Gly Ala Leu Gly Ile Ala Val Ser
            805

<210> SEQ ID NO 45
<211> LENGTH: 4264
<212> TYPE: DNA
<213> ORGANISM: Artificial Sequence
<220> FEATURE:
<223> OTHER INFORMATION: Synthetic primer

<400> SEQUENCE: 45
gaggagattt ccacccagct ttcccccacc acactgctgc ccccacctcc ctgtaccaga        60
catggattga gtccttataa ctatgtagca agtgcttttc ccactgagca tctcctcagc       120
tcctccctgt gttgctttct tacacatttg tagagagtta caggcagggt actggccctg       180
gtactggttc tcaggtcact cctggcatct ccatttcctt agagacttgc tcatatctag       240
gcttcaggca tgtgggacac aatagagacc aaggacatcc ctcagcacgg gaccccttgt       300
gactccttca ccagcagtct tgggcctcct gcctaccctc atgcccaag cacccaattc        360

```
taacatatga ttttaagagc agtgtgtaca gagtctttta acattccccet gttgcaggtg      420 cctggacatg attctgttag ctaggctgct ctgaggagct ggaggtacgt ggccccgggt      480
ggagctggtg tggtctgggc tgttgaggga agtgatggta cctggcctca ttcctcttgt      540
aggaatgact ccagccacag agtgtggagg gtggcccagt ccacatcagc agcccaagac      600
atcttgcagc tccagaatga gttttcaaaa ctgagcctat aaagaccct tgatggatgt       660 cattccctat aggaggggt ctttactact gtgtccacac ctgggggtca gaggacccct       720
aaaatggaat ggaaaacaaa gtgtctgcct tgctcacgag ggcttggctt gtacccatgc      780
tcacatgagt ctgtgaccct tctgacagta aggatttggg cttctggaag tcaggggctc      840
caccatgaga acaaattcaa atcccagggc cacctataca gctgtgcaac ctccggcaag      900
tcactcaacc tccctgtgcc tttgtccctt catctgaaaa tgagggaact gactgtacct      960
ccatgataaa gctgggttaa gtggtgggaa gggacagagg gagagatgat cagaagaaaa     1020
cttagcatgg cgttaatagc agtgctagtg aggattgcca gagggcagag gtcctccggg     1080
acatcaggcc accagagtgt tctccaagag atgcacaggt tccacttggg cgatgtcacc     1140
ccctggtcct ggggctcgga ttctgttaat aggaccatga agaccactgt tcctaaacaa     1200
ttgctctgcc atcagccacc tcttcctccc tccctccctc cctccccct cctcccttc       1260 ttcttctctc tctctctctc tctctctctc tctctctctc tctctttctt agtctagaat     1320
agagtttatt aagggcatgg ggaaggaagc taagaaggta gtagaggcag agagagagag     1380
aagagagaag tagaggggta gaggcaggcc atgagcacat gaagagagag ggggaaggga     1440
atggggagag gggaaggggt gaggggacag agtgggagca agaaggcaag aaaccaagag     1500
agaaacaaga gggcaagagg ctcgaagccc tttcttggcc ttcccacagc ttagccaggc     1560
ttcagtgcgt cacacaggct gttgacattt gaagttgaca ggtacaaggg ttattttcat     1620
ggctcatttt atttcattgt taggttctgg ctggacttct cgaagctgag gagaagcaga     1680
gggacctggc ttctgatttt ggatctgcgt gcttgctggt tctggcgcct gctggtcttg     1740
ttcctgtaac ctaggactcg gggcttgcac atgcttttt tttgaagttg ctggagaggg      1800
agcccaggac cttgtgcagg tgagccaggt atcctgacac tgcaggattg ttcatggcat     1860
gagacactgg tggctggaac tggatgcgtg tatgactggg tgtccacctt gggcattact     1920
tcctctctgc agctctgccg ggcccagcct gacagacagg tccacgaagc agaaggaggc     1980
agaactccag aggctgaaga acccagctgt agactcacag ctgctcggag gcaaaatggg     2040
tctgggactg acccatttag atacagcctc cagataatga ggggagcggg ggactgagga     2100
ctgacccatt gcaggggggt cactgaggac tgacccattg ctgcaggggg gggtactgg      2160 ggtctgaccc attgctgcag gggtcactgg ggattgtccc actgctgcgg gtggggcact     2220
ggggactgac ccattgcttt gggaaggcac ttgggactga cccactgctg ttcatagagt     2280
agcacacagc tccccatttg cagggcttct ctctctccca tcctccctcc caatttcttt     2340
tctttgcttt gatcctcttc ctcccgaatg ctggggttg gaacccagga cctggaacat      2400
accaggcaag cctactgaat ttgtgtgttc atttaagctt ccagaacctc taagatgggg     2460
ctgtcagtgg atggccactt agcagacagg gaaactgagg ccctgggtac agcttgctca     2520
ggttcacagc tggtatggga gggagccagg atttgaactt gagaaagtta tgaatgtatg     2580
ccacagctct cctgggacag gcgaatagag gtatgctcgc gtgctctgtg tgcagagggc     2640
acagagacat ggggggaggga ggccatgaca caaatgaaat ggaccccgct gacccaggat    2700
```

```
cagcatctgc ccactcttct ttctgcaggc accttttgtg tccccaatgg ggcggctttg    2760
caccaagttc ctgacctctg tgggctgtct gattttgctg ttggtgactg gatctggtaa    2820
gtcactcatt cattcatcaa ccactaatga catgtcaagg tcctgcagtc ctcacggaat    2880
agaacaaagc tcttgtgggg attgggggggg aggggggagg aagcagccga tgacaaatca    2940
ccatgactaa gttattttca ttgacactaa ttcaaattgg aaattggggc tgtccgggaa    3000
ttgagtagaa aataatttga gttatatgcc aaaggttatc aaaagatggt gggaaaacgc    3060
agctcaggac tgagtaaggg aggcttgggg gaggggtgga gagggagagg gcattgcact    3120
ttaaagcagg gtgcacaggg acactggtgt caacttagag gaaggcaggg gagggcacac    3180
agtgtctgtg gtgtgtcttt ggtgaggccc cagggaggg cctgcctggc atgggttggg    3240
aggacgtgtc gcagggtcat tgagtcagaa gaccttgcag agtctgatca gaggaattga    3300
gtgaaggcca gggtcgctca gtgatctgga aagagagttt ctagatcaat ctagaaggtc    3360
agcatgaaga cacgtgggaa ttgacctgaa ggtttctcat ccatgtggcc aggtgtggct    3420
tacacctgtc agcctagcac ttgggagact gaggcaggag gattgtgagt ttgagcccag    3480
cctgggctac aagttactgt aaaaaaacaa aacaaagaa aaaacaaaa aaaaaaaaa    3540 ccaaatggac acacaaattc taccccaagc ccagacaagg gtggattatt ctgtatgacg    3600
ggaaaaccca gggtagctgt tgaaggagag ggttcaggag gttagaattt tgtttgctgt    3660
atgaaaactt cctgcatggt ggaccacacc cgctggcatg tgtattgtga ctttgtctgg    3720
acagtggcca tgtagggctt gggtcaaaaa gctcttgagg gtcccacact cactggctgt    3780
tacacacaca cacacacaca cacacacaca cacacatact cacacacaca ccacatctga    3840
attcctggca gggagctgat gggtaagtgt ctgtccccctc ctccttccct tccctctttc    3900
ctgctcttcc attggctaag cctcttgggt accaaagggt cagagcctga gcctgagccg    3960
tacagattgc agagtcaatc tcttgcctca gtggagaagg gaggtaggga aggagatgtg    4020
ggagtggggg gcgggatggg gggtggggcg cggtggacaa cactgtagga cactgccccct   4080 tcctcccctgt gctttaacgt ggtgcttctg agggagagtg gcacctaggt aggtgtgtgc    4140
gtgtgcaggc atgtgtgtca tgatcctgat gcactagcct ccctctgacc ttagtggtgg    4200
gagcccctga ccatgccacc actgatctgg ccgttctgtc tctgcaggga gcatcaaggt    4260
cctg                                                                 4264

<210> SEQ ID NO 46
<211> LENGTH: 4525
<212> TYPE: DNA
<213> ORGANISM: Artificial Sequence
<220> FEATURE:
<223> OTHER INFORMATION: Synthetic primer

<400> SEQUENCE: 46
tgcgcagtag cacgcatgcg taatcctgat ggagcaatta ggagaagccg gtggccggct      60
agcctgtgca gactgtgaaa acagagcatc tgaagctgtg tgaaaggcta gctcgcctgt     120
gctcctcaga tcctgacata cgccatctcg agcaaaagat taacaatcga ttaaaaccca     180
cacatgaaaa caaagaaacc agttagctcc agataaaagc aaatgccagg aaggaaagga     240
ggcagagggc agggtggag gagcaggtgg gagaggatga cgtcagagaa atctcagtgg     300
ccgtgaacaa ggaagatatt ccagggcttg ttctgaatgt gtgatctttt aaaccatgtg     360
gccctcttag cctgtgagaa aagtccattt ctagccctgc tgaacagaga gcccagggg     420 agcaaccaac tggccttcgg tcactcagca aggacctagt agaggctggc tttgaacttg     480
```

| | |
|---|---|
| agccctccag ggcacttgac ctctgagctt tgggaaaaca agcgaggcag cttcacgctg | 540 |
| ttgtgatctg gacttggatc agggccagtg aggacaggga cagggatggg tgtgataagg | 600 |
| acttggtgtg taagagggag agttggggag acaggtggga gggctatctg tagccaggta | 660 |
| accaagggtc ccaggggaac ccccagtgtg gacgcggact gcacatgaca cagggcggcc | 720 |
| tccccattca tgactgtttt tctccttgca gacttccagc tgcccctgat acagcgcctt | 780 |
| ccactggggg tcaccatctc ctgcctctgc atcccgttgt tttgcctgtt ctgttacttc | 840 |
| agcattacca agtgagttcc tgctttggct ggtgtctctg gctggcccct cagcagtgct | 900 |
| ctcagaggtc acagtcattg tgctggctga aaaaggctg aagtctgcc tcgaagggca | 960 |
| gggcagggca gcctgtggct ggaggcttct ccacagtggc tgtgctctgg aataaagaga | 1020 |
| gctaggttgg gggacagtaa tggtggctgc tctggagaga aggagctggc ttggggctag | 1080 |
| ggagggggttg tttggggcat agagaagatg ggagctctgt ccctctcaat gcccatggta | 1140 |
| tggtcccggc actgggcatg tggtaggagc agaggaattt gagcagatgc tgtgaatata | 1200 |
| gtagggtttg agtgagaccc ggaagtggcg cttgctggca ggtagctggt cagctacctg | 1260 |
| ggctcctctg tgggctcaga gtgaccatga gaacaagacc tccagaggag tctgggcaga | 1320 |
| gccggtagag ggggaagatt cacttctggt gagttctacc ttggagtctc agacccagag | 1380 |
| ccatgttctt ttagaagtga gattagaagt cacttcgaat tagggctgtg caggtacccg | 1440 |
| gtacccgccg cctggctaag tgcagggagt gccagagcct ctcctctccg tggcttgcca | 1500 |
| ctcataacct cgtcagtcac ccggggctag gcactgctgt tctgatgcag gtttctctg | 1560 |
| tgtcctgttg cccttccctt ctcccacgtg atgcccctgc accccgcagc ccgcagttct | 1620 |
| caaaggcaca tggcacgttc ttccatagag tcttagccat gccccaccc taaacgttct | 1680 |
| gccccttcac ttttctgggc tgttccctgc aaccccaac tctgcttctc tctcctacct | 1740 |
| tcctctctta tacattgtgg tcttcttgtt tgtcttttta attgttttga acccagggt | 1800 |
| cttacacatg ccaccctatc tctgagctcc actctagcct cctgcttact tttgcttgga | 1860 |
| gacagggtct tgccaagtta cctaggctgg tctccaactc tcctcagctc aggaaggtct | 1920 |
| ggcactttga ctcttcctgc cctgtctcct gagtggcagg gatgatttcc ggtcaccatc | 1980 |
| cctggctgtg gttttgctc atcagcactt atggtggtga atgagtgtca tgtgatcatg | 2040 |
| cctgcatttg cttcttgttt ctcttgaagg cgacccacag gggcttctcc actggctgtt | 2100 |
| tttctggctt agtccctgtg gccctagtac cttgatgctc agaaaatact atgggaagac | 2160 |
| ggaagagtga aagtcatagg ggccagttag cccaggaaga aggaaatgc ccgcttccac | 2220 |
| acggcccctg acctctcaag cctgttaaag ccagcatggt caaagggac ttttgaggga | 2280 |
| gcgggatcct tgctgtatag cttgaggctt tggtagtgtg gataggtcaa gcagccctgc | 2340 |
| cagcatcagg ctctccctgg gcacctctcc caattcagaa tggtagtggt gatggacagt | 2400 |
| taggaccaag attgttccat atccaaaatg ggatcagtgt ggccttcgtg ccctgggagg | 2460 |
| agtgacggcc aggacacttg aagagcacc ttggccactg tacattcgga gaccaaccta | 2520 |
| cttcctttcc accctcagga ttaagaagat atggtgggac cagattccca ccccagcacg | 2580 |
| cagtcccttg gtggccatca tcattcagga tgcacaggta agagggtaca ggcgttgcat | 2640 |
| agtgtgactc ccagccatgg gtagggtggg tgggtgcgag gagcaaacgg ccagggtaa | 2700 |
| gcagggtggt gcacgggtgg taacaaagcc catgcccaca tctgtgtggg cttggtatta | 2760 |
| ttcctgccat gttctgctag tcacagtgaa gtcctgtgtc cagatcagag agtccaagat | 2820 |

| | |
|---|---|
| ggcaccggca agctggagca tctgagggca tttgctatct ctgatgccct ttcactggtg | 2880 |
| tgggggggcag ggagggcaga ggctgagact cccagagctc tgtggggcct gtgtggatct | 2940 |
| cagctctcta ggcatggttg ctgtctgtga aaacactgag ccttctgtga ctgggttgtg | 3000 |
| ctggcacccc ccaccccccac tgattggctg tctattttag gtgcccctct gggataagca | 3060 |
| gacccgaagc caggagtcaa ccaagtaccc gtatgtatct gaacttgaac ttgggtcata | 3120 |
| gttttttgtgg gtttgtgtga gaatgtgata gttactcggc tggtggcaat caattcccct | 3180 |
| tccttgcccc cccccccccac acacaattgc cttctctctt cctggcccca agggggagag | 3240 |
| aggggggcaat catgggtggc tgagtctcca ttctgcagca agaacaggct aagtgttgat | 3300 |
| tttaagagtc agaaccacat ctataacacc ccaatatcaa tacagggtga ttccgtgtgg | 3360 |
| gattctaaag gatgaatagt tttttaaatg tggcaaaact taaccctcag ctttacctct | 3420 |
| gcaggcactg gaaaacttgt ctagacaagc tgctgccttg cttgctgaag cacagagtaa | 3480 |
| agaagaagac agacttcccg aaggctgccc caaccaagtc tctccagagt cctggaaagg | 3540 |
| caggctggtg tcccatggag gtcagcagga ccgtcctctg gccagagaat gttagtgtca | 3600 |
| gtgtggtgcg ctgtatggag ctgtttgagg ccccagtaca gaatgtggag gaggaagaag | 3660 |
| atgagatagt caaagaggac ctgagcatgt cacctgagaa cagcggaggc tgcggcttcc | 3720 |
| aggagagcca ggcagacatc atggctcggc tcactgagaa cctgttttcc gacttgttgg | 3780 |
| aggctgagaa tgggggcctt ggccagtcag ccttggcaga gtcatgctcc cctctgcctt | 3840 |
| caggaagtgg gcaggcttct gtatcctggg cctgcctccc catggggccc agtgaggagg | 3900 |
| ccacatgcca ggtcacagag cagccttcac acccaggccc tctttcaggc agcccagccc | 3960 |
| agagtgcacc tactctggct tgcacgcagg tcccacttgt ccttgcagac aatcctgcct | 4020 |
| accggagttt tagtgactgc tgtagcccgg ccccaaatcc tggagagctg gctccagagc | 4080 |
| agcagcaggc tgatcatctg gaagaagagg agcctccaag cccggctgac ccccattctt | 4140 |
| cagggccacc aatgcagcca gtggagagct gggagcagat ccttcacatg agtgtcctgc | 4200 |
| agcatggggc agctgctggc tccaccccag cccctgccgg tggctaccag gagtttgtgc | 4260 |
| aggcagtgaa gcagggtgcc gcccaggatc ctggggtgcc tggtgtcagg ccttctggag | 4320 |
| accccggtta caaggccttc tcgagcctgc tcagcagcaa tggcatccgc ggggacacag | 4380 |
| cagcagcggg gactgacgat gggcatggag gctacaagcc cttccagaat cctgttccta | 4440 |
| accagtcccc tagctccgtg cccttattta cttttcggact agacacggag ctgtcaccca | 4500 |
| gtcctctgaa ctcagaccca cccaa | 4525 |

<210> SEQ ID NO 47
<211> LENGTH: 10537
<212> TYPE: DNA
<213> ORGANISM: Artificial Sequence
<220> FEATURE:
<223> OTHER INFORMATION: Synthetic primer

<400> SEQUENCE: 47

| | |
|---|---|
| caggagccca cctgcgtctc cgactacatg agcatctcta cttgcgagtg gaagatgaat | 60 |
| ggtcccacca attgcagcac cgagctccgc ctgttgtacc agctggtttt tctgctctcc | 120 |
| gagtaagcct gcgctggagc tggaggtttg gggaggttgt gcccaaaggg tttgccccaa | 180 |
| gagtgagctg gtccaggtg gtgcgctgga gtgcaggatg ctgagtatgg tttgctgctg | 240 |
| tttatatggt gttagagggg aggtcccatc tccaggaca tgttatgtaa gatacagtgg | 300 |
| agcgcatggt gggagtgttg gtccacgtgg cacatggata cggctggaat actggactag | 360 |

```
accagcagtt ctcacacttt ttggtctcag gacccttttt cacacttaaa aatgagtgag      420
gacccaaagg gctttggtgt aggtaacaca tcattctatg tttacctaat tagaacttgc      480
aatgaagaaa tggtgtaatt tttaaaaaat taaaacaatt aaaaattttt tttcttactg      540
aaatggaggt ctcactgtgt tgcccaggct gctctcaaac tcctgggctc cagtgatcct      600
cctgcctccg cctcccaaag tgctgggatt acaagcgtga gccgctgtat ccggcccaaa      660
atggagaaat tttaagtccc aacaacatgc aagcccgcat tcaacaaatc ttcagatcaa      720
ttacatgatc acaggtcatg tagcctctag aaaattccac tgtacgccag tgagagagag      780
tgaaaaggca aataacgtcc ctgtattatg atgaaaagag ttttacctgg tgggcccaga      840
ccacactttg agaaccactg gactagaccc ttgattgagg agtacggtgt tgagagtgga      900
gtcctctgtg atggtggatg gaccaggaca catggcatag gagtcaggtg gttccctggg      960
ctactccatg gtgcacagga tgcttcgtta cactggtgcc caggacataa tcacgtacac     1020
aagacacaca gttacggggc agactgggga tatacggcac accagcatgc agcgttcacc     1080
agtaaaggtg gtattccatg attattctaa ggtagatggg ctgtgctttg tttccattgg     1140
cttagtccag ggattggcaa actatggccc gtgagccaaa tccggcccac tgcttgtttt     1200
tgtaaataaa gttttattgg aacacactgg ctgctgtagt tgtaacagaa actgcatggc     1260
cctcctttat gttttttgtt tgtttgtttg tttgtttgtt ttctttgaga cagagtttcg     1320
ctcttgttgc ccaggctgga gtgcagtggc acaatctcgg ctcactgcaa cctctgcctc     1380
ccgggttcaa gcgattctcc tgtctcagcc tcccgagtag ttgggattaa tggtgcctgc     1440
caccacaccc ggctaatttt tcgtattttt agtagagacc ggttttcatc atgttggcca     1500
agctggtctc gaactcctga actcaggtga tccacccgcc tcagcgtccc aaagtgctgg     1560
gattacaggc atgagccact gagcccggcc tcctccttta tcttaattga ataattcag      1620 aaatggaaag tcaaatactg catgttctca cttataagta agagttaaat aatgtgtaca     1680
catgggcatt attccatgta ccatggaata acagacattg aagacttggg agggtgggag     1740
aggggtgaag gaagagaagt tacttaatgg gcatagtgta caccatttgg gtgacggacc     1800
caccagaacc ccagacttca ccactaggca gcatatccag tgagaacaga tctgaggctt     1860
gccatcaaaa ttgcacttgt aaggccgggc actgtggtgg ctcgcggctg taatcccagc     1920
cctttgggag gccgaggtgg gcagatcact tgaggtcagg agttcgagac cggcctggcc     1980
aacatggtga agctccatct ctactaaaaa tacaacaatt aactgggtgt agtggcgcac     2040
acctgtaatc ccagctacta gggaggctga ggcgggagaa ttgcttgagc ccaggaggtg     2100
gaggttgcag tgagccgaga tcacatcact gtactctagc ctgggtgaca gtgagacttt     2160
gtctcaggaa aaaaaacaa aaacaaaaa caaaaaactc gtacccccta aatttataca      2220
aataaccaaa aaaaaaaaaa aaaaggaaa ttgtgtggcc tttgaagtcc aaaatattaa      2280
ctatctggcc tgttacagaa aaagtttgca gaccccctggc ctagcccgtg agatgtgggt    2340
tggctgttaa ggtggaacat tggaattatc ttacgatggc caaactgtgc gatgcagagc     2400
ttatgttgtt ctaaattaat tagtgccacc ggttcttccc tttcatgggc tttcaggaac     2460
aagctaagtc ccaggaccag ggccggcagc taggcaggtg tgaggagcat ccttggtgca     2520
tgtggtaaga ggctgtggcc agcaagagag gcaaccctag tcggctgccc cagcacaccc     2580
tggccgctcc caagccccca gatctgtcct cacatccgtg atcgggaagc tggaagagtc     2640
tgatgcggtt cctggaggca tgtcccggac acagctgtgg ggcccagcca gcctacaggt     2700
```

```
gaccagccta acccagcccc tgtgtctgca gagcccacac gtgtatccct gagaacaacg    2760
gaggcgcggg gtgcgtgtgc cacctgctca tggatgacgt ggtcagtgcg gataactata    2820
cactggacct gtgggctggg cagcagctgc tgtggaaggg ctccttcaag cccagcgagc    2880
atggtgagca gggcggagtg cggcaggggt ggctgggtgt gttcccacag ctgcctgggc    2940
tgagggtggg gtgggcaggg gaggaggtgg ggtcatagca acagcaggag gaagccgcct    3000
gtatttcccc aaatctgatg ggattcctgc ccctgcctgg gcctcagtcc tcccaccttt    3060
gaaacggagc tggtcgcagt agaccaccaa gccccttca gcccagctgt ttccacccct     3120
gaacttaagt gcccaggaag gcgtattgag atgaggtgtg cttgctggaa ggcatgcctg    3180
ctgctgattg aaaaccgaac tgggaacatt ccttccattc tgtgtccact ggtcagctgc    3240
tgcggctttg gatggtcttg accgtggaag gctgaccttc ttctggtacc cggagtccct    3300
gcaggaatcc cccttgagct tgctgggctg tggtgacagg agtttaaaac atgcgttgta    3360
ttccagtgat gcatgatatg acatgcatca caggaataaa aacctgaggt ctcatggata    3420
tgattgcttc aaaggagacc aagttttaaa acagatgaat caaaataaag aaaaatactc    3480
agtaaatcat cataaagtac agagatgtgg ccaaaggtgt gaaggatgca gctgtaaaag    3540
ctgaagtttg aggccgggtg tggtggttca tgcctataat cccagcactt tgggaggccg    3600
agcccagcgg atcaccggag gtcaggagtt cgagaccagc ctggacaaca tggtaaaacc    3660
ccgtctctac taaaaataca aaaaattagt ctggcatggt ggcaggcgcc tgtaatccca    3720
gctacttggg aggctgaggt aggagaatgg cttgaaccca ggagaaggag gttgcagtga    3780
gcttagatca tgctactgcc ctccagcctg ggcgacagag tgagattacg tctcaaaaaa    3840
ataaaaataa ataaaaataa aaagattttt taaaaggctg aagtttgggt tactttggct    3900
catacacttt gccttcactg tagaaaggtg gttagtaaag accaggcgcg gtggctcatg    3960
cctggaatcc cagcactttg ggagcccagc gcaggcagat cacttgagcc ctgggctatt    4020
gaggctgcag tgagctggga ttgtgccact gcactccagc ctgggcaaca gagtgggacc    4080
ctgtctcaaa aagaagaaa aaaagggtaa ttaataaaca ctaaagttct atgtagaatt     4140
ttagcaacat tattgttatt ataatcttct ttgctatggc tctgaatctg tgtggtgctc    4200
cagaagtatg ctatggaggt tttgtcgacc aaaaatctgg gtggtggctg tggtttgtag    4260
gccggggctg ggctgggtga tgggggagtc actgcataga tcctcacata gaggccgctt    4320
ctcccgcagt gaaacccagg gccccaggaa acctgacagt tcacaccaat gtctccgaca    4380
ctctgctgct gacctggagc aacccgtatc ccctgacaa ttacctgtat aatcatctca     4440
cctatgcagt caacatttgg agtgaaaacg acccggcaga tgtgagtggg catgctttga    4500 cgttttctg tgacctctgg ggaacagggt gggtgaccag cagaggccca gtccctggag     4560
ccaggagcct gggaggcaag ccctggggct ggatagcaaa tcccaggagc tagagacctg    4620
gcttctcacc tggctctgca ctaggcaagt ccctttgctt cctggccccc cacccctcac    4680
atcagagaag gggagttatc tctgcatgcc gctcctcctc tgtaaaggta gggctgtggg    4740
ccacatctgt gtttcccagt ttgggggaca caagtgatcg taggtggcac attgacagct    4800
cacttgaata accctattat tgaagagaat aatactgact caagagacag tgaccgtgt    4860 cagttccctt ttgaggccaa cgggttaagg aggaagtccc catacagctg actcgtttac    4920
taattcctct taatgaagag agcagaggcc acacccagg cttagacttt cccaagaaaa     4980
caagatcagt ttgttggttg ttccccatgg aagctggtcc tgacattccc ttcacagtag    5040
tgttggtgga gttttgttg ttgtttgttt tgagacagag tctcactctg tcacccaggg     5100
```

```
tggaacacag tggcgtgatc ttggctcact gcaacctccg cctcctgggt tctagcgatt    5160
ctcctgcctc agcctcctga gcagccggga ctacaggcac ctgccaccgt gcccagctaa    5220
tttttgtata tttagtagag atggggtttc actgcgttgg ccaggctggt ctcaaactcc    5280
tgacctcaga tgatccactc gccttggcct cccaaagtgc tgggattaca ggtgtgagcc    5340
accgcacctg gccagtggag ttccttctta agtacatgta ttgacatctt taaaagggc    5400 gagaggattt acaggaaact atcaggtcag taatggcagg ggccgtccac agtgggtggc    5460
tgagtccccc tattttctg ctggtgtgca gggaggtcat ttcctgccac ccatgtttcc     5520
ccaccctgaa tccaccttcc tcacattccc attggaggga caatctctgg acatatggga    5580
cctggggtcc cacagggctg caatccaatg cctgctgtgc cactcgccag ctgtgtgatg    5640
ttgggcatat cccataacct ctttgtgcct cagtttcctc atctgtaaca caggagtgac    5700
aagagcaccc gcccacaggg ctatgacagt acaaggtgtg tgatacagat gagctcccct    5760
gtttggccca catgtgtcct aaaagccatg tgccctttct cttgagtgcc ccaggccaca    5820
gagatcccca tctgcccgct gtcccacaca ctggtctgtc atttgttcct tgaggtttgt    5880
gagggccggc tctgtgcatc ccaggggccc aggctgggcc tggttggctc tcagggagca    5940
ggcacccgcc accttaagct cccatgctgg tgtctgtcac tgcttcctct caatctggcc    6000
aagccagggg tgtcgattta tatctctcag gtctggtttc ccctttggca ctgggccagg    6060 tatgggaaa gagcaggaat ggggcagttg gctcacacag cagaggctca gaaagcgggg     6120
ggcatggggg gaaggagtgc acagatgcta gagagtgggg caagttttgt ttggtcaata    6180
aatctccttc tcatgcccca ggcctgtgca agacctacag agagtcccaa ggatgggctg    6240
gggggaagag aaaggtacca ccttcagagt ccaaagatat gttatttaat attttcatat    6300
ttctagatct gccttcaggc atggctggat ccagcttcta ggaacctgtc cagctctgcg    6360
ccctgcttta ttctgtactg gcttcgtttt taggcaggct cttccctcat gtagtggcag    6420
atatgcctac tagttgctcc aggcctacat cccaaagcca cagtgggaaa agggttttt    6480 ttcttgacgg ttctaataag agtcctaagg ctgctgctca gtggcctggc ttcgatgctg    6540
tgccagcctc tgaaccaatc actggctgtg ggtggagaga gggtgctggt ggagggccct    6600
gcttgtccag ggaggagtca catacctgcc tctagggctg caggtgggct cagctccatc    6660
caaaccagat gaactgaaaa taaggcagga gtggcttccc caggggaaac tggggaagag    6720
gaagcaggac tgtgctggct aaaatgccag ccaggtttaa gacgtggcac cagatgccag    6780
tcatgggatt ggattggtca gcatgcctgg gctatggctt aggggtatgt tggtgctcag    6840
ggatgccaca ggcctccaga taccaggtct gaggcagaag aatgaagtcc agcttctctt    6900
gtgggtggaa cagtggcaac tgagataccc catctctccc ttcccaagaa cagagctgaa    6960
cataaagaat ttagtgattg ccagagcttt ggccacatgc tcccctctga tgaatgatag    7020
gccaggtgat gggattggca caattggctt agactaatga gggttggccc tggagttgca    7080
ggcagtggag ttctgtccta agcagtgggc acctaaaccc gatggcataa agctgggcg     7140 ggtgtccacc tgcatctgcc acagcactat aggcaccaac tgtggctcat actgagtggg    7200
ataaattcca gaaagaaaca ttaggaactt actatagaat tttggggcta gagctactca    7260
ttcattcccc tagataattt ctaggcaagg ttccatagtg gagggggagt tttggcttgg    7320
gcattgaagg atgcatagga gttttctaga tggggaaaga agggaacggt agaccaggca    7380
gagggaactg catgataaaa ggtttatggg tgtgaaaatt catggaatgt ttgaggatta    7440
```

```
tggggttggg ggatgtggga atatgtgtag cgataaagca ccaaacaaag ccaaaagttt      7500
agttagagcc ctgaatgcct gcctcataat ggtttccata ttttatatgc ctactatgtg      7560
ccaggcacat tgctcagggt cacacagctg gaaatggcag ggctgagttt ttgttgttgt      7620
tgttgttgtt gagacagagt ctcactctat cacccaggct ggaatgcagg ggcgtgatca      7680
tggctcactg catccttgac ttcctgggat caggtgattc tcccacctct gcctcccagg      7740
tagctgggac tacaggcaca ggccaccacg ccaggctaat ttttgtatt tttagtagcg       7800 acagggtctc gccatgttgt ccgggctggt ctggatctcc tggcttcaag tgatccccct      7860
ggctcagcct cccaaggtgc tgggattaca ggcttgagcc accgcatcca gcccagatct      7920
gagatttgca cccagtattt gaactcccaa gcctgtgctc ttttcctcc catggacatt       7980 tctctcagag atggtctccc aaacacctgt ccttcttgtt aaaaaacaga caaaccgcaa      8040
gtagttcttt ggaagctcag atttctcttt tgtttcttag taaaacattt cccagttccc      8100
agctcccttc cagggtgtaa gatttcttcg gtaacttaca tctagctgtt gcttcttgtt      8160
tgctcatgtt tagaaagaaa gacaaaagag agtgagaatt ttctctccct tccccagtct      8220
ccccacaact cacaccccac cctcagctcc ctctgtaata ggaaaatctc tgaactctct      8280
gtagttgctc cagcaatctt ttggaacttt gcttctttct tgtgaaaaaa cctccccttg      8340
gctcactttg caccaggttt ccccaaatgt gcttccaacc acaagcagaa atggagctgc      8400
cagtaaccag gaagaaactg ccgggggctg aggaagagga gagggaggtg catagccctg      8460
gatctcgcag ggagaggggt gacaggatga gaactcaggt tgctcacttg ccatcagggt      8520
cagtcatgaa tatagcgttc atgtatcact ttttaaagct tttttggagg gtaaaagtaa      8580
tagttacaca aaataaaaat acaaatggta caaaaggact tagaatggaa acatgtttct      8640
ctcccgactc cagcctcctg ttttcttcc cagagactga ccactgctgt ctgtctcttg        8700
ccagaaggga aagggaggca aggttagggc aggcagaggg catgtgcatc ctttagagag      8760
agcttatgtc tatacaagca aatgtgtgtg ttcagtcatc gctgtcttag ttttctattg      8820
ctgcataata atggtactac cagcttcaca gctttaaaca acacccattt attatctcat      8880
agtttctgtg gttgggagtc tggacatagc ttagccaggt tctctgcttt agagtctcgt     8940
gaggctataa tcaaggtgtg ggatggggct gcagtttcat ctgaggctca attggggaag     9000
ggtcacttct aagctcatac aatattggtg acattcagtc cctggcaggc tgttgaactg     9060
agagcctcag tttcgtgctg gctgttggtt gtagttaacc ctgaattcct tcccatgtgc     9120
cctttgcaaa gccatcaagg cagagagact tgcctagcaa gtaggatatt acagtcttct     9180
gtaatataat cacatccatg aaatcctcta tatatcccat caccttacc atattctgtg       9240 ggttagaaac aagtagcagg tcctgcccac actcgagaag accagatgac acaaagatgt     9300
gattcaaagt ggggatcatc ggggccatct taggtttgtc tgcagtgatc actgtgccat     9360
ctctctctct ctcttttttt tttttttttt ttccgagacg aagtcgtcac tctgtcaccc     9420
aggctggagt gcagtggcat gatctcagct taccacaatc tctgcctccc aggttcaaat      9480
gattcttctg cctcagcctc ctgagtagct gggattacag gtgcccgcca ccacacccag     9540 ctaattttg tattttagt agagacagag tttcaccatg ttggccaggc tggtcttgaa       9600
ctcctcacct caagtgatcc acccacttcg gcctcccaaa gtgctgggat tacaggcatg      9660
agccaccatg cccagcccca tctctcttta aaaacaaaac aaacaaacaa aaaacataaa      9720
aagaagcaga gaacacatac acatctgcat cttcccttgt ttacttaaca atagatcttg      9780
gaagtcactt ctcagtagag gctaggttgg gcagagcatt ggattctagg ccagtgagtt     9840
```

```
tggacttgac catggagaca ctaggaagcc catgaaggac agagagagat gcctcgaccc    9900
tgccagtcct ttagaaagat cacccagtgc tttttgtata ccaaacccta tttgaaatac    9960
ttacgtatat taacccattt ccttatcacc acaaccctgc gggaagggag ataggcactt   10020
ttattatctt cattttgcag atgaggacat tgaggtccag agaggttatg tcacttactt   10080
aaggtcacac agccaggaag tggtagtagg gactcttacc cttgttttac agatgagatt   10140
gaattatctc acgaaaactc agaaaggtta acaacttgc  ctaagtaaca tacagctaat   10200
tagtcgagga gcctgacgca tgttgctgta gcctggtcac agttacagag gtggcaagca   10260
atggcctgaa caggacgaac aaccaaatac ccaggctggt ggctcttaaa catggtgggg   10320
tcagctaacg acagcaacca gggtgggcac tggtgcccct cgccccggc  tggtgcccta   10380 acatctccct tttctctacc agttcagaat ctataacgtg acctacctag aaccctccct   10440
ccgcatcgca gccagcaccc tgaagtctgg gatttcctac agggcacggg tgagggcctg   10500
ggctcagtgc tataacacca cctggagtga gtggagc                           10537

<210> SEQ ID NO 48
<211> LENGTH: 183
<212> TYPE: DNA
<213> ORGANISM: Artificial Sequence
<220> FEATURE:
<223> OTHER INFORMATION: Synthetic primer

<400> SEQUENCE: 48
cctccctctg accttagtgg tgggagcccc tgaccatgcc accactgatc tggccgttct      60
gtctctgcag ggagcatcaa ggtcctgcag gagcccacct gcgtctccga ctacatgagc    120
atctctactt gcgagtggaa gatgaatggt cccaccaatt gcagcaccga gctccgcctg    180
ttg                                                                 183

<210> SEQ ID NO 49
<211> LENGTH: 183
<212> TYPE: DNA
<213> ORGANISM: Artificial Sequence
<220> FEATURE:
<223> OTHER INFORMATION: Synthetic primer

<400> SEQUENCE: 49
cagcaccctg aagtctggga tttcctacag ggcacgggtg agggcctggg ctcagtgcta     60
taacaccacc tggagtgagt ggagccctag catcacgtgg tacaaccgtg agtatcaggg    120
tcgtaggctg tgaggatctc tacagccgtg tatattctct gttcagaaat tccctctggc    180
tga                                                                 183

<210> SEQ ID NO 50
<211> LENGTH: 87
<212> TYPE: DNA
<213> ORGANISM: Artificial Sequence
<220> FEATURE:
<223> OTHER INFORMATION: Synthetic primer

<400> SEQUENCE: 50
aggcccggag tttaaatccc cagagcccac gtaaaagcct gatatcgaat tccgaagttc     60
ctattctcta gaaagtatag gaacttc                                        87

<210> SEQ ID NO 51
<211> LENGTH: 183
<212> TYPE: DNA
```

```
<213> ORGANISM: Artificial Sequence
<220> FEATURE:
<223> OTHER INFORMATION: Synthetic primer

<400> SEQUENCE: 51
gaagttccta ttctctagaa agtataggaa cttcatcagt caggtacata atggtggatc    60
caagctttgc gcagtagcac gcatgcgtaa tcctgatgga gcaattagga gaagccggtg   120
gccggctagc ctgtgcagac tgtgaaaaca gagcatctga agctgtgtga aaggctagct   180
cgc                                                                 183

<210> SEQ ID NO 52
<211> LENGTH: 21
<212> TYPE: DNA
<213> ORGANISM: Artificial Sequence
<220> FEATURE:
<223> OTHER INFORMATION: Synthetic primer

<400> SEQUENCE: 52
cgcattgtct gagtaggtgt c                                              21

<210> SEQ ID NO 53
<211> LENGTH: 24
<212> TYPE: DNA
<213> ORGANISM: Artificial Sequence
<220> FEATURE:
<223> OTHER INFORMATION: Synthetic primer

<400> SEQUENCE: 53
gctgttcaat gaatggcctc tgtg                                           24

<210> SEQ ID NO 54
<211> LENGTH: 21
<212> TYPE: DNA
<213> ORGANISM: Artificial Sequence
<220> FEATURE:
<223> OTHER INFORMATION: Synthetic primer

<400> SEQUENCE: 54
gtggccaccg tttctgggaa c                                              21

<210> SEQ ID NO 55
<211> LENGTH: 22
<212> TYPE: DNA
<213> ORGANISM: Artificial Sequence
<220> FEATURE:
<223> OTHER INFORMATION: Synthetic primer

<400> SEQUENCE: 55
tcaacaatct aagcacggac ct                                             22

<210> SEQ ID NO 56
<211> LENGTH: 21
<212> TYPE: DNA
<213> ORGANISM: Artificial Sequence
<220> FEATURE:
<223> OTHER INFORMATION: Synthetic primer

<400> SEQUENCE: 56
gtgctgaggc cagggttcct c                                              21

<210> SEQ ID NO 57
<211> LENGTH: 24
<212> TYPE: DNA
<213> ORGANISM: Artificial Sequence
```

```
<220> FEATURE:
<223> OTHER INFORMATION: Synthetic primer

<400> SEQUENCE: 57
gctgttcaat gaatggcctc tgtg                                         24

<210> SEQ ID NO 58
<211> LENGTH: 24
<212> TYPE: DNA
<213> ORGANISM: Artificial Sequence
<220> FEATURE:
<223> OTHER INFORMATION: Synthetic primer

<400> SEQUENCE: 58
gacacacgtg tctgccagct ctgt                                         24

<210> SEQ ID NO 59
<211> LENGTH: 25
<212> TYPE: DNA
<213> ORGANISM: Artificial Sequence
<220> FEATURE:
<223> OTHER INFORMATION: Synthetic primer

<400> SEQUENCE: 59
cacggtcagc cagagggaat ttctg                                        25

<210> SEQ ID NO 60
<211> LENGTH: 24
<212> TYPE: DNA
<213> ORGANISM: Artificial Sequence
<220> FEATURE:
<223> OTHER INFORMATION: Synthetic primer

<400> SEQUENCE: 60
gtggggtcag ctaacgacag caac                                         24

<210> SEQ ID NO 61
<211> LENGTH: 25
<212> TYPE: DNA
<213> ORGANISM: Artificial Sequence
<220> FEATURE:
<223> OTHER INFORMATION: Synthetic primer

<400> SEQUENCE: 61
cgtgtcaaaa gcagaaacgc aggag                                        25

<210> SEQ ID NO 62
<211> LENGTH: 25
<212> TYPE: DNA
<213> ORGANISM: Artificial Sequence
<220> FEATURE:
<223> OTHER INFORMATION: Synthetic primer

<400> SEQUENCE: 62
gcgtatgtca ggatctgagg agcac                                        25

<210> SEQ ID NO 63
<211> LENGTH: 25
<212> TYPE: DNA
<213> ORGANISM: Artificial Sequence
<220> FEATURE:
<223> OTHER INFORMATION: Synthetic primer

<400> SEQUENCE: 63
gacaagcgtt agtaggcaca tatac                                        25
```

<210> SEQ ID NO 64
<211> LENGTH: 24
<212> TYPE: DNA
<213> ORGANISM: Artificial Sequence
<220> FEATURE:
<223> OTHER INFORMATION: Synthetic primer

<400> SEQUENCE: 64
gctccaattt cccacaacat tagt                                            24

<210> SEQ ID NO 65
<211> LENGTH: 23
<212> TYPE: DNA
<213> ORGANISM: Artificial Sequence
<220> FEATURE:
<223> OTHER INFORMATION: Synthetic primer

<400> SEQUENCE: 65
aacatagact ggcgttcacc tgg                                             23

<210> SEQ ID NO 66
<211> LENGTH: 23
<212> TYPE: DNA
<213> ORGANISM: Artificial Sequence
<220> FEATURE:
<223> OTHER INFORMATION: Synthetic primer

<400> SEQUENCE: 66
tccgcacttc cacgtgtgag tgg                                             23

<210> SEQ ID NO 67
<211> LENGTH: 23
<212> TYPE: DNA
<213> ORGANISM: Artificial Sequence
<220> FEATURE:
<223> OTHER INFORMATION: Synthetic primer

<400> SEQUENCE: 67
gtggttcctg gatagcgctg tgg                                             23

<210> SEQ ID NO 68
<211> LENGTH: 23
<212> TYPE: DNA
<213> ORGANISM: Artificial Sequence
<220> FEATURE:
<223> OTHER INFORMATION: Synthetic primer

<400> SEQUENCE: 68
atccaggaac cactcacacg tgg                                             23

<210> SEQ ID NO 69
<211> LENGTH: 23
<212> TYPE: DNA
<213> ORGANISM: Artificial Sequence
<220> FEATURE:
<223> OTHER INFORMATION: Synthetic primer

<400> SEQUENCE: 69
tatgttgtgc tgtatgcttg tgg                                             23

<210> SEQ ID NO 70
<211> LENGTH: 23
<212> TYPE: DNA
<213> ORGANISM: Artificial Sequence
<220> FEATURE:
<223> OTHER INFORMATION: Synthetic primer

```
<400> SEQUENCE: 70
ctcagctctg cctacactac agg                                              23

<210> SEQ ID NO 71
<211> LENGTH: 23
<212> TYPE: DNA
<213> ORGANISM: Artificial Sequence
<220> FEATURE:
<223> OTHER INFORMATION: Synthetic primer

<400> SEQUENCE: 71
agaacatcag cctgtagtgt agg                                              23

<210> SEQ ID NO 72
<211> LENGTH: 23
<212> TYPE: DNA
<213> ORGANISM: Artificial Sequence
<220> FEATURE:
<223> OTHER INFORMATION: Synthetic primer

<400> SEQUENCE: 72
ctactatacg gcgcgtgtga ggg                                              23

<210> SEQ ID NO 73
<211> LENGTH: 23
<212> TYPE: DNA
<213> ORGANISM: Artificial Sequence
<220> FEATURE:
<223> OTHER INFORMATION: Synthetic primer

<400> SEQUENCE: 73
gatgtcaggg gtctactata cgg                                              23

<210> SEQ ID NO 74
<211> LENGTH: 23
<212> TYPE: DNA
<213> ORGANISM: Artificial Sequence
<220> FEATURE:
<223> OTHER INFORMATION: Synthetic primer

<400> SEQUENCE: 74
tatagtagac ccctgacatc agg                                              23

<210> SEQ ID NO 75
<211> LENGTH: 23
<212> TYPE: DNA
<213> ORGANISM: Artificial Sequence
<220> FEATURE:
<223> OTHER INFORMATION: Synthetic primer

<400> SEQUENCE: 75
acgtgtgtcg gttcccagcc tgg                                              23

<210> SEQ ID NO 76
<211> LENGTH: 23
<212> TYPE: DNA
<213> ORGANISM: Artificial Sequence
<220> FEATURE:
<223> OTHER INFORMATION: Synthetic primer

<400> SEQUENCE: 76
ctgacatcag gatgttgatc ggg                                              23

<210> SEQ ID NO 77
```

```
<211> LENGTH: 23
<212> TYPE: DNA
<213> ORGANISM: Artificial Sequence
<220> FEATURE:
<223> OTHER INFORMATION: Synthetic primer

<400> SEQUENCE: 77
gttgatcggg aagctcagcc tgg                                            23

<210> SEQ ID NO 78
<211> LENGTH: 23
<212> TYPE: DNA
<213> ORGANISM: Artificial Sequence
<220> FEATURE:
<223> OTHER INFORMATION: Synthetic primer

<400> SEQUENCE: 78
atgtgaccta caaggaaccc agg                                            23

<210> SEQ ID NO 79
<211> LENGTH: 23
<212> TYPE: DNA
<213> ORGANISM: Artificial Sequence
<220> FEATURE:
<223> OTHER INFORMATION: Synthetic primer

<400> SEQUENCE: 79
agtctataat gtgacctaca agg                                            23

<210> SEQ ID NO 80
<211> LENGTH: 644
<212> TYPE: DNA
<213> ORGANISM: Artificial Sequence
<220> FEATURE:
<223> OTHER INFORMATION: Synthetic primer

<400> SEQUENCE: 80
ttgttagcat ctcttgataa acttaattgt ctctcgtcac tgacggcaca gagctattga    60
tgggtctcac ctcccaactg cttcccccte tgttcttcct gctagcatgt gccggcaact   120
ttgtccacgg acacaagtgc gatatcacct tacaggagat catcaaaact ttgaacagcc   180
tcacagagca gaagactctg tgcaccgagt tgaccgtaac agacatcttt gctgcctcca   240
agaacacaac tgagaaggaa accttctgca gggctgcgac tgtgctccgg cagttctaca   300
gccaccatga aaggacact cgctgcctgg gtgcgactgc acagcagttc cacaggcaca   360
agcagctgat ccgattcctg aaacggctcg acaggaacct ctggggcctg gcgggcttga   420
attcctgtcc tgtgaaggaa gccaaccaga gtacgttgga aaacttcttg gaaaggctaa   480
agacgatcat gagagagaaa tattcaaagt gttcgagctg atactgagcc accatgcttt   540
aacttatgaa tttttaatgg ttttattttt aatatttata tatttataat tcataaaata   600
aaatatttgt ataatgtaac agaaaaaaaa aaaaaaaaa aaaa                     644

<210> SEQ ID NO 81
<211> LENGTH: 21
<212> TYPE: DNA
<213> ORGANISM: Artificial Sequence
<220> FEATURE:
<223> OTHER INFORMATION: Synthetic primer

<400> SEQUENCE: 81
gggagggtga gtggagtccc a                                              21
```

```
<210> SEQ ID NO 82
<211> LENGTH: 22
<212> TYPE: DNA
<213> ORGANISM: Artificial Sequence
<220> FEATURE:
<223> OTHER INFORMATION: Synthetic primer

<400> SEQUENCE: 82
cagcgcaggc ttactcggag ag                                            22
```